US011467153B2

(12) United States Patent
Belhocine et al.

(10) Patent No.: US 11,467,153 B2
(45) Date of Patent: Oct. 11, 2022

(54) METHODS FOR PROCESSING NUCLEIC ACID MOLECULES

(71) Applicant: 10x Genomics, Inc., Pleasanton, CA (US)

(72) Inventors: Zahra Kamila Belhocine, Fremont, CA (US); Jason Bell, Palo Alto, CA (US); Jerald Sapida, San Jose, CA (US); Katrina Sullivan-Bibee, Palo Alto, CA (US)

(73) Assignee: 10X GENOMICS, INC., Pleasanton, CA (US)

( * ) Notice: Subject to any disclaimer, the term of this patent is extended or adjusted under 35 U.S.C. 154(b) by 0 days.

(21) Appl. No.: 17/393,107

(22) Filed: Aug. 3, 2021

(65) Prior Publication Data
US 2021/0364502 A1 Nov. 25, 2021

Related U.S. Application Data

(63) Continuation of application No. PCT/US2020/018010, filed on Feb. 12, 2020.
(Continued)

(51) Int. Cl.
*G01N 33/532* (2006.01)
*C12N 15/85* (2006.01)
(Continued)

(52) U.S. Cl.
CPC ..... *G01N 33/532* (2013.01); *C07K 14/70539* (2013.01); *C12N 15/1037* (2013.01);
(Continued)

(58) Field of Classification Search
None
See application file for complete search history.

(56) References Cited

U.S. PATENT DOCUMENTS

| 4,124,638 A | 11/1978 | Hansen |
| 5,137,829 A | 8/1992 | Nag et al. |

(Continued)

FOREIGN PATENT DOCUMENTS

| EP | 1019496 B1 | 9/2004 |
| EP | 1841879 A2 | 10/2007 |

(Continued)

OTHER PUBLICATIONS

10X Genomics, Inc. CG000153 Rev A. Chromium Single Cell DNA Reagent Kits User Guide. 2018.
(Continued)

*Primary Examiner* — Kaijiang Zhang
(74) *Attorney, Agent, or Firm* — Wilson Sonsini Goodrich & Rosati

(57) ABSTRACT

The present disclosure provides methods, systems, and kits for processing nucleic acid molecules. A method may comprise providing a template nucleic acid fragment (e.g., within a cell, cell bead, or cell nucleus) within a partition (e.g., a droplet or well) and subjecting the template nucleic acid fragment to one or more processes including a barcoding process and a single primer extension or amplification process. The processed template nucleic acid fragment may then be recovered from the partition and subjected to further amplification to provide material for subsequent sequencing analysis. The methods provided herein may permit simultaneous processing and analysis of both DNA and RNA molecules originating from the same cell, cell bead, or cell nucleus.

30 Claims, 25 Drawing Sheets

Related U.S. Application Data

(60) Provisional application No. 62/804,644, filed on Feb. 12, 2019.

(51) Int. Cl.

| | | |
|---|---|---|
| *G01N 33/543* | (2006.01) | |
| *G01N 33/548* | (2006.01) | |
| *C12N 15/10* | (2006.01) | |
| *C12Q 1/6806* | (2018.01) | |
| *C12Q 1/6881* | (2018.01) | |
| *C40B 50/06* | (2006.01) | |
| *C07K 14/74* | (2006.01) | |
| *C12Q 1/6804* | (2018.01) | |
| *G01N 33/50* | (2006.01) | |
| *G01N 33/53* | (2006.01) | |
| *G01N 33/58* | (2006.01) | |
| *C12Q 1/6818* | (2018.01) | |
| *C12Q 1/6827* | (2018.01) | |
| *C12N 15/11* | (2006.01) | |
| *G01N 33/569* | (2006.01) | |
| *C40B 70/00* | (2006.01) | |
| *C40B 30/04* | (2006.01) | |

(52) U.S. Cl.
CPC ..... *C12N 15/1055* (2013.01); *C12N 15/1065* (2013.01); *C12N 15/1075* (2013.01); *C12N 15/11* (2013.01); *C12N 15/85* (2013.01); *C12Q 1/6804* (2013.01); *C12Q 1/6806* (2013.01); *C12Q 1/6818* (2013.01); *C12Q 1/6827* (2013.01); *C12Q 1/6881* (2013.01); *G01N 33/505* (2013.01); *G01N 33/5032* (2013.01); *G01N 33/5304* (2013.01); *G01N 33/5306* (2013.01); *G01N 33/5308* (2013.01); *G01N 33/548* (2013.01); *G01N 33/54306* (2013.01); *G01N 33/54366* (2013.01); *G01N 33/56977* (2013.01); *G01N 33/58* (2013.01); *C12N 2310/20* (2017.05); *C12N 2320/10* (2013.01); *C12Q 2537/164* (2013.01); *C12Q 2563/179* (2013.01); *C12Q 2563/185* (2013.01); *C12Q 2565/1015* (2013.01); *C40B 30/04* (2013.01); *C40B 50/06* (2013.01); *C40B 70/00* (2013.01)

(56) References Cited

U.S. PATENT DOCUMENTS

| | | |
|---|---|---|
| 5,185,099 A | 2/1993 | Delpuech et al. |
| 5,270,183 A | 12/1993 | Corbett et al. |
| 5,478,893 A | 12/1995 | Ghosh et al. |
| 5,736,330 A | 4/1998 | Fulton |
| 5,756,334 A | 5/1998 | Perler et al. |
| 5,846,719 A | 12/1998 | Brenner et al. |
| 5,900,481 A | 5/1999 | Lough et al. |
| 5,942,609 A | 8/1999 | Hunkapiller et al. |
| 5,965,443 A | 10/1999 | Reznikoff et al. |
| 5,994,056 A | 11/1999 | Higuchi |
| 6,033,880 A | 3/2000 | Haff et al. |
| 6,057,149 A | 5/2000 | Burns et al. |
| 6,123,798 A | 9/2000 | Gandhi et al. |
| 6,171,850 B1 | 1/2001 | Nagle et al. |
| 6,172,218 B1 | 1/2001 | Brenner |
| 6,176,962 B1 | 1/2001 | Soane et al. |
| 6,207,384 B1 | 3/2001 | Mekalanos et al. |
| 6,294,385 B1 | 9/2001 | Goryshin et al. |
| 6,306,590 B1 | 10/2001 | Mehta et al. |
| 6,327,410 B1 | 12/2001 | Walt et al. |
| 6,379,929 B1 | 4/2002 | Burns et al. |
| 6,406,848 B1 | 6/2002 | Bridgham et al. |
| 6,409,832 B2 | 6/2002 | Weigl et al. |
| 6,492,118 B1 | 12/2002 | Abrams et al. |
| 6,524,456 B1 | 2/2003 | Ramsey et al. |
| 6,586,176 B1 | 7/2003 | Trnovsky et al. |
| 6,632,655 B1 | 10/2003 | Mehta et al. |
| 6,915,679 B2 | 7/2005 | Chien et al. |
| 7,041,481 B2 | 5/2006 | Anderson et al. |
| 7,115,400 B1 | 10/2006 | Adessi et al. |
| 7,129,091 B2 | 10/2006 | Ismagilov et al. |
| 7,138,267 B1 | 11/2006 | Jendrisak et al. |
| 7,262,056 B2 | 8/2007 | Wooddell et al. |
| 7,268,167 B2 | 9/2007 | Higuchi et al. |
| 7,282,370 B2 | 10/2007 | Bridgham et al. |
| 7,294,503 B2 | 11/2007 | Quake et al. |
| 7,323,305 B2 | 1/2008 | Leamon et al. |
| 7,544,473 B2 | 6/2009 | Brenner |
| 7,608,434 B2 | 10/2009 | Reznikoff et al. |
| 7,622,076 B2 | 11/2009 | Davies et al. |
| 7,622,280 B2 | 11/2009 | Holliger et al. |
| 7,645,596 B2 | 1/2010 | Williams et al. |
| 7,708,949 B2 | 5/2010 | Stone et al. |
| 7,772,287 B2 | 8/2010 | Higuchi et al. |
| 7,776,927 B2 | 8/2010 | Chu et al. |
| 7,842,457 B2 | 11/2010 | Berka et al. |
| 7,910,354 B2 | 3/2011 | Drmanac et al. |
| 7,927,797 B2 | 4/2011 | Nobile et al. |
| 7,960,104 B2 | 6/2011 | Drmanac et al. |
| 7,968,287 B2 | 6/2011 | Griffiths et al. |
| 8,053,192 B2 | 11/2011 | Bignell et al. |
| 8,133,719 B2 | 3/2012 | Drmanac et al. |
| 8,168,385 B2 | 5/2012 | Brenner |
| 8,268,564 B2 | 9/2012 | Roth et al. |
| 8,273,573 B2 | 9/2012 | Ismagilov et al. |
| 8,298,767 B2 | 10/2012 | Brenner et al. |
| 8,304,193 B2 | 11/2012 | Ismagilov et al. |
| 8,318,433 B2 | 11/2012 | Brenner |
| 8,329,407 B2 | 12/2012 | Ismagilov et al. |
| 8,592,150 B2 | 11/2013 | Drmanac et al. |
| 8,658,430 B2 | 2/2014 | Miller et al. |
| 8,822,148 B2 | 9/2014 | Ismagliov et al. |
| 8,835,358 B2 | 9/2014 | Fodor et al. |
| 8,871,444 B2 | 10/2014 | Griffiths et al. |
| 8,889,083 B2 | 11/2014 | Ismagilov et al. |
| 8,927,218 B2 | 1/2015 | Forsyth |
| 8,975,302 B2 | 3/2015 | Light et al. |
| 9,005,935 B2 | 4/2015 | Belyaev |
| 9,012,390 B2 | 4/2015 | Holtze et al. |
| 9,029,083 B2 | 5/2015 | Griffiths et al. |
| 9,029,085 B2 | 5/2015 | Agresti et al. |
| 9,080,211 B2 | 7/2015 | Grunenwald et al. |
| 9,085,798 B2 | 7/2015 | Chee |
| 9,089,844 B2 | 7/2015 | Hiddessen et al. |
| 9,126,160 B2 | 9/2015 | Ness et al. |
| 9,156,010 B2 | 10/2015 | Colston et al. |
| 9,194,861 B2 | 11/2015 | Hindson et al. |
| 9,216,392 B2 | 12/2015 | Hindson et al. |
| 9,238,206 B2 | 1/2016 | Rotem et al. |
| 9,238,671 B2 | 1/2016 | Goryshin et al. |
| 9,266,104 B2 | 2/2016 | Link |
| 9,290,808 B2 | 3/2016 | Fodor et al. |
| 9,328,382 B2 | 5/2016 | Drmanac et al. |
| 9,347,059 B2 | 5/2016 | Saxonov |
| 9,371,598 B2 | 6/2016 | Chee |
| 9,388,465 B2 | 7/2016 | Hindson et al. |
| 9,417,190 B2 | 8/2016 | Hindson et al. |
| 9,486,757 B2 | 11/2016 | Romanowsky et al. |
| 9,498,761 B2 | 11/2016 | Holtze et al. |
| 9,500,664 B2 | 11/2016 | Ness et al. |
| 9,567,631 B2 | 2/2017 | Hindson et al. |
| 9,574,226 B2 | 2/2017 | Gormley et al. |
| 9,593,365 B2 | 3/2017 | Frisen et al. |
| 9,623,384 B2 | 4/2017 | Hindson et al. |
| 9,637,799 B2 | 5/2017 | Fan et al. |
| 9,644,204 B2 | 5/2017 | Hindson et al. |
| 9,689,024 B2 | 6/2017 | Hindson et al. |
| 9,694,361 B2 | 7/2017 | Bharadwaj et al. |
| 9,701,998 B2 | 7/2017 | Hindson et al. |
| 9,764,322 B2 | 9/2017 | Hiddessen et al. |
| 9,822,396 B2 | 11/2017 | Litterst et al. |
| 9,824,068 B2 | 11/2017 | Wong |
| 9,868,979 B2 | 1/2018 | Chee et al. |
| 9,879,313 B2 | 1/2018 | Chee et al. |

(56) References Cited

U.S. PATENT DOCUMENTS

| | | |
|---|---|---|
| 9,946,577 B1 | 4/2018 | Stafford et al. |
| 9,951,386 B2 | 4/2018 | Hindson et al. |
| 9,957,558 B2 | 5/2018 | Leamon et al. |
| 9,975,122 B2 | 5/2018 | Masquelier et al. |
| 10,011,872 B1 | 7/2018 | Belgrader et al. |
| 10,017,759 B2 | 7/2018 | Kaper et al. |
| 10,030,261 B2 | 7/2018 | Frisen et al. |
| 10,059,989 B2 | 8/2018 | Giresi et al. |
| 10,221,436 B2 | 3/2019 | Hardenbol et al. |
| 10,221,442 B2 | 3/2019 | Hindson et al. |
| 10,253,364 B2 | 4/2019 | Hindson et al. |
| 10,273,541 B2 | 4/2019 | Hindson et al. |
| 10,323,279 B2 | 6/2019 | Hindson et al. |
| 10,347,365 B2 | 7/2019 | Wong et al. |
| 10,357,771 B2 | 7/2019 | Bharadwaj et al. |
| 10,395,758 B2 | 8/2019 | Schnall-Levin |
| 10,400,280 B2 | 9/2019 | Hindson et al. |
| 10,428,326 B2 | 10/2019 | Belhocine et al. |
| 10,533,221 B2 | 1/2020 | Hindson et al. |
| 10,544,413 B2 | 1/2020 | Bharadwaj et al. |
| 10,549,279 B2 | 2/2020 | Bharadwaj et al. |
| 10,590,244 B2 | 3/2020 | Delaney et al. |
| 10,633,691 B2 | 4/2020 | Wu |
| 10,745,742 B2 | 8/2020 | Bent et al. |
| 10,752,949 B2 | 8/2020 | Hindson et al. |
| 10,774,374 B2 | 9/2020 | Frisen et al. |
| 10,815,525 B2 | 10/2020 | Lucero et al. |
| 10,829,815 B2 | 11/2020 | Bharadwaj et al. |
| 10,874,997 B2 | 12/2020 | Weitz et al. |
| 10,927,370 B2 | 2/2021 | Belhocine et al. |
| 10,995,333 B2 | 5/2021 | Pfeiffer |
| 2002/0005354 A1 | 1/2002 | Spence et al. |
| 2002/0051971 A1 | 5/2002 | Stuelpnagel et al. |
| 2002/0092767 A1 | 7/2002 | Bjornson et al. |
| 2002/0119455 A1 | 8/2002 | Chan |
| 2002/0127736 A1 | 9/2002 | Chou et al. |
| 2003/0036206 A1 | 2/2003 | Chien et al. |
| 2003/0075446 A1 | 4/2003 | Culbertson et al. |
| 2003/0124509 A1 | 7/2003 | Kenis et al. |
| 2003/0215862 A1 | 11/2003 | Parce et al. |
| 2005/0130188 A1 | 6/2005 | Walt et al. |
| 2005/0250147 A1 | 11/2005 | Macevicz |
| 2005/0266582 A1 | 12/2005 | Modlin et al. |
| 2005/0287572 A1 | 12/2005 | Mathies et al. |
| 2006/0177832 A1 | 8/2006 | Brenner |
| 2006/0275782 A1 | 12/2006 | Gunderson et al. |
| 2007/0020640 A1 | 1/2007 | McCloskey et al. |
| 2007/0042419 A1 | 2/2007 | Barany et al. |
| 2007/0172873 A1 | 7/2007 | Brenner et al. |
| 2007/0190543 A1 | 8/2007 | Livak |
| 2007/0196397 A1 | 8/2007 | Torii et al. |
| 2007/0264320 A1 | 11/2007 | Lee et al. |
| 2008/0056948 A1 | 3/2008 | Dale et al. |
| 2008/0166720 A1 | 7/2008 | Hsieh et al. |
| 2008/0242560 A1 | 10/2008 | Gunderson et al. |
| 2009/0011943 A1 | 1/2009 | Drmanac et al. |
| 2009/0047713 A1 | 2/2009 | Handique |
| 2009/0099041 A1 | 4/2009 | Church et al. |
| 2009/0131543 A1 | 5/2009 | Weitz et al. |
| 2009/0148961 A1 | 6/2009 | Luchini et al. |
| 2009/0155563 A1 | 6/2009 | Petsev et al. |
| 2009/0202984 A1 | 8/2009 | Cantor |
| 2009/0235990 A1 | 9/2009 | Beer |
| 2009/0269248 A1 | 10/2009 | Falb et al. |
| 2009/0286687 A1 | 11/2009 | Dressman et al. |
| 2010/0035254 A1 | 2/2010 | Williams |
| 2010/0069263 A1 | 3/2010 | Shendure et al. |
| 2010/0086914 A1 | 4/2010 | Bentley et al. |
| 2010/0105866 A1 | 4/2010 | Fraden et al. |
| 2010/0184928 A1 | 7/2010 | Kumacheva |
| 2010/0216153 A1 | 8/2010 | Lapidus et al. |
| 2010/0248991 A1 | 9/2010 | Roesler et al. |
| 2010/0304982 A1 | 12/2010 | Hinz et al. |
| 2011/0217736 A1 | 9/2011 | Hindson |
| 2011/0305761 A1 | 12/2011 | Shum et al. |
| 2012/0071331 A1 | 3/2012 | Casbon et al. |
| 2012/0172259 A1 | 7/2012 | Rigatti et al. |
| 2012/0196288 A1 | 8/2012 | Beer |
| 2012/0219947 A1 | 8/2012 | Yurkovetsky et al. |
| 2013/0028812 A1 | 1/2013 | Prieto et al. |
| 2013/0109575 A1 | 5/2013 | Kleinschmidt et al. |
| 2014/0065234 A1 | 3/2014 | Shum et al. |
| 2014/0093916 A1 | 4/2014 | Belyaev |
| 2014/0155295 A1 | 6/2014 | Hindson et al. |
| 2014/0221239 A1 | 8/2014 | Carman et al. |
| 2014/0272996 A1 | 9/2014 | Bemis |
| 2014/0274740 A1 | 9/2014 | Srinivasan et al. |
| 2014/0302503 A1 | 10/2014 | Lowe et al. |
| 2014/0338753 A1 | 11/2014 | Sperling et al. |
| 2014/0378345 A1 | 12/2014 | Hindson et al. |
| 2015/0111788 A1 | 4/2015 | Fernandez et al. |
| 2015/0267191 A1 | 9/2015 | Steelman et al. |
| 2015/0291942 A1 | 10/2015 | Gloeckner et al. |
| 2015/0361418 A1 | 12/2015 | Reed |
| 2015/0368638 A1 | 12/2015 | Steemers et al. |
| 2015/0368694 A1 | 12/2015 | Pan et al. |
| 2015/0376605 A1 | 12/2015 | Jarosz et al. |
| 2015/0376609 A1 | 12/2015 | Hindson et al. |
| 2015/0376700 A1 | 12/2015 | Schnall-Levin et al. |
| 2015/0379196 A1 | 12/2015 | Schnall-Levin et al. |
| 2016/0008778 A1 | 1/2016 | Weitz et al. |
| 2016/0024558 A1 | 1/2016 | Hardenbol et al. |
| 2016/0024572 A1 | 1/2016 | Shishkin et al. |
| 2016/0053253 A1 | 2/2016 | Salathia et al. |
| 2016/0059204 A1 | 3/2016 | Hindson et al. |
| 2016/0060621 A1 | 3/2016 | Agresti et al. |
| 2016/0115474 A1 | 4/2016 | Jelinek et al. |
| 2016/0122753 A1 | 5/2016 | Mikkelsen et al. |
| 2016/0122817 A1 | 5/2016 | Jarosz et al. |
| 2016/0203196 A1 | 7/2016 | Schnall-Levin et al. |
| 2016/0208323 A1 | 7/2016 | Bernstein et al. |
| 2016/0232291 A1 | 8/2016 | Kyriazopoulou-Panagiotopoulou et al. |
| 2016/0244809 A1 | 8/2016 | Belgrader et al. |
| 2016/0281160 A1 | 9/2016 | Jarosz et al. |
| 2016/0289769 A1 | 10/2016 | Schwartz et al. |
| 2016/0314242 A1 | 10/2016 | Schnall-Levin et al. |
| 2016/0348093 A1 | 12/2016 | Price et al. |
| 2016/0362724 A1 | 12/2016 | Bailey et al. |
| 2017/0016041 A1 | 1/2017 | Greenfield et al. |
| 2017/0128937 A1 | 5/2017 | Hung et al. |
| 2017/0144161 A1 | 5/2017 | Hindson et al. |
| 2017/0145476 A1 | 5/2017 | Ryvkin et al. |
| 2017/0159109 A1 | 6/2017 | Zheng et al. |
| 2017/0235876 A1 | 8/2017 | Jaffe et al. |
| 2017/0260584 A1 | 9/2017 | Zheng et al. |
| 2018/0030515 A1 | 2/2018 | Regev et al. |
| 2018/0080075 A1 | 3/2018 | Brenner et al. |
| 2018/0105808 A1 | 4/2018 | Mikkelsen et al. |
| 2018/0112212 A1 | 4/2018 | Nicol et al. |
| 2018/0195112 A1 | 7/2018 | Lebofsky et al. |
| 2018/0312822 A1 | 11/2018 | Lee et al. |
| 2018/0312873 A1 | 11/2018 | Zheng |
| 2018/0340169 A1 | 11/2018 | Belhocine et al. |
| 2018/0340171 A1* | 11/2018 | Belhocine et al. ............ C12N 15/1096 |
| 2018/0355348 A1 | 12/2018 | Adey et al. |
| 2018/0371538 A1 | 12/2018 | Blauwkamp et al. |
| 2018/0371545 A1 | 12/2018 | Wong et al. |
| 2019/0002967 A1 | 1/2019 | Chen et al. |
| 2019/0032128 A1 | 1/2019 | Chen et al. |
| 2019/0040382 A1 | 2/2019 | Steemers et al. |
| 2019/0060890 A1 | 2/2019 | Bharadwaj et al. |
| 2019/0060905 A1 | 2/2019 | Bharadwaj et al. |
| 2019/0064173 A1 | 2/2019 | Bharadwaj et al. |
| 2019/0071656 A1 | 3/2019 | Chang et al. |
| 2019/0127731 A1 | 5/2019 | McDermott |
| 2019/0134633 A1 | 5/2019 | Bharadwaj et al. |
| 2019/0153532 A1 | 5/2019 | Bharadwaj et al. |
| 2019/0176152 A1 | 6/2019 | Bharadwaj et al. |
| 2019/0177800 A1 | 6/2019 | Boutet et al. |
| 2019/0323088 A1 | 10/2019 | Boutet et al. |
| 2019/0345636 A1 | 11/2019 | McDermott et al. |
| 2019/0352717 A1 | 11/2019 | Schnall-Levin |

(56) References Cited

U.S. PATENT DOCUMENTS

| | | |
|---|---|---|
| 2019/0367997 A1 | 12/2019 | Bent et al. |
| 2019/0376118 A1 | 12/2019 | Belhocine et al. |
| 2020/0005902 A1 | 1/2020 | Mellen et al. |
| 2020/0032335 A1 | 1/2020 | Martinez |
| 2020/0033237 A1 | 1/2020 | Hindson et al. |
| 2020/0033366 A1 | 1/2020 | Alvarado Martinez |
| 2020/0056223 A1 | 2/2020 | Bell |
| 2020/0105373 A1 | 4/2020 | Zheng |
| 2020/0263232 A1 | 8/2020 | Bell et al. |
| 2020/0291454 A1 | 9/2020 | Belhocine et al. |
| 2020/0407775 A1 | 12/2020 | Bharadwaj et al. |

FOREIGN PATENT DOCUMENTS

| | | |
|---|---|---|
| EP | 1967592 B1 | 4/2010 |
| EP | 2540389 A1 | 1/2013 |
| EP | 2635679 B1 | 4/2017 |
| GB | 2097692 A | 11/1982 |
| GB | 2097692 B | 5/1985 |
| WO | WO-84/02000 | 5/1984 |
| WO | WO-95/30782 | 11/1995 |
| WO | WO-99/52708 | 10/1999 |
| WO | WO-2000008212 A1 | 2/2000 |
| WO | WO-2001002850 A1 | 1/2001 |
| WO | WO-0114589 A2 | 3/2001 |
| WO | WO-0190418 A1 | 11/2001 |
| WO | WO-2001089787 A2 | 11/2001 |
| WO | WO-2004002627 A2 | 1/2004 |
| WO | WO-2004065617 A2 | 8/2004 |
| WO | WO-2004069849 A2 | 8/2004 |
| WO | WO-2004091763 A2 | 10/2004 |
| WO | WO-2005021151 A1 | 3/2005 |
| WO | WO-2005049787 A9 | 6/2005 |
| WO | WO-2005082098 A2 | 9/2005 |
| WO | WO-2006040551 A2 | 4/2006 |
| WO | WO-2006078841 A1 | 7/2006 |
| WO | WO-2006096571 A2 | 9/2006 |
| WO | WO-2007081385 A2 | 7/2007 |
| WO | WO-2007081387 A1 | 7/2007 |
| WO | WO-2007089541 A2 | 8/2007 |
| WO | WO-2007133710 A2 | 11/2007 |
| WO | WO-2007140015 A2 | 12/2007 |
| WO | WO-2007147079 A2 | 12/2007 |
| WO | WO-2008021123 A1 | 2/2008 |
| WO | WO-2008109176 A2 | 9/2008 |
| WO | WO-2008121342 A2 | 10/2008 |
| WO | WO-2008134153 A1 | 11/2008 |
| WO | WO-2008150432 A1 | 12/2008 |
| WO | WO-2009011808 A1 | 1/2009 |
| WO | WO-2009015296 A1 | 1/2009 |
| WO | WO-2009085215 A1 | 7/2009 |
| WO | WO-2009147386 A1 | 12/2009 |
| WO | WO-2009152928 A2 | 12/2009 |
| WO | WO-2010033200 A2 | 3/2010 |
| WO | WO-2010048605 A1 | 4/2010 |
| WO | WO-2010104604 A1 | 9/2010 |
| WO | WO-2010117620 A2 | 10/2010 |
| WO | WO-2010148039 A2 | 12/2010 |
| WO | WO-2011028539 A1 | 3/2011 |
| WO | WO-2011047870 A1 | 4/2011 |
| WO | WO-2011056546 A1 | 5/2011 |
| WO | WO-2011066476 A1 | 6/2011 |
| WO | WO-2011156529 A2 | 12/2011 |
| WO | WO-2012048341 A1 | 4/2012 |
| WO | WO-2012061832 A1 | 5/2012 |
| WO | WO-2012083225 A2 | 6/2012 |
| WO | WO-2012106546 A2 | 8/2012 |
| WO | WO-2012112804 A1 | 8/2012 |
| WO | WO-2012112970 A2 | 8/2012 |
| WO | WO-2012116331 A2 | 8/2012 |
| WO | WO-2012142531 A2 | 10/2012 |
| WO | WO-2012142611 A2 | 10/2012 |
| WO | WO-2012149042 A2 | 11/2012 |
| WO | WO-2012166425 A2 | 12/2012 |
| WO | WO-2012167142 A2 | 12/2012 |
| WO | WO-2013019751 A1 | 2/2013 |
| WO | WO-2013036929 A1 | 3/2013 |
| WO | WO-2013055955 A1 | 4/2013 |
| WO | WO-2013096643 A1 | 6/2013 |
| WO | WO-2013126741 A1 | 8/2013 |
| WO | WO-2013134261 A1 | 9/2013 |
| WO | WO-2014028378 A2 | 2/2014 |
| WO | WO-2014108810 A2 | 7/2014 |
| WO | WO-2014165559 A2 | 10/2014 |
| WO | WO-2014189957 A2 | 11/2014 |
| WO | WO-2015015199 A2 | 2/2015 |
| WO | WO-2015044428 A1 | 4/2015 |
| WO | WO-2015095226 A2 | 6/2015 |
| WO | WO-2015164212 A1 | 10/2015 |
| WO | WO-2015200893 A2 | 12/2015 |
| WO | WO-2016040476 A1 | 3/2016 |
| WO | WO-2016061517 A2 | 4/2016 |
| WO | WO-2016126871 A2 | 8/2016 |
| WO | WO-2016191618 A1 | 12/2016 |
| WO | WO-2016207647 A1 | 12/2016 |
| WO | WO-2016207653 A2 | 12/2016 |
| WO | WO-2017015075 A1 | 1/2017 |
| WO | WO-2017025594 A1 | 2/2017 |
| WO | WO-2017034970 A1 | 3/2017 |
| WO | WO-2017075265 A1 | 5/2017 |
| WO | WO-2017171985 A1 | 10/2017 |
| WO | WO-2017197343 A2 | 11/2017 |
| WO | WO-2018031631 A1 | 2/2018 |
| WO | WO-2018039338 A1 | 3/2018 |
| WO | WO-2018039969 A1 | 3/2018 |
| WO | WO-2018064640 A1 | 4/2018 |
| WO | WO-2018091676 A1 | 5/2018 |
| WO | WO-2018103025 A1 | 6/2018 |
| WO | WO-2018119301 A1 | 6/2018 |
| WO | WO-2018119447 A2 | 6/2018 |
| WO | WO-2018129368 A2 | 7/2018 |
| WO | WO-2018172726 A1 | 9/2018 |
| WO | WO-2018191701 A1 | 10/2018 |
| WO | WO-2018213643 A1 | 11/2018 |
| WO | WO-2018217912 A1 | 11/2018 |
| WO | WO-2018218226 A1 | 11/2018 |
| WO | WO-2018226546 A1 | 12/2018 |
| WO | WO-2018236615 A1 | 12/2018 |
| WO | WO-2019028166 A1 | 2/2019 |
| WO | WO-2019040637 A1 | 2/2019 |
| WO | WO-2019060907 A1 | 3/2019 |
| WO | WO-2019083852 A1 | 5/2019 |
| WO | WO-2019084043 A1 | 5/2019 |
| WO | WO-2019084165 A1 | 5/2019 |
| WO | WO-2019099751 A1 | 5/2019 |
| WO | WO-2019108851 A1 | 6/2019 |
| WO | WO-2019113235 A1 | 6/2019 |
| WO | WO-2019118355 A1 | 6/2019 |
| WO | WO-2019126789 A1 | 6/2019 |
| WO | WO-2019148042 A1 | 8/2019 |
| WO | WO-2019152108 A1 | 8/2019 |
| WO | WO-2019157529 A1 | 8/2019 |
| WO | WO-2019165318 A1 | 8/2019 |
| WO | WO-2019169028 A1 | 9/2019 |
| WO | WO-2019169347 A1 | 9/2019 |
| WO | WO-2019191321 A1 | 10/2019 |
| WO | WO-2019217758 A1 | 11/2019 |
| WO | WO-2020028882 A1 | 2/2020 |
| WO | WO-2020041148 A1 | 2/2020 |
| WO | WO-2020142779 A1 | 7/2020 |
| WO | WO-2020167862 A1 | 8/2020 |
| WO | WO-2020167866 A1 | 8/2020 |
| WO | WO-2020168013 A1 | 8/2020 |
| WO | WO-2020198532 A1 | 10/2020 |
| WO | WO-2021046475 A1 | 3/2021 |
| WO | WO-2021/222302 A1 | 11/2021 |
| WO | WO-2021222301 A | 11/2021 |

OTHER PUBLICATIONS

10X Genomics, Inc. CG000184 Rev A. Chromium Single Cell 3' Reagent Kits v3 User Guide with Feature Barcoding Technology for CRISPR Screening. 2018.

(56) References Cited

OTHER PUBLICATIONS

10X Genomics, Inc. CG000185 Rev B. Chromium Single Cell 3' Reagent Kits User Guide with Feature Barcoding Technology for Cell Surface Protein. 2018.
10X Genomics, Inc. CG000208 Rev E. Chromium Next GEM Single Cell V(D)J reagent Kits v1.1 User Guide with Feature Barcode Technology for Cell Surface Protein. 2020.
10X Genomics, Inc. CG000209 Rev D. Chromium Next GEM Single Cell ATAC Reagent Kits v1.1 User Guide. 2020.
10X Genomics, Inc. CG000239 Rev B. Visium Spatial Gene Expression Reagent Kits User Guide. 2020.
10X Genomics, Inc. CG00026. Chromium Single Cell 3' Reagent Kit User Guide. 2016.
10X Genomics, Inc. LIT00003 Rev B Chromium Genome Solution Application Note. 2017.
Abate, A.R. et al. "Beating Poisson encapsulation statistics using close-packed ordering" Lab on a Chip (Sep. 21, 2009) 9(18):2628-2631.
Ackermann, et al. Integration of ATAC-seq and RNA-seq identifies human alpha cell and beta cell signature genes. Mol Metab. Jan. 11, 2016;5(3):233-244. doi: 10.1016/j.molmet.2016.01.002. eCollection Mar. 2016.
Adamson et al., "Production of arrays of chemically distinct nanolitre plugs via repeated splitting in microfluidic devices", Lab Chip 6(9): 1178-1186 (Sep. 2006).
Adey, et al. Rapid, low-input, low-bias construction of shotgun fragment libraries by high-density in vitro transposition. Genome Biology 11:R119 (2010).
Adey, et al., "Ultra-low-input, tagmentation-based whole-genome bisulfite sequencing", Genome Research, 2012, 22 ;6): 1139-1143.
Agasti, S.S. et al. "Photocleavable DNA barcode-antibody conjugates allow sensitive and multiplexed protein analysis in single cell" J Am Chem Soc (2012) 134(45):18499-18502.
Amini, S. et al. "Haplotype-resolved whole-genome sequencing by contiguity-preserving transposition and combinatorial indexing" Nature Genetics (2014) 46:1343-1349 doi:10.1038/ng.3119.
Anna et al.: Formation of dispersions using "flow focusing" in microchannels: Applied Physics Letters, vol. 82, No. 3, pp. 364-366 (2003).
Ason et al. DNA sequence bias during Tn5 transposition. Journal of molecular biology 335.5 (2004): 1213-1225.
Baret, "Surfactants in droplet-based microfluidics" Lab Chip (12(3):422-433 (2012).
Beer et al. On-Chip, Real-Time, Single-Copy Polymerase Chain Reaction in Picoliter Droplets. Anal Chem 79:8471-8475 (2007).
Berkum, et al. Hi-C: a method to study the three-dimensional architecture of genomes. J Vis Exp. May 6, 2010;(39). pii: 1869. doi: 10.3791/1869.
Boyle, et al. "High-resolution genome-wide in vivo footprinting of diverse transcription factors in human cells", Genome Res. Mar. 2011;21(3):456-64.
Braeckmans et al., Scanning the Code. Modern Drug Discovery. 2003:28-32.
Brenner, et al. "In vitro cloning of complex mixtures of DNA on microbeads: physical separation of differentially expressed cDNAs." Proc Natl Acad Sci U S A. Feb. 15, 2000;97(4):1665-70.
Buchman GW, et al. Selective RNA amplification: a novel method using dUMP-containing primers and uracil DNA glycosylase. PCR Methods Appl. Aug. 1993; 3(1):28-31.
Buenrostro, et al. ATAC-seq: A Method for Assaying Chromatin Accessibility Genome-Wide. Curr Protoc Mol Biol. Jan. 5, 2015;109: 21.29.1-21.29.9. doi:10.1002/0471142727.mb2129s109.
Buenrostro, et al. Single-cell chromatin accessibility reveals principles of regulatory variation. Nature. Jul. 23, 2015;523(7561):486-90. doi: 10.1038/nature14590. Epub Jun. 17, 2015.
Buenrostro, et al. "Transposition of native chromatin for fast and sensitive epigenomic profiling of open chromatin, DNA-binding proteins and nucleosome position." Nat Methods. Dec. 2013;10(12):1213-8. doi: 10.1038/nmeth.2688. Epub Oct. 6, 2013.
Burns, et al. An Integrated Nanoliter DNA Analysis Device. Science. Oct. 16, 1998;282(5388):484-7.
Burns, et al. Microfabricated structures for integrated DNA analysis. Proc Natl Acad Sci U S A. May 28, 1996; 93(11): 5556-5561.
Burns, et al. The intensification of rapid reactions in multiphase systems using slug flow in capillaries. Lab Chip. Sep. 2001;1(1):10-15. Epub Aug. 9, 2001.
Cao, et al. Joint profiling of chromatin accessibility and gene expression in thousands of single cells. Science. Sep. 28, 2018;361(6409):1380-1385. doi: 10.1126/science.aau0730. Epub Aug. 30, 2018.
Caruccio, et al. Nextera Technology for NGS DNA Library Preparation: Simultaneous Fragmentation and Tagging by In Vitro Transposition, Nextera Technology, 2009, 16-3. (Year: 2009).
Caruccio N., Preparation of Next-Generation Sequencing Libraries Using Nextera Technology: Simultaneous DNA Fragmentation and Adaptor Tagging by In Vitro Transposition. Ch. 17 Methods in Microbiology 733:241-55 (2011).
Chen, et al. Chemical transfection of cells in picoliter aqueous droplets in fluorocarbon oil. Anal Chem. Nov. 15, 2011;83(22):8816-20. doi: 10.1021/ac2022794. Epub Oct. 17, 2011.
Chen et al. High-throughput sequencing of the transcriptome and chromatin accessibility in the same cell. Nat Biotechnol. Oct. 14, 2019. doi: 10.1038/s41587-019-0290-0. [Epub ahead of print].
Chien et al. "Multiport flow-control system for lab-on-a-chip microfluidic devices", Fresenius J. Anal Chem, 371:106-111 (Jul. 27, 2001).
Chu, et al. Controllable monodisperse multiple emulsions. Angew Chem Int Ed Engl. 2007;46(47):8970-4.
Clark, et al. Single-cell epigenomics: powerful new methods for understanding gene regulation and cell identity. Genome Biol. Apr. 18, 2016;17:72. doi: 10.1186/s13059-016-0944-x.
Clausell-Tormos et al., "Droplet-based microfluidic platforms for the encapsulation and screening of mammalian cells and multicellular organisms", Chem. Biol. 15:427-437 (2008).
Co-pending U.S. Appl. No. 16/434,076, inventor Giresi; Paul, filed Jun. 6, 2019.
Co-pending U.S. Appl. No. 16/434,084, inventor Giresi; Paul, filed Jun. 6, 2019.
Co-pending U.S. Appl. No. 16/434,102, inventors Price; Andrew D. et al., filed Jun. 6, 2019.
Co-pending U.S. Appl. No. 16/708,214, inventors Wheeler; Tobias Daniel et al., filed Dec. 9, 2019.
Co-pending U.S. Appl. No. 16/737,762, inventors Price; Andrew D. et al., filed Jan. 8, 2020.
Co-pending U.S. Appl. No. 16/737,770, inventors Belhocine; Zahara Kamila et al., filed Jan. 8, 2020.
Co-pending U.S. Appl. No. 16/789,273, inventors Maheshwari; Arundhati Shamoni et al., filed Feb. 12, 2020.
Co-pending U.S. Appl. No. 16/800,450, inventor Katherine; Pfeiffer, filed Feb. 25, 2020.
Co-pending U.S. Appl. No. 17/014,909, inventor Giresi; Paul, filed Sep. 8, 2020.
Co-pending U.S. Appl. No. 17/148,942, inventors McDermott; Geoffrey et al., filed Jan. 14, 2021.
Co-pending U.S. Appl. No. 17/166,982, inventors McDermott; Geoffrey et al., filed Feb. 3, 2021.
Co-pending U.S. Appl. No. 17/175,542, inventors Maheshwari; Arundhati Shamoni et al., filed Feb. 12, 2021.
Co-pending U.S. Appl. No. 17/220,303, inventor Walter; Dagmar, filed Apr. 1, 2021.
Co-pending U.S. Appl. No. 17/381,612, inventor Martinez; Luigi Jhon Alvarado, filed Jul. 21, 2021.
Co-pending U.S. Appl. No. 17/499,039, inventors Pfeiffer; Katherine et al., filed Oct. 12, 2021.
Co-pending U.S. Appl. No. 17/512,241, inventors Hill; Andrew John et al., filed Oct. 27, 2021.
Co-pending U.S. Appl. No. 17/522,741, inventors Zheng; Xinying et al., filed Nov. 9, 2021.
Corces, et al. Lineage-specific and single cell chromatin accessibility charts human hematopoiesis and leukemia evolution. Nat Genet. Oct. 2016; 48(10): 1193-1203. Published online Aug. 15, 2016.doi: 10.1038/ng.3646.

(56) References Cited

OTHER PUBLICATIONS

Craig. Unity in Transposition Reactions. Science. Oct. 13, 1995;270(5234):253-4.
Cusanovich, et al. A Single-Cell Atlas of In Vivo Mammalian Chromatin Accessibility. Cell. Aug. 23, 2018;174(5):1309-1324. e18. doi: 10.1016/j.cell.2018.06.052. Epub Aug. 2, 2018.
Cusanovich, et al. Multiplex single-cell profiling of chromatin accessibility by combinatorial cellular indexing. Sciencexpress. May 7, 2014. p. 1-9. doi: 10.1126/science.aab1601.
Cusanovich, et al. Supplementary materials for Multiplex single-cell profiling of chromatin accessibility by combinatorial cellular indexing. Science. May 22, 2015;348(6237):910-4. doi: 10.1126/science.aab1601. Epub May 7, 2015.
Damean, et al. Simultaneous measurement of reactions in microdroplets filled by concentration gradients. Lab Chip. Jun. 21, 2009;9(12):1707-13. doi: 10.1039/b821021g. Epub Mar. 19, 2009.
Dekker, et al. Capturing chromosome conformation. Science. Feb. 15, 2002;295(5558):1306-11.
Drmanac et al., Sequencing by hybridization (SBH): advantages, achievements, and opportunities. Adv Biochem Eng Biotechnol. 2002;77 :75-101.
Duffy et al., Rapid Protyping of Microfluidic Systems and Polydimethylsiloxane, Anal Chem 70:4974-4984 (1998).
Eastburn, et al. Ultrahigh-throughput mammalian single-cell reverse-transcriptase polymerase chain reaction in microfluidic droplets. Anal Chem. Aug. 20, 2013;85(16):8016-21. doi: 10.1021/ac402057q. Epub Aug. 8, 2013.
Epicentre., "EZ-Tn5TM Custom Transposome Construction Kits", www.epicentre.com, pp. 1-17, 2012.
Esser-Kahn, et al. Triggered release from polymer capsules. Macromolecules. 2011;44:5539-5553.
Gaiti, et al. Epigenetic evolution and lineage histories of chronic lymphocytic leukaemia. Nature. May 2019;569(7757):576-580. doi: 10.1038/s41586-019-1198-z. Epub May 15, 2019.
Gangadharan et al., DNA transposon Hermes insert into DNA in nucleosome-free regions in vivo, Proc nat Ad Sci, Dec. 21, 2010, vol. 107, No. 51, pp. 21966-21972.
Gaublomme, et al. Nuclei multiplexing with barcoded antibodies for single-nucleus genomics. Nat Commun. Jul. 2, 2019;10(1):2907. doi: 10.1038/s41467-019-10756-2.
Gericke, et al. Functional cellulose beads: preparation, characterization, and applications. Chemical reviews 113.7 (2013): 4812-4836.
Gravina, et al. Single-cell genome-wide bisulfite sequencing uncovers extensive heterogeneity in the mouse liver methylome. Genome Biol. Jul. 5, 2016;17(1):150. doi: 10.1186/s13059-016-1011-3.
Gravina, et al. Single-cell, locus-specific bisulfite sequencing (SLBS) for direct detection of epimutations in DNA methylation patterns. Nucleic Acids Res. Aug. 18, 2015;43(14):e93. doi: 10.1093/nar/gkv366. Epub Apr. 19, 2015.
Green et al. Insertion site preference of Mu, Tn5, and Tn7 transposons. Mobile DNA 3.1 (2012): 3.
Greenleaf, et al. Assaying the epigenome in limited numbers of cells. Methods. Jan. 15, 2015;72:51-6. doi: 10.1016/j.ymeth.2014.10.010. Epub Oct. 22, 2014.
Guo, et al. Droplet microfluidics for high-throughput biological assays. Lab Chip. Jun. 21, 2012;12(12):2146-55. doi: 10.1039/c2lc21147e. Epub Feb. 9, 2012.
Gyarmati, et al. Reversible disulphide formation in polymer networks: a versatile functional group from synthesis to applications. European Polymer Journal. 2013; 49:1268-1286.
Hashimshony, et al. CEL-Seq: Single-Cell RNA-Seq by Multiplexed Linear Amplification. Cell Rep. Sep. 27, 2012;2(3):666-73. doi: 10.1016/j.celrep.2012.08.003. Epub Aug. 30, 2012.
Holtze, et al. Biocompatible surfactants for water-in-fluorocarbon emulsions. Lab Chip. Oct. 2008;8(10):1632-9. doi: 10.1039/b806706f. Epub Sep. 2, 2008.
Hrdlickova, R. et al. "RNA-Seq methods for transcriptome analysis" Wiley Interdiscip Rev RNA (2016) 8(1):e1364 (17 pages).

Hug, et al. Measurement of the number of molecules of a single mRNA species in a complex mRNA preparation. J Theor Biol. Apr. 21, 2003;221(4):615-24.
Islam, et al. Highly multiplexed and strand-specific single-cell RNA 5' end sequencing. Nat Protoc. Apr. 5, 2012;7(5):813-28. doi: 10.1038/nprot.2012.022.
Jaitin, et al. Massively parallel single-cell RNA-seq for marker-free decomposition of tissues into cell types. Science. Feb. 14, 2014;343(6172):776-9. doi: 10.1126/science.1247651.
Jarosz, M. et al. "Using 1ng of DNA to detect haplotype phasing and gene fusions from whole exome sequencing of cancer cell lines" Cancer Res (2015) 75(supp15):4742.
Jia, et al. Single cell RNA-seq and ATAC-seq analysis of cardiac progenitor cell transition states and lineage settlement. Nat Commun. Nov. 19, 2018;9(1):4877. doi: 10.1038/s41467-018-07307-6.
Jin, et al. Genome-wide detection of DNase I hypersensitive sites in single cells and FFPE tissue samples. Nature. Dec. 3, 2015;528(7580):142-6. doi: 10.1038/nature15740.
Kaper, et al. Supporting Information for "Whole-genome haplotyping by dilution, amplification, and sequencing." Proc Natl Acad Sci U S A. Apr. 2, 2013;110(14):5552-7. doi: 10.1073/pnas.1218696110. Epub Mar. 18, 2013.
Kaper, et al. Whole-genome haplotyping by dilution, amplification, and sequencing. Proc Natl Acad Sci U S A. Apr. 2, 2013;110(14):5552-7. doi: 10.1073/pnas.1218696110. Epub Mar. 18, 2013.
Kenis, et al. Microfabrication Inside Capillaries Using Multiphase Laminar Flow Patterning. Science. 1999; 285:83-85.
Kilgore, et al. Single-molecule and population probing of chromatin structure using DNA methyltransferases. Methods. Mar. 2007;41(3):320-32.
Kivioja, et al. Counting absolute numbers of molecules using unique molecular identifiers. Nat Methods. Nov. 20, 2011;9(1):72-4.
Klein, et al. Droplet barcoding for single-cell transcriptomics applied to embryonic stem cells. Cell. May 21, 2015; 161:1187-1201.
Korlach et al., Methods in Enzymology, Real-Time DNA Sequencing from Single Polymerase Molecules, (2010) 472:431-455.
Koster et al., "Drop-based microfluidic devices for encapsulation of single cells", Lab on a Chip The Royal Soc. of Chem. 8: 1110-1115 (2008).
Lagally, et al. Single-Molecular DNA Amplification and Analysis in an Integrated Microfluidic Device. Anal Chem. Feb. 1, 2001;73(3):565-70.
Laird et al., Hairpin-bisulfite PCR: Assessing epigenetic methylation patterns on complementary strands of individual DNA molecules, 2004, PNAS, 101, 204-209.
Lake, et al. "Integrative Single-Cell Analysis By Transcriptional And Epigenetic States In Human Adult Brain". Apr. 19, 2017. doi: https://doi.org/10.1101/128520.
Lennon et al. A scalable, fully automated process for construction of sequence-ready barcoded libraries for 454. Genome Biology 11:R15 (2010).
Macosko, et al. Highly Parallel Genome-wide Expression Profiling of Individual Cells Using Nanoliter Droplets. Cell. May 21, 2015;161(5):1202-14. doi: 10.1016/j.cell.2015.05.002.
Madl, et al. "Bioorthogonal Strategies for Engineering Extracellular matrices", Madal, Chritopher, Adv. Funct. Master. Jan. 19, 2018, vol. 28, 1706046, pp. 1-21.
Mair, et al. Injection molded microfluidic chips featuring integrated interconnects. Lab Chip. Oct. 2006;6(10):1346-54. Epub Jul. 31, 2006.
McCoy, R. et al. "Illumina TruSeq Synthetic Long-Reads Empower De Novo Assembly and Resolve Complex, Highly-Repetitive Transposable Elements" PLOS (2014) 9(9):e1016689.
Microfluidic ChipShop. Microfluidic product catalogue. Oct. 2009.
Nagano, et al. Single-cell Hi-C reveals cell-to-cell variability in chromosome structure. Nature. Oct. 3, 2013;502(7469):59-64. doi: 10.1038/nature12593. Epub Sep. 25, 2013.
Navin. The first five years of single-cell cancer genomics and beyond. Genome Res. Oct. 2015;25(10):1499-507. doi: 10.1101/gr.191098.115.
Nisisako, et al. Droplet formation in a microchannel network. Lab Chip. Feb. 2002;2(1):24-6. Epub Jan. 18, 2002.

(56) References Cited

OTHER PUBLICATIONS

Nisisako, T. et al. Droplet Formation in a Microchannel on PMMA Plate. Micro Total Analysis Systems. 2001. Kluwer Academic Publishers. pp. 137-138.
Nisisako, T. et al., Microfluidics large-scale integration on a chip for mass production of monodisperse droplets and particles, The Royal Society of Chemistry: Lab Chip, (Nov. 23, 2007) 8:287-293.
Novak, R. et al., "Single cell multiplex gene detection and sequencing using microfluidicallygenerated agarose emulsions" Angew. Chem. Int. Ed. Engl. (2011) 50(2):390-395.
Orakdogen, N. "Novel responsive poly(N,N-dimethylaminoethyl methacrylate) gel beads: preparation, mechanical properties and pH-dependent swelling behavior" J Polym Res (2012) 19:9914.
Park. ChIP-seq: advantages and challenges of a maturing technology. Nature Reviews Genetics vol. 10, pp. 669-680 (2009).
Perrott, Jimmy. Optimization and Improvement of Emulsion PCR for the Ion Torrent Next-Generation Sequencing Platform. (2011) Thesis.
Peters, B.A. et al. Accurate whole-genome sequencing and haplotyping from 10 to 20 human cells. Nature, 487(7406):190-195 (Jul. 11, 2012).
Plunkett, et al. Chymotrypsin responsive hydrogel: application of a disulfide exchange protocol for the preparation of methacrylamide containing peptides. Biomacromolecules. Mar.-Apr. 2005;6(2):632-7.
Ponnaluri, et al. NicE-seq: high resolution open chromatin profiling. Genome Biol. Jun. 28, 2017;18(1):122. doi: 10.1186/s13059-017-1247-6.
Pott, et al. Single-cell ATAC-seq: strength in numbers. Genome Biol. Aug. 21, 2015;16:172. doi: 10.1186/s13059-015-0737-7.
Preissl, et al. Single nucleus analysis of the chromatin landscape in mouse forebrain development. Posted Jul. 4, 2017. bioRxiv 159137; doi: https://doi.org/10.1101/159137.
Priest, et al. Generation of Monodisperse Gel Emulsions in a Microfluidic Device, Applied Physics Letters, 88:024106 (2006).
Pushkarev et al. "Single-molecule sequencing of an individual human genome," Nature Biotech (2009) 27:847-850.
Ramani, et al. Massively multiplex single-cell Hi-C. Nat Methods. Mar. 2017; 14(3): 263-266. Published online Jan. 30, 2017.doi: 10.1038/nmeth.4155.
Ramsey, J.M. "The burgeoning power of the shrinking laboratory" Nature Biotech (1999) 17:1061-1062.
Ramskold et al. (2012) "Full-length mRNA-Seq from single-cell levels of RNA and individual circulating tumor cells" Nature Biotechnology 30(8):777-782.
Reuter, J.A. et al. "Simul-seq: combined DNA and RNA sequencing for whole-genome and transcriptome profiling" Nature Methods (2016) 13(11):953-958.
Roche. Using Multiplex Identifier (MID) Adaptors for the GS FLX Titanium Chemistry Basic MID Set Genome Sequencer FLX System, Technical Bulletin 004-2009, (Apr. 1, 2009) pp. 1-11. URL:http://454.com/downloads/my454/documentation/technical-bulletins/TCB-09004 Using MultiplexIdentifierAdaptorsForTheGSFLXTitaniumSeriesChemistry-BasicMIDSet.pdf.
Rotem, A. et al., "High-throughput single-cell labeling (Hi-SCL) for RNA-Seq using drop-based microfluidics" PLOS One (May 22, 2015) 0116328 (14 pages).
Rotem, et al. Single-cell ChIP-seq reveals cell subpopulations defined by chromatin state. Nat Biotechnol. Nov. 2015;33(11):1165-72. doi: 10.1038/nbt.3383. Epub Oct. 12, 2015.
Saikia, et al. Simultaneous multiplexed amplicon sequencing and transcriptome profiling in single cells. Nat Methods. Jan. 2019;16(1):59-62. doi: 10.1038/s41592-018-0259-9. Epub Dec. 17, 2018.
Schubert, et al. Microemulsifying fluorinated oils with mixtures of fluorinated and hydrogenated surfactants. Colloids and Surfaces A; Physicochemical and Engineering Aspects, 84(1994) 97-106.
Schutsky, et al. APOBEC3A efficiently deaminates methylated, but not TET-oxidized, cytosine bases in DNA. Nucleic Acids Res. Jul. 27, 2017;45(13):7655-7665. doi: 10.1093/nar/gkx345.

Seiffert, et al. Microfluidic fabrication of smart microgels from macromolecular precursors. Polymer. vol. 51, Issue 25, Nov. 26, 2010, pp. 5883-5889.
Seiffert, et al. Microfluidic fabrication of smart microgels from macromolecular precursors. 2010. Polymer.
Seiffert, S. et al., "Smart microgel capsules from macromolecular precursors" J. Am. Chem. Soc. (2010) 132:6606-6609.
Shah, et al. "Fabrication of mono disperse thermosensitive microgels and gel capsules in micro fluidic devices", Soft Matter, 4:2303-2309 (2008).
Shendure, et al., Accurate Multiplex Polony Sequencing of an Evolved Bacterial Genome. Science 309.5741 (Sep. 2005): 1728-1732. XP002427180, ISSN: 0036-8075, DOI: 10.1126/SCIENCE.1117839.
Simon, et al., "Using formaldehyde-assisted isolation of regulatory elements (FAIRE) to isolate active regulatory DNA", Nature Protocols, 2012, 7(2): 256-267.
Smallwood, et al. Single-cell genome-wide bisulfite sequencing for assessing epigenetic heterogeneity. Nat Methods. Aug. 2014;11(8):817-820. doi: 10.1038/nmeth.3035. Epub Jul. 20, 2014.
Smith, et al. Highly-multiplexed barcode sequencing: an efficient method for parallel analysis of pooled samples. Nucleic Acids Research, 38(13): e142 (2010).
Song, et al., "DNase-seq: A High-Resolution Technique for Mapping Active Gene Regulatory Elements across the Senome from Mammalian Cells", Cold Spring Harbor Laboratory Press, 2010, 2010(2), doi:10.1101/pdb.prot5384.
Song, et al. Reactions in droplets in microfluidic channels. Angew Chem Int Ed Engl. Nov. 13, 2006;45(44):7336-56.
Thaxton, C.S. et al. "A Bio-Bar-Code Assay Based Upon Dithiothreitol Oligonucleotide Release" Anal Chem (2005) 77:8174-8178.
Theberge, et al. Microdroplets in microfluidics: an evolving platform for discoveries in chemistry and biology. Angew Chem Int Ed Engl. Aug. 9, 2010;49(34):5846-68. doi: 10.1002/anie.200906653.
Thorsen, et al. Dynamic pattern formation in a vesicle-generating microfluidic device. Physical Review Letters. American Physical Society. 2001; 86(18):4163-4166.
Tonelli, et al. Perfluoropolyether functional oligomers: unusual reactivity in organic chemistry. Journal of fluorine chemistry. 2002; 118(1)"107-121.
Turchinovich, et al. "Capture and Amplification by Tailing and Switching (CATS): An Ultrasensitive Ligation-Independent Method for Generation of DNA Libraries for Deep Sequencing from Picogram Amounts of DNA and RNA." RNA Biology 11.7 (2014): 817-828. PMC. Web. Nov. 13, 2017.
Ushijima et al, Detection and interpretation of altered methylation patterns in cancer cells, 2005, Nature reviews, 5, 223-231.
Uttamapinant, et al. Fast, cell-compatible click chemistry with copper-chelating azides for biomolecular labeling. Angew. Chem. Int. End. Engl., Jun. 11, 2012: 51(24) pp. 5852-5856.
Wagner, et al. Biocompatible fluorinated polyglycerols for droplet microfluidics as an alternative to PEG-based copolymer surfactants. Lab Chip. Jan. 7, 2016;16(1):65-9. doi: 10.1039/c5lc00823a. Epub Dec. 2, 2015.
Wang, et al. CoBATCH for High-Throughput Single-Cell Epigenomic Profiling. Mol Cell. Oct. 3, 2019;76(1):206-216.e7. doi: 10.1016/j.molcel.2019.07.015. Epub Aug. 27, 2019.
Weigl, et al. Microfluidic Diffusion-Based Separation and Detection. Science. 1999; pp. 346-347.
Williams, et al. Amplification of complex gene libraries by emulsion PCR. Nature Methods. 2006;3(7):545-50.
Xu, et al. Single-cell lineage tracing by endogenous mutations enriched in transposase accessible mitochondrial DNA Elife. Apr. 9, 2019;8. pii: e45105. doi: 10.7554/eLife.45105.
Zentner, et al. Surveying the epigenomic landscape, one base at a time. Genome Biol. Oct. 22, 2012;13(10):250. doi: 10.1186/gb4051.
Zhang, et al. One-step fabrication of supramolecular microcapsules from microfluidic droplets. Science. Feb. 10, 2012;335(6069):690-4. doi: 10.1126/science.1215416.
Zheng, et al. Massively parallel digital transcriptional profiling of single cells. Nat Commun. Jan. 16, 2017;8:14049. doi: 10.1038/ncomms14049.

(56) References Cited

OTHER PUBLICATIONS

Zheng et al. Multiplex chromatin interactions with single-molecule precision. Nature 566(7745):558-562 (Feb. 2019).

Zheng, X.Y. et al. "Haplotyping germline and cancer genomes with high-throughput linked-read sequencing" Nature Biotech (Feb. 1, 2016) 34(3):303-311.

Zhu, et al. Reverse transcriptase template switching: a SMART approach for full-length cDNA library construction. Biotechniques. Apr. 2001;30(4):892-7.

Zhu, et al. An ultra high-throughput method for single-cell joint analysis of open chromatin and transcriptome. Nat Struct Mol Biol. Nov. 2019;26(11):1063-1070. doi: 10.1038/s41594-019-0323-x. Epub Nov. 6, 2019.

Co-pending U.S. Appl. No. 17/545,862, inventor Katherine Pfeiffer, filed Dec. 8, 2021.

Co-pending U.S. Appl. No. 17/573,350, inventor Corey M. Nemec, filed Jan. 11, 2022.

Co-pending PCT application No. PCT/US2022/017558, inventors Dagmar et al., filed on Feb. 23, 2022.

Co-pending PCT application No. PCT/US2022/017377, inventors Pfeiffer et al., filed on Feb. 22, 2022.

\* cited by examiner

METHODS FOR PROCESSING NUCLEIC ACID MOLECULES

CROSS-REFERENCE

This application is a continuation of International application Ser. No. PCT/US2020/018010, filed Feb. 12, 2020, which claims the benefit of U.S. Provisional Application No. 62/804,644, filed Feb. 12, 2019, each of which applications is entirely incorporated herein by reference.

BACKGROUND

A sample may be processed for various purposes, such as detection, identification, quantitation, and characterization of a type of moiety within the sample. The sample may be a biological sample. Biological samples may be processed, such as for detection of a disease (e.g., cancer) or identification of a particular species. There are various approaches for processing samples, such as polymerase chain reaction (PCR) and sequencing.

Biological samples may be processed within various reaction environments, such as partitions. Partitions may be wells or droplets. Droplets or wells may be employed to process biological samples in a manner that enables the biological samples to be partitioned and processed separately. For example, such droplets may be fluidically isolated from other droplets, enabling accurate control of respective environments in the droplets.

Biological samples in partitions may be subjected to various processes, such as chemical processes or physical processes. Samples in partitions may be subjected to heating or cooling, or chemical reactions, such as to yield species that may be qualitatively or quantitatively processed.

A biological sample may comprise one or more nucleic acid molecules, such as one or more deoxyribonucleic acid (DNA) molecules and/or one or more ribonucleic acid (RNA) molecules. Methods of processing such a biological sample may vary depending on the types of nucleic acid molecules included therein.

SUMMARY

The present disclosure provides methods, systems, and kits for processing multiple different types of nucleic acid molecules in tandem. The methods provided herein may allow for analysis of both deoxyribonucleic acid (DNA) molecules and ribonucleic acid (RNA) molecules originating from the same cells or cell beads or components thereof (e.g., nuclei). Analysis of different types of nucleic acid molecules may be performed simultaneously or near simultaneously. The methods provided herein may comprise use of a partitioning scheme in which materials (e.g., different types of target nucleic acid molecules, such as target nucleic acid molecules included within a cell, cell bead, or nucleus) are distributed between a plurality of partitions, such as a plurality of droplets or wells. Materials (e.g., target nucleic acid molecules) may be co-partitioned with one or more reagents to facilitate processing of target nucleic acid molecules, such as one or more enzymes, beads (e.g., beads comprising nucleic acid barcode molecules), primers, oligos, lysing or permeabilizing agents, buffers, or other reagents. The methods provided herein may comprise generating a barcoded nucleic acid product (e.g., within a partition of a plurality of partitions) corresponding to each of various different target nucleic acid molecules (e.g., DNA and RNA molecules), prior to subjecting the barcoded nucleic acid products to one or more amplification processes (e.g., polymerase chain reaction (PCR), which may optionally be performed in bulk).

Target nucleic acid molecules (e.g., DNA and RNA molecules) may initially be included in a cell, cell bead, or cell nucleus. Accordingly, the methods provided herein provide sample preparation techniques that permit sequencing of nucleic acid molecules from single cells, cell beads, and nuclei of interest.

In eukaryotic genomes, chromosomal DNA winds itself around histone proteins (i.e., "nucleosomes"), thereby forming a complex known as chromatin. The tight or loose packaging of chromatin contributes to the control of gene expression. Tightly packed chromatin ("closed chromatin") is usually not permissive for gene expression while more loosely packaged, accessible regions of chromatin ("open chromatin") is associated with the active transcription of gene products. Methods for probing genome-wide DNA accessibility have proven extremely effective in identifying regulatory elements across a variety of cell types and quantifying changes that lead to both activation or repression of gene expression.

One such method is the Assay for Transposase Accessible Chromatin with high-throughput sequencing (ATAC-seq). The ATAC-seq method probes DNA accessibility with an artificial transposon, which inserts specific sequences into accessible regions of chromatin. Because the transposase can only insert sequences into accessible regions of chromatin not bound by transcription factors and/or nucleosomes, sequencing reads can be used to infer regions of increased chromatin accessibility.

Traditional approaches to the ATAC-seq methodology requires large pools of cells, processes cells in bulk, and result in data representative of an entire cell population, but lack information about cell-to-cell variation inherently present in a cell population (see, e.g., Buenrostro, et al., Curr. Protoc. Mol. Biol., 2015 Jan. 5; 21.29.1-21.29.9). While single cell ATAC-seq (scATAC-seq) methods have been developed, they suffer from several limitations. For example, scATAC-seq methods that utilize sample pooling, cell indexing, and cell sorting (see, e.g., Cusanovich, et al., Science, 2015 May 22; 348(6237):910-14) result in high variability and a low number of reads associated with any single cell. Other scATAC-seq methods that utilize a programmable microfluidic device to isolate single cells and perform scATAC-seq in nanoliter reaction chambers (see, e.g., Buenrostro, et al., Nature, 2015 Jul. 23; 523(7561): 486-90) are limited by the throughput of the assay and may not generate personal epigenomic profiles on a timescale compatible with clinical decision-making.

In an aspect, the present disclosure provides a method for processing a nucleic acid sample, comprising: (a) providing a biological particle comprising a deoxyribonucleic acid (DNA) molecule and a ribonucleic acid (RNA) molecule within a partition among a plurality of partitions, wherein the partition comprises (i) a first nucleic acid barcode molecule, (ii) a second nucleic acid barcode molecule, and (iii) a splint sequence, wherein the first nucleic acid barcode molecule and the second nucleic acid barcode molecule comprise a common barcode sequence, wherein the first nucleic acid barcode molecule comprises an overhang sequence, and wherein the splint sequence comprises a sequence complementary to the DNA molecule and a sequence complementary to the overhang sequence; (b) within the partition, using the DNA molecule, the first nucleic acid barcode molecule, and the splint sequence to generate a first barcoded nucleic acid product corresponding to the DNA molecule and using the RNA molecule and the second nucleic acid barcode molecule to generate a second barcoded nucleic acid product corresponding to the RNA molecule, wherein the first barcoded nucleic acid product and the second barcoded nucleic acid product comprise the common barcode sequence, or a complement thereof; and (c) recovering the first barcoded nucleic acid product and the second barcoded nucleic acid product from the partition.

In some embodiments, the biological particle is a cell, cell bead, or cell nucleus. In some embodiments, the method further comprises lysing or permeabilizing the biological particle within the partition to provide access to the DNA molecule and the RNA molecule therein.

In some embodiments, the method further comprises, prior to (a), processing an open chromatin structure of the nucleic acid sample with a transposase to yield the DNA molecule. In some embodiments, the transposase is included in a transposase-nucleic acid complex that comprises (i) a first nucleic acid molecule comprising a first transposon end sequence and a first sequencing primer or portion thereof, or a complement thereof and (ii) a second nucleic acid molecule comprising a second transposon end sequence and a second sequencing primer or portion thereof, or a complement thereof. In some embodiments, the first transposon end sequence and the second transposon end sequence are the same, and wherein the first transposon end sequence and the second transposon end sequence are each hybridized to complementary sequences.

In some embodiments, generating the first barcoded nucleic acid product comprises (i) subjecting the DNA molecule and the splint sequence to conditions sufficient to hybridize to the sequence of the DNA molecule to the splint sequence and (ii) subjecting the first nucleic acid barcode molecule and the splint sequence to conditions sufficient to hybridize the overhang sequence of the first nucleic acid barcode molecule to the splint sequence. In some embodiments, the splint sequence is hybridized to the sequence of the DNA molecule outside of the partition. In some embodiments, the method further comprises ligating the first nucleic acid barcode molecule to the DNA molecule.

In some embodiments, the first nucleic acid barcode molecule comprises a flow cell sequence, or complement thereof; a barcode sequence; a sequencing primer, or portion thereof; a unique molecular identifier sequence; or a combination thereof.

In some embodiments, the DNA molecule comprises one or more gaps, and further comprising, prior to (c), subjecting the DNA molecule to an extension process to fill the one or more gaps.

In some embodiments, the second nucleic acid barcode molecule comprises a unique molecular identifier sequence, a barcode sequence, a sequencing primer or portion thereof, or a combination thereof.

In some embodiments, the method further comprises, prior to (b), within the partition, reverse transcribing the RNA molecule to provide a complementary DNA (cDNA) molecule. In some embodiments, prior to reverse transcribing the RNA molecule, the second nucleic acid barcode molecule is hybridized to a sequence of a precursor of the RNA molecule. In some embodiments, the precursor comprises a polyA sequence, and wherein the second nucleic acid barcode molecule comprises a polyT sequence configured to hybridize to the polyA sequence. In some embodiments, the method further comprises appending an additional sequence to the cDNA molecule, wherein the additional sequence is a poly(C) sequence. In some embodiments, the method further comprises contacting the cDNA molecule with a template-switching oligonucleotide under conditions sufficient to hybridize the template-switching oligonucleotide to the cDNA molecule, wherein the template-switching oligonucleotide hybridizes to the additional sequence of the cDNA molecule. In some embodiments, the method further comprises extending the cDNA molecule to generate an extended cDNA molecule, which extended cDNA molecule comprises sequences complementary to sequences of the template-switching oligonucleotide. In some embodiments, the template-switching oligonucleotide comprises a sequencing primer or portion thereof, or complement thereof; a unique molecular identifier sequence, or complement thereof; or a combination thereof. In some embodiments, the template-switching oligonucleotide is the second nucleic acid barcode molecule, and wherein the extended cDNA molecule is the second barcoded nucleic acid product.

In some embodiments, the first nucleic acid barcode molecule and the second nucleic acid barcode molecule comprise a common nucleic acid sequence.

In some embodiments, the partition is a droplet among a plurality of droplets. In some embodiments, the partition is a droplet and wherein (c) comprises breaking or disrupting the droplet.

In some embodiments, the method further comprises, subsequent to (c), using (i) the first barcoded nucleic acid product to generate a first plurality of amplification products and (ii) the second barcoded nucleic acid product to generate a second plurality of amplification products. In some embodiments, generating the first plurality of amplification products and the second plurality of amplification products comprises performing one or more nucleic acid amplification reactions using the first barcoded nucleic acid product or the second barcoded nucleic acid product. In some embodiments, performing the one or more nucleic acid amplification reactions comprises attaching one or more flow cell sequences to the first barcoded nucleic acid product or the second barcoded nucleic acid product, or a derivative thereof.

In some embodiments, the first nucleic acid barcode molecule and the second nucleic acid barcode molecule are coupled to a bead. In some embodiments, the bead is a gel bead. In some embodiments, the first nucleic acid barcode molecule is coupled to the bead via a first labile moiety and the second nucleic acid barcode molecule is coupled to the bead via a second labile moiety. In some embodiments, the first nucleic acid barcode molecule and the second nucleic acid barcode molecule are releasably coupled to the bead. In some embodiments, the first nucleic acid barcode molecule is releasable from the bead upon application of a first stimulus and the second nucleic acid barcode molecule is releasable from the bead upon application of a second stimulus.

In another aspect, the present disclosure provides a method for processing a nucleic acid sample, comprising: (a) providing a biological particle comprising a deoxyribonucleic acid (DNA) molecule and a ribonucleic acid (RNA) molecule within a partition among a plurality of partitions, wherein the partition comprises a first nucleic acid barcode molecule and a second nucleic acid barcode molecule, wherein the first nucleic acid barcode molecule and the second nucleic acid barcode molecule comprise a common barcode sequence; (b) within the partition, generating (i) a first barcoded nucleic acid product from the DNA molecule and the first nucleic acid barcode molecule and (ii) a second barcoded nucleic acid product from the RNA molecule and the second nucleic acid barcode molecule, wherein the first barcoded nucleic acid product and the second barcoded nucleic acid product comprise the common barcode sequence, or a complement thereof; (c) recovering the first barcoded nucleic acid product and the second barcoded nucleic acid product from the partition; (d) processing the first barcoded nucleic acid product to generate a processed nucleic acid product comprising a dA tail; and (e) using (i) the processed nucleic acid product to generate a first plurality of amplification products and (ii) the second barcoded nucleic acid product to generate a second plurality of amplification products.

In some embodiments, the biological particle is a cell, cell bead, or cell nucleus. In some embodiments, the method further comprises lysing or permeabilizing the biological particle within the partition to provide access to the DNA molecule and the RNA molecule therein.

In some embodiments, the method further comprises, prior to (a), processing an open chromatin structure of the nucleic acid sample with a transposase to yield the DNA molecule. In some embodiments, the transposase is included in a transposase-nucleic acid complex that comprises (i) a first nucleic acid molecule comprising a first transposon end sequence and a first sequencing primer or portion thereof, or a complement thereof and (ii) a second nucleic acid molecule comprising a second transposon end sequence and a second sequencing primer or portion thereof, or a complement thereof. In some embodiments, the first transposon end sequence and the second transposon end sequence are the same, and wherein the first transposon end sequence and the second transposon end sequence are each hybridized to complementary sequences.

In some embodiments, the first nucleic acid barcode molecule comprises a sequencing primer or portion thereof, or complement thereof. In some embodiments, (b) comprises subjecting the DNA molecule to conditions sufficient to hybridize the first nucleic acid barcode molecule to the DNA molecule. In some embodiments, the method further comprises (i) extending the first nucleic acid barcode molecule hybridized to the DNA molecule and (ii) ligating the first nucleic acid barcode molecule to the DNA molecule to generate the first barcoded nucleic acid product.

In some embodiments, the method further comprises ligating the first nucleic acid barcode molecule to the DNA molecule.

In some embodiments, the first nucleic acid barcode molecule comprises a flow cell sequence, or complement thereof; a barcode sequence; a unique molecular identifier sequence; or a combination thereof.

In some embodiments, the DNA molecule comprises one or more gaps, and further comprising, prior to (c), subjecting the DNA molecule to an extension process to fill the one or more gaps.

In some embodiments, the second nucleic acid barcode molecule comprises a unique molecular identifier sequence, a barcode sequence, a sequencing primer or portion thereof, or a combination thereof.

In some embodiments, the method further comprises, prior to (b), within the partition, reverse transcribing the RNA molecule to provide a complementary DNA (cDNA) molecule. In some embodiments, prior to reverse transcribing the RNA molecule, the second nucleic acid barcode molecule is hybridized to a sequence of a precursor of the RNA molecule. In some embodiments, the precursor comprises a polyA sequence, and wherein the second nucleic acid barcode molecule comprises a polyT sequence configured to hybridize to the polyA sequence. In some embodiments, the method further comprises appending an additional sequence to the cDNA molecule, wherein the additional sequence is a poly(C) sequence. In some embodiments, the method further comprises contacting the cDNA molecule with a template-switching oligonucleotide under conditions sufficient to hybridize the template-switching oligonucleotide to the cDNA molecule, wherein the template-switching oligonucleotide hybridizes to the additional sequence of the cDNA molecule. In some embodiments, the method further comprises extending the cDNA molecule to generate an extended cDNA molecule, which extended cDNA molecule comprises sequences complementary to sequences of the template-switching oligonucleotide. In some embodiments, the template-switching oligonucleotide comprises a sequencing primer or portion thereof, or complement thereof; a unique molecular identifier sequence, or complement thereof; or a combination thereof. In some embodiments, the template-switching oligonucleotide is the second nucleic acid barcode molecule, and wherein the extended cDNA molecule is the second barcoded nucleic acid product. In some embodiments, the first nucleic acid barcode molecule and the second nucleic acid barcode molecule comprise a common nucleic acid sequence.

In some embodiments, the partition is a droplet among a plurality of droplets. In some embodiments, the partition is a droplet and wherein (c) comprises breaking or disrupting the droplet.

In some embodiments, (e) comprises performing one or more nucleic acid amplification reactions using the first barcoded nucleic acid product or the second barcoded nucleic acid product. In some embodiments, (e) comprises attaching one or more flow cell sequences to the first barcoded nucleic acid product or the second barcoded nucleic acid product, or a derivative thereof.

In some embodiments, the first nucleic acid barcode molecule and the second nucleic acid barcode molecule are coupled to a bead. In some embodiments, the bead is a gel bead. In some embodiments, the first nucleic acid barcode molecule is coupled to the bead via a first labile moiety and the second nucleic acid barcode molecule is coupled to the bead via a second labile moiety. In some embodiments, the first nucleic acid barcode molecule and the second nucleic acid barcode molecule are releasably coupled to the bead. In some embodiments, the first nucleic acid barcode molecule is releasable from the bead upon application of a first stimulus and the second nucleic acid barcode molecule is releasable from the bead upon application of a second stimulus.

In a further aspect, the present disclosure provides a method for processing a nucleic acid sample, comprising: (a) providing a biological particle comprising a deoxyribonucleic acid (DNA) molecule and a ribonucleic acid (RNA) molecule within a partition among a plurality of partitions, wherein the partition comprises a first nucleic acid barcode molecule and a second nucleic acid barcode molecule, wherein the first nucleic acid barcode molecule and the second nucleic acid barcode molecule comprise a common barcode sequence, and wherein the DNA molecule comprises a first hairpin moiety at a first end and a second hairpin moiety at a second end; (b) within the partition, generating (i) a first barcoded nucleic acid product from the DNA molecule and the first nucleic acid barcode molecule and (ii) a second barcoded nucleic acid product from the RNA molecule and the second nucleic acid barcode molecule, wherein the first barcoded nucleic acid product and the second barcoded nucleic acid product comprise the common barcode sequence, or a complement thereof; (c) recovering the first barcoded nucleic acid product and the second barcoded nucleic acid product from the partition; and (d) using (i) the first barcoded nucleic acid product to generate a first plurality of amplification products and (ii) the second barcoded nucleic acid product to generate a second plurality of amplification products.

In some embodiments, the biological particle is a cell, cell bead, or cell nucleus. In some embodiments, the method further comprises lysing or permeabilizing the biological particle within the partition to provide access to the DNA molecule and the RNA molecule therein.

In some embodiments, the method further comprises prior to (a), processing an open chromatin structure of the nucleic acid sample with a transposase to yield the DNA molecule. In some embodiments, the transposase is included in a transposase-nucleic acid complex that comprises (i) a first nucleic acid molecule comprising a first transposon end sequence and a first sequencing primer or portion thereof, or a complement thereof and (ii) a second nucleic acid molecule comprising a second transposon end sequence and a second sequencing primer or portion thereof, or a complement thereof. In some embodiments, the first transposon end sequence and the second transposon end sequence are the same, and wherein the first transposon end sequence and the second transposon end sequence are each hybridized to complementary sequences.

In some embodiments, the first nucleic acid barcode molecule comprises a sequencing primer or portion thereof, or complement thereof. In some embodiments, (b) comprises subjecting the DNA molecule to conditions sufficient to hybridize the first nucleic acid barcode molecule to the DNA molecule. In some embodiments, the method further comprises (i) extending the first nucleic acid barcode molecule hybridized to the DNA molecule and (ii) ligating the first nucleic acid barcode molecule to the DNA molecule to generate the first barcoded nucleic acid product.

In some embodiments, the method further comprises ligating the first nucleic acid barcode molecule to the DNA molecule.

In some embodiments, the first nucleic acid barcode molecule comprises a flow cell sequence, or complement thereof; a barcode sequence; a unique molecular identifier sequence; or a combination thereof.

In some embodiments, the DNA molecule comprises one or more gaps, and further comprising, prior to (c), subjecting the DNA molecule to an extension process to fill the one or more gaps.

In some embodiments, the second nucleic acid barcode molecule comprises a unique molecular identifier sequence, a barcode sequence, a sequencing primer or portion thereof, or a combination thereof.

In some embodiments, the method further comprises, prior to (b), within the partition, reverse transcribing the RNA molecule to provide a complementary DNA (cDNA) molecule. In some embodiments, prior to reverse transcribing the RNA molecule, the second nucleic acid barcode molecule is hybridized to a sequence of a precursor of the RNA molecule. In some embodiments, the precursor comprises a polyA sequence, and wherein the second nucleic acid barcode molecule comprises a polyT sequence configured to hybridize to the polyA sequence. In some embodiments, the method further comprises appending an additional sequence to the cDNA molecule, wherein the additional sequence is a poly(C) sequence. In some embodiments, the method further comprises contacting the cDNA molecule with a template-switching oligonucleotide under conditions sufficient to hybridize the template-switching oligonucleotide to the cDNA molecule, wherein the template-switching oligonucleotide hybridizes to the additional sequence of the cDNA molecule. In some embodiments, the method further comprises extending the cDNA molecule to generate an extended cDNA molecule, which extended cDNA molecule comprises sequences complementary to sequences of the template-switching oligonucleotide. In some embodiments, the template-switching oligonucleotide comprises a sequencing primer or portion thereof, or complement thereof; a unique molecular identifier sequence, or complement thereof; or a combination thereof. In some embodiments, the template-switching oligonucleotide is the second nucleic acid barcode molecule, and wherein the extended cDNA molecule is the second barcoded nucleic acid product.

In some embodiments, the first nucleic acid barcode molecule and the second nucleic acid barcode molecule comprise a common nucleic acid sequence.

In some embodiments, the partition is a droplet among a plurality of droplets. In some embodiments, the partition is a droplet and wherein (c) comprises breaking or disrupting the droplet.

In some embodiments, (e) comprises performing one or more nucleic acid amplification reactions using the first barcoded nucleic acid product or the second barcoded nucleic acid product. In some embodiments, (e) comprises attaching one or more flow cell sequences to the first barcoded nucleic acid product or the second barcoded nucleic acid product, or a derivative thereof.

In some embodiments, the first nucleic acid barcode molecule and the second nucleic acid barcode molecule are coupled to a bead. In some embodiments, the bead is a gel bead. In some embodiments, the first nucleic acid barcode molecule is coupled to the bead via a first labile moiety and the second nucleic acid barcode molecule is coupled to the bead via a second labile moiety. In some embodiments, the first nucleic acid barcode molecule and the second nucleic acid barcode molecule are releasably coupled to the bead. In some embodiments, the first nucleic acid barcode molecule is releasable from the bead upon application of a first stimulus and the second nucleic acid barcode molecule is releasable from the bead upon application of a second stimulus.

In an aspect, the present disclosure provides a method for processing a nucleic acid sample, comprising: (a) providing a partition among a plurality of partitions, wherein the partition comprises a deoxyribonucleic acid (DNA) molecule derived from the nucleic acid sample; (b) transcribing the DNA molecule to generate a ribonucleic acid (RNA) molecule; (c) reverse transcribing the RNA molecule to generate a complementary DNA (cDNA) molecule; and (d) recovering the cDNA molecule or a derivative thereof from the partition.

In some embodiments, the partition is a well among a plurality of wells.

In some embodiments, the partition is a droplet among a plurality of droplets.

In some embodiments, the method further comprises, prior to (a), processing an open chromatin structure of the nucleic acid sample with a transposase to yield the DNA molecule. In some embodiments, the transposase is a Tn5 transposase. In some embodiments, the DNA molecule comprises one or more gaps. In some embodiments, the one or more gaps are filled using a reverse transcriptase. In some embodiments, the processing further comprises attachment of a nucleic acid molecule to the nucleic acid sample, wherein the nucleic acid molecule comprises a sequence having a first sub-sequence and a second sub-sequence, wherein the first sub-sequence is complementary to the second sub-sequence. In some embodiments, the nucleic acid molecule is a hairpin nucleic acid molecule. In some embodiments, the nucleic acid molecule comprises a promoter sequence. In some embodiments, the promoter sequence is a T7 promoter sequence. In some embodiments, the nucleic acid molecule is attached to a 3' end of the nucleic acid sample.

In some embodiments, (b) comprises transcribing the DNA molecule using a T7 polymerase.

In some embodiments, (c) comprises appending a poly(C) sequence to the RNA molecule.

In some embodiments, the method further comprises subsequent to (c), attaching a nucleic acid barcode molecule to a 5' end of the cDNA molecule. In some embodiments, the nucleic acid barcode molecule comprises a unique molecular identifier sequence. In some embodiments, the nucleic acid barcode molecule comprises a barcode sequence. In some embodiments, the nucleic acid barcode molecule comprises a primer sequence. In some embodiments, the nucleic acid barcode molecule comprises a capture sequence. In some embodiments, the capture sequence comprises a poly(G) sequence.

In some embodiments, the nucleic acid barcode molecule is coupled to a bead. In some embodiments, the bead is a gel bead. In some embodiments, the nucleic acid barcode molecule is releasably coupled to the bead. In some embodiments, the nucleic acid barcode molecule is releasable from the bead upon application of a stimulus. In some embodiments, the stimulus is a chemical stimulus. In some embodiments, the chemical stimulus is a reducing agent.

In some embodiments, the cDNA molecule is a single-stranded cDNA molecule. In some embodiments, the method further comprises using the single-stranded cDNA molecule to generate a double-stranded cDNA molecule. In some embodiments, the double-stranded cDNA molecule is generated using a 5' blocked primer and a Klenow fragment. In some embodiments, the Klenow fragment does not have exonuclease activity.

In some embodiments, the cDNA molecule comprises a DNA sequence coupled to an RNA sequence, and wherein subsequent to (d), the cDNA molecule is processed with an RNase enzyme to digest the RNA sequence or remove the RNA sequence from the cDNA molecule.

In some embodiments, the partition is a droplet, and wherein (d) comprises breaking or disrupting the droplet.

In some embodiments, the method further comprises subsequent to (d), attaching one or more flow cell sequences to the cDNA molecule or derivative thereof. In some embodiments, the one or more flow cell sequences are attached via one or more nucleic acid amplification reactions.

In some embodiments, the method further comprises subsequent to (d), attaching a primer to a 3' end of the cDNA molecule or derivative thereof. In some embodiments, the cDNA molecule includes an A tail and wherein the primer attaches to the A tail.

In some embodiments, the nucleic acid sample is from a cell or cell nucleus. In some embodiments, the cell or the cell nucleus is in the partition. In some embodiments, the cell or the cell nucleus comprises the DNA molecule. In some embodiments, the cell or the cell nucleus further comprises a second ribonucleic acid (RNA) molecule. In some embodiments, the method further comprises lysing or permeabilizing the cell or the cell nucleus to provide access to the DNA molecule and/or the second RNA molecule therein.

In some embodiments, the method further comprises prior to (a), processing a messenger RNA (mRNA) molecule to provide the second RNA molecule. In some embodiments, the method further comprises, within the partition, reverse transcribing the second RNA molecule to provide an additional cDNA molecule. In some embodiments, prior to reverse transcribing the second RNA molecule, a primer molecule is hybridized to a sequence of a precursor of the second RNA molecule. In some embodiments, the precursor comprises a polyA sequence, and wherein the primer molecule comprises a polyT sequence configured to hybridize to the polyA sequence. In some embodiments, the primer molecule comprises a unique molecular identifier sequence. In some embodiments, the primer molecule comprises a barcode sequence. In some embodiments, the primer molecule comprises a sequencing primer or portion thereof. In some embodiments, the primer molecule is coupled to an additional bead. In some embodiments, the additional bead is a gel bead. In some embodiments, the primer molecule is coupled to the additional bead via a labile moiety. In some embodiments, the primer molecule is releasably coupled to the additional bead. In some embodiments, the primer molecule is releasable from the additional bead upon application of stimulus. In some embodiments, the stimulus is a chemical stimulus. In some embodiments, the chemical stimulus is a reducing agent.

In some embodiments, the method further comprises appending an additional sequence to the additional cDNA molecule. In some embodiments, the additional sequence comprises a poly(C) sequence. In some embodiments, the method further comprises contacting the additional cDNA molecule with a template-switching oligonucleotide under conditions sufficient to hybridize the template-switching oligonucleotide to the additional cDNA molecule. In some embodiments, the template-switching oligonucleotide hybridizes to the additional sequence of the additional cDNA molecule. In some embodiments, the method further comprises extending the additional cDNA molecule to generate an extended cDNA molecule, which extended cDNA molecule comprises sequences complementary to sequences of the template-switching oligonucleotide. In some embodiments, the template-switching oligonucleotide comprises a sequencing primer, or complement thereof. In some embodiments, the template-switching oligonucleotide comprises a barcode sequence, or complement thereof. In some embodiments, the template-switching oligonucleotide comprises a unique molecular identifier sequence, or complement thereof. In some embodiments, the template-switching oligonucleotide is coupled to a further bead. In some embodiments, the further bead is a gel bead. In some embodiments, the template-switching oligonucleotide is coupled to the further bead via a labile moiety. In some embodiments, the template-switching oligonucleotide is releasably coupled to the further bead. In some embodiments, the template-switching oligonucleotide is releasable from the further bead upon application of stimulus. In some embodiments, the stimulus is a chemical stimulus. In some embodiments, the chemical stimulus is a reducing agent.

In some embodiments, the template-switching oligonucleotide is a further nucleic acid barcode molecule, and wherein the extended cDNA molecule is a barcoded nucleic acid product. In some embodiments, the further nucleic acid barcode molecule comprises a flow cell sequence, or complement thereof. In some embodiments, the method further comprises contacting the extended cDNA molecule with an additional nucleic acid barcode molecule under conditions sufficient to hybridize the additional nucleic acid barcode molecule to a sequence of the extended cDNA molecule. In some embodiments, the method further comprises subjecting the extended cDNA molecule hybridized to the additional nucleic acid barcode molecule to an extension reaction to generate a barcoded nucleic acid product, which barcoded nucleic acid product comprises sequences complementary to sequences of the extended cDNA molecule. In some embodiments, the additional nucleic acid barcode molecule comprises a sequencing primer or portion thereof, or complement thereof. In some embodiments, the additional nucleic acid barcode molecule comprises a flow cell sequence, or complement thereof. In some embodiments, the additional nucleic acid barcode molecule comprises a barcode sequence, or complement thereof. In some embodiments, the additional nucleic acid barcode molecule is coupled to another bead. In some embodiments, the other bead is a gel bead. In some embodiments, the additional nucleic acid barcode molecule is coupled to the other bead via a labile moiety. In some embodiments, the additional nucleic acid barcode molecule is releasably coupled to the other bead. In some embodiments, the additional nucleic acid barcode molecule is releasable from the other bead upon application of stimulus. In some embodiments, the stimulus is a chemical stimulus. In some embodiments, the chemical stimulus is a reducing agent.

In some embodiments, the method further comprises recovering the barcoded nucleic acid product or a derivative thereof from the partition. In some embodiments, the method further comprises attaching one or more flow cell sequences to the barcoded nucleic acid product or derivative thereof. In some embodiments, the one or more flow cell sequences are attached via one or more nucleic acid amplification reactions.

In another aspect, the present disclosure provides a method for processing a nucleic acid sample, comprising: (a) providing a biological particle comprising a deoxyribonucleic acid (DNA) molecule and a ribonucleic acid (RNA) molecule within a partition among a plurality of partitions, wherein the partition comprises a first plurality of nucleic acid barcode molecules and a second plurality of nucleic acid barcode molecules, wherein the first plurality of nucleic acid barcode molecules and the second plurality of nucleic acid barcode molecules comprise a common barcode sequence; (b) within the partition, generating a first barcoded nucleic acid product corresponding to the DNA molecule and a second barcoded nucleic acid product corresponding to the RNA molecule, wherein the first barcoded nucleic acid product and the second barcoded nucleic acid product comprise the common barcode sequence, or a complement thereof; (c) recovering the first barcoded nucleic acid product and the second barcoded nucleic acid product from the partition; and (d) using (i) the first barcoded nucleic acid product to generate a first plurality of amplification products and (ii) the second barcoded nucleic acid product to generate a second plurality of amplification products, wherein in (b), the generating does not comprise performing an exponential amplification reaction.

In some embodiments, the partition is a droplet among a plurality of droplets.

In some embodiments, the partition is a well among a plurality of wells.

In some embodiments, the biological particle is a cell, cell bead, or cell nucleus.

In some embodiments, the method further comprises lysing or permeabilizing the biological particle within the partition to provide access to the DNA molecule and the RNA molecule therein.

In some embodiments, the method further comprises, prior to (a), processing an open chromatin structure of the nucleic acid sample with a transposase to yield the DNA molecule. In some embodiments, the transposase is a Tn5 transposase. In some embodiments, the transposase is included in a transposase-nucleic acid complex. In some embodiments, the transposase-nucleic acid complex comprises (i) a first nucleic acid molecule comprising a first transposon end sequence and a first sequencing primer or portion thereof, or a complement thereof and (ii) a second nucleic acid molecule comprising a second transposon end sequence and a second sequencing primer or portion thereof, or a complement thereof. In some embodiments, the first transposon end sequence and the second transposon end sequence are the same, and wherein the first transposon end sequence and the second transposon end sequence are each hybridized to complementary sequences. In some embodiments, the first sequencing primer or portion thereof, or complement thereof, is different than the second sequencing primer or portion thereof, or complement thereof.

In some embodiments, the first plurality of nucleic acid barcode molecules each comprise a sequencing primer or portion thereof, or complement thereof. In some embodiments, (b) comprises subjecting the DNA molecule to conditions sufficient to hybridize a first nucleic acid barcode molecule of the first plurality of nucleic acid barcode molecules to the DNA molecule. In some embodiments, the method further comprises extending the first nucleic acid barcode molecule hybridized to the DNA molecule to generate the first barcoded nucleic acid product. In some embodiments, the method further comprises ligating the first nucleic acid barcode molecule to the DNA molecule.

In some embodiments, the first plurality of nucleic acid barcode molecules each comprise an overhang sequence. In some embodiments, (b) comprises subjecting the DNA molecule to conditions sufficient to hybridize to a splint sequence, wherein the splint sequence comprises a sequence complementary to the DNA molecule and a sequence complementary to the overhang sequence. In some embodiments, the splint sequence comprises a 3' blocking group. In some embodiments, (b) comprises subjecting the DNA molecule hybridized to the splint sequence to conditions sufficient to hybridize the overhang sequence of a first nucleic acid barcode molecule of the first plurality of nucleic acid barcode molecules to the sequence complementary to the overhang sequence. In some embodiments, the method further comprises ligating the first nucleic acid barcode molecule to the DNA molecule. In some embodiments, the split sequence is hybridized to the overhang sequence outside of the partition.

In some embodiments, the first plurality of nucleic acid barcode molecules each comprise a flow cell sequence, or complement thereof.

In some embodiments, the DNA molecule comprises one or more gaps. In some embodiments, the method further comprises, prior to (c), subjecting the DNA molecule to an extension process to fill the one or more gaps. In some embodiments, filling of the one or more gaps is blocked by the presence of a transposase. In some embodiments, the method further comprises subsequent to (c), subjecting the DNA molecule to an extension process to fill the one or more gaps.

In some embodiments, the method further comprises, prior to (a), processing a messenger RNA (mRNA) molecule to provide the RNA molecule. In some embodiments, the method further comprises, prior to (b), within the partition, reverse transcribing the RNA molecule to provide an additional cDNA molecule. In some embodiments, prior to reverse transcribing the RNA molecule, a primer molecule is hybridized to a sequence of a precursor of the second RNA molecule. In some embodiments, the precursor comprises a polyA sequence, and wherein the primer molecule comprises a polyT sequence configured to hybridize to the polyA sequence. In some embodiments, the primer molecule comprises a unique molecular identifier sequence. In some embodiments, the primer molecule comprises a barcode sequence. In some embodiments, the primer molecule comprises a sequencing primer or portion thereof. In some embodiments, the primer molecule is a second nucleic acid barcode molecule of the plurality of second nucleic acid barcode molecules. In some embodiments, the method further comprises appending an additional sequence to the additional cDNA molecule. In some embodiments, the additional sequence is a poly(C) sequence. In some embodiments, the method further comprises contacting the additional cDNA molecule with a template-switching oligonucleotide under conditions sufficient to hybridize the template-switching oligonucleotide to the additional cDNA molecule. In some embodiments, the template-switching oligonucleotide hybridizes to the additional sequence of the additional cDNA molecule. In some embodiments, the method further comprises extending the additional cDNA molecule to generate an extended cDNA molecule, which extended cDNA molecule comprises sequences complementary to sequences of the template-switching oligonucleotide. In some embodiments, the template-switching oligonucleotide comprises a sequencing primer or portion thereof, or complement thereof. In some embodiments, the template-switching oligonucleotide comprises a unique molecular identifier sequence, or complement thereof. In some embodiments, the method further comprises contacting the extended cDNA molecule with a second nucleic acid barcode molecule of the second plurality of nucleic acid barcode molecules under conditions sufficient to hybridize the second nucleic acid barcode molecule to a sequence of the extended cDNA molecule. In some embodiments, the method further comprises subjecting the extended cDNA molecule hybridized to the second nucleic acid barcode molecule to an extension reaction to generate the second barcoded nucleic acid product, which second barcoded nucleic acid product comprises sequences complementary to sequences of the extended cDNA molecule. In some embodiments, the second nucleic acid barcode molecule comprises a sequencing primer or portion thereof, or complement thereof. In some embodiments, the second nucleic acid barcode molecule comprises a flow cell sequence, or complement thereof.

In some embodiments, the first plurality of nucleic acid barcode molecules and the second plurality of nucleic acid barcode molecules are the same.

In some embodiments, the template-switching oligonucleotide is a second nucleic acid barcode molecule of the second plurality of nucleic acid barcode molecules, and wherein the extended cDNA molecule is the second barcoded nucleic acid product. In some embodiments, the second nucleic acid barcode molecule comprises a flow cell sequence, or complement thereof.

In some embodiments, the partition is a droplet and wherein (c) comprises breaking or disrupting the droplet.

In some embodiments, (d) comprises performing one or more nucleic acid amplification reactions using the first barcoded nucleic acid product or the second barcoded nucleic acid product. In some embodiments, the one or more nucleic acid amplification reactions comprise one or more polymerase chain reactions (PCR). In some embodiments, (d) comprises attaching one or more flow cell sequences to the first barcoded nucleic acid product or the second barcoded nucleic acid product, or a derivative thereof.

In some embodiments, the first plurality of nucleic acid barcode molecules are coupled to a first bead and the second plurality of nucleic acid barcode molecules are coupled to a second bead. In some embodiments, the first bead and the second bead are gel beads. In some embodiments, the first bead is linked to the second bead. In some embodiments, the first plurality of nucleic acid barcode molecules are coupled to the first bead via a first labile moiety and the second plurality of nucleic acid barcode molecules are coupled to the second bead via a second labile moiety. In some embodiments, the first labile moiety and the second labile moiety are the same. In some embodiments, the first plurality of nucleic acid barcode molecules are releasably coupled to the first bead and the second plurality of nucleic acid barcode molecules are releasably coupled to the second bead. In some embodiments, the first plurality of nucleic acid barcode molecules are releasable from the first bead upon application of a first stimulus and the second plurality of nucleic acid barcode molecules are releasable from the second bead upon application of a second stimulus. In some embodiments, the first stimulus and the second stimulus are the same. In some embodiments, the first stimulus and the second stimulus are chemical stimuli.

In some embodiments, the first plurality of nucleic acid barcode molecules and the second plurality of nucleic acid barcode molecules are coupled to a bead. In some embodiments, the bead is a gel bead. In some embodiments, the first plurality of nucleic acid barcode molecules are coupled to the bead via a first labile moiety and the second plurality of nucleic acid barcode molecules are coupled to the bead via a second labile moiety. In some embodiments, the first labile moiety and the second labile moiety are the same. In some embodiments, the first plurality of nucleic acid barcode molecules and the second plurality of nucleic acid barcode molecules are releasably coupled to the bead. In some embodiments, the first plurality of nucleic acid barcode molecules are releasable from the bead upon application of a first stimulus and the second plurality of nucleic acid barcode molecules are releasable from the bead upon application of a second stimulus. In some embodiments, the first stimulus and the second stimulus are the same. In some embodiments, the first stimulus and the second stimulus are chemical stimuli.

In some embodiments, the method further comprises, subsequent to (d), sequencing the first plurality of amplification products and the second plurality of amplification products to identify sequences of the DNA molecule and the RNA molecule, respectively.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

DETAILED DESCRIPTION

Figure 1:
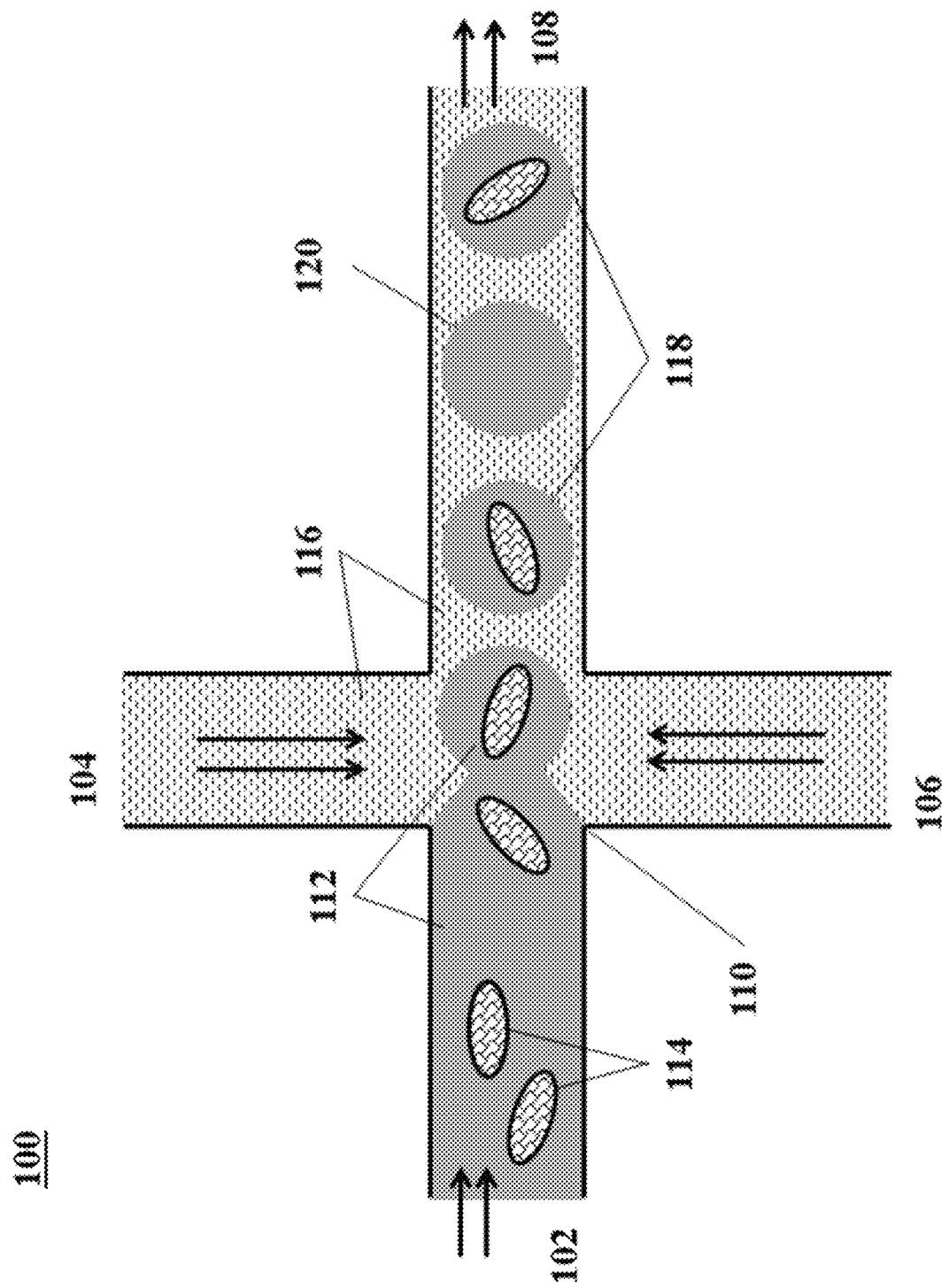
FIG. 1 shows an example of a microfluidic channel structure for partitioning individual biological particles.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The terms "a," "an," and "the," as used herein, generally refers to singular and plural references unless the context clearly dictates otherwise.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

Where values are described as ranges, it will be understood that such disclosure includes the disclosure of all possible sub-ranges within such ranges, as well as specific numerical values that fall within such ranges irrespective of whether a specific numerical value or specific sub-range is expressly stated.

The term "barcode," as used herein, generally refers to a label, or identifier, that conveys or is capable of conveying information about an analyte. A barcode can be part of an analyte. A barcode can be independent of an analyte. A barcode can be a tag attached to an analyte (e.g., nucleic acid molecule) or a combination of the tag in addition to an endogenous characteristic of the analyte (e.g., size of the analyte or end sequence(s)). A barcode may be unique. Barcodes can have a variety of different formats. For example, barcodes can include: polynucleotide barcodes; random nucleic acid and/or amino acid sequences; and synthetic nucleic acid and/or amino acid sequences. A barcode can be attached to an analyte in a reversible or irreversible manner. A barcode can be added to, for example, a fragment of a deoxyribonucleic acid (DNA) or ribonucleic acid (RNA) sample before, during, and/or after sequencing of the sample. Barcodes can allow for identification and/or quantification of individual sequencing-reads.

The term "real time," as used herein, can refer to a response time of less than about 1 second, a tenth of a second, a hundredth of a second, a millisecond, or less. The response time may be greater than 1 second. In some instances, real time can refer to simultaneous or substantially simultaneous processing, detection or identification.

The term "subject," as used herein, generally refers to an animal, such as a mammal (e.g., human) or avian (e.g., bird), or other organism, such as a plant. For example, the subject can be a vertebrate, a mammal, a rodent (e.g., a mouse), a primate, a simian or a human. Animals may include, but are not limited to, farm animals, sport animals, and pets. A subject can be a healthy or asymptomatic individual, an individual that has or is suspected of having a disease (e.g., cancer) or a pre-disposition to the disease, and/or an individual that is in need of therapy or suspected of needing therapy. A subject can be a patient. A subject can be a microorganism or microbe (e.g., bacteria, fungi, archaea, viruses).

The term "genome," as used herein, generally refers to genomic information from a subject, which may be, for example, at least a portion or an entirety of a subject's hereditary information. A genome can be encoded either in DNA or in RNA. A genome can comprise coding regions (e.g., that code for proteins) as well as non-coding regions. A genome can include the sequence of all chromosomes together in an organism. For example, the human genome ordinarily has a total of 46 chromosomes. The sequence of all of these together may constitute a human genome.

The terms "adaptor(s)", "adapter(s)" and "tag(s)" may be used synonymously. An adaptor or tag can be coupled to a polynucleotide sequence to be "tagged" by any approach, including ligation, hybridization, or other approaches.

The term "sequencing," as used herein, generally refers to methods and technologies for determining the sequence of nucleotide bases in one or more polynucleotides. The polynucleotides can be, for example, nucleic acid molecules such as deoxyribonucleic acid (DNA) or ribonucleic acid (RNA), including variants or derivatives thereof (e.g., single stranded DNA). Sequencing can be performed by various systems currently available, such as, without limitation, a sequencing system by Illumina®, Pacific Biosciences (PacBio®), Oxford Nanopore®, or Life Technologies (Ion Torrent®). Alternatively or in addition, sequencing may be performed using nucleic acid amplification, polymerase chain reaction (PCR) (e.g., digital PCR, quantitative PCR, or real time PCR), or isothermal amplification. Such systems may provide a plurality of raw genetic data corresponding to the genetic information of a subject (e.g., human), as generated by the systems from a sample provided by the subject. In some examples, such systems provide sequencing reads (also "reads" herein). A read may include a string of nucleic acid bases corresponding to a sequence of a nucleic acid molecule that has been sequenced. In some situations, systems and methods provided herein may be used with proteomic information.

The term "bead," as used herein, generally refers to a particle. The bead may be a solid or semi-solid particle. The bead may be a gel bead. The gel bead may include a polymer matrix (e.g., matrix formed by polymerization or cross-linking). The polymer matrix may include one or more polymers (e.g., polymers having different functional groups or repeat units). Polymers in the polymer matrix may be randomly arranged, such as in random copolymers, and/or have ordered structures, such as in block copolymers. Cross-linking can be via covalent, ionic, or inductive, interactions, or physical entanglement. The bead may be a macromolecule. The bead may be formed of nucleic acid molecules bound together. The bead may be formed via covalent or non-covalent assembly of molecules (e.g., macromolecules), such as monomers or polymers. Such polymers or monomers may be natural or synthetic. Such polymers or monomers may be or include, for example, nucleic acid molecules (e.g., DNA or RNA). The bead may be formed of a polymeric material. The bead may be magnetic or non-magnetic. The bead may be rigid. The bead may be flexible and/or compressible. The bead may be disruptable or dissolvable. The bead may be a solid particle (e.g., a metal-based particle including but not limited to iron oxide, gold or silver) covered with a coating comprising one or more polymers. Such coating may be disruptable or dissolvable.

The term "sample," as used herein, generally refers to a biological sample of a subject. The biological sample may comprise any number of macromolecules, for example, cellular macromolecules. The sample may be a cell sample. The sample may be a cell line or cell culture sample. The sample can include one or more cells. The sample can include one or more microbes. The biological sample may be a nucleic acid sample or protein sample. The biological sample may also be a carbohydrate sample or a lipid sample. The biological sample may be derived from another sample. The sample may be a tissue sample, such as a biopsy, core biopsy, needle aspirate, or fine needle aspirate. The sample may be a fluid sample, such as a blood sample, urine sample, or saliva sample. The sample may be a skin sample. The sample may be a cheek swab. The sample may be a plasma or serum sample. The sample may be a cell-free or cell free sample. A cell-free sample may include extracellular polynucleotides. Extracellular polynucleotides may be isolated from a bodily sample that may be selected from the group consisting of blood, plasma, serum, urine, saliva, mucosal excretions, sputum, stool and tears.

The term "biological particle," as used herein, generally refers to a discrete biological system derived from a biological sample. The biological particle may be a macromolecule. The biological particle may be a small molecule. The biological particle may be a virus. The biological particle may be a cell or derivative of a cell. The biological particle may be an organelle. The biological particle may be a rare cell from a population of cells. The biological particle may be any type of cell, including without limitation prokaryotic cells, eukaryotic cells, bacterial, fungal, plant, mammalian, or other animal cell type, mycoplasmas, normal tissue cells, tumor cells, or any other cell type, whether derived from single cell or multicellular organisms. The biological particle may be a constituent of a cell. The biological particle may be or may include DNA, RNA, organelles, proteins, or any combination thereof. The biological particle may be or may include a matrix (e.g., a gel or polymer matrix) comprising a cell or one or more constituents from a cell (e.g., cell bead), such as DNA, RNA, organelles, proteins, or any combination thereof, from the cell. The biological particle may be obtained from a tissue of a subject. The biological particle may be a hardened cell. Such hardened cell may or may not include a cell wall or cell membrane. The biological particle may include one or more constituents of a cell, but may not include other constituents of the cell. An example of such constituents is a nucleus or an organelle. A cell may be a live cell. The live cell may be capable of being cultured, for example, being cultured when enclosed in a gel or polymer matrix, or cultured when comprising a gel or polymer matrix. For a description of exemplary cell beads, polymer or cross-linked matrices, and cell bead generation methods, see, e.g., U.S. Pat. Pub. 20180216162 and U.S. Pat. Pub. 20190100632, each of which is herein incorporated by reference in their entireties.

The term "macromolecular constituent," as used herein, generally refers to a macromolecule contained within or from a biological particle. The macromolecular constituent may comprise a nucleic acid. In some cases, the biological particle may be a macromolecule. The macromolecular constituent may comprise DNA. The macromolecular constituent may comprise RNA. The RNA may be coding or non-coding. The RNA may be messenger RNA (mRNA), ribosomal RNA (rRNA) or transfer RNA (tRNA), for example. The RNA may be a transcript. The RNA may be small RNA that are less than 200 nucleic acid bases in length, or large RNA that are greater than 200 nucleic acid bases in length. Small RNAs may include 5.8S ribosomal RNA (rRNA), 5S rRNA, transfer RNA (tRNA), microRNA (miRNA), small interfering RNA (siRNA), small nucleolar RNA (snoRNAs), Piwi-interacting RNA (piRNA), tRNA-derived small RNA (tsRNA) and small rDNA-derived RNA (srRNA). The RNA may be double-stranded RNA or single-stranded RNA. The RNA may be circular RNA. The macromolecular constituent may comprise a protein. The macromolecular constituent may comprise a peptide. The macromolecular constituent may comprise a polypeptide.

The term "molecular tag," as used herein, generally refers to a molecule capable of binding to a macromolecular constituent. The molecular tag may bind to the macromolecular constituent with high affinity. The molecular tag may bind to the macromolecular constituent with high specificity. The molecular tag may comprise a nucleotide sequence. The molecular tag may comprise a nucleic acid sequence. The nucleic acid sequence may be at least a portion or an entirety of the molecular tag. The molecular tag may be a nucleic acid molecule or may be part of a nucleic acid molecule. The molecular tag may be an oligonucleotide or a polypeptide. The molecular tag may comprise a DNA aptamer. The molecular tag may be or comprise a primer. The molecular tag may be, or comprise, a protein. The molecular tag may comprise a polypeptide. The molecular tag may be a barcode.

The term "partition," as used herein, generally refers to a space or volume that may be suitable to contain one or more species or conduct one or more reactions. A partition may be a physical compartment, such as a droplet or well. The partition may isolate space or volume from another space or volume. The droplet may be a first phase (e.g., aqueous phase) in a second phase (e.g., oil) immiscible with the first phase. The droplet may be a first phase in a second phase that does not phase separate from the first phase, such as, for example, a capsule or liposome in an aqueous phase. A partition may comprise one or more other (inner) partitions. In some cases, a partition may be a virtual compartment that can be defined and identified by an index (e.g., indexed libraries) across multiple and/or remote physical compartments. For example, a physical compartment may comprise a plurality of virtual compartments.

The present disclosure provides methods, systems, and kits for processing multiple types of nucleic acid molecules. The methods, systems, and kits provided herein may facilitate sample preparation for sequencing of nucleic acid molecules included in cells, cell beads, or cell nuclei of interest. For example, the present disclosure provides methods for processing both deoxyribonucleic acid (DNA) and ribonucleic acid (RNA) molecules included within a cell, cell bead, or cell nucleus. The methods may comprise performing Assay for Transposase Accessible Chromatin with high-throughput sequencing (ATAC-seq) and RNA sequencing (RNA-seq) assays in tandem. Partitioning and barcoding schemes may be utilized to facilitate identification of resultant sequencing reads with the cell, cell bead, or cell nucleus from which they are derived.

The present disclosure also provides methods, systems, and kits for processing biological samples comprising nucleic acid molecules. The method may comprise providing one or more nucleic acid molecules (e.g., deoxyribonucleic acid (DNA) molecules and/or ribonucleic acid (RNA) molecules) from a nucleic acid sample (e.g., a sample comprising a cell, cell bead, or cell nucleus) in a partition of a plurality of partitions (e.g., a plurality of droplets or wells). The one or more nucleic acid molecules may be one or more DNA molecules. The one or more DNA molecules may be transcribed to generate one or more RNA molecules, where the one or more RNA molecules may be reverse transcribed to generate one or more complementary DNA (cDNA) molecules. The one or more cDNA molecules, or derivatives thereof, may then be recovered from the partition of the plurality of partitions (e.g., by pooling the contents of the plurality of partitions). The one or more cDNA molecules, or derivatives thereof, may comprise one or more nucleic acid barcode sequences, or complements thereof, where the one or more nucleic acid barcode sequences, or complements thereof, may be incorporated into nucleic acid molecules during any processing step (e.g., during transcription of a DNA molecule, reverse transcription of an RNA molecule, etc.). The one or more nucleic acid barcode sequences, or complements thereof, may be used to identify sequencing reads (e.g., sequencing reads obtained using a nucleic acid sequencing assay) corresponding to the one or more cDNA molecules from a nucleic acid molecule of the one or more nucleic acid molecules from the nucleic acid sample.

Tandem DNA and RNA Barcoding

In an aspect, the present disclosure provides a method for processing nucleic acid molecules from a cell, cell bead, or cell nucleus. The method may comprise contacting a cell, cell bead, or cell nucleus with a transposase-nucleic acid complex comprising a transposase molecule and one or more transposon end oligonucleotide molecules. The cell, cell bead or cell nucleus may be contacted with a transposase-nucleic acid complex in bulk solution, such that the cell, cell bead or cell nucleus undergoes "tagmentation" via a tagmentation reaction. Contacting the cell, cell bead, or cell nucleus with the transposase-nucleic acid complex may generate one or more template nucleic acid fragments (e.g., "tagmented fragments"). The one or more template nucleic acid fragments may correspond to one or more target nucleic acid molecules (e.g., deoxyribonucleic acid (DNA) molecules) within the cell, cell bead, or cell nucleus. In parallel, the cell, cell bead, or cell nucleus may be contacted with a primer molecule (e.g., a primer molecule comprising a poly-T sequence) configured to interact with one or more additional target nucleic acid molecules (e.g., ribonucleic acid (RNA) molecules, such as messenger RNA (mRNA) molecules). The cell, cell bead, or cell nucleus may be contacted with a primer molecule in bulk solution. Alternatively or in addition to, the cell, cell bead, or cell nucleus may be contacted with a primer molecule within a partition. Interaction between these moieties may yield one or more additional template nucleic acid fragments (e.g., RNA fragments). For example, the primer molecule may have at least partial sequence complementarity to the one or more additional target nucleic acid molecules (e.g., mRNA molecules). The primer molecule may hybridize to a sequence of an additional target nucleic acid molecule of the one or more additional target nucleic acid molecules. The cell, cell bead, or cell nucleus may be partitioned (e.g., co-partitioned with one or more reagents) into a partition (e.g., of a plurality of partitions). The partition may be, for example, a droplet or a well. The partition may comprise one or more reagents, including, for example, one or more particles (e.g., beads) comprising one or more nucleic acid barcode molecules. The cell, cell bead, or cell nucleus may be lysed, permeabilized, fixed, cross-linked or otherwise manipulated to provide access to the one or more template nucleic acid fragments and the one or more additional template nucleic acid fragments therein. The one or more template nucleic acid fragments and the one or more additional template nucleic acid fragments therein may undergo one or more processing steps within the partition. For example, the one or more template nucleic acid fragments and/or the one or more additional template nucleic acid fragments may undergo a barcoding process, a ligation process, a reverse transcription process, a template switching process, a linear amplification process, and/or a gap filling process. The resultant one or more processed template nucleic acid fragments (e.g., tagmented fragments) and/or the one or more processed additional template nucleic acid fragments (e.g., RNA fragments) may each include a barcode sequence (e.g., nucleic acid barcode sequence, as described herein). The one or more processed template nucleic acid fragments and/or the one or more processed additional template nucleic acid fragments may be released from the partition (e.g., pooled with contents of other partitions of a plurality of partitions) and may undergo one or more additional processing steps in bulk. For example, the one or more processed template nucleic acid fragments and/or the one or more processed additional template nucleic acid fragments may undergo a gap filling process, a dA tailing process, a terminal-transferase process, a phosphorylation process, a ligation process, a nucleic acid amplification process, or a combination thereof. For example, the one or more processed template nucleic acid fragments and/or the one or more processed additional template nucleic acid fragments may be subjected to conditions sufficient to undergo one or more polymerase chain reactions (PCR, such as sequence independent PCR) to generate amplification products corresponding to the one or more processed template nucleic acid fragments (e.g., tagmented fragments) and/or the one or more processed additional template nucleic acid fragments (e.g., RNA fragments). Sequences of such amplification products can be detected using, for example, a nucleic acid sequencing assay and used to identify sequences of the one or more target nucleic acid molecules (e.g., DNA molecules) and the one or more additional target nucleic acid molecules (e.g., RNA molecules) of the cell, cell bead, or cell nucleus from which they derive.

A biological sample (e.g., a nucleic acid sample) may comprise one or more cells, cell beads, and/or cell nuclei. A biological sample may also comprise tissue, which tissue may comprise one or more cells, cell beads, and/or cell nuclei. In some cases, a biological sample may comprise a plurality of cells comprising a plurality of cell nuclei. In some cases, a biological sample may comprise a plurality of cell nuclei, which plurality of cell nuclei are not included within cells (e.g., other components of the cell have degraded, dissociated, dissolved, or otherwise been removed). A biological sample may comprise a plurality of cell-free nucleic acid molecules (e.g., nucleic acid molecules that are not included within cells). For example, a biological sample may comprise a plurality of cell-free fetal DNA (cffDNA) or circulating tumor DNA (ctDNA) or other cell-free nucleic acid molecules (e.g., deriving from degraded cells). Such a biological sample may be processed to separate such cell-free nucleic acid molecules from cells, cell beads, and/or cell nuclei, which cells, cell beads, and/or cell nuclei may be subjected to further processing (e.g., as described herein).

Nucleic acid molecules included within a biological sample may include, for example, DNA molecules and RNA molecules. For example, a biological sample may comprise genomic DNA comprising chromatin (e.g., within a cell, cell bead, or cell nucleus). A biological sample may comprise a plurality of RNA molecules, such as a plurality of pre-mRNA or mRNA molecules. mRNA molecules and other RNA molecules may comprise a polyA sequence. At least a subset of a plurality of RNA molecules included in a cell or cell bead may be present in a cell nucleus.

A nucleic acid molecule may undergo one or more processing steps within a cell, cell bead, or cell nucleus. For example, chromatin within a cell, cell bead, or cell nucleus may be contacted with a transposase. A transposase may be included within a transposase-nucleic acid complex, which transposase-nucleic acid complex may comprise a transposase molecule and one or more transposon end oligonucleotide molecules. A transposase may be a Tn transposase, such as a Tn3, Tn5, Tn7, Tn10, Tn552, Tn903 transposase. Alternatively, a transposase may be a MuA transposase, a Vibhar transposase (e.g. from *Vibrio harveyi*), Ac-Ds, Ascot-1, Bs1, Cin4, Copia, En/Spm, F element, hobo, Hsmar1, Hsmar2, IN (HIV), IS1, IS2, IS3, IS4, IS5, IS6, IS10, IS21, IS30, IS50, IS51, IS150, IS256, IS407, IS427, IS630, IS903, IS911, IS982, IS1031, ISL2, L1, Mariner, P element, Tam3, Tc1, Tc3, Tel, THE-1, Tn/O, TnA, Tn3, Tn5, Tn7, Tn10, Tn552, Tn903, Tol1, Tol2, Tn10, Ty1, any prokaryotic transposase, or any transposase related to and/or derived from those listed above. For example, a transposase may be a Tn5 transposase or a mutated, hyperactive Tn5 transposase. A transposase related to and/or derived from a parent transposase may comprise a peptide fragment with at least about 50%, about 55%, about 60%, about 65%, about 70%, about 75%, about 80%, about 85%, about 90%, about 91%, about 92%, about 93%, about 94%, about 95%, about 96%, about 97%, about 98%, or about 99% amino acid sequence homology to a corresponding peptide fragment of the parent transposase. The peptide fragment may be at least about 10, about 15, about 20, about 25, about 30, about 35, about 40, about 45, about 50, about 60, about 70, about 80, about 90, about 100, about 150, about 200, about 250, about 300, about 400, or about 500 amino acids in length. For example, a transposase derived from Tn5 may comprise a peptide fragment that is 50 amino acids in length and about 80% homologous to a corresponding fragment in a parent Tn5 transposase. Action of a transposase (e.g., insertion) may be facilitated and/or triggered by addition of one or more cations, such as one or more divalent cations (e.g., $Ca^{2+}$, $Mg^{2+}$, or $Mn^{2+}$).

A transposase-nucleic acid complex may comprise one or more nucleic acid molecules. For example, a transposase-nucleic acid complex may comprise one or more transposon end oligonucleotide molecules. A transposon end oligonucleotide molecule may comprise one or more adapter sequences (e.g., comprising one or more primer sequences) and/or one or more transposon end sequences. A transposon end sequence may be, for example, a Tn5 or modified Tn5 transposon end sequence or a Mu transposon end sequence. A transposon end sequence may have a sequence of, for example,

AGATGTGTATAAGAGACA. (SEQ ID NO: 1)

A primer sequence of a transposon end oligonucleotide molecule may be a sequencing primer, such as an R1 or R2 sequencing primer, or a portion thereof. A sequencing primer may be, for example, a TrueSeq or Nextera sequencing primer. An R1 sequencing primer region may have a sequence of

TCTACACTCTTTCCCTACACGACGCTCTTCCGATCT, (SEQ ID NO: 2)

or some portion thereof. An R1 sequencing primer region may have a sequence of

TCGTCGGCAGCGTCAGATGTGTATAAGAGACAG, (SEQ ID NO: 3)

or some portion thereof. A transposon end oligonucleotide molecule may comprise a partial R1 sequence. A partial R1 sequence may be

ACTACACGACGCTCTTCCGATCT. (SEQ ID NO: 4)

A transposon end oligonucleotide molecule may comprise an R2 sequencing priming region. An R2 sequencing primer region may have a sequence of

GTGACTGGAGTTCAGACGTGTGCTCTTCCGATCT, (SEQ ID NO: 5)

or some portion thereof. An R2 sequencing primer region may have a sequence of

GTCTCGTGGGCTCGGAGATGTGTATAAGAGACAG, (SEQ ID NO: 6)

or some portion thereof. A transposon end oligonucleotide molecule may comprise a T7 promoter sequence. A T7 promoter sequence may be

TAATACGACTCACTATAG. (SEQ ID NO: 7)

A transposon end oligonucleotide molecule may comprise a region at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to any one of SEQ ID NO: 1-7. A transposon end oligonucleotide molecule may comprise a P5 sequence and/or a P7 sequence. A transposon end oligonucleotide molecule may comprise a sample index sequence, such as a barcode sequence or unique molecular identifier sequence. One or more transposon end oligonucleotide molecules of a transposase-nucleic acid complex may be attached to a solid support (e.g., a solid or semi-solid particle such as a bead (e.g., gel bead)). A transposon end oligonucleotide molecule may be releasably coupled to a solid support (e.g., a bead). Examples of transposon end oligonucleotide molecules may be found in, for example, PCT Patent Publications Nos. WO2018/218226, WO2014/189957, US. Pat. Pub. 20180340171, and U.S. Pat. No. 10,059,989; each of which are herein incorporated by reference in their entireties.

Figure 9:
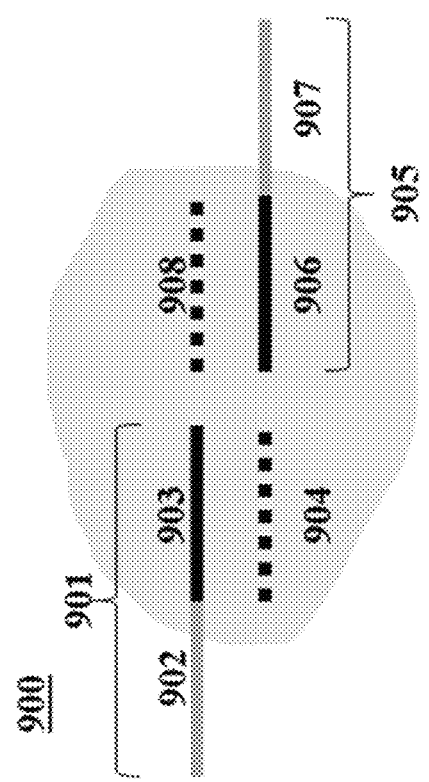
FIG. 9 illustrates a transposase-nucleic acid complex comprising a transposase, a first double-stranded oligonucleotide comprising a transposon end sequence and a first primer sequence and a second double-stranded oligonucleotide comprising a transposon end sequence and a second primer sequence.

FIG. 9 includes an example of a transposase-nucleic acid complex for use in the methods provided herein. Transposase-nucleic acid complex 900 (e.g., comprising a transpose dimer) comprises partially double-stranded oligonucleotide 901 and partially double-stranded oligonucleotide 905. Partially double-stranded oligonucleotide 901 comprises transposon end sequence 903, first primer sequence 902, and a sequence 904 that is complementary to transposon end sequence 903. Partially double-stranded oligonucleotide 905 comprises transposon end sequence 906, first primer sequence 907, and a sequence 908 that is complementary to transposon end sequence 906. Primer sequences 902 and 907 may be the same or different. In some cases, primer sequence 902 may be designated "R1" and primer sequence 907 may be designated "R2". Transposon end sequences 903 and 906 may be the same or different. Transposon end sequences 903 and 906 may alternately be referred to as "mosaic end" or "ME" sequences, while their complementary sequences 904 and 908 may be referred to as "mosaic end reverse complement" or "MErc" sequences.

Figure 10:
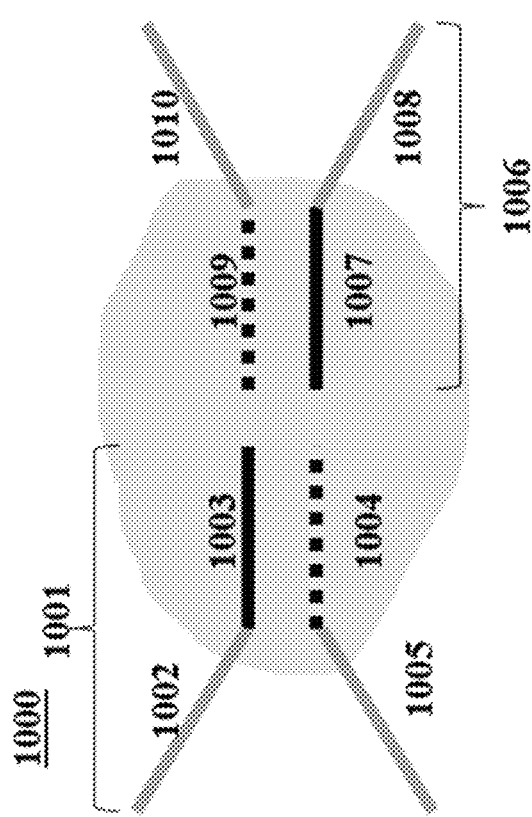
FIG. 10 illustrates a transposase-nucleic acid complex comprising a transposase, a first double-stranded oligonucleotide comprising a transposon end sequence and first and second primer sequences and a second double-stranded oligonucleotide comprising a transposon end sequence and third and fourth primer sequences.

FIG. 10 includes another example of a transposase-nucleic acid complex for use in the methods provided herein. Transposase-nucleic acid complex 1000 (e.g., comprising a transpose dimer) comprises forked adapters 1001 and 1006, which forked adapters are partially double-stranded oligonucleotides. Partially double-stranded oligonucleotide 1001 comprises transposon end sequence 1003, first primer sequence 1002, second primer sequence 1005, and a sequence 1004 that is complementary to transposon end sequence 1003. Partially double-stranded oligonucleotide 1006 comprises transposon end sequence 1007, first primer sequence 1008, second primer sequence 1010, and a sequence 1009 that is complementary to transposon end sequence 1007. Primer sequences 1002, 1005, 1008, and 1010 may be the same or different. In some cases, primer sequences 1002 and 1008 may be designated "R1" and primer sequences 1005 and 1010 may be designated "R2". Alternatively, primer sequences 1002 and 1010 may be designated "R1" and primer sequences 1005 and 1008 may be designated "R2". Alternatively, primer sequences 1002 and 1008 may be designated "R2" and primer sequences 1005 and 1010 may be designated "R1". Alternatively, primer sequences 1002 and 1010 may be designated "R2" and primer sequences 1005 and 1008 may be designated "R1". Transposon end sequences 1003 and 1007 may be the same or different. These sequences may alternately be referred to as "mosaic end" or "ME" sequences, while their complementary sequences 1004 and 1009 may be referred to as "mosaic end reverse complement" or "MErc" sequences.

Figure 11:
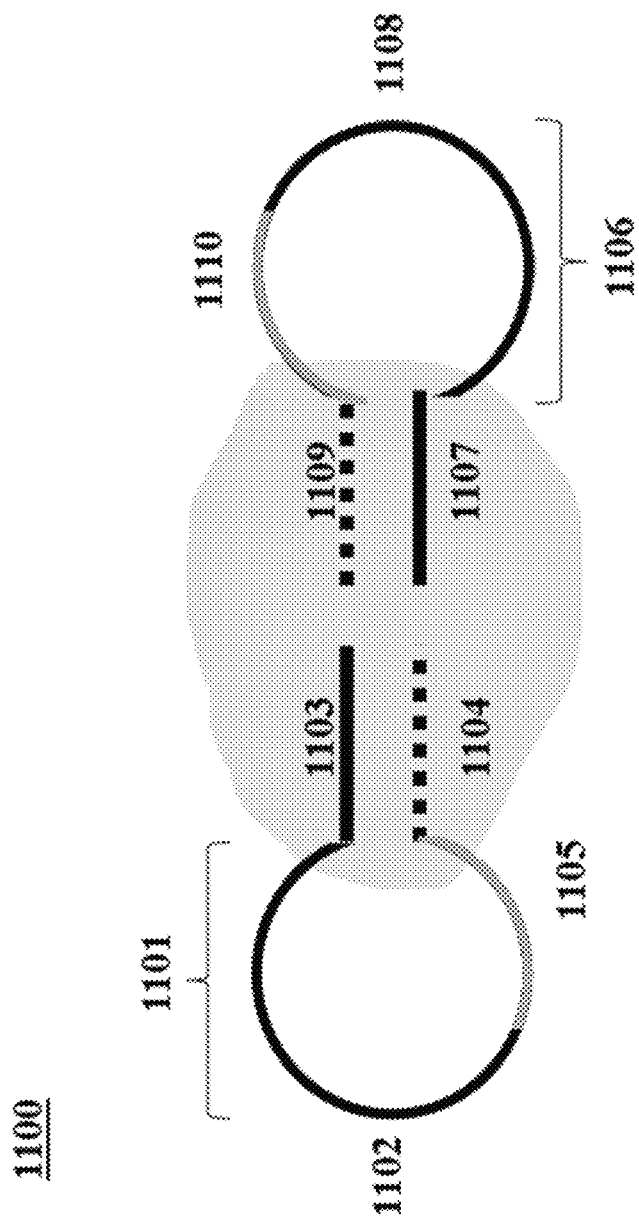
FIG. 11 illustrates a transposase-nucleic acid complex comprising a transposase, a first hairpin molecule, and a second hairpin molecule.

FIG. 11 shows transposase-nucleic acid complex 1100 (e.g., comprising a transpose dimer) comprising hairpin molecules 1101 and 1106. Hairpin molecule 1101 comprises transposon end sequence 1103, first hairpin sequence 1102, second hairpin sequence 1105, and a sequence 1104 that is complementary to transposon end sequence 1103. Hairpin molecule 1106 comprises transposon end sequence 1107, third hairpin sequence 1108, fourth hairpin sequence 1110, and a sequence 1109 that is complementary to transposon end sequence 1107. Hairpin sequences 1102, 1105, 1108, and 1110 may be the same or different. For example, hairpin sequence 1105 may be the same or different as hairpin sequence 1110, and/or hairpin sequence 1102 may be the same or different as hairpin sequence 1108. Hairpin sequences 1102 and 1108 may be spacer sequences or adapter sequences. Hairpin sequences 1105 and 1110 may be a promoter sequence such as T7 recognition or promoter sequences and/or UMI sequences. Transposon end sequences 1103 and 1107 may be the same or different. Transposon end sequences 1103 and 1107 may alternately be referred to as "mosaic end" or "ME" sequences, while their complementary sequences 1104 and 1109 may be referred to as "mosaic end reverse complement" or "MErc" sequences. In some cases, sequence 1104 is a transposon end sequence and 1103 is a sequence complementary to sequence 1104. In some cases, sequence 1109 is a transposon end sequence and 1107 is a sequence complementary to sequence 1109.

Contacting a cell, cell bead, or cell nucleus comprising one or more target nucleic acid molecules (e.g., DNA molecules) with a transposase-nucleic acid complex may generate one or more template nucleic acid fragments (e.g., "tagmented fragments"). The one or more template nucleic acid fragments may each comprise a sequence of the one or more target nucleic acid molecules (e.g., a target sequence). The transposase-nucleic acid complex may be configured to target a specific region of the one or more target nucleic acid molecules to provide one or more template nucleic acid fragments comprising specific target sequences. The one or more template nucleic acid fragments may comprise target sequences corresponding to accessible chromatin. Generation of tagmented fragments may take place within a bulk solution. In other cases, generation of tagmented fragments may take place within a partition (e.g., a droplet or well). A template nucleic acid fragment (e.g., tagmented fragment) may comprise one or more gaps (e.g., between a transposon end sequence or complement thereof and a target sequence on one or both strands of a double-stranded fragment). Gaps may be filled via a gap filling process using, e.g., a polymerase (e.g., DNA polymerase), ligase, or reverse transcriptase. In some cases, a mixture of enzymes may be used to repair a partially double-stranded nucleic acid molecule and fill one or more gaps. Gap filling may not include strand displacement. Gaps may be filled within or outside of a partition.

Alternatively or in addition to, one or more additional nucleic acid molecules may be contacted with one or more capture nucleic acid molecules within a cell, cell bead, or cell nucleus to provide one or more additional template nucleic acid fragments. For example, an RNA molecule (e.g., an mRNA) molecule may be contacted with a primer molecule within a cell, cell bead, or cell nucleus. A primer molecule may comprise a primer sequence, which primer sequence may be a targeted primer sequence or a non-specific primer sequence (e.g., random N-mer). A targeted primer sequence may comprise, for example, a polyT sequence, which polyT sequence may interact with a polyA sequence of an RNA molecule. A primer nucleic acid molecule may also comprise one or more additional sequences, such as one or more sample index sequences, spacer or linker sequences, or one or more additional primer sequences. Generation of additional template nucleic acid fragments (e.g., RNA fragments) may take place within a bulk solution. In other cases, generation of additional template nucleic acid fragments may take place within a partition (e.g., a droplet or well).

Processing of nucleic acid molecules within a cell, cell bead, or cell nucleus (e.g., generation of template nucleic acid fragments using a transposase-nucleic acid complex and/or generation of additional template nucleic acid fragments using a capture nucleic acid molecule) may occur in a bulk solution comprising a plurality of cells, cell beads, and/or cell nuclei. In some cases, template nucleic acid fragments (e.g., tagmented fragments) may be generated in bulk solution and additional template nucleic acid fragments (e.g., RNA fragments) may be generated in a partition.

A plurality of cells, cell beads, and/or cell nuclei (e.g., a plurality of cells, cell beads, and/or cell nuclei that have undergone processing such as a tagmentation process) may be partitioned amongst a plurality of partitions. Partitions may be, for example, droplets or wells. Droplets (e.g., aqueous droplets) may be generated according to the methods provided herein. Partitioning may be performed according to the method provided herein. For example, partitioning a biological particle (e.g., cell, cell bead, or cell nucleus) and one or more reagents may comprise flowing a first phase comprising an aqueous fluid, the biological particle, and the one or more reagents and a second phase comprising a fluid that is immiscible with the aqueous fluid toward a junction. Upon interaction of the first and second phases, a discrete droplet of the first phase comprising the biological particle and the one or more reagents may be formed. The plurality of cells, cell beads, and/or cell nuclei may be partitioned amongst a plurality of partitions such that at least a subset of the plurality of partitions may comprise at most one cell, cell bead, or cell nucleus. Cells, cell beads, and/or cell nuclei may be co-partitioned with one or more reagents such that a partition of at least a subset of the plurality of partitions comprises a single cell, cell bead, or cell nucleus and one or more reagents. The one or more reagents may include, for example, enzymes (e.g., polymerases, reverse transcriptases, ligases, etc.), nucleic acid barcode molecules (e.g., nucleic acid barcode molecules comprising one or more barcode sequences, such as nucleic acid barcode molecules coupled to one or more beads), template switching oligonucleotides, deoxynucleotide triphosphates, buffers, lysis agents, primers, barcodes, detergents, reducing agents, chelating agents, oxidizing agents, nanoparticles, beads, antibodies, or any other useful reagents. Enzymes may include, for example, temperature-sensitive enzymes, pH-sensitive enzymes, light-sensitive enzymes, reverse transcriptases, proteases, ligases, polymerases, kinases, restriction enzymes, nucleases, protease inhibitors, exonucleases, and nuclease inhibitors.

A reagent of the one or more reagents may be useful for lysing or permeabilizing a cell, cell bead, or cell nucleus, or otherwise providing access to nucleic acid molecules and/or template nucleic acid fragments therein. A cell may be lysed using a lysis agent such as a bioactive agent. A bioactive agent useful for lysing a cell may be, for example, an enzyme (e.g., as described herein). An enzyme used to lyse a cell may or may not be capable of carrying out additional actions such as degrading one or more RNA molecules. Alternatively, an ionic, zwitterionic, or non-ionic surfactant may be used to lyse a cell. Examples of surfactants include, but are not limited to, TritonX-100, Tween 20, sarcosyl, or sodium dodecyl sulfate. Cell lysis may also be achieved using a cellular disruption method such as an electroporation or a thermal, acoustic, or mechanical disruption method. Alternatively, a cell may be permeabilized to provide access to a plurality of nucleic acid molecules included therein. Permeabilization may involve partially or completely dissolving or disrupting a cell membrane or a portion thereof. Permeabilization may be achieved by, for example, contacting a cell membrane with an organic solvent or a detergent such as Triton X-100 or NP-40. By lysing or permeabilizing a cell, cell bead, or cell nucleus within a partition (e.g., droplet) to provide access to the plurality of nucleic acid molecules and/or template nucleic acid fragments therein, molecules originating from the same cell, cell bead, or cell nucleus may be isolated within the same partition.

A partition of a plurality of partitions (e.g., a partition comprising a cell, cell bead, and/or cell nucleus) may comprise one or more beads (e.g., gel beads). A bead may be a gel bead. A bead may comprise a plurality of nucleic acid barcode molecules (e.g., nucleic acid molecules each comprising one or more barcode sequences, as described herein). A bead may comprise at least 10,000 nucleic acid barcode molecules attached thereto. For example, the bead may comprise at least 100,000, 1,000,000, or 10,000,000 nucleic acid barcode molecules attached thereto. The plurality of nucleic acid barcode molecules may be releasably attached to the bead. The plurality of nucleic acid barcode molecules may be releasable from the bead upon application of a stimulus. Such a stimulus may be selected from the group consisting of a thermal stimulus, a photo stimulus, and a chemical stimulus. For example, the stimulus may be a reducing agent such as dithiothreitol Application of a stimulus may result in one or more of (i) cleavage of a linkage between nucleic acid barcode molecules of the plurality of nucleic acid barcode molecules and the bead, and (ii) degradation or dissolution of the bead to release nucleic acid barcode molecules of the plurality of nucleic acid barcode molecules from the bead.

A plurality of nucleic acid barcode molecules attached (e.g., releasably attached) to a bead (e.g., gel bead) may be suitable for barcoding template nucleic acid fragments or additional template nucleic acid fragments deriving from DNA and/or RNA molecules of the plurality of cells, cell beads, and/or cell nuclei. For example, a nucleic acid barcode molecule of a plurality of nucleic acid barcode molecule may comprise a barcode sequence, unique molecular identifier (UMI) sequence, primer sequence, universal primer sequence, sequencing adapter or primer, flow cell adapter sequence, or any other useful feature. In an example, a nucleic acid barcode molecule of a plurality of nucleic acid barcode molecules attached to a bead may comprise a flow cell adapter sequence (e.g., a P5 or P7 sequence), a barcode sequence, a capture sequence, and a sequencing primer sequence or portion thereof (e.g., an R1 or R2 sequence or portion thereof), or a complement of any of these sequences. These sequences may be arranged in any useful order and may be linked or may include one or more spacer sequences disposed between them. For instance, the flow cell adapter sequence, where present, may be disposed near (e.g., proximal to) an end of the nucleic acid barcode molecule that is closest to the bead, while the sequencing primer or portion thereof may be disposed at an end of the nucleic acid barcode molecule that is furthest from (e.g., distal to) the bead (e.g., most available to template nucleic acid fragments for interaction). In another example, a nucleic acid barcode molecule of a plurality of nucleic acid barcode molecules attached to a bead may comprise a flow cell adapter sequence (e.g., a P5 or P7 sequence), a barcode sequence, a sequencing primer sequence or portion thereof (e.g., an R1 or R2 sequence or portion thereof), and a UMI sequence, or a complement of any of these sequences. The nucleic acid barcode molecule may further comprise a capture sequence, which capture sequence may be a targeted capture sequence or comprise a template switch sequence (e.g., comprising a polyC or poly G sequence). These sequences may be arranged in any useful order and may be linked or may include one or more spacer sequences disposed between them. For instance, the flow cell adapter sequence may be disposed near (e.g., proximal to) an end of the nucleic acid barcode molecule that is closest to the bead, while the capture sequence or template switch sequence may be disposed at an end of the nucleic acid barcode molecule that is furthest from the bead (e.g., most available to template nucleic acid fragments for interaction).

All of the nucleic acid barcode molecules attached (e.g., releasably attached) to a bead (e.g., gel bead) of a plurality of beads may be the same. For example, all of the nucleic acid barcode molecules attached to the bead may have the same nucleic acid sequence. In such an instance, all of the nucleic acid barcode molecules attached to the bead may comprise the same flow cell adapter sequence, sequencing primer or portion thereof, and/or barcode sequence. The barcode sequence of a plurality of nucleic acid barcode molecules attached to a bead of a plurality of beads may be different from other barcode sequences of other nucleic acid barcode molecules attached to other beads of the plurality of beads. For example, a plurality of beads may comprise a plurality of barcode sequences, such that, for at least a subset of the plurality of beads, each bead comprises a different barcode sequence of the plurality of barcode sequences. This differentiation may permit template nucleic acid fragments (e.g., included within cells, cell beads, and/or cell nuclei) co-partitioned with a plurality of beads between a plurality of partitions to be differentially barcoded within their respective partitions, such that the template nucleic acid fragments or molecules derived therefrom may be identified with the partition (and thus the cell, cell bead, and/or cell nucleus) to which they correspond (e.g., using a nucleic acid sequencing assay, as described herein). A barcode sequence may comprise between 4-20 nucleotides. A barcode sequence may comprise one or more segments, which segments may range in size from 2-20 nucleotides, such as from 4-20 nucleotides. Such segments may be combined to form barcode sequences using a combinatorial assembly method, such as a split-pool method. Details of such methods can be found, for example, in PCT/US2018/061391, filed Nov. 15, 2018, and U.S. Pat. Pub. 20190249226, each of which are herein incorporated by reference in their entireties.

In some cases, nucleic acid barcode molecules attached to a bead may not be the same. For example, the plurality of nucleic acid barcode molecules attached to a bead may each comprise a UMI sequence, which UMI sequence varies across the plurality of nucleic acid barcode molecules. All other sequences of the plurality of nucleic acid barcode molecules attached to the bead may be the same.

In some cases, a bead may comprise multiple different nucleic acid barcode molecules attached thereto. For example, a bead may comprise a first plurality of nucleic acid barcode molecules and a second plurality of nucleic acid barcode molecules, which first plurality of nucleic acid barcode molecules is different than the second plurality of nucleic acid barcode molecules. The first plurality of nucleic acid barcode molecules and the second plurality of nucleic acid barcode molecules coupled to a bead may comprise one or more shared sequences. For example, each nucleic acid barcode molecule of the first plurality of nucleic acid barcode molecules and each nucleic acid barcode molecule of the second plurality of nucleic acid barcode molecules may comprise the same barcode sequence (e.g., as described herein). Such a barcode sequence may be prepared using a combinatorial assembly process (e.g., as described herein). For example, barcode sequences may comprise identical barcode sequence segments. Similarly, each nucleic acid barcode molecule of the first plurality of nucleic acid barcode molecules coupled to a bead may comprise the same flow cell adapter sequence and/or sequencing primer or portion thereof as each nucleic acid barcode molecule of the second plurality of nucleic acid barcode molecules coupled to the bead. In an example, each nucleic acid barcode molecule of the first plurality of nucleic acid barcode molecules coupled to a bead comprises a sequencing primer, and each nucleic acid barcode molecule of the second plurality of nucleic acid barcode molecules coupled to the bead comprises a portion of the same sequencing primer. In some instances, each nucleic acid barcode molecule of the first plurality of nucleic acid barcode molecules coupled to a bead may comprise a first sequencing primer (e.g., a TruSeq R1 sequence), a barcode sequence, and a first functional sequence, and each nucleic acid barcode molecule of the second plurality of nucleic acid barcode molecules coupled to the bead may comprise a second sequencing primer (e.g., a Nextera R1 sequence, or a portion thereof), the barcode sequence, and a second functional sequence. Sequences shared between different sets of nucleic acid barcode molecules coupled to the same bead may be included in the same or different order and may be separated by the same or different sequences. Alternatively or in addition, the first plurality of nucleic acid barcode molecules and the second plurality of nucleic acid barcode molecules coupled to a bead may include one or more different sequences. For example, each nucleic acid barcode molecule of a first plurality of nucleic acid barcode molecules coupled to a bead of a plurality of beads may comprise one or more of a flow cell adapter sequence, a barcode sequence, UMI sequence, capture sequence, and a sequencing primer or portion thereof, while each nucleic acid barcode molecule of a second plurality of nucleic acid barcode molecules coupled to the bead may comprise one or more of a flow cell adapter sequence (e.g., the same flow cell adapter sequence), a barcode sequence (e.g., the same barcode sequence), UMI sequence, capture sequence, and a sequencing primer or portion thereof (e.g., the same sequencing primer or portion thereof). Nucleic acid barcode molecules of the first plurality of nucleic acid barcode molecules may not include a UMI sequence or capture sequence. A bead comprising multiple different populations of nucleic acid barcode molecules, such as a first plurality of nucleic acid molecules and a second plurality of nucleic acid molecules (e.g., as described above), may be referred to as a "multi-functional bead."

A cell, cell bead, or cell nucleus comprising template nucleic acid fragments (e.g., template nucleic acid fragments and additional template nucleic acid fragments deriving from DNA or RNA molecules included within the cell, cell bead, or cell nucleus) may be co-partitioned with one or more beads (e.g., as described herein). For example, a cell, cell bead, or cell nucleus may be co-partitioned with a first bead (e.g., first gel bead) configured to interact with a first set of template nucleic acid fragments (e.g., template nucleic acid fragments deriving from DNA molecules, such as tagmented fragments) and a second bead (e.g., second gel bead) configured to interact with a second set of template nucleic acid fragments (e.g., additional template nucleic acid fragments deriving from RNA molecules). The first bead may comprise a first nucleic acid molecule comprising a flow cell adapter sequence, a barcode sequence, and a sequencing primer or portion thereof, which sequencing primer or portion thereof may be configured to interact with (e.g., anneal or hybridize to) a complementary sequence included in template nucleic acid fragments deriving from DNA molecules of the cell, cell bead, or cell nucleus, or derivatives thereof. The second bead may comprise a second nucleic acid molecule comprising the flow cell adapter sequence, the barcode sequence, the sequencing primer or a portion thereof, a UMI sequence, and a capture sequence, which capture sequence may be configured to interact with (e.g., anneal or hybridize to) a sequence of template nucleic acid fragments deriving from RNA molecules of the cell, cell bead, or cell nucleus, or derivatives thereof. In some cases, the capture sequence may be configured to interact with a sequence of a cDNA molecule generated upon reverse transcription of an RNA fragment. The first and second beads may be linked together (e.g., covalently or non-covalently). The first and second beads may each comprise a plurality of nucleic acid molecules. For example, the first bead may comprise a plurality of first nucleic acid molecules and the second bead may comprise a plurality of second nucleic acid molecules, where each first nucleic acid molecule of the plurality of first nucleic acid molecules comprises a first shared sequence and each second nucleic acid molecule of the plurality of second nucleic acid molecules comprises a second shared sequence. The first shared sequence and the second shared sequence may be the same or different. The first shared sequence and the second shared sequence may comprise one or more shared components, such as a shared barcode sequence or sequencing primer or portion thereof.

Alternatively, a cell, cell bead, or cell nucleus comprising template nucleic acid fragments (e.g., template nucleic acid fragments or additional template nucleic acid fragments deriving from DNA or RNA molecules included within the cell, cell bead, or cell nucleus) may be co-partitioned with a single bead (e.g., gel bead). For example, a cell, cell bead, or cell nucleus may be co-partitioned with a bead comprising (i) a first plurality of nucleic acid barcode molecules configured to interact with a first set of template nucleic acid fragments (e.g., template nucleic acid fragments deriving from DNA molecules, such as tagmented fragments), or derivatives thereof, and (ii) a second plurality of nucleic acid barcode molecules configured to interact with a second set of template nucleic acid fragments (e.g., additional template nucleic acid fragments deriving from RNA molecules), or derivatives thereof (such as cDNA generated from an RNA fragment). A nucleic acid barcode molecule of the first plurality of nucleic acid barcode molecules may comprise a flow cell adapter sequence, a barcode sequence, and a sequencing primer or portion thereof, which sequencing primer or portion thereof may be configured to interact with (e.g., anneal or hybridize to) a complementary sequence included in template nucleic acid fragments deriving from DNA molecules of the cell, cell bead, or cell nucleus, or derivatives thereof. A nucleic acid barcode molecule of the second plurality of nucleic acid barcode molecules may comprise the flow cell adapter sequence, the barcode sequence, the sequencing primer or a portion thereof, a UMI sequence, and a capture sequence, which capture sequence may be configured to interact with (e.g., anneal or hybridize to) a sequence of template nucleic acid fragments deriving from RNA molecules of the cell, cell bead, or cell nucleus, or derivatives thereof, such as cDNA generated from an RNA fragment. The first plurality of nucleic acid barcode molecules may comprise approximately the same number of nucleic acid barcode molecules as the second plurality of nucleic acid barcode molecules. Alternatively, the first plurality of nucleic acid barcode molecules may comprise a greater number of nucleic acid barcode molecules than the second plurality of nucleic acid barcode molecules, or vice versa. The distribution of nucleic acid barcode molecules on a bead may be controlled by, for example, sequence control, concentration control, and or blocking methods during assembly of the nucleic acid barcode molecules on the bead. Details of such processes are provided in, for example, PCT/US2018/061391, filed Nov. 15, 2018, and U.S. Pat. Pub. 20190249226, each of which are incorporated by reference in their entireties.

Figures 24A, 24B:
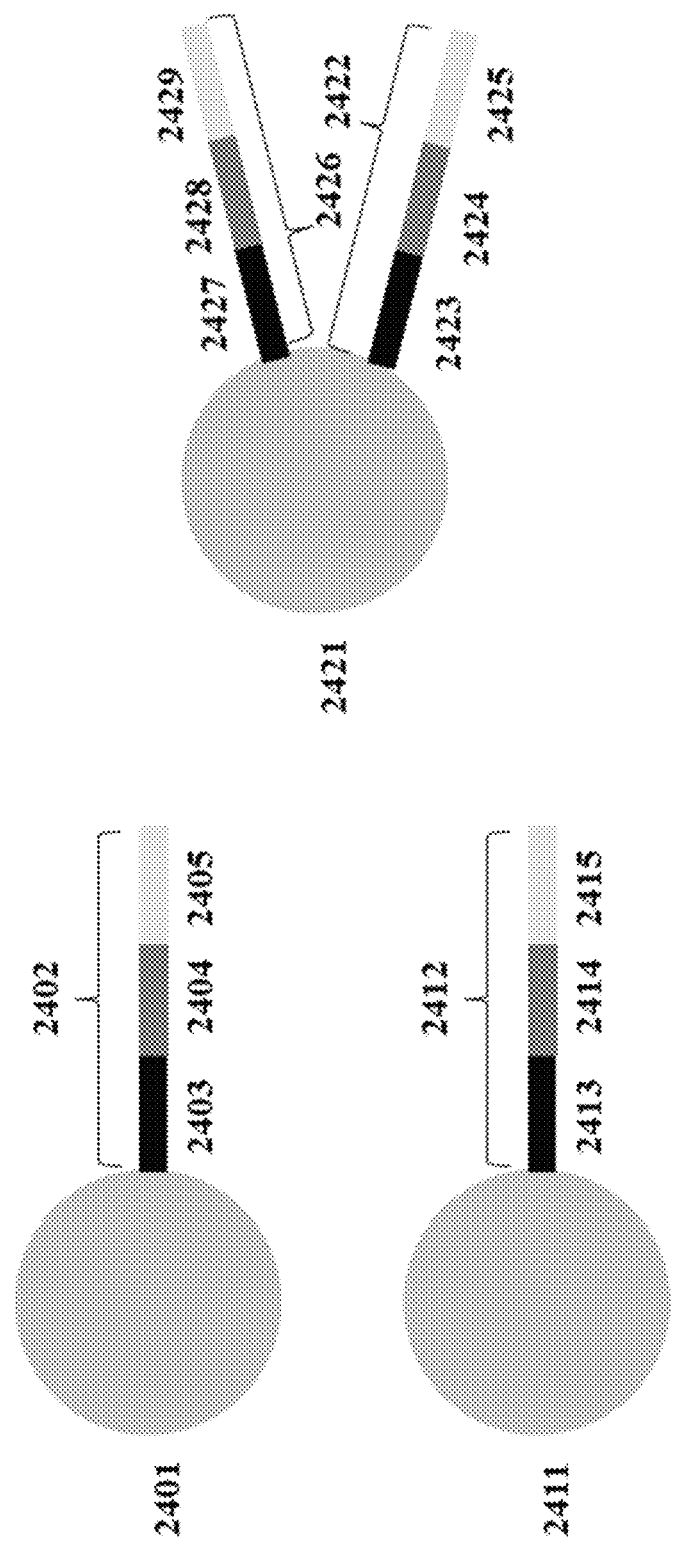
FIGS. 24A and 24B show beads for use according to the methods of the present disclosure.

FIGS. 24A and 24B show examples of beads for use according to the method provided herein. FIG. 24A shows a first bead 2401 and a second bead 2411 that may be co-partitioned with a cell, cell bead, or cell nucleus into a partition of a plurality of partitions (e.g., droplets or wells). First bead 2401 may comprise nucleic acid molecule 2402. Nucleic acid molecule 2402 may comprise sequences 2403, 2404, and 2405. Sequence 2403 may be, for example, a flow cell adapter sequence (e.g., a P5 or P7 sequence). Sequence 2404 may be, for example, a barcode sequence. Sequence 2405 may be, for example, a sequencing primer sequence or portion thereof (e.g., an R1 or R2 primer sequence, or portion thereof). Nucleic acid molecule 2402 may also include additional sequences, such as a UMI sequence. First bead 2401 may comprise a plurality of nucleic acid molecules 2402. Second bead 2411 may comprise nucleic acid molecule 2412. Nucleic acid molecule 2412 may comprise sequences 2413, 2414, and 2415. Sequence 2413 may be, for example, a flow cell adapter sequence (e.g., a P5 or P7 sequence). Sequence 2414 may be, for example, a barcode sequence. Sequence 2415 may be, for example, a sequencing primer sequence or portion thereof (e.g., an R1 or R2 primer sequence, or portion thereof). Nucleic acid molecule 2412 may also include additional sequences, such as a UMI sequence and a capture sequence. Second bead 2401 may comprise a plurality of nucleic acid molecules 2412.

FIG. 24B shows a bead 2421 (e.g., a multifunctional bead having two or more species of nucleic acid barcode molecules attached or coupled thereto) that may be co-partitioned with a cell, cell bead, or cell nucleus into a partition of a plurality of partitions (e.g., droplets or wells). Bead 2421 may comprise nucleic acid molecule 2422 and nucleic acid molecule 2426. Nucleic acid molecule 2422 may comprise sequences 2423, 2424, and 2425. Sequence 2423 may be, for example, a flow cell adapter sequence (e.g., a P5 or P7 sequence). Sequence 2424 may be, for example, a barcode sequence. Sequence 2425 may be, for example, a sequencing primer or portion thereof (e.g., an R1 or R2 primer sequence, or portion thereof, such as a Nextera R1 sequence or portion thereof). In some instances, sequence 2425 may also be, for example, a sequence configured to hybridize to a splint oligonucleotide as described elsewhere herein. Nucleic acid molecule 2426 may comprise sequences 2427, 2428, and 2429. Sequence 2427 may be, for example, a flow cell adapter sequence (e.g., a P5 or P7 sequence). Sequence 2428 may be, for example, a barcode sequence (e.g., the same barcode sequence as sequence 2424). Sequence 2429 may be, for example, a sequencing primer or portion thereof (e.g., an R1 or R2 primer sequence, or portion thereof). Sequence 2427 may be, for example, a sequencing primer or portion thereof (e.g., an R1 or R2 primer sequence, or portion thereof, such as a TruSeq R1 sequence, or portion thereof). Sequence 2428 may be, for example, a barcode sequence (e.g., the same barcode sequence as 2424). Sequence 2429 may be, for example, a capture sequence (e.g., a poly-T sequence), such as a capture sequence that is configured to hybridize with a target nucleic acid molecule (e.g., mRNA molecule). Sequence 2429 may be, for example, a template switching oligonucleotide (TSO) sequence configured to facilitate a template switching reaction with a target nucleic acid molecule (e.g., mRNA molecule). Sequence 2423 and sequence 2427 may be the same. Alternatively, sequence 2423 and sequence 2427 may be different. Sequence 2424 and sequence 2428 may be the same. Alternatively, sequence 2424 and sequence 2428 may be different. Sequence 2425 and sequence 2429 may be the same. Alternatively, sequence 2425 and sequence 2429 may be different. Nucleic acid molecules 2422 and 2426 may also include additional sequences, such as a UMI sequence and a capture sequence. Bead 2421 may comprise a plurality of nucleic acid molecules 2422 and a plurality of nucleic acid molecules 2426.

Within a partition (e.g., as described herein), an RNA fragment (e.g., a molecule comprising a sequence of an RNA molecule of a cell, cell bead, or cell nucleus that is hybridized to a primer molecule) may be processed to provide a barcoded molecule. The RNA fragment may be reverse transcribed to generate a complementary cDNA strand, which cDNA strand may be barcoded. In some cases, template switching can be used to increase the length of a cDNA (e.g., via incorporation of one or more sequences, such as one or more barcode or unique molecular identifier sequences). In one example of template switching, cDNA can be generated from reverse transcription of a template (e.g., an mRNA molecule) where a reverse transcriptase with terminal transferase activity can add additional nucleotides, e.g., polyC, to the cDNA that are not encoded by the template, such, as at an end of the cDNA. Template switch oligonucleotides (e.g., switch oligos) can include sequences complementary to the additional nucleotides, e.g. polyG (such as poly-riboG). The additional nucleotides (e.g., poly-C) on the cDNA can hybridize to the sequences complementary to the additional nucleotides (e.g., polyG) on the template switch oligonucleotide, whereby the template switch oligonucleotide can be used by the reverse transcriptase as template to further extend the cDNA. Template switch oligonucleotides may comprise deoxyribonucleic acids, ribonucleic acids, modified nucleic acids including locked nucleic acids (INA), or any combination thereof. A template switch oligonucleotide may comprise one or more sequences including, for example, one or more sequences selected from the group consisting of a sequencing primer, a barcode sequence, a unique molecular identifier sequence, and a homopolymer sequence (e.g., a polyG sequence), or a complement of any of the preceding sequence.

In some cases, the length of a template switch oligonucleotide may be 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 705, 206, 707, 208, 709, 210, 711, 212, 213, 214, 215, 216, 217, 218, 219, 220, 221, 222, 223, 224, 225, 226, 227, 228, 229, 230, 231, 232, 233, 234, 235, 236, 237, 2, 38, 239, 240, 241, 242, 243, 244, 245, 246, 247, 248, 249, 250 nucleotides or longer.

In some cases, an adapter and/or barcode sequence may be added to an RNA molecule via a method other than template switching. For example, one or more sequences may be ligated to an end of an RNA molecule. Similarly, one or more sequences may be ligated to an end of a cDNA molecule generated via reverse transcription of an RNA molecule.

In an example, a cell, cell bead, or cell nucleus comprising chromatin and one or more RNA molecules is provided. The chromatin in the cell, cell bead, or cell nucleus may be processed to provide a first template nucleic acid fragment derived from the chromatin (e.g., a tagmented fragment, as described herein). The chromatin may be processed in bulk solution. An RNA molecule may be processed to provide a second template nucleic acid fragment derived from the RNA molecule (e.g., as described herein). The RNA molecule may be processed within a partition. The configuration of the first template nucleic acid fragment may be at least partially dependent on the structure of the transposase-nucleic acid complex used to generate the first template nucleic acid fragment. For example, a transposase-nucleic acid complex such as that shown in FIG. 9 may be used to prepare the first template nucleic acid fragment. The first template nucleic acid fragment may be at least partially double-stranded. The first template nucleic acid fragment may comprise a double-stranded region comprising sequences of chromatin of the cell, cell bead, or cell nucleus. A first end of a first strand of the double-stranded region may be linked to a first transposon end sequence (e.g., mosaic end sequence), which first transposon end sequence may be linked to a first sequencing primer or portion thereof. A first end of the second strand of the double-stranded region, which end is opposite the first end of the first strand, may be linked to a second transposon end sequence (e.g., mosaic end sequence), which second transposon end sequence may be linked to a second sequencing primer or portion thereof. The second transposon end sequence may be the same as or different from the first transposon end sequence. The first sequencing primer or portion thereof may be the same as or different from the second sequencing primer or portion thereof. In some cases, the first sequencing primer or portion thereof may be an R1 sequence or portion thereof, and the second sequencing primer or portion thereof may be an R2 sequence or portion thereof. The first transposon end sequence may be hybridized to a first complementary sequence (e.g., mosaic end reverse complement sequence), which first complementary sequence may not be linked to a second end of the second strand of the double-stranded region of the first template nucleic acid fragment. Similarly, the second transposon end sequence may be hybridized to a second complementary sequence (e.g., mosaic end reverse complement sequence), which second complementary sequence may not be linked to a second end of the first strand of the double-stranded region of the first template nucleic acid fragment. In other words, the first template nucleic acid fragment may comprise one or more gaps. In some cases, the one or more gaps may be approximately 9 bp in length each. The second template nucleic acid fragment (e.g., an additional template nucleic acid fragment) may comprise a sequence of an RNA molecule of the cell, cell bead, or cell nucleus and a sequence hybridized to a primer molecule (e.g., a capture nucleic acid molecule). For example, the second template nucleic acid fragment may comprise a sequence of an RNA molecule of the cell, cell bead, or cell nucleus and a polyA sequence hybridized to a polyT sequence of a primer molecule. The primer molecule may also comprise an additional primer sequence.

The cell, cell bead, or cell nucleus comprising the first template nucleic acid fragment (e.g., tagmented fragment) may be co-partitioned with one or more reagents into a partition of a plurality of partitions (e.g., as described herein). The partition may be, for example, a droplet or well. The partition may comprise one or more beads (e.g., as described herein). A bead of the one or more beads may comprise a first plurality of nucleic acid barcode molecules. A nucleic acid barcode molecule of the first plurality of nucleic acid barcode molecules may comprise one or more of a flow cell adapter sequence (e.g., P5 sequence), a barcode sequence, a sequencing primer or portion thereof (e.g., R1 sequence or portion thereof, or a complement thereof), and a sequence configured to hybridize to a splint oligonucleotide as described elsewhere herein. The sequencing primer or portion thereof may be complementary to a sequence of the first template nucleic acid fragment. A bead of the one or more beads may also comprise a second plurality of nucleic acid barcode molecules. A nucleic acid barcode molecule of the second plurality of nucleic acid barcode molecules may comprise one or more of a flow cell adapter sequence (e.g., P5 sequence), a barcode sequence, a sequencing primer or portion thereof (e.g., R1 sequence or portion thereof, or a complement thereof), and a sequence configured to hybridize to a splint oligonucleotide as described elsewhere herein. For example, a nucleic acid barcode molecule of the first plurality of nucleic acid barcode molecules may comprise one or more of a flow cell adapter sequence (e.g., P5 sequence), a barcode sequence, and a sequence configured to hybridize to a splint oligonucleotide as described elsewhere herein. A nucleic acid barcode molecule of the second plurality of nucleic acid barcode molecules may comprise a sequencing primer or portion thereof (e.g., R1 sequence or portion thereof, or a complement thereof), a barcode sequence, and a capture sequence (e.g., a poly T sequence) configured to hybridize to a nucleic acid molecule (e.g., RNA molecule). In some cases, the first plurality of nucleic acid barcode molecules and the second plurality of nucleic acid barcode molecules may be same.

Within the partition, the RNA molecule may be processed to provide the second template nucleic acid fragment (e.g., as described herein).

Within the partition, the cell, cell bead, or cell nucleus may be lysed or permeabilized to provide access to the first and/or second template nucleic acid fragments therein (e.g., as described herein). The second template nucleic acid fragment may be generated after the cell, cell bead, or cell nucleus is lysed or permeabilized.

The first and second template nucleic acid fragments may undergo processing within the partition. Within the partition, the gaps in the first template nucleic acid molecule may be filled via a gap filling extension process (e.g., using a DNA polymerase or reverse transcriptase). The resultant double-stranded nucleic acid molecule may be denatured to provide a single strand comprising a chromatin sequence flanked by transposon end sequences and/or sequences complementary to transposon end sequences. Each transposon end sequence and/or sequence complementary to transposon end sequence may be linked to a sequencing primer or portion thereof, or a complement thereof (e.g., an R1 or R2 sequence or a portion thereof, or a complement thereof). A nucleic acid barcode molecule of the first plurality of nucleic acid barcode molecules may hybridize to a sequencing primer or portion thereof, or a complement thereof, of the single strand. A primer extension reaction may then be used to generate a complement of the single strand (e.g., using a DNA polymerase or reverse transcriptase). Such a process may amount to a linear amplification process. This process incorporates the barcode sequence of the nucleic acid barcode molecule of the first plurality of nucleic acid barcode molecules, or a complement thereof. The resultant double-stranded molecule may be denatured to provide a single strand comprising the flow cell adapter sequence, or complement thereof, of the nucleic acid barcode molecule of the first plurality of nucleic acid barcode molecules; barcode sequence, or complement thereof, of the nucleic acid barcode molecule of the first plurality of nucleic acid barcode molecules; sequencing primer or portion thereof, or complement thereof, of the nucleic acid barcode molecule of the first plurality of nucleic acid barcode molecules; transposon end sequences, and/or complements thereof; second sequencing primer or portion thereof, or complement thereof. An additional amplification process may or may not be performed within a partition. For example, exponential amplification may or may not be performed within a partition.

Within the partition, the second template nucleic acid fragment derived from the RNA molecule of the cell, cell bead, or cell nucleus may be reverse transcribed (e.g., using a reverse transcriptase) to provide a cDNA strand. The reverse transcription process may append a sequence to an end of a strand of the resultant double-stranded nucleic acid molecule comprising the RNA strand and the cDNA strand, such as a polyC sequence. A template switching oligonucleotide may comprise a sequence (e.g., a polyG sequence) that may hybridize to at least a portion of the double-stranded nucleic acid molecule (e.g., to the appended polyC sequence) and be used to further extend the strand of the double-stranded nucleic acid molecule to provide an extended double-stranded nucleic acid molecule. Such a sequence may comprise ribobases. The template switching oligonucleotide may comprise a UMI sequence, or complement thereof, and a sequencing primer or portion thereof, or complement thereof. The extended double-stranded nucleic acid molecule comprising the template switching oligonucleotide and a complement thereof, and the prior double-stranded nucleic acid molecule may be denatured to provide a single strand comprising a sequencing primer or portion thereof, or complement thereof, of the nucleic acid barcode molecule of the second plurality of nucleic acid barcode molecules; the UMI sequence, or complement thereof; the poly(C) or poly(G) sequence; the sequence corresponding to the RNA molecule of the cell, cell bead, or cell nucleus, or complement thereof; and sequences of the capture nucleic acid molecule, or complements thereof. A nucleic acid barcode molecule of the second plurality of nucleic acid barcode molecules may hybridize to a sequencing primer or portion thereof, or a complement thereof, of the single strand. A primer extension reaction may then be used to generate a complement of the single strand (e.g., using a DNA polymerase). Such a process may amount to a linear amplification process. This process incorporates the barcode sequence of the nucleic acid barcode molecule of the second plurality of nucleic acid barcode molecules, or a complement thereof. The resultant double-stranded molecule may be denatured to provide a single strand comprising a flow cell adapter sequence, or complement thereof, of the nucleic acid barcode molecule of the second plurality of nucleic acid barcode molecules; a barcode sequence, or complement thereof, of the nucleic acid barcode molecule of the second plurality of nucleic acid barcode molecules; a sequencing primer or portion thereof, or complement thereof, of the nucleic acid barcode molecule of the second plurality of nucleic acid barcode molecules; the UMI sequence, or complement thereof; the poly(C) or poly(G) sequence; the sequence corresponding to the RNA molecule of the cell, cell bead, or cell nucleus, or complement thereof; and sequences of the capture nucleic acid molecule, or complements thereof. An additional amplification process may or may not be performed within a partition. For example, exponential amplification may or may not be performed within a partition.

The linear amplification products corresponding to the chromatin and the RNA molecule of the cell, cell bead, or cell nucleus included within the partition of the plurality of partitions may be recovered from the partition. For example, the contents of the plurality of partitions may be pooled to provide the linear amplification products in a bulk solution. The linear amplification product corresponding to the chromatin may then be subjected to conditions sufficient to undergo one or more nucleic acid amplification reactions (e.g., PCR) to generate one or more amplification products corresponding to the chromatin. A nucleic acid amplification process may incorporate one or more additional sequences, such as one or more additional flow cell adapter sequences. The linear amplification product corresponding to the RNA molecule may be subjected to fragmentation, end repair, and dA tailing processes. An additional primer sequence (e.g., a sequencing primer or portion thereof, such as an R2 sequence) may then be ligated to the resultant molecule. A nucleic acid amplification reaction (e.g., PCR) may then be performed to generate one or more amplification products corresponding to the RNA molecule. A nucleic acid amplification process may incorporate one or more additional sequences, such as one or more additional flow cell adapter sequences (see, for example, FIG. 12).

In an RNA workflow, in-partition template switching may attach a sequencing primer (e.g., a TruSeq R1 or R2 sequence) to the 3' or 5' end of an RNA transcript. A bead (e.g., gel bead) carrying the sequencing primer, or portion thereof (e.g., partial TruSeq R1 or R2 sequence) may be also used for priming in a DNA (e.g., chromatin) workflow. This may allow for differential amplification of DNA (e.g., ATAC) and RNA libraries after removing materials from partitions (e.g., breaking emulsions) and sample splitting. Another advantage of this method is that the same enzyme (e.g. DNA polymerase or reverse transcriptase) may be used to barcode nucleic acid fragments derived from both DNA (e.g., chromatin) and RNA.

Figure 12:
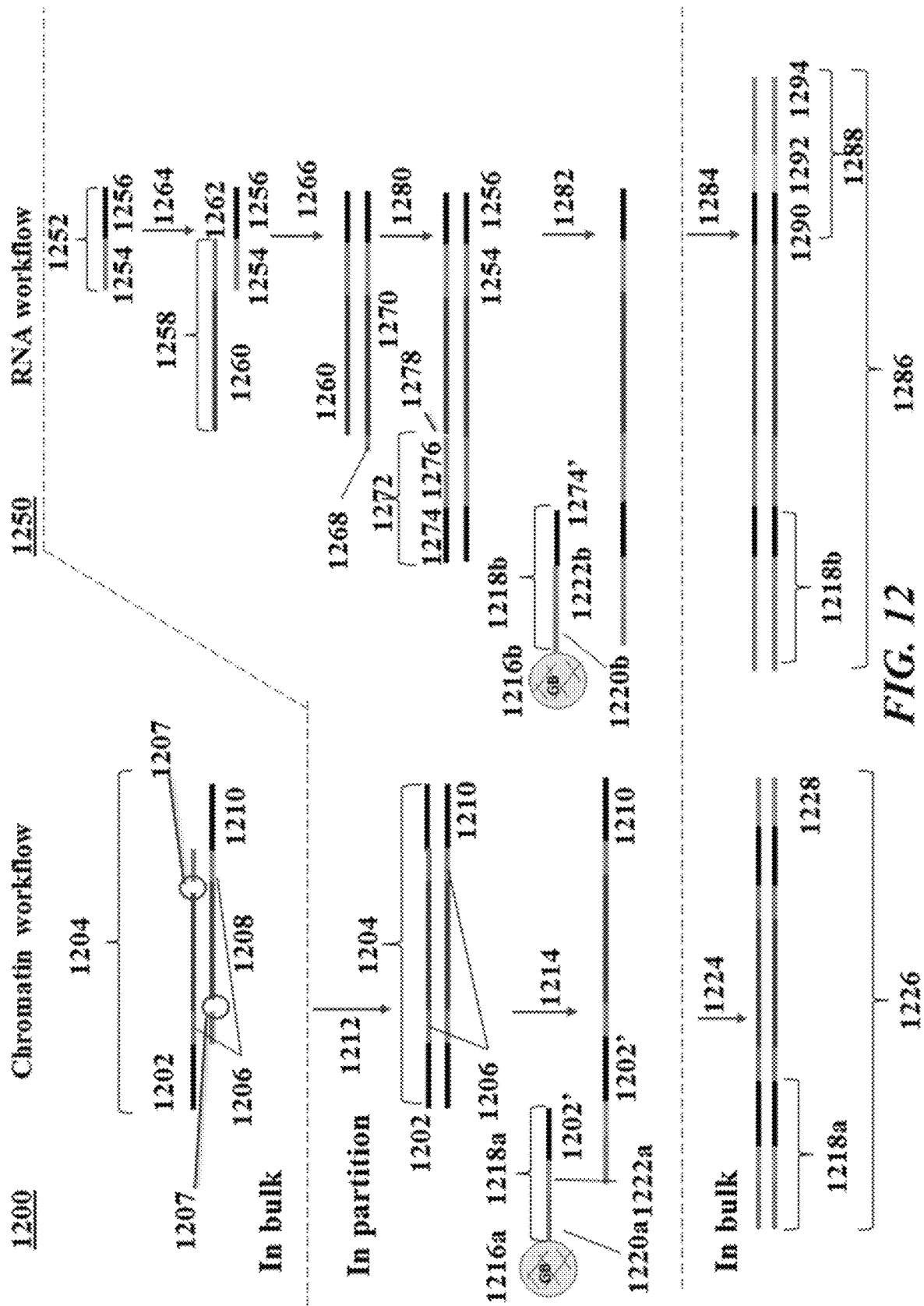
FIG. 12 illustrates a scheme for tandem ATAC ligation and RNA template switching.

FIG. 12 shows an example schematic corresponding to the preceding example. Panel 1200 shows a workflow corresponding to processing of chromatin from a cell, cell bead, or cell nucleus, and panel 1250 shows a workflow corresponding to processing of an mRNA molecule from the cell, cell bead, or cell nucleus. In the figure, two distinct beads (e.g., gel beads) are shown. However, the same bead (e.g., a single gel bead that may be a multifunctional bead) may be used in each workflow.

As shown in panel 1200, in bulk solution, chromatin included within a cell, cell bead, or cell nucleus is processed (e.g., as described herein) to provide a template nucleic acid fragment (e.g., tagmented fragment) 1204 comprising insert sequence 1208 (e.g., region of open chromatin) and a complement thereof, transposon end sequences 1206 and complements thereof, sequencing primer or portion thereof 1202 (e.g., an R1 sequence), sequencing primer or portion thereof 1210 (e.g., an R2 sequence), and gaps 1207. Template nucleic acid fragment 1204 may then be partitioned within a partition (e.g., a droplet or well, as described herein). Within the partition, the cell, cell bead, or cell nucleus comprising template nucleic acid fragment 1204 may be lysed, permeabilized, or otherwise processed to provide access to template nucleic acid fragment 1204 (and one or more RNA molecules) therein. Gaps 1207 may be filled 1212 via a gap filling extension process (e.g., using a DNA polymerase). The partition may include a bead (e.g., gel bead) 1216a coupled to a nucleic acid barcode molecule 1218a. Nucleic acid barcode molecule 1218a may comprise a flow cell adapter sequence 1220a (e.g., a P5 sequence), a barcode sequence 1222a, and a sequencing primer or portion thereof or complement thereof 1202'. Sequence 1202' may hybridize to sequence 1202 of template nucleic acid fragment 1204, or its complement, and undergo primer extension 1214 to yield a strand comprising sequences 1220a, 1222a, 1202', 1210, and insert sequence 1208 or a complement thereof. The contents of the partition may then be recovered in bulk solution (e.g., a droplet may be broken) to provide the strand in bulk solution. This strand may undergo amplification (e.g., PCR) 1224 to provide a double-stranded amplification product 1226 that includes sequences of the nucleic acid barcode molecule 1218a, the original chromatin molecule, and, optionally, an additional sequence 1228 that may be a flow cell adapter sequence (e.g., a P7 sequence).

In parallel to the chromatin workflow of panel 1200, an RNA molecule deriving from the same cell, cell bead, or cell nucleus may be processed. As shown in panel 1250, RNA molecule 1258 comprising RNA sequence 1260 and polyA sequence 1262 may be contacted 1264 with primer molecule 1252 comprising polyT sequence 1254 and additional primer sequence 1256. RNA molecule 1258 may then be reverse transcribed 1266 off of polyT sequence 1254 using a reverse transcriptase with terminal transferase activity, which reverse transcriptase may append sequence 1268 to the resultant cDNA molecule comprising cDNA sequence 1270. Sequence 1268 may be a polyC sequence. A template switch oligonucleotide 1272 comprising sequencing primer or portion thereof or complement thereof 1274, unique molecule identifier sequence or complement thereof 1276, and capture sequence (e.g., polyG sequence) 1278 may then hybridize 1280 to the RNA-cDNA molecule and template switching may take place. The partition may include a bead (e.g., gel bead) 1216b coupled to a nucleic acid barcode molecule 1218b. Nucleic acid barcode molecule 1218b may comprise a flow cell adapter sequence 1220b (e.g., a P5 sequence), a barcode sequence 1222b, and a sequencing primer or portion thereof or complement thereof 1274'. Bead 1216b may be the same as bead 1216a such that partition comprises a single bead (e.g., 1218a and 1218b are attached to a single bead). In such a case, nucleic acid barcode molecule 1218b and nucleic acid barcode molecule 1218a may have the same sequences. Sequence 1274' may hybridize to sequence 1274 of the cDNA molecule, or its complement, and undergo primer extension 1282 to yield a strand comprising sequences 1220b, 1222b, 1274', 1276 or a complement thereof, 1268 or a complement thereof, and insert sequence 1270 or a complement thereof. The contents of the partition may then be recovered in bulk solution (e.g., a droplet may be broken) to provide the strand in bulk solution. This strand may undergo amplification (e.g., PCR) 1284 to provide a double-stranded amplification product 1286 that includes sequences of the nucleic acid barcode molecule 1218b, the original RNA molecule or cDNA corresponding thereto, and, optionally, an additional sequence 1288 that may comprise a sequencing primer or portion thereof (e.g., an R2 sequence) 1290, a sample index sequence 1292, and a flow cell adapter sequence (e.g., a P7 sequence) 1294.

Figure 13:
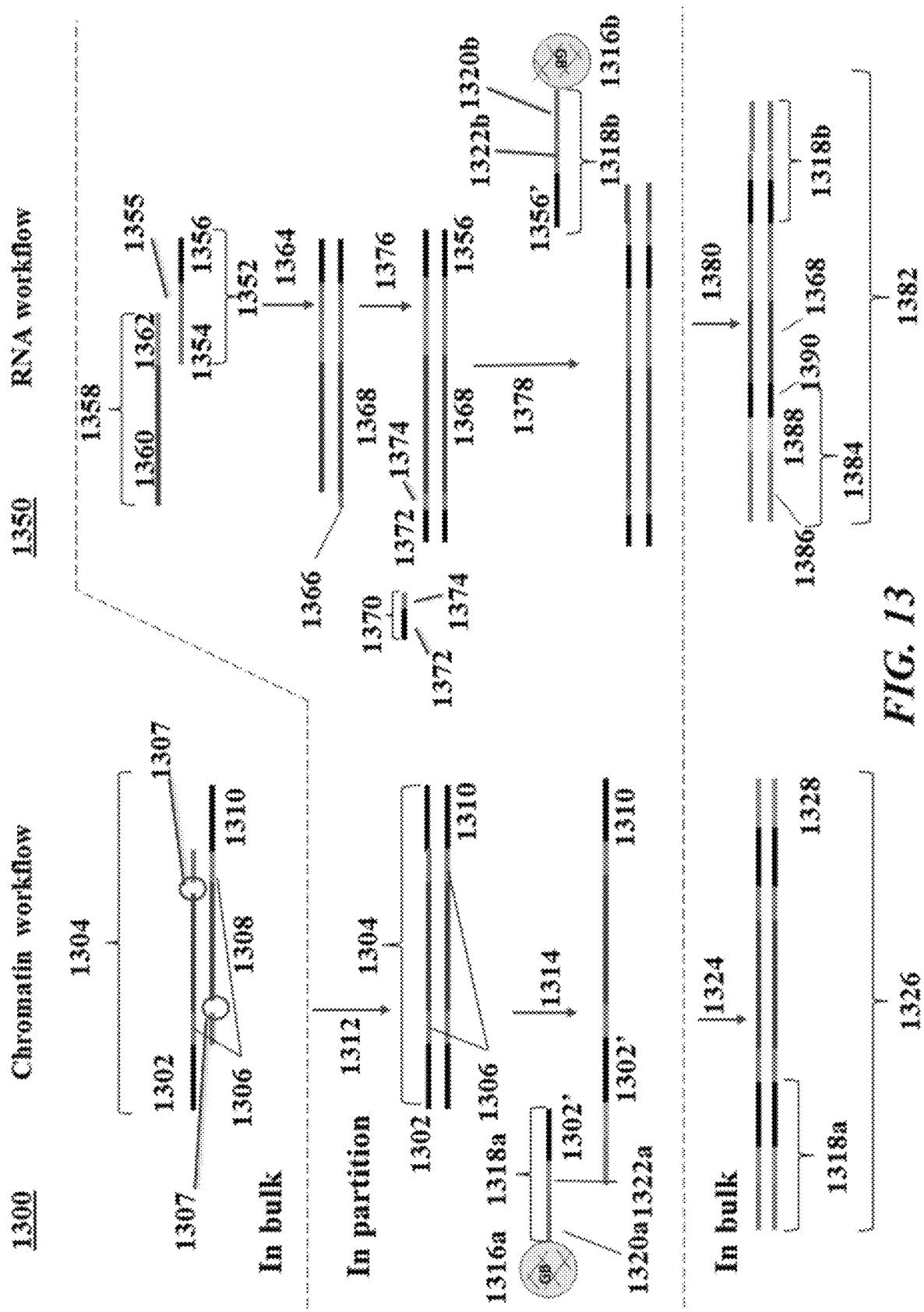
FIG. 13 illustrates an additional scheme for tandem ATAC ligation and RNA template switching.

FIG. 13 shows another example schematic corresponding to the preceding example. Panel 1300 shows a workflow corresponding to processing of chromatin from a cell, cell bead, or cell nucleus, and panel 1350 shows a workflow corresponding to processing of an mRNA molecule from the cell, cell bead, or cell nucleus. In the figure, two distinct beads (e.g., gel beads) are shown. However, the same bead (e.g., gel bead) may be used in each workflow.

As shown in panel 1300, in bulk solution, chromatin included within a cell, cell bead, or cell nucleus is processed (e.g., as described herein) to provide a template nucleic acid fragment (e.g., tagmented fragment) 1304 comprising insert sequence 1308 (e.g., region of open chromatin) and a complement thereof, transposon end sequences 1306 and complements thereof, sequencing primer or portion thereof 1302 (e.g., an R1 sequence), sequencing primer or portion thereof 1310 (e.g., an R2 sequence), and gaps 1307. Template nucleic acid fragment 1304 may then be partitioned within a partition (e.g., a droplet or well, as described herein). Within the partition, the cell, cell bead, or cell nucleus comprising template nucleic acid fragment 1304 may be lysed, permeabilized, or otherwise processed to provide access to template nucleic acid fragment 1304 (and one or more RNA molecules) therein. Gaps 1307 may be filled 1312 via a gap filling extension process (e.g., using a DNA polymerase). The partition may include a bead (e.g., gel bead) 1316a coupled to a nucleic acid barcode molecule 1318a. Nucleic acid barcode molecule 1318a may comprise a flow cell adapter sequence 1320a (e.g., a P5 sequence), a barcode sequence 1322a, and a sequencing primer or portion thereof or complement thereof 1302'. Sequence 1302' may hybridize to sequence 1302 of template nucleic acid fragment 1304, or its complement, and undergo primer extension 1314 to yield a strand comprising sequences 1320a, 1322a, 1302', 1310, and insert sequence 1308 or a complement thereof. The contents of the partition may then be recovered in bulk solution (e.g., a droplet may be broken) to provide the strand in bulk solution. This strand may undergo amplification (e.g., PCR) 1324 to provide a double-stranded amplification product 1326 that includes sequences of the nucleic acid barcode molecule 1318a, the original chromatin molecule, and, optionally, an additional sequence 1328 that may be a flow cell adapter sequence (e.g., a P7 sequence).

In parallel to the chromatin workflow of panel 1300, an RNA molecule deriving from the same cell, cell bead, or cell nucleus may be processed. As shown in panel 1350, RNA molecule 1358 comprising RNA sequence 1360 and polyA sequence 1362 may be contacted with primer molecule 1352 comprising polyT sequence 1354, UMI sequence 1355, and sequencing primer or portion thereof (e.g., R1 sequence) 1356. RNA molecule 1358 may be reverse transcribed 1364 off of polyT sequence 1354 using a reverse transcriptase with terminal transferase activity, which reverse transcriptase may append sequence 1366 (e.g., a polyC sequence) to the resultant cDNA molecule comprising cDNA sequence 1368. A template switch oligonucleotide 1370 comprising additional primer sequence 1372 and a homopolymer sequence 1374 (e.g., a polyG) sequence that is complementary to sequence 1366 may then hybridize 1376 to the cDNA molecule and template switching may take place. The partition may include a bead (e.g., gel bead) 1316b coupled to a nucleic acid barcode molecule 1318b.

Nucleic acid barcode molecule 1318b may comprise a flow cell adapter sequence 1320b (e.g., a P5 sequence), a barcode sequence 1322b, and a sequencing primer or portion thereof or complement thereof 1356'. Bead (e.g., gel bead) 1316b may be the same as bead (e.g., gel bead) 1316a such that partition comprises a single bead (i.e., 1318a and 1318b are attached to a single bead). In such a case, nucleic acid barcode molecule 1318b and nucleic acid barcode molecule 1318a may have the same sequences. Sequence 1356' may hybridize to sequence 1356 of the cDNA molecule, or its complement, and undergo primer extension 1378 to yield a strand comprising sequences 1320b, 1322b, 1356', 1355 or a complement thereof, 1366 or a complement thereof, and insert sequence 1368 or a complement thereof. The contents of the partition may then be recovered in bulk solution (e.g., a droplet may be broken) to provide the strand in bulk solution. This strand may undergo amplification (e.g., PCR) 1380 to provide a double-stranded amplification product 1382 that includes sequences of the nucleic acid barcode molecule 1318b, the original RNA molecule or cDNA corresponding thereto, and, optionally, an additional sequence 1384 that may comprise a sequencing primer or portion thereof (e.g., an R2 sequence) 1390, a sample index sequence 1388, and a flow cell adapter sequence (e.g., a P7 sequence) 1386.

In another example, a cell, cell bead, or cell nucleus comprising chromatin and one or more RNA molecules is provided. The chromatin in the cell, cell bead, or cell nucleus may be processed to provide a first template nucleic acid fragment derived from the chromatin (e.g., a tagmented fragment, as described herein). The chromatin may be processed in bulk solution. An RNA molecule may be processed to provide a second template nucleic acid fragment derived from the RNA molecule (e.g., as described herein). The RNA molecule may be processed within a partition. The configuration of the first template nucleic acid fragment may be at least partially dependent on the structure of the transposase-nucleic acid complex used to generate the first template nucleic acid fragment. For example, a transposase-nucleic acid complex such as that shown in FIG. 9 may be used to prepare the first template nucleic acid fragment. The first template nucleic acid fragment may be at least partially double-stranded. The first template nucleic acid fragment may comprise a double-stranded region comprising sequences of chromatin of the cell, cell bead, or cell nucleus. A first end of a first strand of the double-stranded region may be linked to a first transposon end sequence (e.g., mosaic end sequence), which first transposon end sequence may be linked to a first sequencing primer or portion thereof. A first end of the second strand of the double-stranded region, which end is opposite the first end of the first strand, may be linked to a second transposon end sequence (e.g., mosaic end sequence), which second transposon end sequence may be linked to a second sequencing primer or portion thereof. The second transposon end sequence may be the same as or different from the first transposon end sequence. The first sequencing primer or portion thereof may be the same as or different from the second sequencing primer or portion thereof. In some cases, the first sequencing primer or portion thereof may be an R1 sequence or portion thereof, and the second sequencing primer or portion thereof may be an R2 sequence or portion thereof. The first transposon end sequence may be hybridized to a first complementary sequence (e.g., mosaic end reverse complement sequence), which first complementary sequence may not be linked to a second end of the second strand of the double-stranded region of the first template nucleic acid fragment.

Similarly, the second transposon end sequence may be hybridized to a second complementary sequence (e.g., mosaic end reverse complement sequence), which second complementary sequence may not be linked to a second end of the first strand of the double-stranded region of the first template nucleic acid fragment. In other words, the first template nucleic acid fragment may comprise one or more gaps. In some cases, the one or more gaps may be approximately 9 bp in length each. For example, one or more gaps may be at least about 1, 2, 3, 4, 5, 6, 7, 8, 9, 10, or more bp in length. For example, one or more gaps may be at most about 10, 9, 8, 7, 6, 5, 4, 3, 2, or 1 bp in length. The second template nucleic acid fragment (e.g., an additional template nucleic acid fragment) may comprise a sequence of an RNA molecule of the cell, cell bead, or cell nucleus and a sequence hybridized to a primer molecule (e.g., a capture nucleic acid molecule). For example, the second template nucleic acid fragment may comprise a sequence of an RNA molecule of the cell, cell bead, or cell nucleus and a polyA sequence hybridized to a polyT sequence of a primer molecule. The primer molecule may also comprise an additional primer sequence.

The cell, cell bead, or cell nucleus comprising the first template nucleic acid fragment (e.g., tagmented fragment) may be co-partitioned with one or more reagents into a partition of a plurality of partitions (e.g., as described herein). The partition may be, for example, a droplet or well. The partition may comprise one or more beads (e.g., as described herein). A bead (e.g., gel bead) of the one or more beads may comprise a first plurality of nucleic acid barcode molecules. A nucleic acid barcode molecule of the first plurality of nucleic acid barcode molecules may comprise a flow cell adapter sequence (e.g., P5 sequence), a barcode sequence, and a sequencing primer or portion thereof (e.g., R1 sequence or portion thereof, or a complement thereof). The sequencing primer or portion thereof may be complementary to a sequence of the first template nucleic acid fragment. The flow cell adapter sequence and/or barcode sequence may be hybridized to their complementary sequences. A bead (e.g., gel bead) of the one or more beads may also comprise a second plurality of nucleic acid barcode molecules. A nucleic acid barcode molecule of the second plurality of nucleic acid barcode molecules may comprise a flow cell adapter sequence (e.g., P5 sequence), a barcode sequence, a sequencing primer or portion thereof (e.g., R1 sequence or portion thereof, or a complement thereof), a UMI sequence, and a capture sequence (e.g., a polyG sequence, a polydT sequence or target specific sequence). In some cases, the first plurality of nucleic acid barcode molecules and the second plurality of nucleic acid barcode molecules may be coupled to the same bead, and the partition may comprise a single bead.

Within the partition, the RNA molecule may be processed to provide the second template nucleic acid fragment (e.g., as described herein).

Within the partition, the cell, cell bead, or cell nucleus may be lysed or permeabilized to provide access to the first and/or second template nucleic acid fragments therein (e.g., as described herein). The second template nucleic acid fragment may be generated after the cell, cell bead, or cell nucleus is lysed or permeabilized.

The first and second template nucleic acid fragments may undergo processing within the partition. Within the partition, a sequencing primer or portion thereof of the first template nucleic acid fragment corresponding to the chromatin of the cell, cell bead, or cell nucleus may hybridize to a sequencing primer or portion thereof of the nucleic acid barcode molecule of the first plurality of nucleic acid barcode molecules. The sequencing primer or portion thereof of the nucleic acid barcode molecule may then be ligated (e.g., using a ligase) to a transposon end sequence of the first template nucleic acid fragment, or a complement thereof to provide a partially double-stranded nucleic acid molecule corresponding to the chromatin of the cell, cell bead, or cell nucleus.

Within the partition, the second template nucleic acid fragment derived from the RNA molecule of the cell, cell bead, or cell nucleus may be reverse transcribed (e.g., using a reverse transcriptase) to provide a cDNA strand. The reverse transcription process may append a sequence to an end of a strand of the resultant double-stranded nucleic acid molecule comprising the RNA strand and the cDNA strand, such as a polyC sequence. The capture sequence of the nucleic acid barcode molecule of the second plurality of nucleic acid barcode molecules may hybridize to the appended sequence (e.g., polyC sequence) of the double-stranded nucleic acid molecule and a template switching process may take place to provide an extended double-stranded nucleic acid molecule. Such a sequence may comprise ribobases. The sequence of the nucleic acid barcode molecule of the second plurality of nucleic acid barcode molecules may be considered a template switching oligonucleotide. Accordingly, barcoding and template switching may take place contemporaneously to provide a barcoded cDNA molecule. The cDNA strand of the barcoded cDNA molecule (e.g., a molecule comprising both a cDNA strand and an RNA strand) may comprise the polyC sequence, a sequence complementary to the sequence of the template switch oligonucleotide or a portion thereof (e.g., sequences complementary to the sequencing primer, barcode sequence, and UMI sequence of the template switch oligonucleotide), the cDNA sequence, the polyT sequence, and the additional primer sequence of the primer molecule. The RNA strand of the barcoded cDNA molecule may comprise the sequence of the template switch oligonucleotide, the mRNA sequence, and a sequence complementary to the additional primer sequence of the primer molecule.

The partially double-stranded molecule corresponding to the chromatin of the cell, cell bead, or cell nucleus and the barcoded cDNA molecule corresponding to the RNA molecule of the cell, cell bead, or cell nucleus included within the partition (e.g., droplet or well) of the plurality of partitions may be recovered from the partition. For example, the contents of the plurality of partitions may be pooled to provide these products in a bulk solution.

Outside of the partition, the gaps in the partially double-stranded nucleic acid molecule corresponding to the chromatin may be filled using via a gap filling extension process (e.g., using a DNA polymerase or reverse transcriptase). The gap filling extension process may not include strand displacement. The resultant gap-filled double-stranded nucleic acid molecule may be denatured to provide a single strand, which single strand may be subjected to conditions sufficient to perform one or more nucleic acid amplification reactions (e.g., PCR) to generate amplification products corresponding to the chromatin of the cell, cell bead, or cell nucleus. A nucleic acid amplification process may incorporate one or more additional sequences, such as one or more additional flow cell adapter sequences.

Outside of the partition, the barcoded cDNA molecule corresponding to the RNA molecule may be subjected to fragmentation, end repair, a dA tailing process, tagmentation, or a combination thereof. An additional primer sequence (e.g., a sequencing primer or portion thereof, such as an R2 sequence) may be ligated to the resultant molecule. Alternatively or in addition, a nucleic acid amplification reaction (e.g., PCR) may be performed to generate one or more amplification products corresponding to the RNA molecule or the cDNA molecule generated therefrom. A nucleic acid amplification process may incorporate one or more additional sequences, such as one or more additional flow cell adapter sequences.

Figure 14:
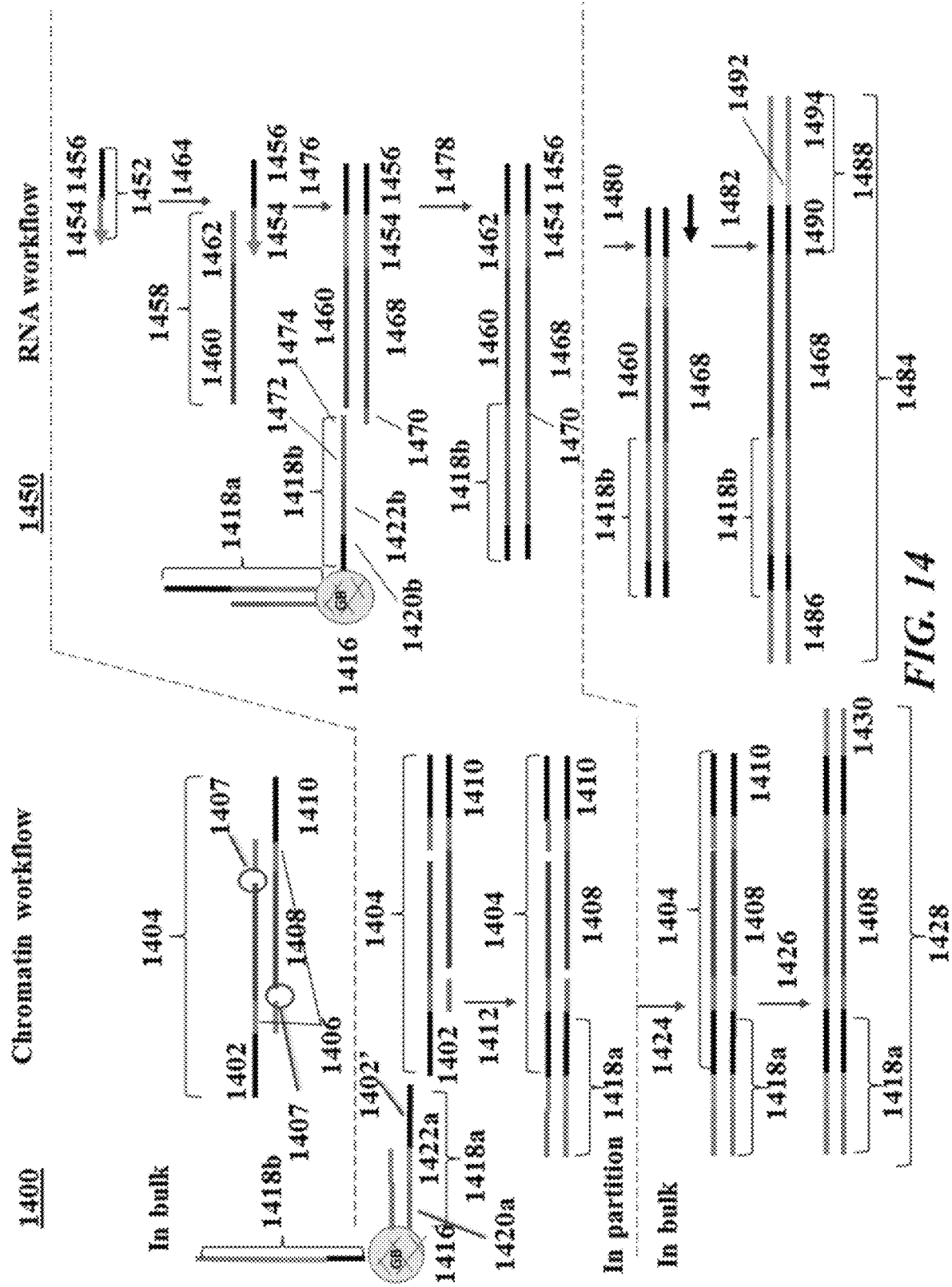
FIG. 14 illustrates an exemplary scheme for tandem ATAC ligation and RNA template switching.

FIG. 14 shows an example schematic corresponding to the preceding example. Panel 1400 shows a workflow corresponding to processing of chromatin from a cell, cell bead, or cell nucleus, and panel 1450 shows a workflow corresponding to processing of an mRNA molecule from the cell, cell bead, or cell nucleus.

As shown in panel 1400, in bulk solution, chromatin included within a cell, cell bead, or cell nucleus is processed (e.g., as described herein) to provide a template nucleic acid fragment (e.g., tagmented fragment) 1404 comprising insert sequence 1408 (e.g., region of open chromatin) and a complement thereof, transposon end sequences 1406 and complements thereof, sequencing primer or portion thereof 1402 (e.g., an R1 sequence), sequencing primer or portion thereof 1410 (e.g., an R2 sequence), and gaps 1407. Template nucleic acid fragment 1404 may then be partitioned within a partition (e.g., a droplet or well, as described herein). Within the partition, the cell, cell bead, or cell nucleus comprising template nucleic acid fragment 1404 may be lysed, permeabilized, or otherwise processed to provide access to template nucleic acid fragment 1404 (and one or more RNA molecules) therein. The partition may include a bead (e.g., gel bead) 1416 coupled to nucleic acid barcode molecules 1418a and 1418b. Nucleic acid barcode molecule 1418a may comprise a flow cell adapter sequence 1420a (e.g., a P5 sequence), a barcode sequence 1422a, and a sequencing primer or portion thereof or complement thereof 1402'. Sequences 1420a and 1422a may be hybridized to complementary sequences 1420' and 1422', respectively. Sequence 1402' may hybridize to sequence 1402 of template nucleic acid fragment 1404, or its complement, and sequence 1422' may be ligated 1412 to sequence 1402 of template nucleic acid fragment 1404. In some instances, template nucleic acid fragment 1404 may be phosphorylated using a suitable kinase enzyme (e.g., polynucleotide kinase (PNK), such as T4 PNK). In some instances, PNK and ATP may be added in bulk in the tagmentation (e.g., ATAC) reaction and/or prior to partitioning a cell, cell bead, or cell nucleus, or a plurality thereof. 15 U of PNK with 1 mM of ATP may be spiked into the tagmentation reaction. For example, less than 95 U of PNK may be spiked into the tagmentation reaction. The contents of the partition may then be recovered in bulk solution (e.g., a droplet may be broken) to provide the partially double-stranded nucleic acid molecule comprising nucleic acid barcode molecule 1418a attached to template nucleic acid fragment 1404 in bulk solution. In bulk solution, gaps 1407 may be filled 1424 via a gap filling extension process (e.g., using a DNA polymerase) to provide a double-stranded nucleic acid molecule. This molecule may undergo amplification (e.g., PCR) 1426 to provide a double-stranded amplification product 1428 that includes sequences of the nucleic acid barcode molecule 1418a, the original chromatin molecule, and, optionally, an additional sequence 1430 that may be a flow cell adapter sequence (e.g., a P7 sequence). Gaps may be filled in the partition prior to bulk processing.

In parallel to the chromatin workflow of panel 1400, an RNA molecule deriving from the same cell, cell bead, or cell nucleus may be processed. As shown in panel 1450, RNA molecule 1458 comprising RNA sequence 1460 and polyA sequence 1462 may be contacted 1464 with primer molecule 1452 comprising polyT sequence 1454 and additional primer sequence 1456. RNA molecule 1458 may then be reverse transcribed 1476 off of polyT sequence 1454 using a reverse transcriptase with terminal transferase activity, which reverse transcriptase may append sequence 1470 to the resultant cDNA molecule comprising cDNA sequence 1468. Sequence 1470 may be a polyC sequence. Bead (e.g., gel bead) 1416 (e.g., the same bead described in panel 1400) may be included within the partition and may be coupled to nucleic acid barcode molecule 1418b. Nucleic acid barcode molecule 1418b may comprise a flow cell adapter sequence 1420b (e.g., a P5 sequence), a barcode sequence 1422b, UMI sequence 1472, and a sequence 1474 complementary to sequence 1470 (e.g., a polyG sequence). In some instances, nucleic acid barcode molecule 1418b may comprise a sequencing primer sequence 1420b (e.g., an R1 sequence or partial R1 sequence), a barcode sequence 1422b, UMI sequence 1472, and a template switching sequence 1474 complementary to sequence 1470 (e.g., a polyG sequence). Nucleic acid barcode molecule 1418b may be used to perform template switching 1478, which process may also result in the generation of a barcoded cDNA molecule. The contents of the partition may then be recovered in bulk solution (e.g., a droplet may be broken) to provide the barcoded cDNA molecule in bulk solution. The barcoded cDNA molecule may undergo amplification (e.g., PCR) 1480 to provide a double-stranded amplification product 1484 that includes sequences of the nucleic acid barcode molecule 1418b, the original RNA molecule or cDNA corresponding thereto, a flow cell adapter sequence 1486, and an additional sequence 1488 that may comprise a sequencing primer or portion thereof (e.g., an R2 sequence) 1490, a sample index sequence 1492, and a flow cell adapter sequence (e.g., a P7 sequence) 1494. The barcoded cDNA molecule may also or alternatively undergo fragmentation, end repair, dA tailing, ligation of one or more adapter sequences, and/or nucleic acid amplification.

Figure 15:
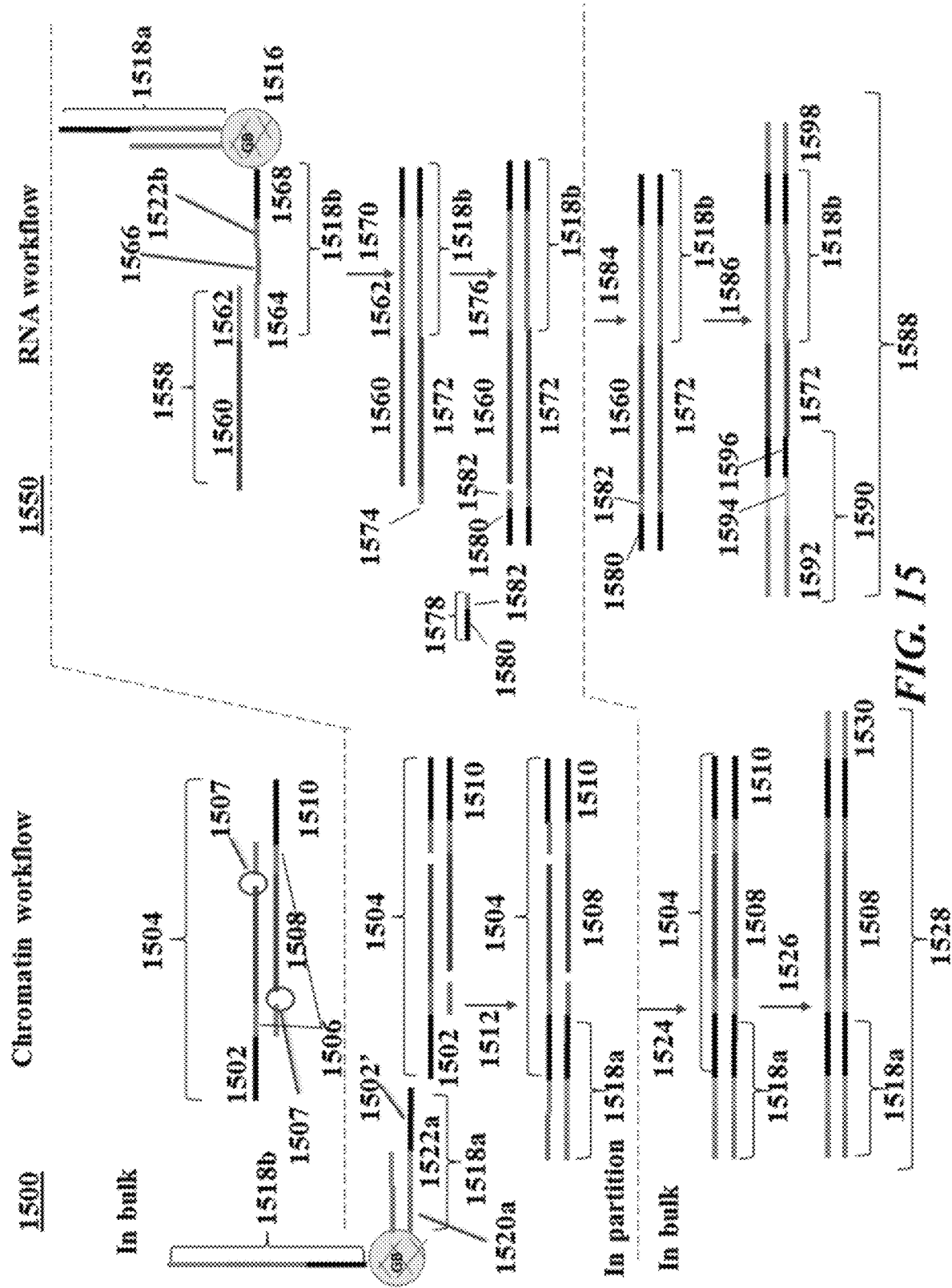
FIG. 15 illustrates an additional scheme for tandem ATAC ligation and RNA template switching.

FIG. 15 shows another example schematic corresponding to the preceding example. Panel 1500 shows a workflow corresponding to processing of chromatin from a cell, cell bead, or cell nucleus, and panel 1550 shows a workflow corresponding to processing of an mRNA molecule from the cell, cell bead, or cell nucleus.

As shown in panel 1500, in bulk solution, chromatin included within a cell, cell bead, or cell nucleus is processed (e.g., as described herein) to provide a template nucleic acid fragment (e.g., tagmented fragment) 1504 comprising insert sequence 1508 (e.g., region of open chromatin) and a complement thereof, transposon end sequences 1506 and complements thereof, sequencing primer or portion thereof 1502 (e.g., an R1 sequence), sequencing primer or portion thereof 1510 (e.g., an R2 sequence), and gaps 1507. Template nucleic acid fragment 1504 may then be partitioned within a partition (e.g., a droplet or well, as described herein). Within the partition, the cell, cell bead, or cell nucleus comprising template nucleic acid fragment 1504 may be lysed, permeabilized, or otherwise processed to provide access to template nucleic acid fragment 1504 (and one or more RNA molecules) therein. The partition may include a bead (e.g., gel bead) 1516 coupled to nucleic acid barcode molecules 1518a and 1518b. Nucleic acid barcode molecule 1518a may comprise a flow cell adapter sequence 1520a (e.g., a P5 sequence), a barcode sequence 1522a, and a sequencing primer or portion thereof or complement thereof 1502'. Sequences 1520a and 1522a may be hybridized to complementary sequences 1520' and 1522', respectively. Sequence 1502' may hybridize to sequence 1502 of template nucleic acid fragment 1504, or its complement, and sequence 1522' may be ligated 1512 to sequence 1502 of template nucleic acid fragment 1504. In some instances, template nucleic acid fragment 1504 may be phosphorylated using a suitable kinase enzyme (e.g., polynucleotide kinase (PNK), such as T4 PNK). PNK and ATP may be added in bulk in the tagmentation (e.g., ATAC) reaction and/or prior to partitioning a cell, cell bead, or cell nucleus, or plurality thereof. 15 U of PNK with 1 mM of ATP may be spiked into the tagmentation reaction. For example, less than 95 U of PNK may be spiked into the tagmentation reaction. The contents of the partition may then be recovered in bulk solution (e.g., a droplet may be broken) to provide the partially double-stranded nucleic acid molecule comprising nucleic acid barcode molecule 1518a attached to template nucleic acid fragment 1504 in bulk solution. In bulk solution, gaps 1507 may be filled 1524 via a gap filling extension process (e.g., using a DNA polymerase) to provide a double-stranded nucleic acid molecule. This molecule may undergo amplification (e.g., PCR) 1526 to provide a double-stranded amplification product 1528 that includes sequences of the nucleic acid barcode molecule 1518a, the original chromatin molecule, and, optionally, an additional sequence 1530 that may be a flow cell adapter sequence (e.g., a P7 sequence). Gaps may be filled in the partition prior to bulk processing.

In parallel to the chromatin workflow of panel 1500, an RNA molecule deriving from the same cell, cell bead, or cell nucleus may be processed. As shown in panel 1550, RNA molecule 1558 comprising RNA sequence 1560 and polyA sequence 1562 and bead (e.g., gel bead) 1516 may be provided within a partition. Bead (e.g., gel bead) 1516 (e.g., the same bead described in panel 1500) may be included within the partition and may be coupled to nucleic acid barcode molecule 1518b. Nucleic acid barcode molecule 1518b may comprise a flow cell adapter sequence 1568 (e.g., a P5 sequence), a barcode sequence 1522b (e.g., the same barcode sequence as barcode sequence 1522a), UMI sequence 1566, and a polyT sequence 1564 complementary to polyA sequence 1562. In some instances, nucleic acid barcode molecule 1518b may comprise a sequencing primer sequence 1568 (e.g., an R1 sequence or partial R1 sequence), a barcode sequence 1522b (e.g., the same barcode sequence as barcode sequence 1522a), UMI sequence 1566, and a polyT sequence 1564 complementary to polyA sequence 1562. PolyT sequence 1564 may hybridize to polyA sequence 1562 of RNA molecule 1558. RNA molecule 1558 may be reverse transcribed 1570 off of polyT sequence 1564 to provide an cDNA molecule comprising cDNA sequence 1572. The reverse transcription process may use a reverse transcriptase with terminal transferase activity, which reverse transcriptase may append sequence 1574 to the resultant cDNA molecule comprising cDNA sequence 1572. Sequence 1574 may be a polyC sequence. A template switch oligonucleotide 1578 comprising a primer sequence 1580 and a sequence complementary to sequence 1574 (e.g., a polyG sequence) may hybridize to the cDNA molecule and facilitate a template switching reaction onto template switch oligonucleotide 1578. The contents of the partition may then be recovered in bulk solution (e.g., a droplet may be broken) to provide the cDNA molecule in bulk solution. The cDNA molecule may undergo amplification (e.g., PCR) 1584. Additional amplification (e.g., PCR) 1586 may to performed to provide a double-stranded amplification product 1588 that includes sequences of the nucleic acid barcode molecule 1518b, the original RNA molecule or cDNA corresponding thereto, a flow cell adapter sequence 1598 (e.g., a P7 sequence), and an additional sequence 1590 that may comprise a sequencing primer or portion thereof (e.g., an R2 sequence) 1596, a sample index sequence 1594, and a flow cell adapter sequence (e.g., a P5 sequence) 1592. The barcoded cDNA molecule may also or alternatively undergo fragmentation, end repair, dA tailing, ligation of one or more adapter sequences, and/or nucleic acid amplification.

In another example, a cell, cell bead, or cell nucleus comprising chromatin and one or more RNA molecules is provided. The chromatin in the cell, cell bead, or cell nucleus may be processed to provide a first template nucleic acid fragment derived from the chromatin (e.g., a tagmented fragment, as described herein). The chromatin may be processed in bulk solution. An RNA molecule may be processed to provide a second template nucleic acid fragment derived from the RNA molecule (e.g., an additional nucleic acid fragment, as described herein). The RNA molecule may be processed within a partition. The second template nucleic acid fragment derived from the RNA molecule may be processed according to the preceding examples. The configuration of the first template nucleic acid fragment may be at least partially dependent on the structure of the transposase-nucleic acid complex used to generate the first template nucleic acid fragment. For example, a transposase-nucleic acid complex such as that shown in FIG. 9 may be used to prepare the first template nucleic acid fragment. Relative to the preceding examples, the polarities of the transposase-nucleic acid may be reversed such that sequencing primers (e.g., R1 and R2 sequencing primers) are not directly linked to the chromatin (see, e.g., FIG. 17). The first template nucleic acid fragment may be at least partially double-stranded. The first template nucleic acid fragment may comprise a double-stranded region comprising sequences of chromatin of the cell, cell bead, or cell nucleus. A first end of a first strand of the double-stranded region may be linked to a first transposon end sequence (e.g., mosaic end sequence). A first end of the second strand of the double-stranded region, which end is opposite the first end of the first strand, may be linked to a second transposon end sequence (e.g., mosaic end sequence). The second transposon end sequence may be the same as or different from the first transposon end sequence. The first transposon end sequence may be hybridized to a first complementary sequence (e.g., mosaic end reverse complement sequence), which first complementary sequence may not be linked to a second end of the second strand of the double-stranded region of the first template nucleic acid fragment. The first complementary sequence may be linked to a first sequencing primer or portion thereof. Similarly, the second transposon end sequence may be hybridized to a second complementary sequence (e.g., mosaic end reverse complement sequence), which second complementary sequence may not be linked to a second end of the first strand of the double-stranded region of the first template nucleic acid fragment. The second complementary sequence may be linked to a second sequencing primer or portion thereof. In other words, the first template nucleic acid fragment may comprise one or more gaps. In some cases, the one or more gaps may be approximately 9 bp in length each. For example, one or more gaps may be at least about 1, 2, 3, 4, 5, 6, 7, 8, 9, 10, or more bp in length. For example, one or more gaps may be at most about 10, 9, 8, 7, 6, 5, 4, 3, 2, or 1 bp in length. The first sequencing primer or portion thereof may be the same as or different from the second sequencing primer or portion thereof. In some cases, the first sequencing primer or portion thereof may be an R1 sequence or portion thereof, and the second sequencing primer or portion thereof may be an R2 sequence or portion thereof.

The cell, cell bead, or cell nucleus comprising the first template nucleic acid fragment (e.g., tagmented fragment) may be co-partitioned with one or more reagents into a partition of a plurality of partitions (e.g., as described herein). The partition may be, for example, a droplet or well. The partition may comprise one or more beads (e.g., as described herein). A bead (e.g., gel bead) of the one or more beads may comprise a first plurality of nucleic acid barcode molecules. A nucleic acid barcode molecule of the first plurality of nucleic acid barcode molecules may comprise a flow cell adapter sequence (e.g., P5 sequence), a barcode sequence, and a sequencing primer or portion thereof (e.g., R1 sequence or portion thereof, or a complement thereof). The sequencing primer or portion thereof may be complementary to a sequence of the first template nucleic acid fragment. The flow cell adapter sequence and/or barcode sequence may be hybridized to their complementary sequences. The same bead or another bead may comprise a second plurality of nucleic acid barcode molecules. A nucleic acid barcode molecule of the second plurality of nucleic acid barcode molecules may comprise a sequencing primer or portion thereof (e.g., an R1 sequence or portion thereof, or complement thereof), a barcode sequence, a unique molecular identifier sequence, and a capture sequence.

Within the partition, the RNA molecule may be processed to provide the second template nucleic acid fragment (e.g., as described herein). For example, the RNA molecule (e.g., mRNA molecule) may be contacted with a primer molecule comprising a first primer sequence (e.g., a polyT sequence) and an additional primer sequence.

Within the partition, the cell, cell bead, or cell nucleus may be lysed or permeabilized to provide access to the first and/or second template nucleic acid fragments therein (e.g., as described herein). The second template nucleic acid fragment may be generated after the cell, cell bead, or cell nucleus is lysed or permeabilized.

The first and second template nucleic acid fragments may undergo processing within the partition. Within the partition, a sequencing primer or portion thereof of the first template nucleic acid fragment corresponding to the chromatin of the cell, cell bead, or cell nucleus may hybridize to a sequencing primer or portion thereof of the nucleic acid barcode molecule of the first plurality of nucleic acid barcode molecules. The sequencing primer or portion thereof of the nucleic acid barcode molecule may then be ligated (e.g., using a ligase) to a transposon end sequence of the first template nucleic acid fragment, or a complement thereof to provide a partially double-stranded nucleic acid molecule corresponding to the chromatin of the cell, cell bead, or cell nucleus. The second template nucleic acid fragment corresponding to the RNA molecule may be reverse transcribed using a reverse transcriptase with terminal transferase activity, which reverse transcriptase may append a sequence (e.g., a polyC sequence) to the cDNA strand of the resultant cDNA molecule. The cDNA molecule may then be contacted with a nucleic acid barcode molecule of the second plurality of nucleic acid barcode molecules that may be a template switch oligonucleotide. The nucleic acid barcode molecule may comprise a sequencing primer or portion thereof (e.g., an R1 sequence or portion thereof, or complement thereof), a barcode sequence, a unique molecular identifier sequence, and a capture sequence. The capture sequence may be a sequence that is complementary to the sequence appended to the cDNA strand (e.g., a polyG sequence). Template switching and barcoding may then take place to provide a barcoded cDNA molecule.

The partially double-stranded molecule corresponding to the chromatin of the cell, cell bead, or cell nucleus and the barcoded cDNA molecule corresponding to the RNA molecule (e.g., prepared as described above) of the cell, cell bead, or cell nucleus included within the partition of the plurality of partitions may be recovered from the partition. For example, the contents of the plurality of partitions may be pooled to provide the linear amplification products in a bulk solution.

Outside of the partition, the gaps in the partially double-stranded nucleic acid molecule corresponding to the chromatin may be filled using via a gap filling extension process (e.g., using a DNA polymerase). Gaps may be filled in the partition prior to bulk processing. The resultant gap-filled double-stranded nucleic acid molecule may be denatured to provide a single strand, which single strand may be subjected to conditions sufficient to perform one or more nucleic acid amplification reactions (e.g., PCR) to generate amplification products corresponding to the chromatin of the cell, cell bead, or cell nucleus. A nucleic acid amplification process may incorporate one or more additional sequences, such as one or more additional flow cell adapter sequences. The barcoded cDNA molecule corresponding to the RNA molecule may also be processed and amplified according to the preceding examples.

Figure 16:
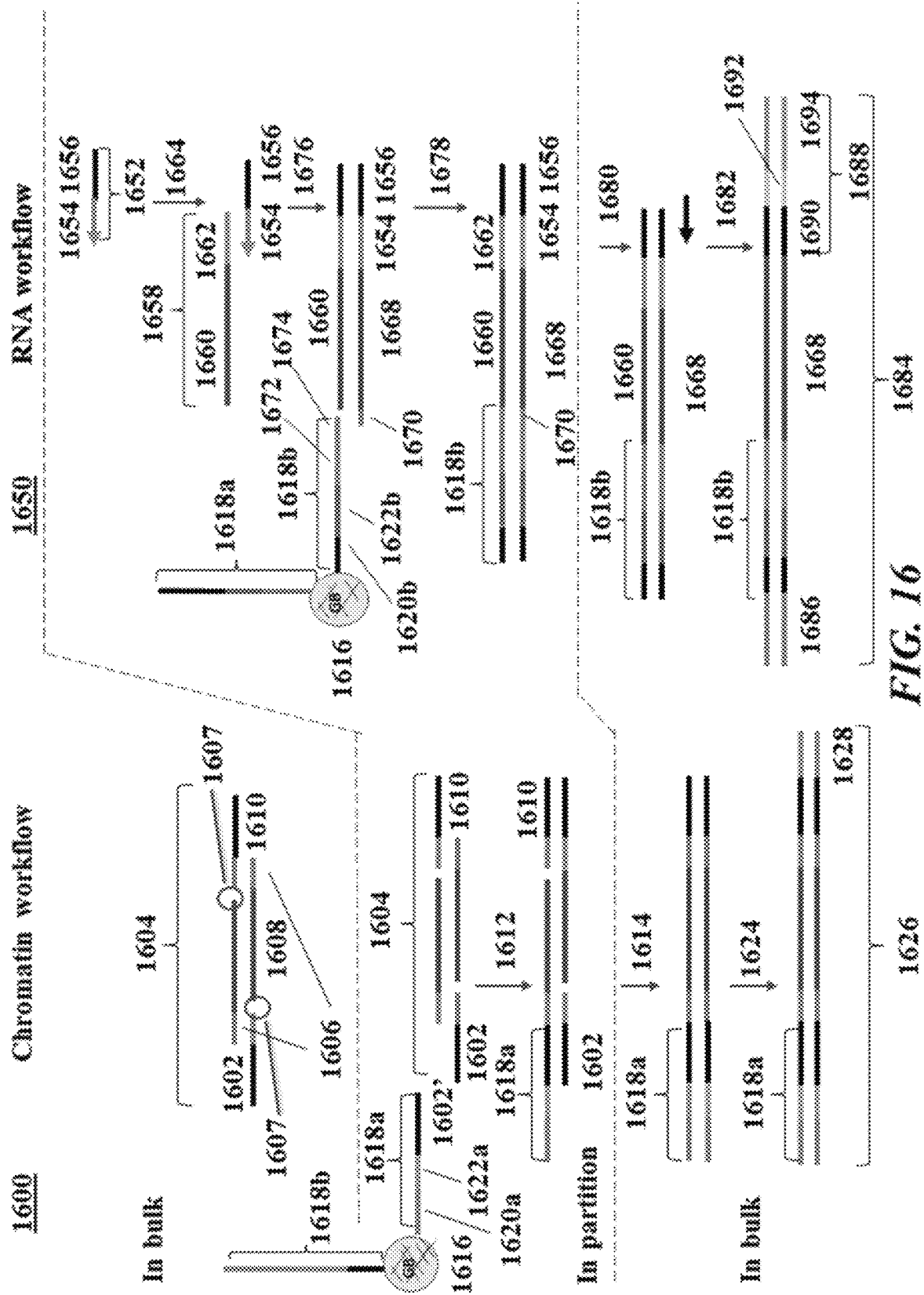
FIG. 16 illustrates an additional scheme for tandem ATAC ligation and RNA template switching.

FIG. 16 shows an example schematic corresponding to the preceding example. Panel 1600 shows a workflow corresponding to processing of chromatin from a cell, cell bead, or cell nucleus, and panel 1650 shows a workflow corresponding to processing of an mRNA molecule from the cell, cell bead, or cell nucleus.

As shown in panel 1600, in bulk solution, chromatin included within a cell, cell bead, or cell nucleus is processed (e.g., as described herein) to provide a template nucleic acid fragment (e.g., tagmented fragment) 1604 comprising insert sequence 1608 (e.g., region of open chromatin) and a complement thereof, transposon end sequences 1606 and complements thereof, sequencing primer or portion thereof 1602 (e.g., an R1 sequence), sequencing primer or portion thereof 1610 (e.g., an R2 sequence), and gaps 1607. Template nucleic acid fragment 1604 may then be partitioned within a partition (e.g., a droplet or well, as described herein). Within the partition, the cell, cell bead, or cell nucleus comprising template nucleic acid fragment 1604 may be lysed, permeabilized, or otherwise processed to provide access to template nucleic acid fragment 1604 (and one or more RNA molecules) therein. The partition may include a bead (e.g., gel bead) 1616 coupled to nucleic acid barcode molecules 1618a and 1618b. Nucleic acid barcode molecule 1618a may comprise a flow cell adapter sequence 1620a (e.g., a P5 sequence), a barcode sequence 1622a, and a sequencing primer or portion thereof or complement thereof 1602'. Sequence 1602' may hybridize to sequence 1602 of template nucleic acid fragment 1604, or its complement. Sequence 1602' may then be ligated 1612 to a transposon end sequence 1606 of template nucleic acid fragment 1604. In some instances, 1604 may be phosphorylated using a suitable kinase enzyme (e.g., polynucleotide kinase (PNK), such as T4 PNK). In some instances, PNK and ATP may be added in bulk in the tagmentation (e.g., ATAC) reaction and/or prior to partitioning a cell, cell bead, or cell nucleus, or plurality thereof 15 U of PNK with 1 mM of ATP may be spiked into the tagmentation reaction. For example, less than 95 U of PNK may be spiked into the tagmentation reaction. The contents of the partition may then be recovered in bulk solution (e.g., a droplet may be broken) to provide the partially double-stranded nucleic acid molecule comprising nucleic acid barcode molecule 1618a attached to template nucleic acid fragment 1604 in bulk solution. In bulk solution, gaps 1607 may be filled 1614 via a gap filling extension process (e.g., using a DNA polymerase) and the molecule extended from sequence 1602 to provide a double-stranded nucleic acid molecule. This molecule may undergo amplification (e.g., PCR) 1624 to provide a double-stranded amplification product 1626 that includes sequences of the nucleic acid barcode molecule 1618a, the original chromatin molecule, and, optionally, an additional sequence 1628 that may be a flow cell adapter sequence (e.g., a P7 sequence). Gaps may be filled in the partition prior to bulk processing.

In parallel to the chromatin workflow of panel 1600, an RNA molecule deriving from the same cell, cell bead, or cell nucleus may be processed. As shown in panel 1650, RNA molecule 1658 comprising RNA sequence 1660 and polyA sequence 1662 may be contacted 1664 with primer molecule 1652 comprising polyT sequence 1654 and additional primer sequence 1656. RNA molecule 1658 may then be reverse transcribed 1676 off of polyT sequence 1654 using a reverse transcriptase with terminal transferase activity, which reverse transcriptase may append sequence 1670 to the resultant cDNA molecule comprising cDNA sequence 1668. Sequence 1670 may be a polyC sequence. Bead (e.g., gel bead) 1616 (e.g., the same bead described in panel 1600) may be included within the partition and may be coupled to nucleic acid barcode molecule 1618b. Nucleic acid barcode molecule 1618b may comprise a flow cell adapter sequence 1620b (e.g., a P5 sequence), a barcode sequence 1622b, UMI sequence 1672, and a sequence 1674 complementary to sequence 1670 (e.g., a polyG sequence). In some instances, nucleic acid barcode molecule 1618b may comprise a sequencing primer sequence 1620b (e.g., an R1 sequence or partial R1 sequence), a barcode sequence 1622b, UMI sequence 1672, and a template switching sequence 1674 complementary to sequence 1670 (e.g., a polyG sequence). Nucleic acid barcode molecule 1618b may be used to perform template switching 1678, which process may also result in the generation of a barcoded cDNA molecule. The contents of the partition may then be recovered in bulk solution (e.g., a droplet may be broken) to provide the barcoded cDNA molecule in bulk solution. The barcoded cDNA molecule may undergo amplification (e.g., PCR) 1680 to provide a double-stranded amplification product 1684 that includes sequences of the nucleic acid barcode molecule 1618b, the original RNA molecule or cDNA corresponding thereto, a flow cell adapter sequence 1686, and an additional sequence 1688 that may comprise a sequencing primer or portion thereof (e.g., an R2 sequence) 1690, a sample index sequence 1692, and a flow cell adapter sequence (e.g., a P7 sequence) 1694. The barcoded cDNA molecule may also or alternatively undergo fragmentation, end repair, dA tailing, ligation of one or more adapter sequences, and/or nucleic acid amplification.

Figure 17:
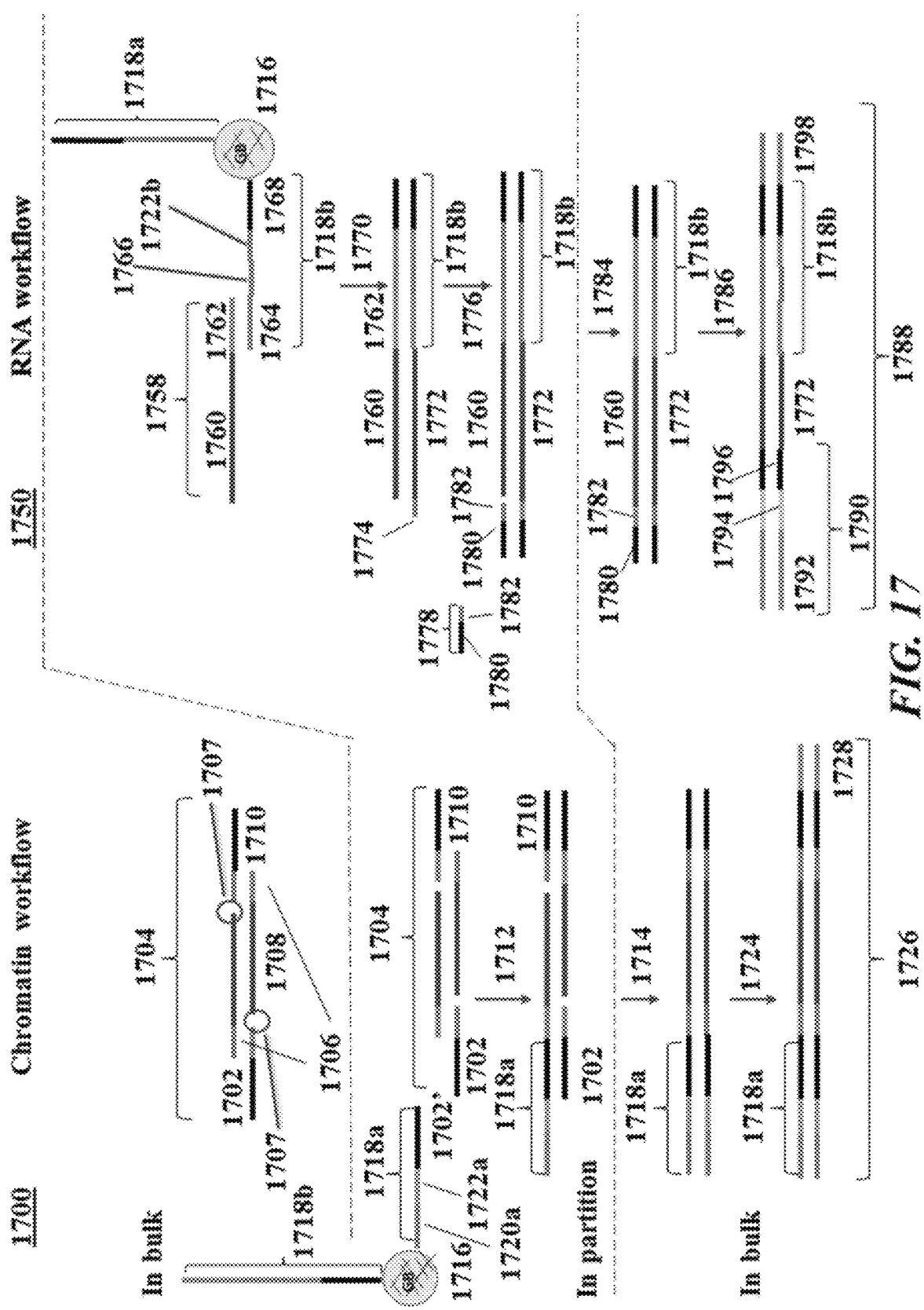
FIG. 17 illustrates an additional scheme for tandem ATAC ligation and RNA template switching.

FIG. 17 shows another example schematic corresponding to the preceding example. Panel 1700 shows a workflow corresponding to processing of chromatin from a cell, cell bead, or cell nucleus, and panel 1750 shows a workflow corresponding to processing of an mRNA molecule from the cell, cell bead, or cell nucleus.

As shown in panel 1700, in bulk solution, chromatin included within a cell, cell bead, or cell nucleus is processed (e.g., as described herein) to provide a template nucleic acid fragment (e.g., tagmented fragment) 1704 comprising insert sequence 1708 (e.g., region of open chromatin) and a complement thereof, transposon end sequences 1706 and complements thereof, sequencing primer or portion thereof 1702 (e.g., an R1 sequence), sequencing primer or portion thereof 1710 (e.g., an R2 sequence), and gaps 1707. Template nucleic acid fragment 1704 may then be partitioned within a partition (e.g., a droplet or well, as described herein). Within the partition, the cell, cell bead, or cell nucleus comprising template nucleic acid fragment 1704 may be lysed, permeabilized, or otherwise processed to provide access to template nucleic acid fragment 1704 (and one or more RNA molecules) therein. The partition may include a bead (e.g., gel bead) 1716 coupled to nucleic acid barcode molecules 1718a and 1718b. Nucleic acid barcode molecule 1718a may comprise a flow cell adapter sequence 1720a (e.g., a P5 sequence), a barcode sequence 1722a, and a sequencing primer or portion thereof or complement thereof 1702'. Sequence 1702' may hybridize to sequence 1702 of template nucleic acid fragment 1704, or its complement. Sequence 1702' may then be ligated 1712 to a transposon end sequence 1706 of template nucleic acid fragment 1704. In some instances, 1704 may be phosphorylated using a suitable kinase enzyme (e.g., polynucleotide kinase (PNK), such as T4 PNK). In some instances, PNK and ATP may be added in bulk in the tagmentation reaction (e.g., ATAC) and/or prior to partitioning a cell, cell bead or cell nucleus, or plurality thereof 15 U of PNK with 1 mM of ATP may be spiked into the tagmentation reaction. For example, less than 95 U of PNK may be spiked into the tagmentation reaction. The contents of the partition may then be recovered in bulk solution (e.g., a droplet may be broken) to provide the partially double-stranded nucleic acid molecule comprising nucleic acid barcode molecule 1718a attached to template nucleic acid fragment 1704 in bulk solution. In bulk solution, gaps 1707 may be filled 1714 via a gap filling extension process (e.g., using a DNA polymerase) and the molecule extended from sequence 1702 to provide a double-stranded nucleic acid molecule. This molecule may undergo amplification (e.g., PCR) 1724 to provide a double-stranded amplification product 1726 that includes sequences of the nucleic acid barcode molecule 1718a, the original chromatin molecule, and, optionally, an additional sequence 1728 that may be a flow cell adapter sequence (e.g., a P7 sequence). Gaps may be filled in the partition prior to bulk processing.

In parallel to the chromatin workflow of panel 1700, an RNA molecule deriving from the same cell, cell bead, or cell nucleus may be processed. As shown in panel 1750, RNA molecule 1758 comprising RNA sequence 1760 and polyA sequence 1762 and bead (e.g., gel bead) 1716 may be provided within a partition. Bead (e.g., gel bead) 1716 (e.g., the same bead described in panel 1700) may be included within the partition and may be coupled to nucleic acid barcode molecule 1718b. Nucleic acid barcode molecule 1718b may comprise a flow cell adapter sequence 1768 (e.g., a P5 sequence), a barcode sequence 1722b (e.g., the same barcode sequence as barcode sequence 1722a), UMI sequence 1766, and a polyT sequence 1764 complementary to polyA sequence 1762. In some entrances, nucleic acid barcode molecule 1718b may comprise a sequencing primer sequence 1768 (e.g., an R1 sequence or partial R1 sequence), a barcode sequence 1722b (e.g., the same barcode sequence as barcode sequence 1722a), UMI sequence 1766, and a polyT sequence 1764 complementary to polyA sequence 1762. PolyT sequence 1764 may hybridize to polyA sequence 1762 of RNA molecule 1758. RNA molecule 1758 may be reverse transcribed 1770 off of polyT sequence 1764 to provide an cDNA molecule comprising cDNA sequence 1772. The reverse transcription process may use a reverse transcriptase with terminal transferase activity, which reverse transcriptase may append sequence 1774 to the resultant cDNA molecule comprising cDNA sequence 1772. Sequence 1774 may be a polyC sequence. A template switch oligonucleotide 1778 comprising a primer sequence 1780 and a sequence complementary to sequence 1774 (e.g., a polyG sequence) may hybridize to the cDNA molecule. The contents of the partition may then be recovered in bulk solution (e.g., a droplet may be broken) to provide the cDNA molecule in bulk solution. The cDNA molecule may undergo amplification (e.g., PCR) 1784. Additional amplification (e.g., PCR) 1786 may to performed to provide a double-stranded amplification product 1788 that includes sequences of the nucleic acid barcode molecule 1718b, the original RNA molecule or cDNA corresponding thereto, a flow cell adapter sequence 1798 (e.g., a P7 sequence), and an additional sequence 1790 that may comprise a sequencing primer or portion thereof (e.g., an R2 sequence) 1796, a sample index sequence 1794, and a flow cell adapter sequence (e.g., a P5 sequence) 1792. The barcoded cDNA molecule may also or alternatively undergo fragmentation, end repair, dA tailing, ligation of one or more adapter sequences, and/or nucleic acid amplification.

In another example, a cell, cell bead, or cell nucleus comprising chromatin and one or more RNA molecules is provided. The chromatin in the cell, cell bead, or cell nucleus may be processed to provide a first template nucleic acid fragment derived from the chromatin (e.g., a tagmented fragment, as described herein). The chromatin may be processed in bulk solution. An RNA molecule may be processed to provide a second template nucleic acid fragment derived from an RNA molecule (e.g., as described herein). The RNA molecule may be processed within a partition. The configuration of the first template nucleic acid fragment may be at least partially dependent on the structure of the transposase-nucleic acid complex used to generate the first template nucleic acid fragment. For example, a transposase-nucleic acid complex such as that shown in FIG. 9 may be used to prepare the first template nucleic acid fragment. The first template nucleic acid fragment may be at least partially double-stranded. The first template nucleic acid fragment may comprise a double-stranded region comprising sequences of chromatin of the cell, cell bead, or cell nucleus. A first end of a first strand of the double-stranded region may be linked to a first transposon end sequence (e.g., mosaic end sequence), which first transposon end sequence may be linked to a first sequencing primer or portion thereof. A first end of the second strand of the double-stranded region, which end is opposite the first end of the first strand, may be linked to a second transposon end sequence (e.g., mosaic end sequence), which second transposon end sequence may be linked to a second sequencing primer or portion thereof. The second transposon end sequence may be the same as or different from the first transposon end sequence. The first sequencing primer or portion thereof may be the same as or different from the second sequencing primer or portion thereof. In some cases, the first sequencing primer or portion thereof may be an R1 sequence or portion thereof, and the second sequencing primer or portion thereof may be an R2 sequence or portion thereof. The first transposon end sequence may be hybridized to a first complementary sequence (e.g., mosaic end reverse complement sequence), which first complementary sequence may not be linked to a second end of the second strand of the double-stranded region of the first template nucleic acid fragment. Similarly, the second transposon end sequence may be hybridized to a second complementary sequence (e.g., mosaic end reverse complement sequence), which second complementary sequence may not be linked to a second end of the first strand of the double-stranded region of the first template nucleic acid fragment. In other words, the first template nucleic acid fragment may comprise one or more gaps. In some cases, the one or more gaps may be approximately 9 bp in length each. For example, one or more gaps may be at least about 1, 2, 3, 4, 5, 6, 7, 8, 9, 10, or more bp in length. For example, one or more gaps may be at most about 10, 9, 8, 7, 6, 5, 4, 3, 2, or 1 bp in length. The second template nucleic acid fragment (e.g., an additional template nucleic acid fragment) may comprise a sequence of an RNA molecule of the cell, cell bead, or cell nucleus and a sequence hybridized to a primer molecule (e.g., a capture nucleic acid molecule). For example, the second template nucleic acid fragment may comprise a sequence of an RNA molecule of the cell, cell bead, or cell nucleus and a polyA sequence hybridized to a polyT sequence of a primer molecule. The primer molecule may also comprise an additional primer sequence.

The cell, cell bead, or cell nucleus comprising the first template nucleic acid fragment (e.g., tagmented fragment) may be co-partitioned with one or more reagents into a partition of a plurality of partitions (e.g., as described herein). The partition may be, for example, a droplet or well. The partition may comprise one or more beads (e.g., as described herein). A bead (e.g., gel bead) of the one or more beads may comprise a first plurality of nucleic acid barcode molecules. A nucleic acid barcode molecule of the first plurality of nucleic acid barcode molecules may comprise a flow cell adapter sequence (e.g., P5 sequence), a barcode sequence, and an overhang sequence. The partition may also comprise a splint sequence comprising a sequence complementary to the overhang sequence and a sequencing primer or portion thereof that may be complementary to a sequence of the first template nucleic acid fragment. A bead of the one or more beads may also comprise a second plurality of nucleic acid barcode molecules. A nucleic acid barcode molecule of the second plurality of nucleic acid barcode molecules may comprise a flow cell adapter sequence (e.g., P5 sequence), a barcode sequence, a sequencing primer or portion thereof (e.g., R1 sequence or portion thereof, or a complement thereof), a UMI sequence, and a capture sequence (e.g., a polyG sequence or a polydT sequence). In some cases, the first plurality of nucleic acid barcode molecules and the second plurality of nucleic acid barcode molecules may be coupled to the same bead, and the partition may comprise a single bead.

Within the partition, the RNA molecule may be processed to provide the second template nucleic acid fragment (e.g., as described herein).

Within the partition, the cell, cell bead, or cell nucleus may be lysed or permeabilized to provide access to the first and/or second template nucleic acid fragments therein (e.g., as described herein). The second template nucleic acid fragment may be generated after the cell, cell bead, or cell nucleus is lysed or permeabilized.

The first and second template nucleic acid fragments may undergo processing within the partition. Within the partition, a sequencing primer or portion thereof of the first template nucleic acid fragment corresponding to the chromatin of the cell, cell bead, or cell nucleus may hybridize to a complementary sequence of the sequencing primer or portion thereof in the splint sequence. The splint sequence may also hybridize to the overhang sequence of the nucleic acid barcode molecule of the first plurality of nucleic acid barcode molecules. The overhang sequence of the nucleic acid barcode molecule may then be ligated (e.g., using a ligase) to a sequencing primer or portion thereof of the first template nucleic acid fragment. The resultant partially double-stranded nucleic acid molecule may comprise the barcode sequence as well as one or more gaps.

Within the partition, the second template nucleic acid fragment derived from the RNA molecule of the cell, cell bead, or cell nucleus may be reverse transcribed (e.g., using a reverse transcriptase) to provide a cDNA strand. The reverse transcription process may append a sequence to an end of a strand of the resultant double-stranded nucleic acid molecule comprising the RNA strand and the cDNA strand, such as a polyC sequence. The capture sequence of the nucleic acid barcode molecule of the second plurality of nucleic acid barcode molecules may hybridize to the appended sequence (e.g., polyC sequence) of the double-stranded nucleic acid molecule and a template switching process may take place to provide a second double-stranded nucleic acid molecule. The sequence of the nucleic acid barcode molecule of the second plurality of nucleic acid barcode molecules may be considered a template switching oligonucleotide. The template switch process may result in a barcoded cDNA molecule. The barcoded cDNA molecule may comprise the sequencing primer or portion thereof, or complement thereof, of the nucleic acid barcode molecule of the second plurality of nucleic acid barcode molecules; the barcode sequence, or complement thereof, of the nucleic acid barcode molecule of the second plurality of nucleic acid barcode molecules; the UMI sequence, or complement thereof, of the nucleic acid barcode molecule of the second plurality of nucleic acid barcode molecules; the capture sequence, or complement thereof, of the nucleic acid barcode molecule of the second plurality of nucleic acid barcode molecules; the poly(C) or poly(G) sequence; the sequence corresponding to the RNA molecule of the cell, cell bead, or cell nucleus, or complement thereof; and sequences of the capture nucleic acid molecule, or complements thereof.

The partially double-stranded nucleic acid molecule corresponding to the chromatin of the cell, cell bead, or cell nucleus and the barcoded cDNA molecule corresponding to the RNA molecule of the cell, cell bead, or cell nucleus included within the partition of the plurality of partitions may be recovered from the partition. For example, the contents of the plurality of partitions may be pooled to provide the partially double-stranded nucleic acid molecule and the barcoded cDNA molecule in a bulk solution.

Outside of the partition, the gaps in the partially double-stranded nucleic acid molecule corresponding to the chromatin may be filled using via a gap filling extension process (e.g., using a DNA polymerase or reverse transcriptase). The DNA polymerase may lack strand displacement activity. The resultant gap-filled double-stranded nucleic acid molecule may be denatured to provide a single strand, which single strand may be subjected to conditions sufficient to perform one or more nucleic acid amplification reactions (e.g., PCR) to generate amplification products corresponding to the chromatin of the cell, cell bead, or cell nucleus. A nucleic acid amplification process may incorporate one or more additional sequences, such as one or more additional flow cell adapter sequences.

Outside of the partition, the barcoded cDNA molecule corresponding to the RNA molecule may be subjected to fragmentation, end repair, a dA tailing process, tagmentation, or a combination thereof. An additional primer sequence (e.g., a sequencing primer or portion thereof, such as an R2 sequence) may then be ligated to the resultant molecule. A nucleic acid amplification reaction (e.g., PCR) may then be performed to generate one or more amplification products corresponding to the RNA molecule. A nucleic acid amplification process may incorporate one or more additional sequences, such as one or more additional flow cell adapter sequences.

Figure 18:
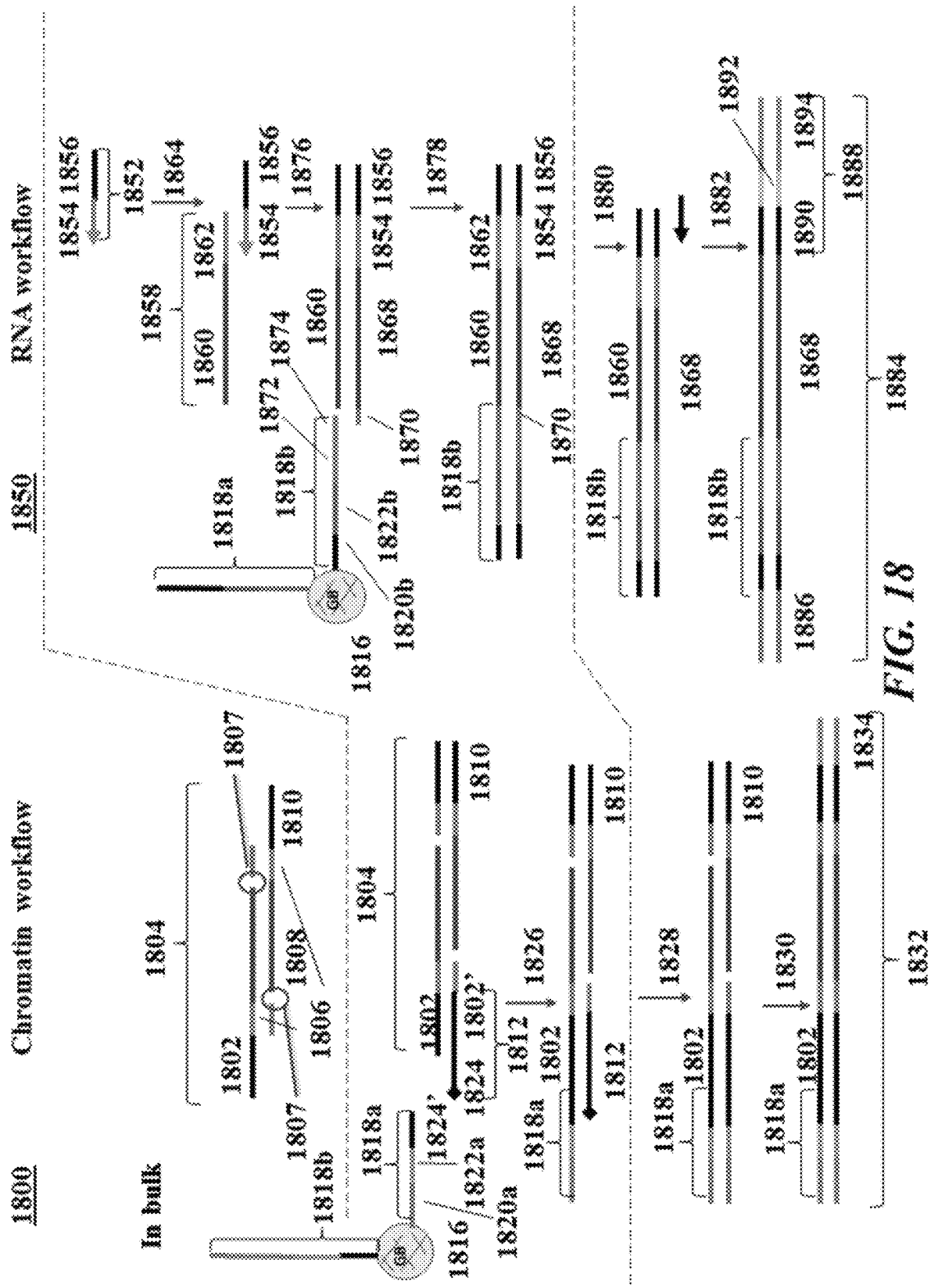
FIG. 18 illustrates an additional scheme for tandem ATAC ligation and RNA template switching.

FIG. 18 shows an example schematic corresponding to the preceding example. Panel 1800 shows a workflow corresponding to processing of chromatin from a cell, cell bead, or cell nucleus, and panel 1850 shows a workflow corresponding to processing of an mRNA molecule from the cell, cell bead, or cell nucleus.

As shown in panel 1800, in bulk solution, chromatin included within a cell, cell bead, or cell nucleus is processed (e.g., as described herein) to provide a template nucleic acid fragment (e.g., tagmented fragment) 1804 comprising insert sequence 1808 (e.g., region of open chromatin) and a complement thereof, transposon end sequences 1806 and complements thereof, sequencing primer or portion thereof 1802 (e.g., an R1 sequence), sequencing primer or portion thereof 1810 (e.g., an R2 sequence), and gaps 1807. Template nucleic acid fragment 1804 may then be partitioned within a partition (e.g., a droplet or well, as described herein). Within the partition, the cell, cell bead, or cell nucleus comprising template nucleic acid fragment 1804 may be lysed, permeabilized, or otherwise processed to provide access to template nucleic acid fragment 1804 (and one or more RNA molecules) therein. The partition may comprise splint sequence 1812, which splint sequence may comprise a first sequence 1802' that is complementary to sequencing primer or portion thereof 1802 and a second sequence 1824. Sequence 1824 may comprise a blocking group (e.g., a 3' blocking group), which blocking group may prevent extension by reverse transcription. The partition may also include a bead (e.g., gel bead) 1816 coupled to nucleic acid barcode molecules 1818a and 1812b. Nucleic acid barcode molecule 1818a may comprise a flow cell adapter sequence 1820a (e.g., a P5 sequence), a barcode sequence 1822a, and an overhang sequence 1824' that is complementary to sequence 1824 of the splint sequence. Sequence 1824 may hybridize to sequence 1824' to provide a partially double-stranded nucleic acid molecule comprising the sequences of nucleic acid barcode molecule 1818a and the template nucleic acid fragment 1804. Sequence 1824' of nucleic acid barcode molecule 1818a may be ligated (e.g., using a ligase) 1826 to sequence 1802 of template nucleic acid fragment 1804. In some instances, 1804 may be phosphorylated using a suitable kinase enzyme (e.g., polynucleotide kinase (PNK), such as T4 PNK). In some instances, PNK and ATP may be added in bulk in the tagmentation reaction (e.g., ATAC) and/or prior to partitioning a cell, cell bead, or cell nucleus, or plurality thereof 15 U of PNK with 1 mM of ATP may be spiked into the tagmentation reaction. For example, less than 95 U of PNK may be spiked into the tagmentation reaction. The contents of the partition may then be recovered in bulk solution (e.g., a droplet may be broken) to provide the partially double-stranded nucleic acid molecule comprising nucleic acid barcode molecule 1818a attached to template nucleic acid fragment 1804 in bulk solution. In bulk solution, gaps 1807 may be filled 1828 via a gap filling extension process (e.g., using a DNA polymerase) to provide a double-stranded nucleic acid molecule. This molecule may undergo amplification (e.g., PCR) 1830 to provide a double-stranded amplification product 1832 that includes sequences of the nucleic acid barcode molecule 1818a, the original chromatin molecule, and, optionally, an additional sequence 1834 that may be a flow cell adapter sequence (e.g., a P7 sequence). Gaps may be filled in the partition prior to bulk processing.

In parallel to the chromatin workflow of panel 1800, an RNA molecule deriving from the same cell, cell bead, or cell nucleus may be processed. As shown in panel 1850, RNA molecule 1858 comprising RNA sequence 1860 and polyA sequence 1862 may be contacted 1864 with primer molecule 1852 comprising polyT sequence 1854 and additional primer sequence 1856. RNA molecule 1858 may then be reverse transcribed 1876 off of polyT sequence 1854 using a reverse transcriptase with terminal transferase activity, which reverse transcriptase may append sequence 1870 to the resultant cDNA molecule comprising cDNA sequence 1868. Sequence 1870 may be a polyC sequence. Bead (e.g., gel bead) 1816 (e.g., the same bead described in panel 1800) may be included within the partition and may be coupled to nucleic acid barcode molecule 1818b. Nucleic acid barcode molecule 1818b may comprise a flow cell adapter sequence 1820b (e.g., a P5 sequence), a barcode sequence 1822b, UMI sequence 1872, and a sequence 1874 complementary to sequence 1870 (e.g., a polyG sequence). In some instances, nucleic acid barcode molecule 1818b may comprise a sequencing primer sequence 1820b (e.g., an R1 sequence or partial R1 sequence), a barcode sequence 1822b, UMI sequence 1872, and a sequence 1874 complementary to sequence 1870 (e.g., a polyG sequence). Nucleic acid barcode molecule 1818b may be used to perform template switching 1878, which process may also result in the generation of a barcoded cDNA molecule. The contents of the partition may then be recovered in bulk solution (e.g., a droplet may be broken) to provide the barcoded cDNA molecule in bulk solution. The barcoded cDNA molecule may undergo amplification (e.g., PCR) 1880 to provide a double-stranded amplification product 1884 that includes sequences of the nucleic acid barcode molecule 1818b, the original RNA molecule or cDNA corresponding thereto, a flow cell adapter sequence 1886, and an additional sequence 1888 that may comprise a sequencing primer or portion thereof (e.g., an R2 sequence) 1890, a sample index sequence 1892, and a flow cell adapter sequence (e.g., a P7 sequence) 1894. The barcoded cDNA molecule may also or alternatively undergo fragmentation, end repair, dA tailing, ligation of one or more adapter sequences, and/or nucleic acid amplification.

Figure 19:
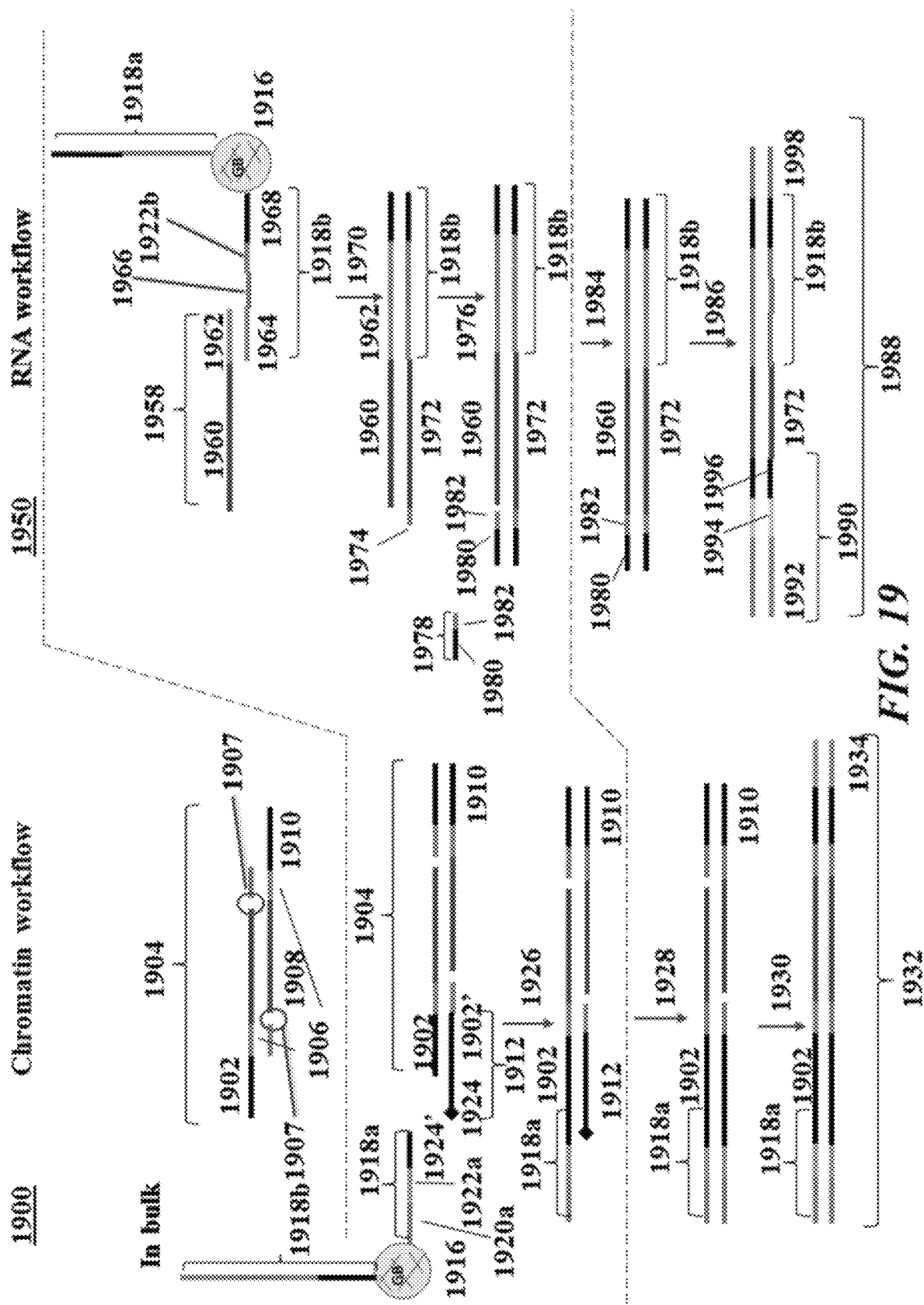
FIG. 19 illustrates an additional scheme for tandem ATAC ligation and RNA template switching.

FIG. 19 shows an example schematic corresponding to the preceding example. Panel 1900 shows a workflow corresponding to processing of chromatin from a cell, cell bead, or cell nucleus, and panel 1950 shows a workflow corresponding to processing of an mRNA molecule from the cell, cell bead, or cell nucleus.

As shown in panel 1900, in bulk solution, chromatin included within a cell, cell bead, or cell nucleus is processed (e.g., as described herein) to provide a template nucleic acid fragment (e.g., tagmented fragment) 1904 comprising insert sequence 1908 (e.g., region of open chromatin) and a complement thereof, transposon end sequences 1906 and complements thereof, sequencing primer or portion thereof 1902 (e.g., an R1 sequence), sequencing primer or portion thereof 1910 (e.g., an R2 sequence), and gaps 1907. Template nucleic acid fragment 1904 may then be partitioned within a partition (e.g., a droplet or well, as described herein). Within the partition, the cell, cell bead, or cell nucleus comprising template nucleic acid fragment 1904 may be lysed, permeabilized, or otherwise processed to provide access to template nucleic acid fragment 1904 (and one or more RNA molecules) therein. The partition may comprise splint sequence 1912, which splint sequence may comprise a first sequence 1902' that is complementary to sequencing primer or portion thereof 1902 and a second sequence 1924. Sequence 1924 may comprise a blocking group (e.g., a 3' blocking group), which blocking group may prevent extension by reverse transcription. The partition may also include a bead (e.g., gel bead) 1916 coupled to nucleic acid barcode molecules 1918a and 1918b. Nucleic acid barcode molecule 1918a may comprise a flow cell adapter sequence 1920a (e.g., a P5 sequence), a barcode sequence 1922a, and an overhang sequence 1924' that is complementary to sequence 1924 of the splint sequence. Sequence 1924 may hybridize to sequence 1924' to provide a partially double-stranded nucleic acid molecule comprising the sequences of nucleic acid barcode molecule 1918a and the template nucleic acid fragment 1904. Sequence 1924' of nucleic acid barcode molecule 1918a may be ligated (e.g., using a ligase) 1926 to sequence 1902 of template nucleic acid fragment 1904. In some instances, 1904 may be phosphorylated using a suitable kinase enzyme (e.g., polynucleotide kinase (PNK), such as T4 PNK). In some instances, PNK and ATP may be added in bulk in the tagmentation reaction (e.g., ATAC) and/or prior to partitioning the cells, cell beads, or cell nuclei. 15 U of PNK with 1 mM of ATP may be spiked into the tagmentation reaction. For example, less than 95 U of PNK may be spiked into the tagmentation reaction. The contents of the partition may then be recovered in bulk solution (e.g., a droplet may be broken) to provide the partially double-stranded nucleic acid molecule comprising nucleic acid barcode molecule 1918a attached to template nucleic acid fragment 1904 in bulk solution. In bulk solution, gaps 1907 may be filled 1928 via a gap filling extension process (e.g., using a DNA polymerase) to provide a double-stranded nucleic acid molecule. This molecule may undergo amplification (e.g., PCR) 1930 to provide a double-stranded amplification product 1932 that includes sequences of the nucleic acid barcode molecule 1918a, the original chromatin molecule, and, optionally, an additional sequence 1934 that may be a flow cell adapter sequence (e.g., a P7 sequence). Gaps may be filled in the partition prior to bulk processing.

In parallel to the chromatin workflow of panel 1900, an RNA molecule deriving from the same cell, cell bead, or cell nucleus may be processed. As shown in panel 1950, RNA molecule 1958 comprising RNA sequence 1960 and polyA sequence 1962 and bead (e.g., gel bead) 1916 may be provided within a partition. Bead (e.g., gel bead 1916 (e.g., the same bead described in panel 1900) may be included within the partition and may be coupled to nucleic acid barcode molecule 1918b. Nucleic acid barcode molecule 1918b may comprise a flow cell adapter sequence 1968 (e.g., a P5 sequence), a barcode sequence 1922b (e.g., the same barcode sequence as barcode sequence 1922a), UMI sequence 1966, and a polyT sequence 1964 complementary to polyA sequence 1962. In some instances, nucleic acid barcode molecule 1918b may comprise a sequencing primer sequence 1968 (e.g., a R1 sequence or partial R1 sequence), a barcode sequence 1922b (e.g., the same barcode sequence as barcode sequence 1922a), UMI sequence 1966, and a polyT sequence 1964 complementary to polyA sequence 1962. PolyT sequence 1964 may hybridize to polyA sequence 1962 of RNA molecule 1958. RNA molecule 1958 may be reverse transcribed 1970 off of polyT sequence 1964 to provide an cDNA molecule comprising cDNA sequence 1972. The reverse transcription process may use a reverse transcriptase with terminal transferase activity, which reverse transcriptase may append sequence 1974 to the resultant cDNA molecule comprising cDNA sequence 1972. Sequence 1974 may be a polyC sequence. A template switch oligonucleotide 1978 comprising a primer sequence 1980 and a sequence complementary to sequence 1974 (e.g., a polyG sequence) may hybridize to the cDNA molecule. The contents of the partition may then be recovered in bulk solution (e.g., a droplet may be broken) to provide the cDNA molecule in bulk solution. The cDNA molecule may undergo amplification (e.g., PCR) 1984. Additional amplification (e.g., PCR) 1986 may to performed to provide a double-stranded amplification product 1988 that includes sequences of the nucleic acid barcode molecule 1918b, the original RNA molecule or cDNA corresponding thereto, a flow cell adapter sequence 1998 (e.g., a P7 sequence), and an additional sequence 1990 that may comprise a sequencing primer or portion thereof (e.g., an R2 sequence) 1996, a sample index sequence 1994, and a flow cell adapter sequence (e.g., a P5 sequence) 1992. The barcoded cDNA molecule may also or alternatively undergo fragmentation, end repair, dA tailing, ligation of one or more adapter sequences, and/or nucleic acid amplification.

In another aspect, the present disclosure provides a method for processing a biological sample (e.g., a nucleic acid sample), which method may comprise performing sequential transcription and reverse transcription processes within a partition. The method may comprise providing a partition (e.g., droplet or well) of a plurality of partitions comprising a nucleic acid molecule (e.g., DNA molecule) derived from a nucleic acid sample. The nucleic acid molecule may be transcribed (e.g., using a transcriptase) to provide an RNA molecule. The RNA molecule may then be reverse transcribed (e.g., using a reverse transcriptase) within the partition to generate a complementary DNA (cDNA) molecule. The cDNA molecule may undergo further processing within the partition to provide a derivative of the cDNA molecule. The cDNA molecule or derivative thereof may be recovered from the partition (e.g., by pooling the contents of the plurality of partitions). The partition may be a well among a plurality of wells. Alternatively, the partition may be a droplet among a plurality of droplets.

A nucleic acid molecule (e.g., DNA molecule) processed according to the method provided herein may derive from a cell, cell bead, or cell nucleus. In some cases, the nucleic acid molecule may be included within the cell, cell bead, or cell nucleus. The nucleic acid molecule may be chromatin. The cell, cell bead, or cell nucleus comprising the nucleic acid molecule may be included within the partition. For example, the cell, cell bead, or cell nucleus may be co-partitioned with one or more reagents (e.g., as described herein) into a partition (e.g., droplet or well). The cell, cell bead, or cell nucleus may be lysed or permeabilized (e.g., within a partition) to provide access to the nucleic acid molecule therein (e.g., as described herein).

A nucleic acid molecule processed according to the method provided herein may be a DNA molecule, such as chromatin. In some cases, the method may further comprise processing an open chromatin structure of the nucleic acid sample with a transposase (e.g., included within a transposase-nucleic acid complex) to provide the nucleic acid molecule. For example, a nucleic acid molecule (e.g., within a cell, cell bead, or cell nucleus) may be contacted with a transposase-nucleic acid complex (e.g., as described herein). A transposase used in such a process may be, for example, a Tn5 transposase. A transposase-nucleic acid complex may have a structure such as that of FIG. 9 or FIG. 10. Alternatively, a transposase-nucleic acid complex may comprise one or more transposon end oligonucleotide molecules, which transposon end oligonucleotide molecules comprise hairpin molecules. An example of such a transposase-nucleic acid complex is shown in FIG. 11.

A nucleic acid molecule processed using a transposase-nucleic acid complex comprising one or more hairpin molecules may be a tagmented fragment comprising a double-stranded region comprising sequences corresponding to the nucleic acid molecule (e.g., chromatin) of the cell, cell bead, or cell nucleus from which it originates or is derived, as well as one or more hairpin molecules appended to either end of the double-stranded region. For example, the double-stranded region may comprise a first hairpin molecule at one end and a second hairpin molecule at a second end. Generally, only one end of a hairpin molecule may be attached to the double-stranded region, such that the tagmented fragment comprises a gap at either end. For example, a hairpin molecule may be attached to a 3' end of the double-stranded region. The hairpin molecule may comprise a promoter sequence, such as a T7 promoter sequence, and/or a UMI sequence.

Within the partition, the nucleic acid molecule (e.g., tagmented fragment) may undergo a gap filling process with a reverse transcriptase. The reverse transcriptase enzyme may be a mutant reverse transcriptase enzyme such as, but not limited to, Moloney Murine Leukemia Virus (MMLV) reverse transcriptase. In one aspect, the reverse transcriptase is a mutant MMLV reverse transcriptase such as, but not limited to, enzyme "42B" (see, US Patent Publication No. 20180312822). Enzyme 42B may reduce inhibition of reverse transcription of mRNAs from a single cell due to one or more unknown components present in cell lysate of the single cell when prepared in reaction volumes of, e.g., less than 1 nanoliter (nL) Enzyme 42B as compared to a commercially available mutant MMLV RT enzyme (CA-MMLV) may show improved reverse transcriptase activity. Such a process may generate a double-stranded nucleic acid molecule comprising the double-stranded region corresponding to the nucleic acid molecule (e.g., chromatin) of the cell, cell bead, or cell nucleus from which it is derived, the sequences of the hairpin molecules at either end of the double-stranded region, and sequences complementary to the sequences of the hairpin molecules. The double-stranded nucleic acid molecule may then undergo transcription with a T7 polymerase, which process begins at an end of a T7 promoter sequences of a hairpin molecules. Both strands may be transcribed in this manner to provide two nucleic acid strands each comprising the T7 promoter sequence, and a complement thereof; one or more transposon end sequences, and one or more complements thereof; and a sequence of the original nucleic acid molecule of the cell, cell bead, or cell nucleus. The strands may also comprise one or more spacer, UMI, or other sequences (e.g., from the hairpin molecules). A strand may then undergo a self-priming process in which the transposon end sequence and complement thereof of a hairpin molecule hybridize to one another to regenerate a hairpin molecule at an end of the strand. The hairpin molecule may serve as the priming site for reverse transcription. A reverse transcriptase process may then be performed (e.g., using a reverse transcriptase). Before, during, or after this process, a sequence may be appended to the end of the molecule, which sequence may be a polyC sequence. A template switching oligonucleotide comprising a sequence complementary to the appended sequence (e.g., a polyG sequence) may hybridize to the appended sequence. The template switching oligonucleotide may comprise a UMI sequence (e.g., a second UMI sequence that may index transcripts that undergo template switching), a barcode sequence, and/or a priming sequence such as a sequencing primer sequence or portion thereof (e.g., an R1 or R2 sequence, or portion thereof). The template switching oligonucleotide may be attached to a bead (e.g., a gel bead) included within the partition. For example, the template switching oligonucleotide may be a nucleic acid barcode molecule of a plurality of nucleic acid barcode molecules attached to the bead (e.g., as described herein). The resultant partially double-stranded nucleic acid molecule may comprise a hairpin moiety; sequences corresponding to the original nucleic acid molecule of the cell, cell bead, or cell nucleus; and the sequences of the template switching oligonucleotide, including a barcode sequence (see, e.g., FIG. 20).

The partially double-stranded nucleic acid molecule may be released from the partition (e.g., droplet or well). Releasing materials from the partition may comprise breaking or disrupting a droplet. The contents of multiple partitions of the plurality of partitions may be pooled together to provide a bulk solution for further processing. Nucleic acid molecules (e.g., partially double-stranded nucleic acid molecule) of the partitions of the plurality of partitions may each be differentially barcoded such that the nucleic acid molecule of each such partition comprises a different barcode sequence.

Outside of the partition, the partially double-stranded nucleic acid molecule may be partially denatured to provide a single-stranded molecule (e.g., a single-stranded cDNA molecule). An RNase treatment may be used to remove the hairpin molecule as well as the shorter strand (e.g., the RNA sequence) of the partially double-stranded nucleic acid molecule. The single-stranded molecule remaining may include the template switching oligonucleotide comprising the barcode sequence and, optionally, UMI sequence. A primer molecule comprising a priming sequence complementary to the priming sequence of the template switching oligonucleotide may be provided and may hybridize to the priming sequence of the template switching oligonucleotide. The priming sequence of the primer molecule may be a 5'-blocked priming sequence. A polymerase with dA tailing activity (e.g., a Klenow fragment having 5'→3' polymerase activity, such as an exo-Klenow fragment lacking exonuclease activity) may be used to generate a second nucleic acid strand. The resultant second strand may be dA tailed. The first strand may also be dA tailed. However, if a 5'-blocking priming sequence is used in the preceding processes, the dA tail appended to the first strand may not be available as a hybridization site for another moiety. Instead, a priming sequence comprising a sequencing primer (e.g., an R1 sequence or complement thereof) and a flow cell adapter sequence (e.g., a P5 sequence or complement thereof) may hybridize to a complementary sequence of the double-stranded nucleic acid molecule. At the opposite end of the double-stranded nucleic acid molecule, the dA moiety appended to the end of the second strand may serve as a site for hybridization of a priming sequence comprising a dT moiety at an end, a sequencing primer (e.g., an R2 sequence or complement thereof), and a flow cell adapter sequence (e.g., a P7 sequence or complement thereof). The double-stranded nucleic acid molecule may then be subjected to conditions sufficient to perform one or more nucleic acid amplification reactions (e.g., PCR) to provide amplification products corresponding to the original nucleic acid molecule of the cell, cell bead, or cell nucleus. The amplification products may comprise flow cell adapter sequences (e.g., P5 and P7 sequences) at either end to facilitate sequencing (e.g., as described herein).

The method provided herein may overcome certain challenges of performing reverse transcription within partitions. For example, reverse transcriptase may have a DNA-dependent DNA polymerase activity, and/or terminal transferase activities. The latter may result in generation of variable overhangs under certain reaction conditions. In the methods provided herein, every insertion site may be provided a T7 promoter, averting losses that may otherwise be encountered via R1-R1 and R2-R2 interactions. Moreover, both mRNA and chromatin-derived fragments may be barcoded using the same biochemistry (e.g., RT template switching). Performance of linear amplification of both such strands of a nucleic acid molecule may provide strand awareness and introduce a new dimension for, e.g., ATAC-seq processes. Further, this method may enable isothermal linear amplification of transposase derived nucleic acid fragments within partitions. Notably, this method may be combined with any of the RNA workflows described elsewhere herein.

Figure 20:
FIG. 20 illustrates a scheme for T7 mediated linear amplification.

FIG. 20 shows a workflow 2000 corresponding to the preceding example. Workflow 2000 may be performed in parallel with an RNA workflow, such as an RNA workflow of any of FIGS. 12-19. Multiple beads, each comprising nucleic acid barcode molecules configured for analysis of DNA or RNA molecules, may be included within a partition. Alternatively, a single bead (e.g., gel bead) comprising nucleic acid barcode molecules configured for analysis of both DNA and RNA molecules (e.g., as described herein) may be included within a partition. The single bead (e.g., in a single partition) may comprise a plurality of identical nucleic acid barcode molecules for both RNA and DNA analysis. In some cases, a single bead (e.g., within a single partition) comprises a first plurality of nucleic acid barcode molecules for DNA analysis and a second plurality of nucleic acid barcode molecules for RNA molecules, where the first and second plurality of nucleic acid barcode molecules comprise a common barcode sequence.

Template nucleic acid fragment (e.g., tagmented fragment) 2002 may be prepared (e.g., using a transposase-nucleic acid complex such as that shown in FIG. 11) and provided in a partition (as described herein). Template nucleic acid fragment 2002 may comprise hairpin moieties 2003 and 2004 and target sequences 2005 and 2006. Template nucleic acid fragment 2002 also comprises gaps 2007. Gaps 2007 may be filled using a reverse transcriptase (e.g., a 42B enzyme), which process may result in the generation of a double-stranded nucleic acid molecule comprising the double-stranded region corresponding to the original nucleic acid molecule (e.g., chromatin) of the cell, cell bead, or cell nucleus comprising sequences 2005 and 2006 and sequences of the hairpin molecules 2003 and 2004. The double-stranded nucleic acid molecule may comprise transposon end sequences 2008, promoter (e.g., T7 promoter) sequences 2010, and UMI sequences 2012. The double-stranded nucleic acid molecule may then undergo transcription with a T7 polymerase, which process begins at an end of a T7 promoter sequences of a hairpin molecule. Both strands may be transcribed in this manner to provide two nucleic acid strands. FIG. 20 shows one such strand comprising T7 promoter sequence 2010, and a complement thereof; one or more transposon end sequences 2008, and one or more complements thereof; UMI sequence 2012, and a complement of a UMI sequence; and an RNA sequence 2006' corresponding to sequence 2006 of the original nucleic acid molecule of the cell, cell bead, or cell nucleus. The strand may then undergo a self-priming process in which the transposon end sequence and complement thereof of hairpin molecule 2004 hybridize to one another to regenerate a hairpin molecule at an end of the strand. Regenerated hairpin molecule 2004 may serve as the priming site for reverse transcription. Reverse transcription and template switching may then be performed (e.g., using a reverse transcriptase). The reverse transcription process may append sequence 2014 (e.g., a polyC sequence) to the resultant cDNA molecule comprising cDNA sequence 2026 and sequences 2012' and 2008' that are complementary to sequences 2012 and 2008, respectively. The template switching process may comprise the use of a template switch oligonucleotide coupled to bead (e.g., gel bead) 2016 included within the partition. Bead (e.g., gel bead) 2016 may be coupled to nucleic acid barcode molecule 2018 that is the template switch oligonucleotide that comprises sequencing primer or portion thereof 2020, barcode sequence 2022, UMI sequence 2024, and a sequence 2014' that is complementary to sequence 2014 (e.g., a polyG sequence). The resultant cDNA molecule may comprise a first strand comprising nucleic acid barcode molecule 2018 and RNA sequence 2006' and a second strand comprising cDNA sequence 2026, appended sequence 2014, and sequences 2020', 2022', and 2024' that are complementary to sequences 2020, 2022, and 2024, respectively.

The cDNA molecule may be released from the partition (e.g., droplet or well). Releasing materials from the partition may comprise breaking or disrupting a droplet. The contents of multiple partitions of the plurality of partitions may be pooled together to provide a bulk solution for further processing. Outside of the partition, the cDNA molecule may be treated with RNase to remove the hairpin molecule as well as the shorter strand (e.g., the RNA sequence) of the partially double-stranded nucleic acid molecule. The single-stranded molecule remaining may include sequences 2020', 2022', 2024', 2014, 2012', 2008', and 2026. Primer molecule 2028 may then hybridize to sequence 2020'. Primer molecule 2028 may be a 5'-blocked priming sequence. A polymerase with dA tailing activity (e.g., a Klenow fragment having polymerase activity, such as an exo-Klenow fragment lacking exonuclease activity) may be used to generate a second nucleic acid strand comprising sequence 2026' that is complementary to cDNA sequence 2026. The resultant second strand may be dA tailed. The first strand may also be dA tailed at an end of sequence 2020'. However, if a 5'-blocking priming sequence is used in the preceding processes, the dA tail appended to the first strand may not be available as a hybridization site for another moiety. A priming sequence 2030 comprising a dT moiety, a sequencing primer (e.g., an R2 sequence or complement thereof) 2032 and a flow cell adapter sequence (e.g., a P7 sequence or complement thereof) 2034 may hybridize to the dA moiety of the double-stranded nucleic acid molecule. A priming sequence 2036 comprising a sequencing primer (e.g., an R1 sequence or complement thereof) 2038 and a flow cell adapter sequence (e.g., a P5 sequence or complement thereof) 2040 may hybridize to sequence 2028 of the double-stranded nucleic acid molecule. The double-stranded nucleic acid molecule may then be amplified to provide amplified product 2042, which amplification product may be subjected to further processing such as nucleic acid sequencing.

Figure 21:
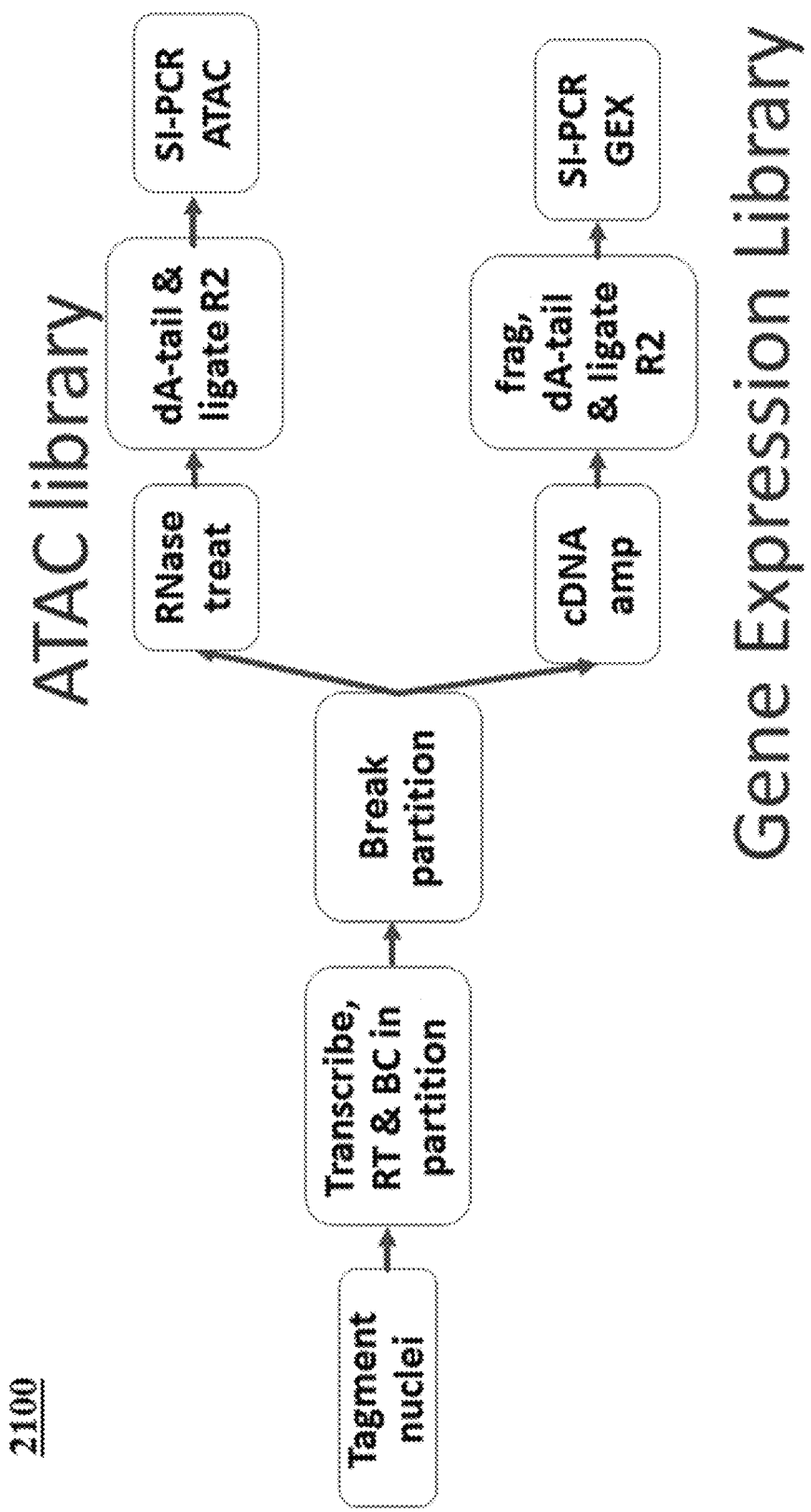
FIG. 21 shows a modified workflow T7 mediated linear amplification.

FIG. 21 provides an overview of a workflow 2100 for processing a nucleic acid molecule (e.g., a nucleic acid molecule included within a cell, cell bead, or cell nucleus). The nucleic acid molecule (e.g., DNA molecule, such as chromatin) is tagmented (e.g., as described herein) to generate a tagmented fragment. The tagmented fragment then undergoes transcription, reverse transcription, and barcoding within a partition (e.g., as described herein). The resultant products are released from the partition and subjected to one of two processes, the first of which provides an ATAC library and the second of which provides a gene expression library. The first process may involve RNase treatment to remove RNA and provide cDNA, dA tailing and ligation of a sequencing primer, and PCR. The second process may involve cDNA amplification; fragmentation, dA tailing, and ligation of a sequencing primer; and PCR.

The present disclosure also provides a method of processing a nucleic acid molecule of a cell, cell bead, or cell nucleus using a reverse transcriptase fill-in process coupled with a barcoding process. The nucleic acid molecule (e.g., DNA molecule) may derive from a cell, cell bead, or cell nucleus. In some cases, the nucleic acid molecule may be included within the cell, cell bead, or cell nucleus. The nucleic acid molecule may be chromatin. The cell, cell bead, or cell nucleus comprising the nucleic acid molecule may be included within the partition. For example, the cell, cell bead, or cell nucleus may be co-partitioned with one or more reagents (e.g., as described herein) into a partition (e.g., droplet or well). The cell, cell bead, or cell nucleus may be lysed or permeabilized (e.g., within a partition) to provide access to the nucleic acid molecule therein (e.g., as described herein).

A nucleic acid molecule processed according to the method provided herein may be a DNA molecule, such as chromatin. In some cases, the method may further comprise processing an open chromatin structure of the nucleic acid sample with a transposase (e.g., included within a transposase-nucleic acid complex) to provide the nucleic acid molecule. For example, a nucleic acid molecule (e.g., within a cell, cell bead, or cell nucleus) may be contacted with a transposase-nucleic acid complex (e.g., as described herein). A transposase used in such a process may be, for example, a Tn5 tranposase. A transposase-nucleic acid complex may have a structure such as that of FIG. 9, 10, or 11. Subsequent to generation of a tagmented fragment (e.g., as described herein), the transposase of the transposase-nucleic acid complex may leave or be removed (e.g., displaced, for example, by an enzyme). Alternatively, the transposase may remain in place. The tagmented fragment may comprise sequences corresponding to the original nucleic acid molecule of the cell, cell bead, or cell nucleus; transposon end sequences and sequences complementary thereto; and one or more sequencing primers or portions thereof. A splint sequence comprising a sequence complementary to a sequencing primer or portion thereof the tagmented fragment may hybridize to the sequencing primer or portion thereof. The splint sequence may be ligated to a transposon end sequence or complement thereof of the tagmented fragment (e.g., using a ligase). Prior to or after hybridization and/or ligation of the splint sequence, the tagmented fragment may be partitioned into a partition of a plurality of partitions (e.g., droplets of wells). The tagmented fragment may be co-partitioned with one or more reagents. The tagmented fragment may be included within a cell, cell bead, or cell nucleus, which cell, cell bead, or cell nucleus may be lysed or permeabilized to provide access to the tagmented fragment therein (e.g., as described herein). A sequence of the splint sequence may then hybridize to a nucleic acid barcode molecule (e.g., a nucleic acid barcode molecule coupled to a bead, as described herein). The bead (e.g., gel bead) may comprise a plurality of nucleic acid barcode molecules, where a nucleic acid barcode molecule of the plurality of nucleic acid barcode molecules may comprise, for example, a flow cell adapter sequence, a barcode sequence, and a UMI sequence. The nucleic acid barcode molecule may also comprise an overhang sequence having sequence complementarity to a sequence of the splint sequence. The overhang sequence may hybridize to the sequence of the splint sequence. A transposase reserved in the tagmented fragment may block gap filling during these processes. The splint sequence may then be extended within the partition (e.g., using a reverse transcriptase).

Subsequent to the barcoding/template switching and extension (e.g., reverse transcription) processes, the contents of the partition of the plurality of partitions may be released from the partition (e.g., as described herein). Prior or subsequent to release of the contents of the partition, the nucleic acid barcode molecule may be ligated to the sequencing primer of the processed tagmented fragment. Outside of the partition, the nucleic acid barcode molecule may hybridize to the sequencing primer or portion thereof of the template nucleic acid fragment. If a transposase is reserved in the tagmented fragment, the transposase may leave the processed tagmented fragment (e.g., via a strand displacing polymerase) and the remaining gaps may be filled to provide a double-stranded nucleic acid molecule. Alternatively, gaps may be filled as described elsewhere herein. The double-stranded nucleic acid molecule may then be subjected to a nucleic acid amplification process (e.g., PCR, as described herein). Amplification may comprise incorporation of one or more additional sequences, such as one or more flow cell adapter sequences (e.g., P7 sequences).

Figure 22:
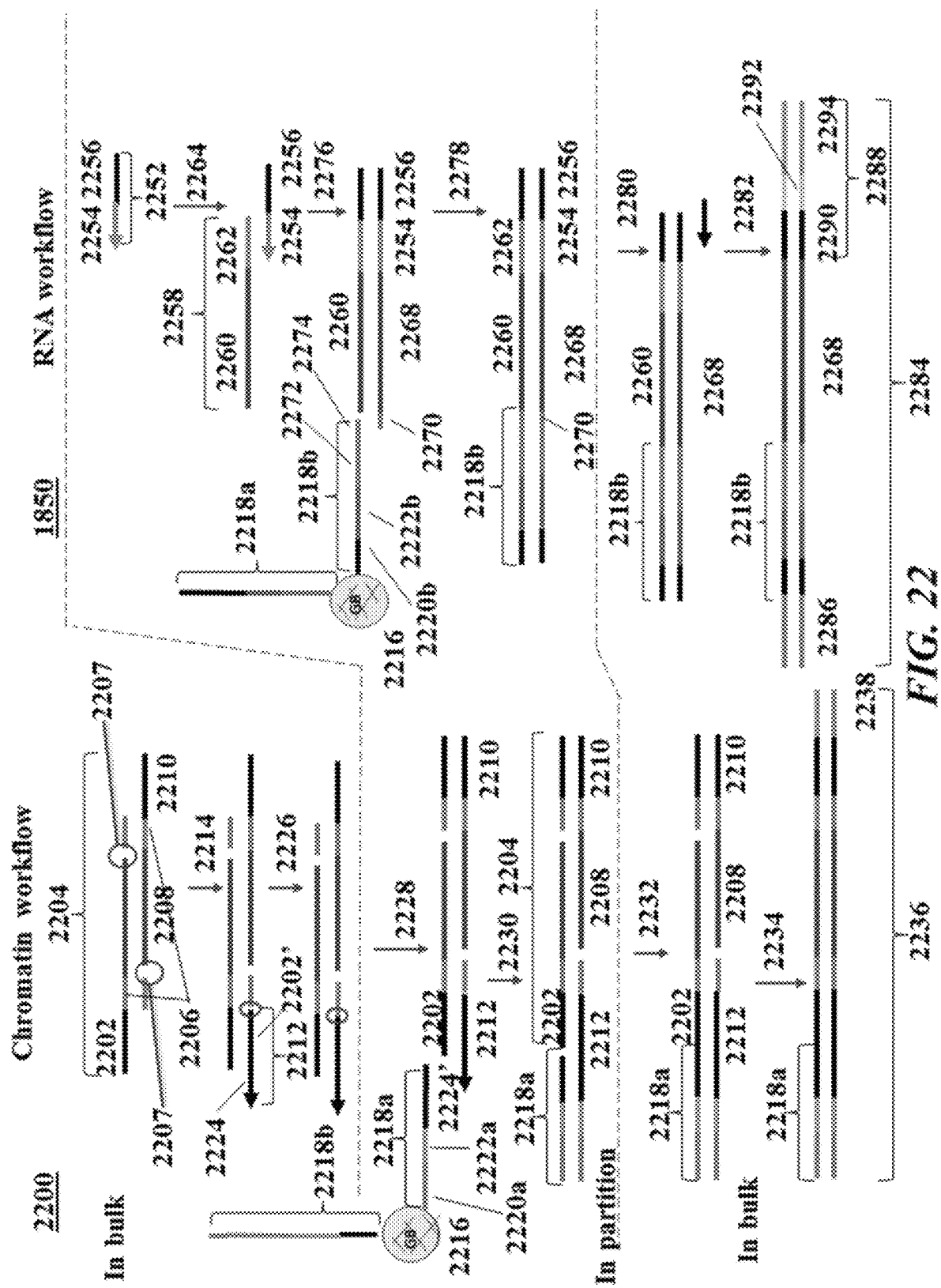
FIG. 22 illustrates a scheme for tandem ATAC and RNA processing.

FIG. 22 shows an example schematic corresponding to the preceding example. Panel 2200 shows a workflow corresponding to processing of chromatin from a cell, cell bead, or cell nucleus, and panel 2250 shows a workflow corresponding to processing of an mRNA molecule from the cell, cell bead, or cell nucleus. Multiple beads (e.g., gel beads), each comprising nucleic acid barcode molecules configured for analysis of DNA or RNA molecules, may be included within a partition. Alternatively, a single bead (e.g., gel bead) comprising nucleic acid barcode molecules configured for analysis of both DNA and RNA molecules (e.g., as described herein) may be included within a given partition.

As shown in panel 2200, in bulk solution, chromatin included within a cell, cell bead, or cell nucleus is processed (e.g., as described herein) to provide a template nucleic acid fragment (e.g., tagmented fragment) 2204 comprising insert sequence 2208 (e.g., region of open chromatin) and a complement thereof, transposon end sequences 2206 and complements thereof, sequencing primer or portion thereof 2202 (e.g., an R1 sequence), sequencing primer or portion thereof 2210 (e.g., an R2 sequence), and gaps 2207. The cell, cell bead, or cell nucleus comprising template nucleic acid fragment 2204 may be lysed, permeabilized, or otherwise processed to provide access to template nucleic acid fragment 2204 (and one or more RNA molecules) therein. Template nucleic acid fragment 2204 may be contacted with splint sequence 2212, which splint sequence may comprise a first sequence 2202' that is complementary to sequencing primer or portion thereof 2202 and a second sequence 2224. Sequence 2224 may comprise a blocking group (e.g., a 3' blocking group), which blocking group may prevent extension by reverse transcription. Sequence 2202' may hybridize 2214 to sequence 2202 of template nucleic acid fragment 2204 to provide a partially double-stranded nucleic acid molecule comprising splint sequence 2212 and template nucleic acid fragment 2204. Sequence 2202' may be ligated 2226 to the complement of transposon end sequence 2206 of template nucleic acid fragment 2204 (e.g., using a ligase). Template nucleic acid fragment 2204 attached to splint sequence 2212 may then be partitioned within a partition (e.g., droplet or well) within a plurality of partitions (e.g., as described herein). The partition may also include a bead (e.g., gel bead) 2216 coupled to nucleic acid barcode molecules 2218a and 2218b. Nucleic acid barcode molecule 2218a may comprise a flow cell adapter sequence 2220a (e.g., a P5 sequence), a barcode sequence 2222a, and an overhang sequence 2224' that is complementary to sequence 2224 of the splint sequence 2212. Sequence 2224 may hybridize 2228 to sequence 2224'. Splint sequence 2212 may then be extended 2230 (e.g., using a reverse transcriptase or DNA polymerase) to provide sequences 2220a' and 2222a' that are complementary to sequences 2220a and 2222a of nucleic acid barcode molecule 2218a. Alternatively, sequence 2224 may hybridize to sequence 2224' to provide a partially double-stranded nucleic acid molecule and nucleic acid barcode molecule 2218a may be ligated (e.g., using a ligase) to sequence 2202 of template nucleic acid fragment 2204. The contents of the partition may then be recovered in bulk solution (e.g., a droplet may be broken) to provide the partially double-stranded nucleic acid molecule comprising nucleic acid barcode molecule 2218a attached to splint sequence 2212 and template nucleic acid fragment 2204 in bulk solution. Sequence 2224' of nucleic acid barcode molecule 2218a may be ligated (e.g., using a ligase) 2232 to sequence 2202 of template nucleic acid fragment 2204. In bulk solution, gaps 2207 may be filled 2234 via a gap filling extension process (e.g., using a DNA polymerase) to provide a double-stranded nucleic acid molecule. This molecule may also undergo amplification (e.g., PCR) to provide a double-stranded amplification product 2236 that includes sequences of the nucleic acid barcode molecule 2218a, the original chromatin molecule, and, optionally, an additional sequence 2238 that may be a flow cell adapter sequence (e.g., a P7 sequence). Gaps may be filled in the partition prior to bulk processing.

In parallel to the chromatin workflow of panel 2200, an RNA molecule deriving from the same cell, cell bead, or cell nucleus may be processed. As shown in panel 2250, RNA molecule 2258 comprising RNA sequence 2260 and polyA sequence 2262 may be contacted 2264 with primer molecule 2252 comprising polyT sequence 2254 and additional primer sequence 2256. RNA molecule 2258 may then be reverse transcribed 2276 off of polyT sequence 2254 using a reverse transcriptase with terminal transferase activity, which reverse transcriptase may append sequence 2270 to the resultant cDNA molecule comprising cDNA sequence 2268. Sequence 2270 may be a polyC sequence. Bead (e.g., gel bead) 2216 (e.g., the same bead described in panel 2200) may be included within the partition and may be coupled to nucleic acid barcode molecule 2218b. Nucleic acid barcode molecule 2218b may comprise a flow cell adapter sequence 2220b (e.g., a P5 sequence), a barcode sequence 2222b, UMI sequence 2272, and a sequence 2274 complementary to sequence 2270 (e.g., a polyG sequence). In some instances, nucleic acid barcode molecule 2218b may comprise a sequencing primer sequence 2220b (e.g., an R1 sequence or partial R1 sequence), a barcode sequence 2222b, UMI sequence 2272, and a sequence 2274 complementary to sequence 2270 (e.g., a polyG sequence). Nucleic acid barcode molecule 2218b may be used to perform template switching 2278, which process may also result in the generation of a barcoded cDNA molecule. The contents of the partition may then be recovered in bulk solution (e.g., a droplet may be broken) to provide the barcoded cDNA molecule in bulk solution. The barcoded cDNA molecule may undergo amplification (e.g., PCR) 2280 to provide a double-stranded amplification product 2284 that includes sequences of the nucleic acid barcode molecule 2218b, the original RNA molecule or cDNA corresponding thereto, a flow cell adapter sequence 2286, and an additional sequence 2288 that may comprise a sequencing primer or portion thereof (e.g., an R2 sequence) 2290, a sample index sequence 2292, and a flow cell adapter sequence (e.g., a P7 sequence) 2294. The barcoded cDNA molecule may also or alternatively undergo fragmentation, end repair, dA tailing, ligation of one or more adapter sequences, and/or nucleic acid amplification.

Figure 23:
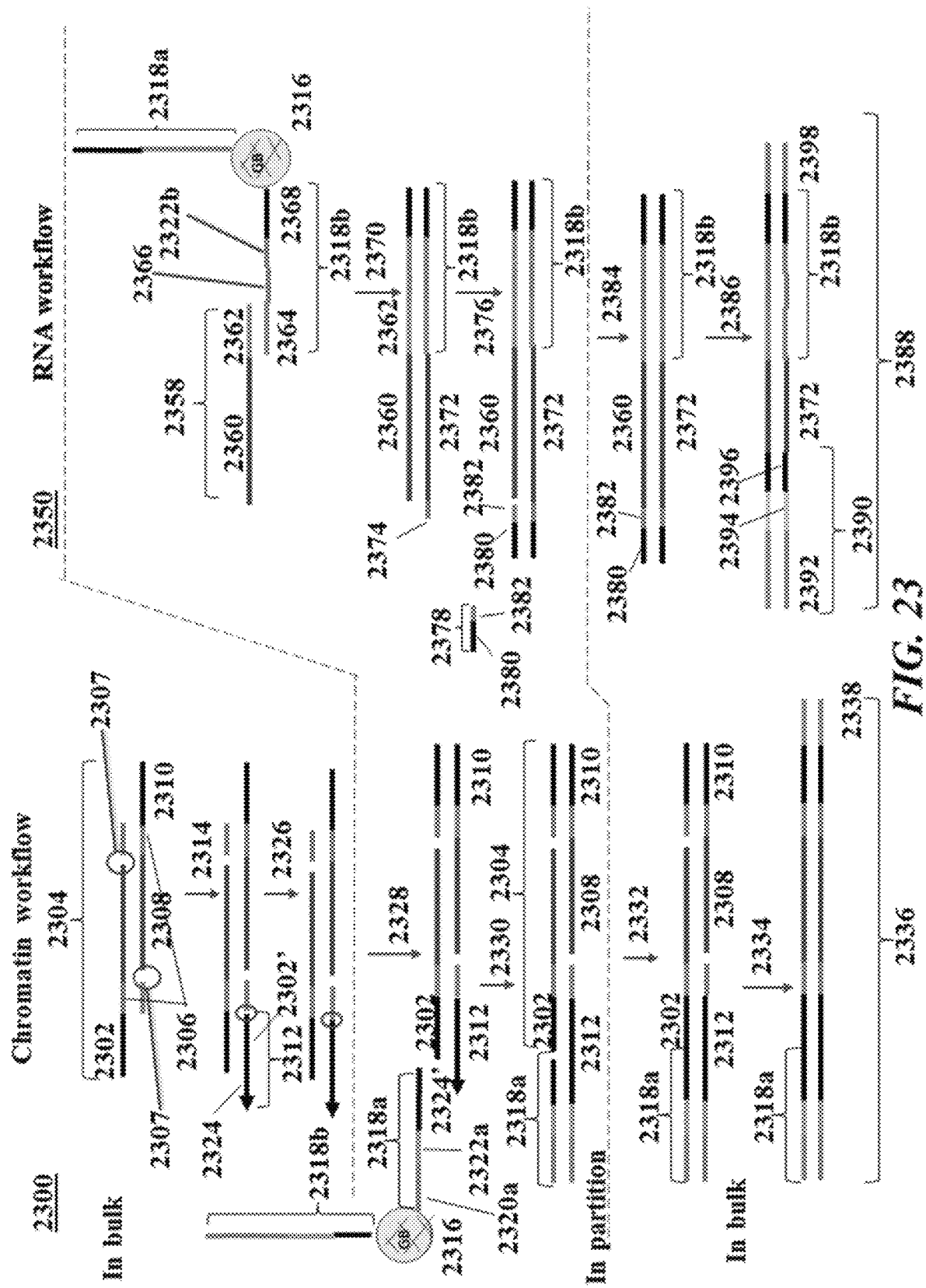
FIG. 23 illustrates a scheme for tandem ATAC and RNA processing.

FIG. 23 shows another example schematic corresponding to the preceding example. Panel 2300 shows a workflow corresponding to processing of chromatin from a cell, cell bead, or cell nucleus, and panel 2350 shows a workflow corresponding to processing of an mRNA molecule from the cell, cell bead, or cell nucleus. Multiple beads (e.g., gel beads), each comprising nucleic acid barcode molecules configured for analysis of DNA or RNA molecules, may be included within a partition. Alternatively, a single bead (e.g., gel bead) comprising nucleic acid barcode molecules configured for analysis of both DNA and RNA molecules (e.g., as described herein) may be included within a given partition.

As shown in panel 2300, in bulk solution, chromatin included within a cell, cell bead, or cell nucleus is processed (e.g., as described herein) to provide a template nucleic acid fragment (e.g., tagmented fragment) 2304 comprising insert sequence 2308 (e.g., region of open chromatin) and a complement thereof, transposon end sequences 2306 and complements thereof, sequencing primer or portion thereof 2302 (e.g., an R1 sequence), sequencing primer or portion thereof 2310 (e.g., an R2 sequence), and gaps 2307. The cell, cell bead, or cell nucleus comprising template nucleic acid fragment 2304 may be lysed, permeabilized, or otherwise processed to provide access to template nucleic acid fragment 2304 (and one or more RNA molecules) therein. Template nucleic acid fragment 2304 may be contacted with splint sequence 2312, which splint sequence may comprise a first sequence 2302' that is complementary to sequencing primer or portion thereof 2302 and a second sequence 2324. Sequence 2324 may comprise a blocking group (e.g., a 3' blocking group), which blocking group may prevent extension by reverse transcription. Sequence 2302' may hybridize 2314 to sequence 2302 of template nucleic acid fragment 2304 to provide a partially double-stranded nucleic acid molecule comprising splint sequence 2312 and template nucleic acid fragment 2304. Sequence 2302' may be ligated 2326 to the complement of transposon end sequence 2306 of template nucleic acid fragment 2304 (e.g., using a ligase). Template nucleic acid fragment 2304 attached to splint sequence 2312 may then be partitioned within a partition (e.g., droplet or well) within a plurality of partitions (e.g., as described herein). The partition may also include a bead (e.g., gel bead) 2316 coupled to nucleic acid barcode molecules 2318a and 2318b. Nucleic acid barcode molecule 2318a may comprise a flow cell adapter sequence 2320a (e.g., a P5 sequence), a barcode sequence 2322a, and an overhang sequence 2324' that is complementary to sequence 2324 of the splint sequence 2312. Sequence 2324 may hybridize 2328 to sequence 2324'. Splint sequence 2312 may then be extended 2330 (e.g., using a reverse transcriptase or DNA polymerase) to provide sequences 2320a' and 2322a' that are complementary to sequences 2320a and 2322a of nucleic acid barcode molecule 2318a. Alternatively, sequence 2324 may hybridize to sequence 2324' to provide a partially double-stranded nucleic acid molecule and nucleic acid barcode molecule 2318a may be ligated (e.g., using a ligase) to sequence 2302 of template nucleic acid fragment 2304. The contents of the partition may then be recovered in bulk solution (e.g., a droplet may be broken) to provide the partially double-stranded nucleic acid molecule comprising nucleic acid barcode molecule 2318a attached to splint sequence 2312 and template nucleic acid fragment 2304 in bulk solution. Sequence 2324' of nucleic acid barcode molecule 2318a may be ligated (e.g., using a ligase) 2332 to sequence 2302 of template nucleic acid fragment 2304. In bulk solution, gaps 2307 may be filled 2334 via a gap filling extension process (e.g., using a DNA polymerase) to provide a double-stranded nucleic acid molecule. This molecule may also undergo amplification (e.g., PCR) to provide a double-stranded amplification product 2336 that includes sequences of the nucleic acid barcode molecule 2318a, the original chromatin molecule, and, optionally, an additional sequence 2338 that may be a flow cell adapter sequence (e.g., a P7 sequence). Gaps may be filled in the partition prior to bulk processing.

In parallel to the chromatin workflow of panel 2300, an RNA molecule deriving from the same cell, cell bead, or cell nucleus may be processed. As shown in panel 2350, RNA molecule 2358 comprising RNA sequence 2360 and polyA sequence 2362 and gel bead 2316 may be provided within a partition. Bead (e.g., gel bead) 2316 (e.g., the same bead described in panel 2300) may be included within the partition and may be coupled to nucleic acid barcode molecule 2318b. Nucleic acid barcode molecule 2318b may comprise a flow cell adapter sequence 2368 (e.g., a P5 sequence), a barcode sequence 2322b (e.g., the same barcode sequence as barcode sequence 2322a), UMI sequence 2366, and a polyT sequence 2364 complementary to polyA sequence 2362. In some instances, nucleic acid barcode molecule 2318b may comprise a sequencing primer sequence 2368 (e.g., a R1 sequence or partial R1 sequence), a barcode sequence 2322b (e.g., the same barcode sequence as barcode sequence 2322a), UMI sequence 2366, and a polyT sequence 2364 complementary to polyA sequence 2362. PolyT sequence 2364 may hybridize to polyA sequence 2362 of RNA molecule 2358. RNA molecule 2358 may be reverse transcribed 2370 off of polyT sequence 2364 to provide an cDNA molecule comprising cDNA sequence 2372. The reverse transcription process may use a reverse transcriptase with terminal transferase activity, which reverse transcriptase may append sequence 2374 to the resultant cDNA molecule comprising cDNA sequence 2372. Sequence 2374 may be a polyC sequence. A template switch oligonucleotide 2378 comprising a primer sequence 2380 and a sequence complementary to sequence 2374 (e.g., a polyG sequence) may hybridize to the cDNA molecule. The contents of the partition may then be recovered in bulk solution (e.g., a droplet may be broken) to provide the cDNA molecule in bulk solution. The cDNA molecule may undergo amplification (e.g., PCR) 2384. Additional amplification (e.g., PCR) 2386 may to performed to provide a double-stranded amplification product 2388 that includes sequences of the nucleic acid barcode molecule 2318b, the original RNA molecule or cDNA corresponding thereto, a flow cell adapter sequence 2398 (e.g., a P7 sequence), and an additional sequence 2390 that may comprise a sequencing primer or portion thereof (e.g., an R2 sequence) 2396, a sample index sequence 2394, and a flow cell adapter sequence (e.g., a P5 sequence) 2392. The barcoded cDNA molecule may also or alternatively undergo fragmentation, end repair, dA tailing, ligation of one or more adapter sequences, and/or nucleic acid amplification.

Systems and Methods for Sample Compartmentalization

In an aspect, the systems and methods described herein provide for the compartmentalization, depositing, or partitioning of one or more particles (e.g., biological particles, macromolecular constituents of biological particles, beads, reagents, etc.) into discrete compartments or partitions (referred to interchangeably herein as partitions), where each partition maintains separation of its own contents from the contents of other partitions. The partition can be a droplet in an emulsion. A partition may comprise one or more other partitions.

A partition may include one or more particles. A partition may include one or more types of particles. For example, a partition of the present disclosure may comprise one or more biological particles and/or macromolecular constituents thereof. A partition may comprise one or more gel beads. A partition may comprise one or more cell beads. A partition may include a single gel bead, a single cell bead, or both a single cell bead and single gel bead. A partition may include one or more reagents. Alternatively, a partition may be unoccupied. For example, a partition may not comprise a bead. A cell bead can be a biological particle and/or one or more of its macromolecular constituents encased inside of a gel or polymer matrix, such as via polymerization of a droplet containing the biological particle and precursors capable of being polymerized or gelled. Unique identifiers, such as barcodes, may be injected into the droplets previous to, subsequent to, or concurrently with droplet generation, such as via a microcapsule (e.g., bead), as described elsewhere herein. Microfluidic channel networks (e.g., on a chip) can be utilized to generate partitions as described herein. Alternative mechanisms may also be employed in the partitioning of individual biological particles, including porous membranes through which aqueous mixtures of cells are extruded into non-aqueous fluids.

The partitions can be flowable within fluid streams. The partitions may comprise, for example, micro-vesicles that have an outer barrier surrounding an inner fluid center or core. In some cases, the partitions may comprise a porous matrix that is capable of entraining and/or retaining materials within its matrix. The partitions can be droplets of a first phase within a second phase, wherein the first and second phases are immiscible. For example, the partitions can be droplets of aqueous fluid within a non-aqueous continuous phase (e.g., oil phase). In another example, the partitions can be droplets of a non-aqueous fluid within an aqueous phase. In some examples, the partitions may be provided in a water-in-oil emulsion or oil-in-water emulsion. A variety of different vessels are described in, for example, U.S. Patent Application Publication No. 2014/0155295, which is entirely incorporated herein by reference for all purposes. Emulsion systems for creating stable droplets in non-aqueous or oil continuous phases are described in, for example, U.S. Patent Application Publication No. 2010/0105112, which is entirely incorporated herein by reference for all purposes.

In the case of droplets in an emulsion, allocating individual particles to discrete partitions may in one non-limiting example be accomplished by introducing a flowing stream of particles in an aqueous fluid into a flowing stream of a non-aqueous fluid, such that droplets are generated at the junction of the two streams. Fluid properties (e.g., fluid flow rates, fluid viscosities, etc.), particle properties (e.g., volume fraction, particle size, particle concentration, etc.), microfluidic architectures (e.g., channel geometry, etc.), and other parameters may be adjusted to control the occupancy of the resulting partitions (e.g., number of biological particles per partition, number of beads per partition, etc.). For example, partition occupancy can be controlled by providing the aqueous stream at a certain concentration and/or flow rate of particles. To generate single biological particle partitions, the relative flow rates of the immiscible fluids can be selected such that, on average, the partitions may contain less than one biological particle per partition in order to ensure that those partitions that are occupied are primarily singly occupied. In some cases, partitions among a plurality of partitions may contain at most one biological particle (e.g., bead, DNA, cell or cellular material). The various parameters (e.g., fluid properties, particle properties, microfluidic architectures, etc.) may be selected or adjusted such that a majority of partitions are occupied, for example, allowing for only a small percentage of unoccupied partitions. The flows and channel architectures can be controlled as to ensure a given number of singly occupied partitions, less than a certain level of unoccupied partitions and/or less than a certain level of multiply occupied partitions.

FIG. 1 shows an example of a microfluidic channel structure 100 for partitioning individual biological particles. The channel structure 100 can include channel segments 102, 104, 106 and 108 communicating at a channel junction 110. In operation, a first aqueous fluid 112 that includes suspended biological particles (or cells) 114 may be transported along channel segment 102 into junction 110, while a second fluid 116 that is immiscible with the aqueous fluid 112 is delivered to the junction 110 from each of channel segments 104 and 106 to create discrete droplets 118, 120 of the first aqueous fluid 112 flowing into channel segment 108, and flowing away from junction 110. The channel segment 108 may be fluidically coupled to an outlet reservoir where the discrete droplets can be stored and/or harvested. A discrete droplet generated may include an individual biological particle 114 (such as droplets 118). A discrete droplet generated may include more than one individual biological particle 114 (not shown in FIG. 1). A discrete droplet may contain no biological particle 114 (such as droplet 120). Each discrete partition may maintain separation of its own contents (e.g., individual biological particle 114) from the contents of other partitions.

The second fluid 116 can comprise an oil, such as a fluorinated oil, that includes a fluorosurfactant for stabilizing the resulting droplets, for example, inhibiting subsequent coalescence of the resulting droplets 118, 120. Examples of particularly useful partitioning fluids and fluorosurfactants are described, for example, in U.S. Patent Application Publication No. 2010/0105112, which is entirely incorporated herein by reference for all purposes.

As will be appreciated, the channel segments described herein may be coupled to any of a variety of different fluid sources or receiving components, including reservoirs, tubing, manifolds, or fluidic components of other systems. As will be appreciated, the microfluidic channel structure 100 may have other geometries. For example, a microfluidic channel structure can have more than one channel junction. For example, a microfluidic channel structure can have 2, 3, 4, or 5 channel segments each carrying particles (e.g., biological particles, cell beads, and/or gel beads) that meet at a channel junction. Fluid may be directed to flow along one or more channels or reservoirs via one or more fluid flow units. A fluid flow unit can comprise compressors (e.g., providing positive pressure), pumps (e.g., providing negative pressure), actuators, and the like to control flow of the fluid. Fluid may also or otherwise be controlled via applied pressure differentials, centrifugal force, electrokinetic pumping, vacuum, capillary or gravity flow, or the like.

The generated droplets may comprise two subsets of droplets: (1) occupied droplets 118, containing one or more biological particles 114, and (2) unoccupied droplets 120, not containing any biological particles 114. Occupied droplets 118 may comprise singly occupied droplets (having one biological particle) and multiply occupied droplets (having more than one biological particle). As described elsewhere herein, in some cases, the majority of occupied partitions can include no more than one biological particle per occupied partition and some of the generated partitions can be unoccupied (of any biological particle). In some cases, though, some of the occupied partitions may include more than one biological particle. In some cases, the partitioning process may be controlled such that fewer than about 25% of the occupied partitions contain more than one biological particle, and in many cases, fewer than about 20% of the occupied partitions have more than one biological particle, while in some cases, fewer than about 10% or even fewer than about 5% of the occupied partitions include more than one biological particle per partition.

In some cases, it may be desirable to minimize the creation of excessive numbers of empty partitions, such as to reduce costs and/or increase efficiency. While this minimization may be achieved by providing a sufficient number of biological particles (e.g., biological particles 114) at the partitioning junction 110, such as to ensure that at least one biological particle is encapsulated in a partition, the Poissonian distribution may expectedly increase the number of partitions that include multiple biological particles. As such, where singly occupied partitions are to be obtained, at most about 95%, 90%, 85%, 80%, 75%, 70%, 65%, 60%, 55%, 50%, 45%, 40%, 35%, 30%, 25%, 20%, 15%, 10%, 5% or less of the generated partitions can be unoccupied.

In some cases, the flow of one or more of the biological particles (e.g., in channel segment 102), or other fluids directed into the partitioning junction (e.g., in channel segments 104, 106) can be controlled such that, in many cases, no more than about 50% of the generated partitions, no more than about 25% of the generated partitions, or no more than about 10% of the generated partitions are unoccupied. These flows can be controlled so as to present a non-Poissonian distribution of single-occupied partitions while providing lower levels of unoccupied partitions. The above noted ranges of unoccupied partitions can be achieved while still providing any of the single occupancy rates described above. For example, in many cases, the use of the systems and methods described herein can create resulting partitions that have multiple occupancy rates of less than about 25%, less than about 20%, less than about 15%, less than about 10%, and in many cases, less than about 5%, while having unoccupied partitions of less than about 50%, less than about 40%, less than about 30%, less than about 20%, less than about 10%, less than about 5%, or less.

Figure 2:
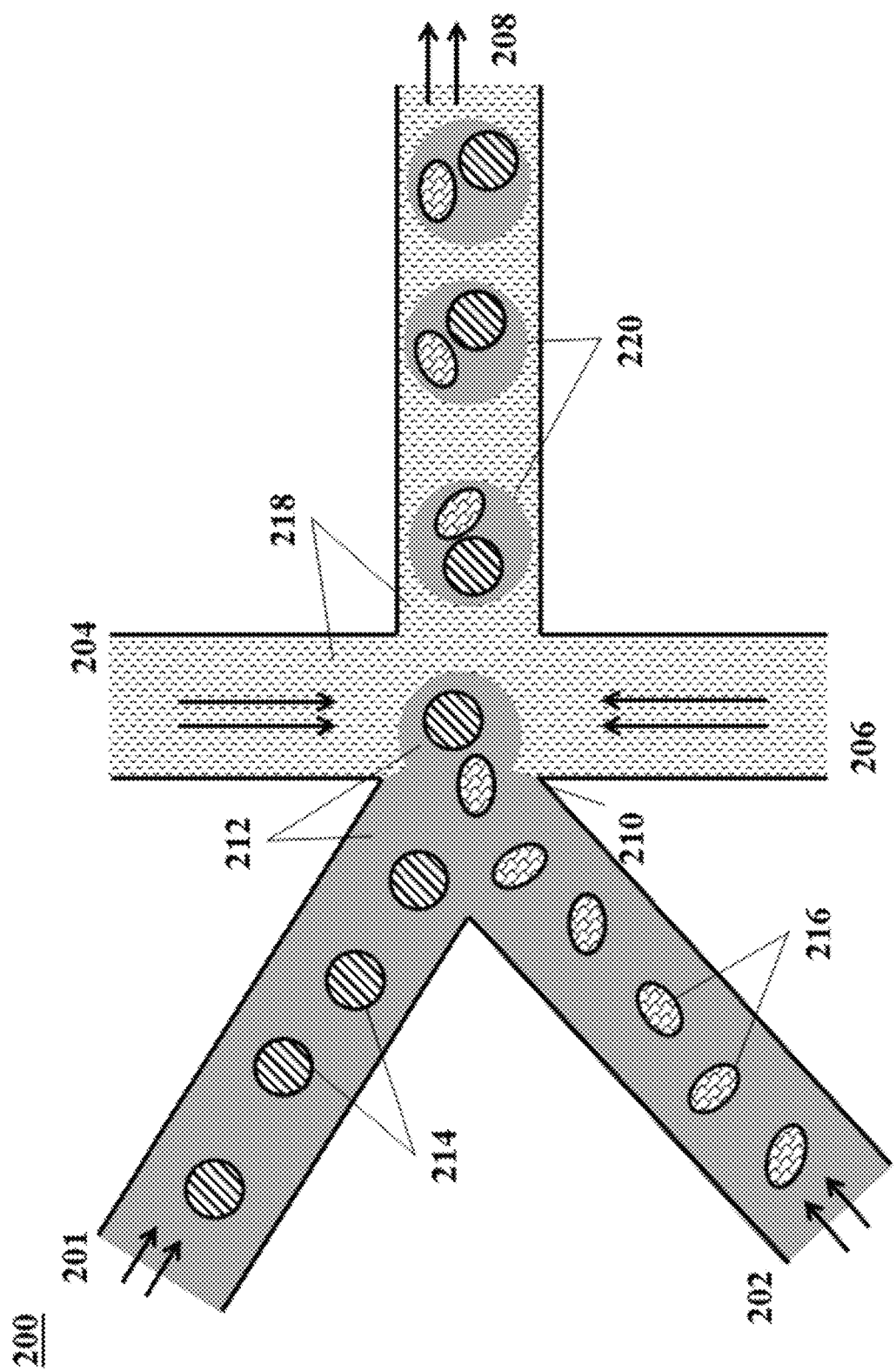
FIG. 2 shows an example of a microfluidic channel structure for delivering barcode carrying beads to droplets.

As will be appreciated, the above-described occupancy rates are also applicable to partitions that include both biological particles and additional reagents, including, but not limited to, microcapsules or beads (e.g., gel beads) carrying barcoded nucleic acid molecules (e.g., oligonucleotides) (described in relation to FIG. 2). The occupied partitions (e.g., at least about 10%, 20%, 30%, 40%, 50%, 60%, 70%, 80%, 90%, 95%, or 99% of the occupied partitions) can include both a microcapsule (e.g., bead) comprising barcoded nucleic acid molecules and a biological particle.

In another aspect, in addition to or as an alternative to droplet based partitioning, biological particles may be encapsulated within a microcapsule that comprises an outer shell, layer or porous matrix in which is entrained one or more individual biological particles or small groups of biological particles. The microcapsule may include other reagents. Encapsulation of biological particles may be performed by a variety of processes. Such processes may combine an aqueous fluid containing the biological particles with a polymeric precursor material that may be capable of being formed into a gel or other solid or semi-solid matrix upon application of a particular stimulus to the polymer precursor. Such stimuli can include, for example, thermal stimuli (e.g., either heating or cooling), photo-stimuli (e.g., through photo-curing), chemical stimuli (e.g., through cross-linking, polymerization initiation of the precursor (e.g., through added initiators)), mechanical stimuli, or a combination thereof.

Preparation of microcapsules comprising biological particles may be performed by a variety of methods. For example, air knife droplet or aerosol generators may be used to dispense droplets of precursor fluids into gelling solutions in order to form microcapsules that include individual biological particles or small groups of biological particles. Likewise, membrane based encapsulation systems may be used to generate microcapsules comprising encapsulated biological particles as described herein. Microfluidic systems of the present disclosure, such as that shown in FIG. 1, may be readily used in encapsulating cells as described herein. In particular, and with reference to FIG. 1, the aqueous fluid 112 comprising (i) the biological particles 114 and (ii) the polymer precursor material (not shown) is flowed into channel junction 110, where it is partitioned into droplets 118, 120 through the flow of non-aqueous fluid 116. In the case of encapsulation methods, non-aqueous fluid 116 may also include an initiator (not shown) to cause polymerization and/or crosslinking of the polymer precursor to form the microcapsule that includes the entrained biological particles. Examples of polymer precursor/initiator pairs include those described in U.S. Patent Application Publication No. 2014/0378345, which is entirely incorporated herein by reference for all purposes.

For example, in the case where the polymer precursor material comprises a linear polymer material, such as a linear polyacrylamide, PEG, or other linear polymeric material, the activation agent may comprise a cross-linking agent, or a chemical that activates a cross-linking agent within the formed droplets. Likewise, for polymer precursors that comprise polymerizable monomers, the activation agent may comprise a polymerization initiator. For example, in certain cases, where the polymer precursor comprises a mixture of acrylamide monomer with a N,N'-bis-(acryloyl) cystamine (BAC) comonomer, an agent such as tetraethylmethylenediamine (TEMED) may be provided within the second fluid streams 116 in channel segments 104 and 106, which can initiate the copolymerization of the acrylamide and BAC into a cross-linked polymer network, or hydrogel.

Upon contact of the second fluid stream 116 with the first fluid stream 112 at junction 110, during formation of droplets, the TEMED may diffuse from the second fluid 116 into the aqueous fluid 112 comprising the linear polyacrylamide, which will activate the crosslinking of the polyacrylamide within the droplets 118, 120, resulting in the formation of gel (e.g., hydrogel) microcapsules, as solid or semi-solid beads or particles entraining the cells 114. Although described in terms of polyacrylamide encapsulation, other 'activatable' encapsulation compositions may also be employed in the context of the methods and compositions described herein. For example, formation of alginate droplets followed by exposure to divalent metal ions (e.g., Ca' ions), can be used as an encapsulation process using the described processes. Likewise, agarose droplets may also be transformed into capsules through temperature based gelling (e.g., upon cooling, etc.).

In some cases, encapsulated biological particles can be selectively releasable from the microcapsule, such as through passage of time or upon application of a particular stimulus, that degrades the microcapsule sufficiently to allow the biological particles (e.g., cell), or its other contents to be released from the microcapsule, such as into a partition (e.g., droplet). For example, in the case of the polyacrylamide polymer described above, degradation of the microcapsule may be accomplished through the introduction of an appropriate reducing agent, such as DTT or the like, to cleave disulfide bonds that cross-link the polymer matrix. See, for example, U.S. Patent Application Publication No. 2014/0378345, which is entirely incorporated herein by reference for all purposes.

The biological particle can be subjected to other conditions sufficient to polymerize or gel the precursors. The conditions sufficient to polymerize or gel the precursors may comprise exposure to heating, cooling, electromagnetic radiation, and/or light. The conditions sufficient to polymerize or gel the precursors may comprise any conditions sufficient to polymerize or gel the precursors. Following polymerization or gelling, a polymer or gel may be formed around the biological particle. The polymer or gel may be diffusively permeable to chemical or biochemical reagents. The polymer or gel may be diffusively impermeable to macromolecular constituents of the biological particle. In this manner, the polymer or gel may act to allow the biological particle to be subjected to chemical or biochemical operations while spatially confining the macromolecular constituents to a region of the droplet defined by the polymer or gel. The polymer or gel may include one or more of disulfide cross-linked polyacrylamide, agarose, alginate, polyvinyl alcohol, polyethylene glycol (PEG)-diacrylate, PEG-acrylate, PEG-thiol, PEG-azide, PEG-alkyne, other acrylates, chitosan, hyaluronic acid, collagen, fibrin, gelatin, or elastin. The polymer or gel may comprise any other polymer or gel.

The polymer or gel may be functionalized to bind to targeted analytes, such as nucleic acids, proteins, carbohydrates, lipids or other analytes. The polymer or gel may be polymerized or gelled via a passive mechanism. The polymer or gel may be stable in alkaline conditions or at elevated temperature. The polymer or gel may have mechanical properties similar to the mechanical properties of the bead. For instance, the polymer or gel may be of a similar size to the bead. The polymer or gel may have a mechanical strength (e.g. tensile strength) similar to that of the bead. The polymer or gel may be of a lower density than an oil. The polymer or gel may be of a density that is roughly similar to that of a buffer. The polymer or gel may have a tunable pore size. The pore size may be chosen to, for instance, retain denatured nucleic acids. The pore size may be chosen to maintain diffusive permeability to exogenous chemicals such as sodium hydroxide (NaOH) and/or endogenous chemicals such as inhibitors. The polymer or gel may be biocompatible. The polymer or gel may maintain or enhance cell viability. The polymer or gel may be biochemically compatible. The polymer or gel may be polymerized and/or depolymerized thermally, chemically, enzymatically, and/or optically.

The polymer may comprise poly(acrylamide-co-acrylic acid) crosslinked with disulfide linkages. The preparation of the polymer may comprise a two-step reaction. In the first activation step, poly(acrylamide-co-acrylic acid) may be exposed to an acylating agent to convert carboxylic acids to esters. For instance, the poly(acrylamide-co-acrylic acid) may be exposed to 4-(4,6-dimethoxy-1,3,5-triazin-2-yl)-4-methylmorpholinium chloride (DMTMM). The polyacrylamide-co-acrylic acid may be exposed to other salts of 4-(4,6-dimethoxy-1,3,5-triazin-2-yl)-4-methylmorpholinium. In the second cross-linking step, the ester formed in the first step may be exposed to a disulfide crosslinking agent. For instance, the ester may be exposed to cystamine (2,2'-dithiobis(ethylamine)). Following the two steps, the biological particle may be surrounded by polyacrylamide strands linked together by disulfide bridges. In this manner, the biological particle may be encased inside of or comprise a gel or matrix (e.g., polymer matrix) to form a "cell bead." A cell bead can contain biological particles (e.g., a cell) or macromolecular constituents (e.g., RNA, DNA, proteins, etc.) of biological particles. A cell bead may include a single cell or multiple cells, or a derivative of the single cell or multiple cells. For example after lysing and washing the cells, inhibitory components from cell lysates can be washed away and the macromolecular constituents can be bound as cell beads. Systems and methods disclosed herein can be applicable to both cell beads (and/or droplets or other partitions) containing biological particles and cell beads (and/or droplets or other partitions) containing macromolecular constituents of biological particles.

Encapsulated biological particles can provide certain potential advantages of being more storable and more portable than droplet-based partitioned biological particles. Furthermore, in some cases, it may be desirable to allow biological particles to incubate for a select period of time before analysis, such as in order to characterize changes in such biological particles over time, either in the presence or absence of different stimuli. In such cases, encapsulation may allow for longer incubation than partitioning in emulsion droplets, although in some cases, droplet partitioned biological particles may also be incubated for different periods of time, e.g., at least 10 seconds, at least 30 seconds, at least 1 minute, at least 5 minutes, at least 10 minutes, at least 30 minutes, at least 1 hour, at least 2 hours, at least 5 hours, or at least 10 hours or more. The encapsulation of biological particles may constitute the partitioning of the biological particles into which other reagents are co-partitioned. Alternatively or in addition, encapsulated biological particles may be readily deposited into other partitions (e.g., droplets) as described above.

Beads

A partition may comprise one or more unique identifiers, such as barcodes. Barcodes may be previously, subsequently or concurrently delivered to the partitions that hold the compartmentalized or partitioned biological particle. For example, barcodes may be injected into droplets previous to, subsequent to, or concurrently with droplet generation. The delivery of the barcodes to a particular partition allows for the later attribution of the characteristics of the individual biological particle to the particular partition. Barcodes may be delivered, for example on a nucleic acid molecule (e.g., an oligonucleotide), to a partition via any suitable mechanism. Barcoded nucleic acid molecules can be delivered to a partition via a microcapsule. A microcapsule, in some instances, can comprise a bead. Beads are described in further detail below.

In some cases, barcoded nucleic acid molecules can be initially associated with the microcapsule and then released from the microcapsule. Release of the barcoded nucleic acid molecules can be passive (e.g., by diffusion out of the microcapsule). In addition or alternatively, release from the microcapsule can be upon application of a stimulus which allows the barcoded nucleic acid nucleic acid molecules to dissociate or to be released from the microcapsule. Such stimulus may disrupt the microcapsule, an interaction that couples the barcoded nucleic acid molecules to or within the microcapsule, or both. Such stimulus can include, for example, a thermal stimulus, photo-stimulus, chemical stimulus (e.g., change in pH or use of a reducing agent(s)), a mechanical stimulus, a radiation stimulus; a biological stimulus (e.g., enzyme), or any combination thereof.

FIG. 2 shows an example of a microfluidic channel structure 200 for delivering barcode carrying beads to droplets. The channel structure 200 can include channel segments 201, 202, 204, 206 and 208 communicating at a channel junction 210. In operation, the channel segment 201 may transport an aqueous fluid 212 that includes a plurality of beads 214 (e.g., with nucleic acid molecules, oligonucleotides, molecular tags) along the channel segment 201 into junction 210. The plurality of beads 214 may be sourced from a suspension of beads. For example, the channel segment 201 may be connected to a reservoir comprising an aqueous suspension of beads 214. The channel segment 202 may transport the aqueous fluid 212 that includes a plurality of biological particles 216 along the channel segment 202 into junction 210. The plurality of biological particles 216 may be sourced from a suspension of biological particles. For example, the channel segment 202 may be connected to a reservoir comprising an aqueous suspension of biological particles 216. In some instances, the aqueous fluid 212 in either the first channel segment 201 or the second channel segment 202, or in both segments, can include one or more reagents, as further described below. A second fluid 218 that is immiscible with the aqueous fluid 212 (e.g., oil) can be delivered to the junction 210 from each of channel segments 204 and 206. Upon meeting of the aqueous fluid 212 from each of channel segments 201 and 202 and the second fluid 218 from each of channel segments 204 and 206 at the channel junction 210, the aqueous fluid 212 can be partitioned as discrete droplets 220 in the second fluid 218 and flow away from the junction 210 along channel segment 208. The channel segment 208 may deliver the discrete droplets to an outlet reservoir fluidly coupled to the channel segment 208, where they may be harvested.

As an alternative, the channel segments 201 and 202 may meet at another junction upstream of the junction 210. At such junction, beads and biological particles may form a mixture that is directed along another channel to the junction 210 to yield droplets 220. The mixture may provide the beads and biological particles in an alternating fashion, such that, for example, a droplet comprises a single bead and a single biological particle.

Beads, biological particles and droplets may flow along channels at substantially regular flow profiles (e.g., at regular flow rates). Such regular flow profiles may permit a droplet to include a single bead and a single biological particle. Such regular flow profiles may permit the droplets to have an occupancy (e.g., droplets having beads and biological particles) greater than 5%, 10%, 20%, 30%, 40%, 50%, 60%, 70%, 80%, 90%, or 95%. Such regular flow profiles and devices that may be used to provide such regular flow profiles are provided in, for example, U.S. Patent Publication No. 2015/0292988, which is entirely incorporated herein by reference.

The second fluid 218 can comprise an oil, such as a fluorinated oil, that includes a fluorosurfactant for stabilizing the resulting droplets, for example, inhibiting subsequent coalescence of the resulting droplets 220.

A discrete droplet that is generated may include an individual biological particle 216. A discrete droplet that is generated may include a barcode or other reagent carrying bead 214. A discrete droplet generated may include both an individual biological particle and a barcode carrying bead, such as droplets 220. In some instances, a discrete droplet may include more than one individual biological particle or no biological particle. In some instances, a discrete droplet may include more than one bead or no bead. A discrete droplet may be unoccupied (e.g., no beads, no biological particles).

Beneficially, a discrete droplet partitioning a biological particle and a barcode carrying bead may effectively allow the attribution of the barcode to macromolecular constituents of the biological particle within the partition. The contents of a partition may remain discrete from the contents of other partitions.

As will be appreciated, the channel segments described herein may be coupled to any of a variety of different fluid sources or receiving components, including reservoirs, tubing, manifolds, or fluidic components of other systems. As will be appreciated, the microfluidic channel structure 200 may have other geometries. For example, a microfluidic channel structure can have more than one channel junctions. For example, a microfluidic channel structure can have 2, 3, 4, or 5 channel segments each carrying beads that meet at a channel junction. Fluid may be directed flow along one or more channels or reservoirs via one or more fluid flow units. A fluid flow unit can comprise compressors (e.g., providing positive pressure), pumps (e.g., providing negative pressure), actuators, and the like to control flow of the fluid. Fluid may also or otherwise be controlled via applied pressure differentials, centrifugal force, electrokinetic pumping, vacuum, capillary or gravity flow, or the like.

A bead may be porous, non-porous, solid, semi-solid, semi-fluidic, fluidic, and/or a combination thereof. In some instances, a bead may be dissolvable, disruptable, and/or degradable. In some cases, a bead may not be degradable. In some cases, the bead may be a gel bead. A gel bead may be a hydrogel bead. A gel bead may be formed from molecular precursors, such as a polymeric or monomeric species. A semi-solid bead may be a liposomal bead. Solid beads may comprise metals including iron oxide, gold, and silver. In some cases, the bead may be a silica bead. In some cases, the bead can be rigid. In other cases, the bead may be flexible and/or compressible.

A bead may be of any suitable shape. Examples of bead shapes include, but are not limited to, spherical, non-spherical, oval, oblong, amorphous, circular, cylindrical, and variations thereof.

Beads may be of uniform size or heterogeneous size. In some cases, the diameter of a bead may be at least about 10 nanometers (nm), 100 nm, 500 nm, 1 micrometer (µm), 5 µm, 10 µm, 20 µm, 30 µm, 40 µm, 50 µm, 60 µm, 70 µm, 80 µm, 90 µm, 100 µm, 250 µm, 500 µm, 1 mm, or greater. In some cases, a bead may have a diameter of less than about 10 nm, 100 nm, 500 nm, 1 µm, 5 µm, 10 µm, 20 µm, 30 µm, 40 µm, 50 µm, 60 µm, 70 µm, 80 µm, 90 µm, 100 µm, 250 µm, 500 µm, 1 mm, or less. In some cases, a bead may have a diameter in the range of about 40-75 µm, 30-75 µm, 20-75 µm, 40-85 µm, 40-95 µm, 20-100 µm, 10-100 µm, 1-100 µm, 20-250 µm, or 20-500 µm.

In certain aspects, beads can be provided as a population or plurality of beads having a relatively monodisperse size distribution. Where it may be desirable to provide relatively consistent amounts of reagents within partitions, maintaining relatively consistent bead characteristics, such as size, can contribute to the overall consistency. In particular, the beads described herein may have size distributions that have a coefficient of variation in their cross-sectional dimensions of less than 50%, less than 40%, less than 30%, less than 20%, and in some cases less than 15%, less than 10%, less than 5%, or less.

A bead may comprise natural and/or synthetic materials. For example, a bead can comprise a natural polymer, a synthetic polymer or both natural and synthetic polymers. Examples of natural polymers include proteins and sugars such as deoxyribonucleic acid, rubber, cellulose, starch (e.g., amylose, amylopectin), proteins, enzymes, polysaccharides, silks, polyhydroxyalkanoates, chitosan, dextran, collagen, carrageenan, ispaghula, acacia, agar, gelatin, shellac, sterculia gum, xanthan gum, Corn sugar gum, guar gum, gum karaya, agarose, alginic acid, alginate, or natural polymers thereof. Examples of synthetic polymers include acrylics, nylons, silicones, spandex, viscose rayon, polycarboxylic acids, polyvinyl acetate, polyacrylamide, polyacrylate, polyethylene glycol, polyurethanes, polylactic acid, silica, polystyrene, polyacrylonitrile, polybutadiene, polycarbonate, polyethylene, polyethylene terephthalate, poly(chlorotrifluoroethylene), poly(ethylene oxide), poly(ethylene terephthalate), polyethylene, polyisobutylene, poly(methyl methacrylate), poly(oxymethylene), polyformaldehyde, polypropylene, polystyrene, poly(tetrafluoroethylene), poly(vinyl acetate), poly(vinyl alcohol), poly(vinyl chloride), poly(vinylidene dichloride), poly(vinylidene difluoride), poly(vinyl fluoride) and/or combinations (e.g., co-polymers) thereof. Beads may also be formed from materials other than polymers, including lipids, micelles, ceramics, glass-ceramics, material composites, metals, other inorganic materials, and others.

In some instances, the bead may contain molecular precursors (e.g., monomers or polymers), which may form a polymer network via polymerization of the molecular precursors. In some cases, a precursor may be an already polymerized species capable of undergoing further polymerization via, for example, a chemical cross-linkage. In some cases, a precursor can comprise one or more of an acrylamide or a methacrylamide monomer, oligomer, or polymer. In some cases, the bead may comprise prepolymers, which are oligomers capable of further polymerization. For example, polyurethane beads may be prepared using prepolymers. In some cases, the bead may contain individual polymers that may be further polymerized together. In some cases, beads may be generated via polymerization of different precursors, such that they comprise mixed polymers, co-polymers, and/or block co-polymers. In some cases, the bead may comprise covalent or ionic bonds between polymeric precursors (e.g., monomers, oligomers, linear polymers), nucleic acid molecules (e.g., oligonucleotides), primers, and other entities. In some cases, the covalent bonds can be carbon-carbon bonds, thioether bonds, or carbon-heteroatom bonds.

Cross-linking may be permanent or reversible, depending upon the particular cross-linker used. Reversible cross-linking may allow for the polymer to linearize or dissociate under appropriate conditions. In some cases, reversible cross-linking may also allow for reversible attachment of a material bound to the surface of a bead. In some cases, a cross-linker may form disulfide linkages. In some cases, the chemical cross-linker forming disulfide linkages may be cystamine or a modified cystamine.

In some cases, disulfide linkages can be formed between molecular precursor units (e.g., monomers, oligomers, or linear polymers) or precursors incorporated into a bead and nucleic acid molecules (e.g., oligonucleotides). Cystamine (including modified cystamines), for example, is an organic agent comprising a disulfide bond that may be used as a crosslinker agent between individual monomeric or polymeric precursors of a bead. Polyacrylamide may be polymerized in the presence of cystamine or a species comprising cystamine (e.g., a modified cystamine) to generate polyacrylamide gel beads comprising disulfide linkages (e.g., chemically degradable beads comprising chemically-reducible cross-linkers). The disulfide linkages may permit the bead to be degraded (or dissolved) upon exposure of the bead to a reducing agent.

In some cases, chitosan, a linear polysaccharide polymer, may be crosslinked with glutaraldehyde via hydrophilic chains to form a bead. Crosslinking of chitosan polymers may be achieved by chemical reactions that are initiated by heat, pressure, change in pH, and/or radiation.

In some cases, a bead may comprise an acrydite moiety, which in certain aspects may be used to attach one or more nucleic acid molecules (e.g., barcode sequence, barcoded nucleic acid molecule, barcoded oligonucleotide, primer, or other oligonucleotide) to the bead. In some cases, an acrydite moiety can refer to an acrydite analogue generated from the reaction of acrydite with one or more species, such as, the reaction of acrydite with other monomers and cross-linkers during a polymerization reaction. Acrydite moieties may be modified to form chemical bonds with a species to be attached, such as a nucleic acid molecule (e.g., barcode sequence, barcoded nucleic acid molecule, barcoded oligonucleotide, primer, or other oligonucleotide). Acrydite moieties may be modified with thiol groups capable of forming a disulfide bond or may be modified with groups already comprising a disulfide bond. The thiol or disulfide (via disulfide exchange) may be used as an anchor point for a species to be attached or another part of the acrydite moiety may be used for attachment. In some cases, attachment can be reversible, such that when the disulfide bond is broken (e.g., in the presence of a reducing agent), the attached species is released from the bead. In other cases, an acrydite moiety can comprise a reactive hydroxyl group that may be used for attachment.

Functionalization of beads for attachment of nucleic acid molecules (e.g., oligonucleotides) may be achieved through a wide range of different approaches, including activation of chemical groups within a polymer, incorporation of active or activatable functional groups in the polymer structure, or attachment at the pre-polymer or monomer stage in bead production.

For example, precursors (e.g., monomers, cross-linkers) that are polymerized to form a bead may comprise acrydite moieties, such that when a bead is generated, the bead also comprises acrydite moieties. The acrydite moieties can be attached to a nucleic acid molecule (e.g., oligonucleotide), which may include a priming sequence (e.g., a primer for amplifying target nucleic acids, random primer, primer sequence for messenger RNA) and/or one or more barcode sequences. The one more barcode sequences may include sequences that are the same for all nucleic acid molecules coupled to a bead and/or sequences that are different across all nucleic acid molecules coupled to the bead. The nucleic acid molecule may be incorporated into the bead.

In some cases, the nucleic acid molecule can comprise a functional sequence, for example, for attachment to a sequencing flow cell, such as, for example, a P5 sequence for Illumina® sequencing. In some cases, the nucleic acid molecule or derivative thereof (e.g., oligonucleotide or polynucleotide generated from the nucleic acid molecule) can comprise another functional sequence, such as, for example, a P7 sequence for attachment to a sequencing flow cell for Illumina sequencing. In some cases, the nucleic acid molecule can comprise a barcode sequence. In some cases, the primer can further comprise a unique molecular identifier (UMI). In some cases, the primer can comprise an R1 primer sequence for Illumina sequencing. In some cases, the primer can comprise an R2 primer sequence for Illumina sequencing. Examples of such nucleic acid molecules (e.g., oligonucleotides, polynucleotides, etc.) and uses thereof, as may be used with compositions, devices, methods and systems of the present disclosure, are provided in U.S. Patent Pub. Nos. 2014/0378345 and 2015/0376609, each of which is entirely incorporated herein by reference.

Figure 8:
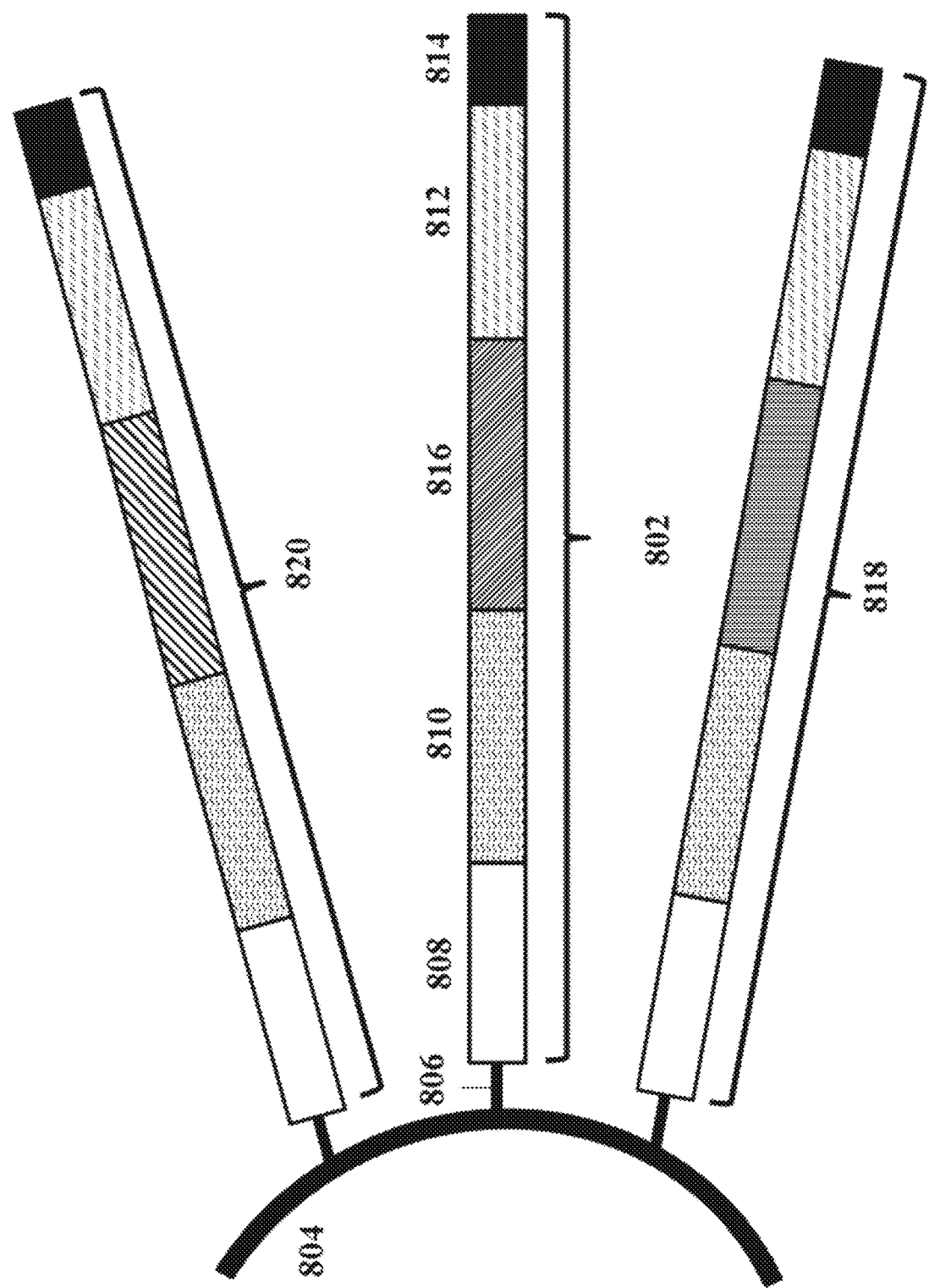
FIG. 8 illustrates an example of a barcode carrying bead.

FIG. 8 illustrates an example of a barcode carrying bead. A nucleic acid molecule 802, such as an oligonucleotide, can be coupled to a bead 804 by a releasable linkage 806, such as, for example, a disulfide linker. The same bead 804 may be coupled (e.g., via releasable linkage) to one or more other nucleic acid molecules 818, 820. The nucleic acid molecule 802 may be or comprise a barcode. As noted elsewhere herein, the structure of the barcode may comprise a number of sequence elements. The nucleic acid molecule 802 may comprise a functional sequence 808 that may be used in subsequent processing. For example, the functional sequence 808 may include one or more of a sequencer specific flow cell attachment sequence (e.g., a P5 sequence for Illumina® sequencing systems) and a sequencing primer sequence (e.g., a R1 primer for Illumina® sequencing systems). The nucleic acid molecule 802 may comprise a barcode sequence 810 for use in barcoding the sample (e.g., DNA, RNA, protein, etc.). In some cases, the barcode sequence 810 can be bead-specific such that the barcode sequence 810 is common to all nucleic acid molecules (e.g., including nucleic acid molecule 802) coupled to the same bead 804. Alternatively or in addition, the barcode sequence 810 can be partition-specific such that the barcode sequence 810 is common to all nucleic acid molecules coupled to one or more beads that are partitioned into the same partition. The nucleic acid molecule 802 may comprise a specific priming sequence 812, such as an mRNA specific priming sequence (e.g., poly-T sequence), a targeted priming sequence, and/or a random priming sequence. The nucleic acid molecule 802 may comprise an anchoring sequence 814 to ensure that the specific priming sequence 812 hybridizes at the sequence end (e.g., of the mRNA). For example, the anchoring sequence 814 can include a random short sequence of nucleotides, such as a 1-mer, 2-mer, 3-mer or longer sequence, which can ensure that a poly-T segment is more likely to hybridize at the sequence end of the poly-A tail of the mRNA.

The nucleic acid molecule 802 may comprise a unique molecular identifying sequence 816 (e.g., unique molecular identifier (UMI)). In some cases, the unique molecular identifying sequence 816 may comprise from about 5 to about 8 nucleotides. Alternatively, the unique molecular identifying sequence 816 may compress less than about 5 or more than about 8 nucleotides. The unique molecular identifying sequence 816 may be a unique sequence that varies across individual nucleic acid molecules (e.g., 802, 818, 820, etc.) coupled to a single bead (e.g., bead 804). In some cases, the unique molecular identifying sequence 816 may be a random sequence (e.g., such as a random N-mer sequence). For example, the UMI may provide a unique identifier of the starting mRNA molecule that was captured, in order to allow quantitation of the number of original expressed RNA. As will be appreciated, although FIG. 8 shows three nucleic acid molecules 802, 818, 820 coupled to the surface of the bead 804, an individual bead may be coupled to any number of individual nucleic acid molecules, for example, from one to tens to hundreds of thousands or even millions of individual nucleic acid molecules. The respective barcodes for the individual nucleic acid molecules can comprise both common sequence segments or relatively common sequence segments (e.g., 808, 810, 812, etc.) and variable or unique sequence segments (e.g., 816) between different individual nucleic acid molecules coupled to the same bead.

In operation, a biological particle (e.g., cell, DNA, RNA, etc.) can be co-partitioned along with a barcode bearing bead 804. The barcoded nucleic acid molecules 802, 818, 820 can be released from the bead 804 in the partition. By way of example, in the context of analyzing sample RNA, the poly-T segment (e.g., 812) of one of the released nucleic acid molecules (e.g., 802) can hybridize to the poly-A tail of a mRNA molecule. Reverse transcription may result in a cDNA transcript of the mRNA, but which transcript includes each of the sequence segments 808, 810, 816 of the nucleic acid molecule 802. Because the nucleic acid molecule 802 comprises an anchoring sequence 814, it will more likely hybridize to and prime reverse transcription at the sequence end of the poly-A tail of the mRNA. Within any given partition, all of the cDNA transcripts of the individual mRNA molecules may include a common barcode sequence segment 810. However, the transcripts made from the different mRNA molecules within a partition may vary at the unique molecular identifying sequence 812 segment (e.g., UMI segment). Beneficially, even following any subsequent amplification of the contents of a partition, the number of different UMIs can be indicative of the quantity of mRNA originating from a given partition, and thus from the biological particle (e.g., cell). As noted above, the transcripts can be amplified, cleaned up and sequenced to identify the sequence of the cDNA transcript of the mRNA, as well as to sequence the barcode segment and the UMI segment. While a poly-T primer sequence is described, other targeted or random priming sequences may also be used in priming the reverse transcription reaction. Likewise, although described as releasing the barcoded oligonucleotides into the partition, in some cases, the nucleic acid molecules bound to the bead (e.g., gel bead) may be used to hybridize and capture the mRNA on the solid phase of the bead, for example, in order to facilitate the separation of the RNA from other cell contents.

In some cases, precursors comprising a functional group that is reactive or capable of being activated such that it becomes reactive can be polymerized with other precursors to generate gel beads comprising the activated or activatable functional group. The functional group may then be used to attach additional species (e.g., disulfide linkers, primers, other oligonucleotides, etc.) to the gel beads. For example, some precursors comprising a carboxylic acid (COOH) group can co-polymerize with other precursors to form a gel bead that also comprises a COOH functional group. In some cases, acrylic acid (a species comprising free COOH groups), acrylamide, and bis(acryloyl)cystamine can be co-polymerized together to generate a gel bead comprising free COOH groups. The COOH groups of the gel bead can be activated (e.g., via 1-Ethyl-3-(3-dimethylaminopropyl)carbodiimide (EDC) and N-Hydroxysuccinimide (NHS) or 4-(4,6-Dimethoxy-1,3,5-triazin-2-yl)-4-methylmorpholinium chloride (DMTMM)) such that they are reactive (e.g., reactive to amine functional groups where EDC/NHS or DMTMM are used for activation). The activated COOH groups can then react with an appropriate species (e.g., a species comprising an amine functional group where the carboxylic acid groups are activated to be reactive with an amine functional group) comprising a moiety to be linked to the bead.

Beads comprising disulfide linkages in their polymeric network may be functionalized with additional species via reduction of some of the disulfide linkages to free thiols. The disulfide linkages may be reduced via, for example, the action of a reducing agent (e.g., DTT, TCEP, etc.) to generate free thiol groups, without dissolution of the bead. Free thiols of the beads can then react with free thiols of a species or a species comprising another disulfide bond (e.g., via thiol-disulfide exchange) such that the species can be linked to the beads (e.g., via a generated disulfide bond). In some cases, free thiols of the beads may react with any other suitable group. For example, free thiols of the beads may react with species comprising an acrydite moiety. The free thiol groups of the beads can react with the acrydite via Michael addition chemistry, such that the species comprising the acrydite is linked to the bead. In some cases, uncontrolled reactions can be prevented by inclusion of a thiol capping agent such as N-ethylmalieamide or iodoacetate.

Activation of disulfide linkages within a bead can be controlled such that only a small number of disulfide linkages are activated. Control may be exerted, for example, by controlling the concentration of a reducing agent used to generate free thiol groups and/or concentration of reagents used to form disulfide bonds in bead polymerization. In some cases, a low concentration (e.g., molecules of reducing agent:gel bead ratios of less than or equal to about 1:100,000,000,000, less than or equal to about 1:10,000,000,000, less than or equal to about 1:1,000,000,000, less than or equal to about 1:100,000,000, less than or equal to about 1:10,000,000, less than or equal to about 1:1,000,000, less than or equal to about 1:100,000, less than or equal to about 1:10,000) of reducing agent may be used for reduction. Controlling the number of disulfide linkages that are reduced to free thiols may be useful in ensuring bead structural integrity during functionalization. In some cases, optically-active agents, such as fluorescent dyes may be coupled to beads via free thiol groups of the beads and used to quantify the number of free thiols present in a bead and/or track a bead.

In some cases, addition of moieties to a gel bead after gel bead formation may be advantageous. For example, addition of an oligonucleotide (e.g., barcoded oligonucleotide) after gel bead formation may avoid loss of the species during chain transfer termination that can occur during polymerization. Moreover, smaller precursors (e.g., monomers or cross linkers that do not comprise side chain groups and linked moieties) may be used for polymerization and can be minimally hindered from growing chain ends due to viscous effects. In some cases, functionalization after gel bead synthesis can minimize exposure of species (e.g., oligonucleotides) to be loaded with potentially damaging agents (e.g., free radicals) and/or chemical environments. In some cases, the generated gel may possess an upper critical solution temperature (UCST) that can permit temperature driven swelling and collapse of a bead. Such functionality may aid in oligonucleotide (e.g., a primer) infiltration into the bead during subsequent functionalization of the bead with the oligonucleotide. Post-production functionalization may also be useful in controlling loading ratios of species in beads, such that, for example, the variability in loading ratio is minimized. Species loading may also be performed in a batch process such that a plurality of beads can be functionalized with the species in a single batch.

A bead injected or otherwise introduced into a partition may comprise releasably, cleavably, or reversibly attached barcodes. A bead injected or otherwise introduced into a partition may comprise activatable barcodes. A bead injected or otherwise introduced into a partition may be degradable, disruptable, or dissolvable beads.

Barcodes can be releasably, cleavably or reversibly attached to the beads such that barcodes can be released or be releasable through cleavage of a linkage between the barcode molecule and the bead, or released through degradation of the underlying bead itself, allowing the barcodes to be accessed or be accessible by other reagents, or both. In non-limiting examples, cleavage may be achieved through reduction of di-sulfide bonds, use of restriction enzymes, photo-activated cleavage, or cleavage via other types of stimuli (e.g., chemical, thermal, pH, enzymatic, etc.) and/or reactions, such as described elsewhere herein. Releasable barcodes may sometimes be referred to as being activatable, in that they are available for reaction once released. Thus, for example, an activatable barcode may be activated by releasing the barcode from a bead (or other suitable type of partition described herein). Other activatable configurations are also envisioned in the context of the described methods and systems.

In addition to, or as an alternative to the cleavable linkages between the beads and the associated molecules, such as barcode containing nucleic acid molecules (e.g., barcoded oligonucleotides), the beads may be degradable, disruptable, or dissolvable spontaneously or upon exposure to one or more stimuli (e.g., temperature changes, pH changes, exposure to particular chemical species or phase, exposure to light, reducing agent, etc.). In some cases, a bead may be dissolvable, such that material components of the beads are solubilized when exposed to a particular chemical species or an environmental change, such as a change temperature or a change in pH. In some cases, a gel bead can be degraded or dissolved at elevated temperature and/or in basic conditions. In some cases, a bead may be thermally degradable such that when the bead is exposed to an appropriate change in temperature (e.g., heat), the bead degrades. Degradation or dissolution of a bead bound to a species (e.g., a nucleic acid molecule, e.g., barcoded oligonucleotide) may result in release of the species from the bead.

As will be appreciated from the above disclosure, the degradation of a bead may refer to the disassociation of a bound or entrained species from a bead, both with and without structurally degrading the physical bead itself. For example, the degradation of the bead may involve cleavage of a cleavable linkage via one or more species and/or methods described elsewhere herein. In another example, entrained species may be released from beads through osmotic pressure differences due to, for example, changing chemical environments. By way of example, alteration of bead pore sizes due to osmotic pressure differences can generally occur without structural degradation of the bead itself. In some cases, an increase in pore size due to osmotic swelling of a bead can permit the release of entrained species within the bead. In other cases, osmotic shrinking of a bead may cause a bead to better retain an entrained species due to pore size contraction.

A degradable bead may be introduced into a partition, such as a droplet of an emulsion or a well, such that the bead degrades within the partition and any associated species (e.g., oligonucleotides) are released within the droplet when the appropriate stimulus is applied. The free species (e.g., oligonucleotides, nucleic acid molecules) may interact with other reagents contained in the partition. For example, a polyacrylamide bead comprising cystamine and linked, via a disulfide bond, to a barcode sequence, may be combined with a reducing agent within a droplet of a water-in-oil emulsion. Within the droplet, the reducing agent can break the various disulfide bonds, resulting in bead degradation and release of the barcode sequence into the aqueous, inner environment of the droplet. In another example, heating of a droplet comprising a bead-bound barcode sequence in basic solution may also result in bead degradation and release of the attached barcode sequence into the aqueous, inner environment of the droplet.

Any suitable number of molecular tag molecules (e.g., primer, barcoded oligonucleotide) can be associated with a bead such that, upon release from the bead, the molecular tag molecules (e.g., primer, e.g., barcoded oligonucleotide) are present in the partition at a pre-defined concentration. Such pre-defined concentration may be selected to facilitate certain reactions for generating a sequencing library, e.g., amplification, within the partition. In some cases, the pre-defined concentration of the primer can be limited by the process of producing nucleic acid molecule (e.g., oligonucleotide) bearing beads.

In some cases, beads can be non-covalently loaded with one or more reagents. The beads can be non-covalently loaded by, for instance, subjecting the beads to conditions sufficient to swell the beads, allowing sufficient time for the reagents to diffuse into the interiors of the beads, and subjecting the beads to conditions sufficient to de-swell the beads. The swelling of the beads may be accomplished, for instance, by placing the beads in a thermodynamically favorable solvent, subjecting the beads to a higher or lower temperature, subjecting the beads to a higher or lower ion concentration, and/or subjecting the beads to an electric field. The swelling of the beads may be accomplished by various swelling methods. The de-swelling of the beads may be accomplished, for instance, by transferring the beads in a thermodynamically unfavorable solvent, subjecting the beads to lower or high temperatures, subjecting the beads to a lower or higher ion concentration, and/or removing an electric field. The de-swelling of the beads may be accomplished by various de-swelling methods. Transferring the beads may cause pores in the bead to shrink. The shrinking may then hinder reagents within the beads from diffusing out of the interiors of the beads. The hindrance may be due to steric interactions between the reagents and the interiors of the beads. The transfer may be accomplished microfluidically. For instance, the transfer may be achieved by moving the beads from one co-flowing solvent stream to a different co-flowing solvent stream. The swellability and/or pore size of the beads may be adjusted by changing the polymer composition of the bead.

In some cases, an acrydite moiety linked to a precursor, another species linked to a precursor, or a precursor itself can comprise a labile bond, such as chemically, thermally, or photo-sensitive bond e.g., disulfide bond, UV sensitive bond, or the like. Once acrydite moieties or other moieties comprising a labile bond are incorporated into a bead, the bead may also comprise the labile bond. The labile bond may be, for example, useful in reversibly linking (e.g., covalently linking) species (e.g., barcodes, primers, etc.) to a bead. In some cases, a thermally labile bond may include a nucleic acid hybridization based attachment, e.g., where an oligonucleotide is hybridized to a complementary sequence that is attached to the bead, such that thermal melting of the hybrid releases the oligonucleotide, e.g., a barcode containing sequence, from the bead or microcapsule.

The addition of multiple types of labile bonds to a gel bead may result in the generation of a bead capable of responding to varied stimuli. Each type of labile bond may be sensitive to an associated stimulus (e.g., chemical stimulus, light, temperature, enzymatic, etc.) such that release of species attached to a bead via each labile bond may be controlled by the application of the appropriate stimulus. Such functionality may be useful in controlled release of species from a gel bead. In some cases, another species comprising a labile bond may be linked to a gel bead after gel bead formation via, for example, an activated functional group of the gel bead as described above. As will be appreciated, barcodes that are releasably, cleavably or reversibly attached to the beads described herein include barcodes that are released or releasable through cleavage of a linkage between the barcode molecule and the bead, or that are released through degradation of the underlying bead itself, allowing the barcodes to be accessed or accessible by other reagents, or both.

The barcodes that are releasable as described herein may sometimes be referred to as being activatable, in that they are available for reaction once released. Thus, for example, an activatable barcode may be activated by releasing the barcode from a bead (or other suitable type of partition described herein). Other activatable configurations are also envisioned in the context of the described methods and systems.

In addition to thermally cleavable bonds, disulfide bonds and UV sensitive bonds, other non-limiting examples of labile bonds that may be coupled to a precursor or bead include an ester linkage (e.g., cleavable with an acid, a base, or hydroxylamine), a vicinal diol linkage (e.g., cleavable via sodium periodate), a Diels-Alder linkage (e.g., cleavable via heat), a sulfone linkage (e.g., cleavable via a base), a silyl ether linkage (e.g., cleavable via an acid), a glycosidic linkage (e.g., cleavable via an amylase), a peptide linkage (e.g., cleavable via a protease), or a phosphodiester linkage (e.g., cleavable via a nuclease (e.g., DNAase)). A bond may be cleavable via other nucleic acid molecule targeting enzymes, such as restriction enzymes (e.g., restriction endonucleases), as described further below.

Species may be encapsulated in beads during bead generation (e.g., during polymerization of precursors). Such species may or may not participate in polymerization. Such species may be entered into polymerization reaction mixtures such that generated beads comprise the species upon bead formation. In some cases, such species may be added to the gel beads after formation. Such species may include, for example, nucleic acid molecules (e.g., oligonucleotides), reagents for a nucleic acid amplification reaction (e.g., primers, polymerases, dNTPs, co-factors (e.g., ionic co-factors), buffers) including those described herein, reagents for enzymatic reactions (e.g., enzymes, co-factors, substrates, buffers), reagents for nucleic acid modification reactions such as polymerization, ligation, or digestion, and/or reagents for template preparation (e.g., tagmentation) for one or more sequencing platforms (e.g., Nextera® for Illumina®). Such species may include one or more enzymes described herein, including without limitation, polymerase, reverse transcriptase, restriction enzymes (e.g., endonuclease), transposase, ligase, proteinase K, DNAse, etc. Such species may include one or more reagents described elsewhere herein (e.g., lysis agents, inhibitors, inactivating agents, chelating agents, stimulus). Trapping of such species may be controlled by the polymer network density generated during polymerization of precursors, control of ionic charge within the gel bead (e.g., via ionic species linked to polymerized species), or by the release of other species. Encapsulated species may be released from a bead upon bead degradation and/or by application of a stimulus capable of releasing the species from the bead. Alternatively or in addition, species may be partitioned in a partition (e.g., droplet) during or subsequent to partition formation. Such species may include, without limitation, the abovementioned species that may also be encapsulated in a bead.

A degradable bead may comprise one or more species with a labile bond such that, when the bead/species is exposed to the appropriate stimuli, the bond is broken and the bead degrades. The labile bond may be a chemical bond (e.g., covalent bond, ionic bond) or may be another type of physical interaction (e.g., van der Waals interactions, dipole-dipole interactions, etc.). In some cases, a crosslinker used to generate a bead may comprise a labile bond. Upon exposure to the appropriate conditions, the labile bond can be broken and the bead degraded. For example, upon exposure of a polyacrylamide gel bead comprising cystamine crosslinkers to a reducing agent, the disulfide bonds of the cystamine can be broken and the bead degraded.

A degradable bead may be useful in more quickly releasing an attached species (e.g., a nucleic acid molecule, a barcode sequence, a primer, etc) from the bead when the appropriate stimulus is applied to the bead as compared to a bead that does not degrade. For example, for a species bound to an inner surface of a porous bead or in the case of an encapsulated species, the species may have greater mobility and accessibility to other species in solution upon degradation of the bead. In some cases, a species may also be attached to a degradable bead via a degradable linker (e.g., disulfide linker). The degradable linker may respond to the same stimuli as the degradable bead or the two degradable species may respond to different stimuli. For example, a barcode sequence may be attached, via a disulfide bond, to a polyacrylamide bead comprising cystamine. Upon exposure of the barcoded-bead to a reducing agent, the bead degrades and the barcode sequence is released upon breakage of both the disulfide linkage between the barcode sequence and the bead and the disulfide linkages of the cystamine in the bead.

As will be appreciated from the above disclosure, while referred to as degradation of a bead, in many instances as noted above, that degradation may refer to the disassociation of a bound or entrained species from a bead, both with and without structurally degrading the physical bead itself. For example, entrained species may be released from beads through osmotic pressure differences due to, for example, changing chemical environments. By way of example, alteration of bead pore sizes due to osmotic pressure differences can generally occur without structural degradation of the bead itself. In some cases, an increase in pore size due to osmotic swelling of a bead can permit the release of entrained species within the bead. In other cases, osmotic shrinking of a bead may cause a bead to better retain an entrained species due to pore size contraction.

Where degradable beads are provided, it may be beneficial to avoid exposing such beads to the stimulus or stimuli that cause such degradation prior to a given time, in order to, for example, avoid premature bead degradation and issues that arise from such degradation, including for example poor flow characteristics and aggregation. By way of example, where beads comprise reducible cross-linking groups, such as disulfide groups, it will be desirable to avoid contacting such beads with reducing agents, e.g., DTT or other disulfide cleaving reagents. In such cases, treatment to the beads described herein will, in some cases be provided free of reducing agents, such as DTT. Because reducing agents are often provided in commercial enzyme preparations, it may be desirable to provide reducing agent free (or DTT free) enzyme preparations in treating the beads described herein. Examples of such enzymes include, e.g., polymerase enzyme preparations, reverse transcriptase enzyme preparations, ligase enzyme preparations, as well as many other enzyme preparations that may be used to treat the beads described herein. The terms "reducing agent free" or "DTT free" preparations can refer to a preparation having less than about 1/10th, less than about 1/50th, or even less than about 1/100th of the lower ranges for such materials used in degrading the beads. For example, for DTT, the reducing agent free preparation can have less than about 0.01 millimolar (mM), 0.005 mM, 0.001 mM DTT, 0.0005 mM DTT, or even less than about 0.0001 mM DTT. In many cases, the amount of DTT can be undetectable.

Numerous chemical triggers may be used to trigger the degradation of beads. Examples of these chemical changes may include, but are not limited to pH-mediated changes to the integrity of a component within the bead, degradation of a component of a bead via cleavage of cross-linked bonds, and depolymerization of a component of a bead.

A bead may be formed from materials that comprise degradable chemical crosslinkers, such as BAC or cystamine. Degradation of such degradable crosslinkers may be accomplished through a number of mechanisms. In some examples, a bead may be contacted with a chemical degrading agent that may induce oxidation, reduction or other chemical changes. For example, a chemical degrading agent may be a reducing agent, such as dithiothreitol (DTT). Additional examples of reducing agents may include β-mercaptoethanol, (2S)-2-amino-1,4-dimercaptobutane (dithiobutylamine or DTBA), tris(2-carboxyethyl) phosphine (TCEP), or combinations thereof. A reducing agent may degrade the disulfide bonds formed between gel precursors forming the bead, and thus, degrade the bead. In other cases, a change in pH of a solution, such as an increase in pH, may trigger degradation of a bead. In other cases, exposure to an aqueous solution, such as water, may trigger hydrolytic degradation, and thus degradation of the bead. In some cases, any combination of stimuli may trigger degradation of a bead. For example, a change in pH may enable a chemical agent (e.g., DTT) to become an effective reducing agent.

Beads may also be induced to release their contents upon the application of a thermal stimulus. A change in temperature can cause a variety of changes to a bead. For example, heat can cause a solid bead to liquefy. A change in heat may cause melting of a bead such that a portion of the bead degrades. In other cases, heat may increase the internal pressure of the bead components such that the bead ruptures or explodes. Heat may also act upon heat-sensitive polymers used as materials to construct beads.

Any suitable agent may degrade beads. For example, changes in temperature or pH may be used to degrade thermo-sensitive or pH-sensitive bonds within beads. Alternatively or in addition to, chemical degrading agents may be used to degrade chemical bonds within beads by oxidation, reduction or other chemical changes. For example, a chemical degrading agent may be a reducing agent, such as DTT, wherein DTT may degrade the disulfide bonds formed between a crosslinker and gel precursors, thus degrading the bead. A reducing agent may be added to degrade the bead, which may or may not cause the bead to release its contents. Examples of reducing agents may include dithiothreitol (DTT), β-mercaptoethanol, (2S)-2-amino-1,4-dimercaptobutane (dithiobutylamine or DTBA), tris(2-carboxyethyl) phosphine (TCEP), or combinations thereof. The reducing agent may be present at a concentration of about 0.1 mM, 0.5 mM, 1 mM, 5 mM, 10 mM. The reducing agent may be present at a concentration of at least about 0.1 mM, 0.5 mM, 1 mM, 5 mM, 10 mM, or greater than 10 mM. The reducing agent may be present at concentration of at most about 10 mM, 5 mM, 1 mM, 0.5 mM, 0.1 mM, or less.

Any suitable number of molecular tag molecules (e.g., primer, barcoded oligonucleotide) can be associated with a bead such that, upon release from the bead, the molecular tag molecules (e.g., primer, e.g., barcoded oligonucleotide) are present in the partition at a pre-defined concentration. Such pre-defined concentration may be selected to facilitate certain reactions for generating a sequencing library, e.g., amplification, within the partition. In some cases, the pre-defined concentration of the primer can be limited by the process of producing oligonucleotide bearing beads.

Although FIG. 1 and FIG. 2 have been described in terms of providing substantially singly occupied partitions, above, in certain cases, it may be desirable to provide multiply occupied partitions, e.g., containing two, three, four or more cells and/or microcapsules (e.g., beads) comprising barcoded nucleic acid molecules (e.g., oligonucleotides) within a single partition. Accordingly, as noted above, the flow characteristics of the biological particle and/or bead containing fluids and partitioning fluids may be controlled to provide for such multiply occupied partitions. In particular, the flow parameters may be controlled to provide a occupancy rate at greater than about 50% of the partitions, greater than about 75%, and in some cases greater than about 80%, 90%, 95%, or higher.

In some cases, additional microcapsules can be used to deliver additional reagents to a partition. In such cases, it may be advantageous to introduce different beads into a common channel or droplet generation junction, from different bead sources (e.g., containing different associated reagents) through different channel inlets into such common channel or droplet generation junction (e.g., junction 210). In such cases, the flow and frequency of the different beads into the channel or junction may be controlled to provide for a certain ratio of microcapsules from each source, while ensuring a pairing or combination of such beads into a partition with a given number of biological particles (e.g., one biological particle and one bead per partition).

The partitions described herein may comprise small volumes, for example, less than about 10 microliters (μL), 5 μL, 1 μL, 900 picoliters (pL), 800 pL, 700 pL, 600 pL, 500 pL, 400 pL, 300 pL, 200 pL, 100 pL, 50 pL, 20 pL, 10 pL, 1 pL, 500 nanoliters (nL), 100 nL, 50 nL, or less.

For example, in the case of droplet based partitions, the droplets may have overall volumes that are less than about 1000 pL, 900 pL, 800 pL, 700 pL, 600 pL, 500 pL, 400 pL, 300 pL, 200 pL, 100 pL, 50 pL, 20 pL, 10 pL, 1 pL, or less. Where co-partitioned with microcapsules, it will be appreciated that the sample fluid volume, e.g., including co-partitioned biological particles and/or beads, within the partitions may be less than about 90% of the above described volumes, less than about 80%, less than about 70%, less than about 60%, less than about 50%, less than about 40%, less than about 30%, less than about 20%, or less than about 10% of the above described volumes.

As is described elsewhere herein, partitioning species may generate a population or plurality of partitions. In such cases, any suitable number of partitions can be generated or otherwise provided. For example, at least about 1,000 partitions, at least about 5,000 partitions, at least about 10,000 partitions, at least about 50,000 partitions, at least about 100,000 partitions, at least about 500,000 partitions, at least about 1,000,000 partitions, at least about 5,000,000 partitions at least about 10,000,000 partitions, at least about 50,000,000 partitions, at least about 100,000,000 partitions, at least about 500,000,000 partitions, at least about 1,000,000,000 partitions, or more partitions can be generated or otherwise provided. Moreover, the plurality of partitions may comprise both unoccupied partitions (e.g., empty partitions) and occupied partitions.

Reagents

In accordance with certain aspects, biological particles may be partitioned along with lysis reagents in order to release the contents of the biological particles within the partition. In such cases, the lysis agents can be contacted with the biological particle suspension concurrently with, or immediately prior to, the introduction of the biological particles into the partitioning junction/droplet generation zone (e.g., junction 210), such as through an additional channel or channels upstream of the channel junction. In accordance with other aspects, additionally or alternatively, biological particles may be partitioned along with other reagents, as will be described further below.

Figure 3:
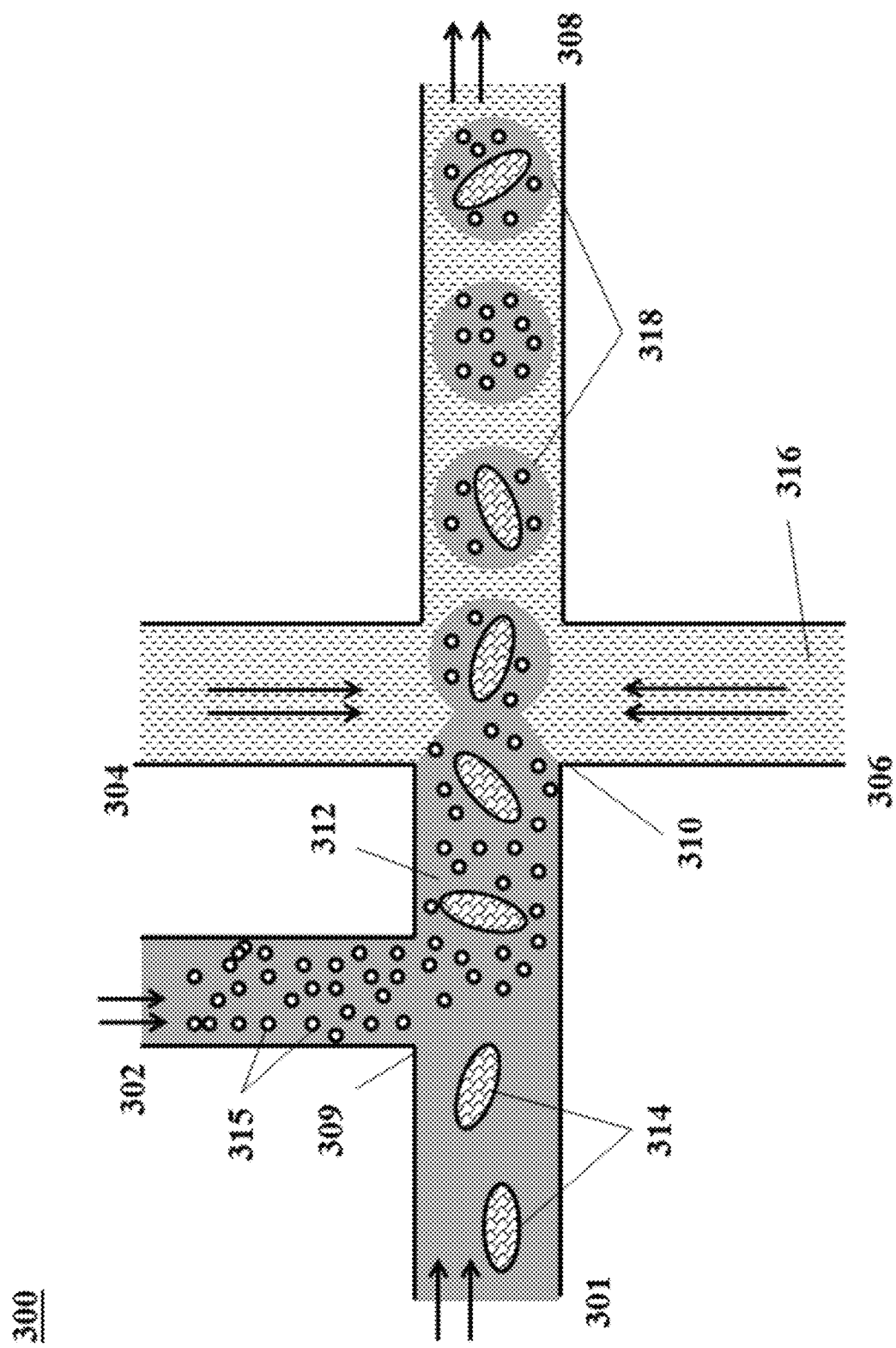
FIG. 3 shows an example of a microfluidic channel structure for co-partitioning biological particles and reagents.

FIG. 3 shows an example of a microfluidic channel structure 300 for co-partitioning biological particles and reagents. The channel structure 300 can include channel segments 301, 302, 304, 306 and 308. Channel segments 301 and 302 communicate at a first channel junction 309. Channel segments 302, 304, 306, and 308 communicate at a second channel junction 310.

In an example operation, the channel segment 301 may transport an aqueous fluid 312 that includes a plurality of biological particles 314 along the channel segment 301 into the second junction 310. As an alternative or in addition to, channel segment 301 may transport beads (e.g., gel beads). The beads may comprise barcode molecules.

For example, the channel segment 301 may be connected to a reservoir comprising an aqueous suspension of biological particles 314. Upstream of, and immediately prior to reaching, the second junction 310, the channel segment 301 may meet the channel segment 302 at the first junction 309. The channel segment 302 may transport a plurality of reagents 315 (e.g., lysis agents) suspended in the aqueous fluid 312 along the channel segment 302 into the first junction 309. For example, the channel segment 302 may be connected to a reservoir comprising the reagents 315. After the first junction 309, the aqueous fluid 312 in the channel segment 301 can carry both the biological particles 314 and the reagents 315 towards the second junction 310. In some instances, the aqueous fluid 312 in the channel segment 301 can include one or more reagents, which can be the same or different reagents as the reagents 315. A second fluid 316 that is immiscible with the aqueous fluid 312 (e.g., oil) can be delivered to the second junction 310 from each of channel segments 304 and 306. Upon meeting of the aqueous fluid 312 from the channel segment 301 and the second fluid 316 from each of channel segments 304 and 306 at the second channel junction 310, the aqueous fluid 312 can be partitioned as discrete droplets 318 in the second fluid 316 and flow away from the second junction 310 along channel segment 308. The channel segment 308 may deliver the discrete droplets 318 to an outlet reservoir fluidly coupled to the channel segment 308, where they may be harvested.

The second fluid 316 can comprise an oil, such as a fluorinated oil, that includes a fluorosurfactant for stabilizing the resulting droplets, for example, inhibiting subsequent coalescence of the resulting droplets 318.

A discrete droplet generated may include an individual biological particle 314 and/or one or more reagents 315. In some instances, a discrete droplet generated may include a barcode carrying bead (not shown), such as via other microfluidics structures described elsewhere herein. In some instances, a discrete droplet may be unoccupied (e.g., no reagents, no biological particles).

Beneficially, when lysis reagents and biological particles are co-partitioned, the lysis reagents can facilitate the release of the contents of the biological particles within the partition. The contents released in a partition may remain discrete from the contents of other partitions.

As will be appreciated, the channel segments described herein may be coupled to any of a variety of different fluid sources or receiving components, including reservoirs, tubing, manifolds, or fluidic components of other systems. As will be appreciated, the microfluidic channel structure 300 may have other geometries. For example, a microfluidic channel structure can have more than two channel junctions. For example, a microfluidic channel structure can have 2, 3, 4, 5 channel segments or more each carrying the same or different types of beads, reagents, and/or biological particles that meet at a channel junction. Fluid flow in each channel segment may be controlled to control the partitioning of the different elements into droplets. Fluid may be directed flow along one or more channels or reservoirs via one or more fluid flow units. A fluid flow unit can comprise compressors (e.g., providing positive pressure), pumps (e.g., providing negative pressure), actuators, and the like to control flow of the fluid. Fluid may also or otherwise be controlled via applied pressure differentials, centrifugal force, electrokinetic pumping, vacuum, capillary or gravity flow, or the like.

Examples of lysis agents include bioactive reagents, such as lysis enzymes that are used for lysis of different cell types, e.g., gram positive or negative bacteria, plants, yeast, mammalian, etc., such as lysozymes, achromopeptidase, lysostaphin, labiase, kitalase, lyticase, and a variety of other lysis enzymes available from, e.g., Sigma-Aldrich, Inc. (St Louis, Mo.), as well as other commercially available lysis enzymes. Other lysis agents may additionally or alternatively be co-partitioned with the biological particles to cause the release of the biological particle's contents into the partitions. For example, in some cases, surfactant-based lysis solutions may be used to lyse cells, although these may be less desirable for emulsion based systems where the surfactants can interfere with stable emulsions. In some cases, lysis solutions may include non-ionic surfactants such as, for example, TritonX-100 and Tween 20. In some cases, lysis solutions may include ionic surfactants such as, for example, sarcosyl and sodium dodecyl sulfate (SDS). Electroporation, thermal, acoustic or mechanical cellular disruption may also be used in certain cases, e.g., non-emulsion based partitioning such as encapsulation of biological particles that may be in addition to or in place of droplet partitioning, where any pore size of the encapsulate is sufficiently small to retain nucleic acid fragments of a given size, following cellular disruption.

Alternatively or in addition to the lysis agents co-partitioned with the biological particles described above, other reagents can also be co-partitioned with the biological particles, including, for example, DNase and RNase inactivating agents or inhibitors, such as proteinase K, chelating agents, such as EDTA, and other reagents employed in removing or otherwise reducing negative activity or impact of different cell lysate components on subsequent processing of nucleic acids. In addition, in the case of encapsulated biological particles, the biological particles may be exposed to an appropriate stimulus to release the biological particles or their contents from a co-partitioned microcapsule. For example, in some cases, a chemical stimulus may be co-partitioned along with an encapsulated biological particle to allow for the degradation of the microcapsule and release of the cell or its contents into the larger partition. In some cases, this stimulus may be the same as the stimulus described elsewhere herein for release of nucleic acid molecules (e.g., oligonucleotides) from their respective microcapsule (e.g., bead). In alternative aspects, this may be a different and non-overlapping stimulus, in order to allow an encapsulated biological particle to be released into a partition at a different time from the release of nucleic acid molecules into the same partition.

Additional reagents may also be co-partitioned with the biological particles, such as endonucleases to fragment a biological particle's DNA, DNA polymerase enzymes and dNTPs used to amplify the biological particle's nucleic acid fragments and to attach the barcode molecular tags to the amplified fragments. Other enzymes may be co-partitioned, including without limitation, polymerase, transposase, ligase, proteinase K, DNAse, etc. Additional reagents may also include reverse transcriptase enzymes, including enzymes with terminal transferase activity, primers and oligonucleotides, and switch oligonucleotides (also referred to herein as "switch oligos" or "template switching oligonucleotides") which can be used for template switching. In some cases, template switching can be used to increase the length of a cDNA. In some cases, template switching oligonucleotides can be used to append a predefined nucleic acid sequence to the cDNA. In an example of template switching, cDNA can be generated from reverse transcription of a template, e.g., cellular mRNA, where a reverse transcriptase with terminal transferase activity can add additional nucleotides, e.g., polyC, to the cDNA in a template independent manner. Switch oligos can include sequences complementary to the additional nucleotides, e.g., polyG. The additional nucleotides (e.g., polyC) on the cDNA can hybridize to the additional nucleotides (e.g., polyG) on the switch oligo, whereby the switch oligo can be used by the reverse transcriptase as template to further extend the cDNA. Template switching oligonucleotides may comprise a hybridization region and a template region. The hybridization region can comprise any sequence capable of hybridizing to the target. In some cases, as previously described, the hybridization region comprises a series of G bases to complement the overhanging C bases at the 3' end of a cDNA molecule. The series of G bases may comprise 1 G base, 2 G bases, 3 G bases, 4 G bases, 5 G bases or more than 5 G bases. The template sequence can comprise any sequence to be incorporated into the cDNA. In some cases, the template region comprises at least 1 (e.g., at least 2, 3, 4, 5 or more) tag sequences and/or functional sequences. Switch oligos may comprise deoxyribonucleic acids; ribonucleic acids; modified nucleic acids including 2-Aminopurine, 2,6-Diaminopurine (2-Amino-dA), inverted dT, 5-Methyl dC, 2'-deoxyInosine, Super T (5-hydroxybutynl-2'-deoxyuridine), Super G (8-aza-7-deazaguanosine), locked nucleic acids (LNAs), unlocked nucleic acids (UNAs, e.g., UNA-A, UNA-U, UNA-C, UNA-G), Iso-dG, Iso-dC, 2' Fluoro bases (e.g., Fluoro C, Fluoro U, Fluoro A, and Fluoro G), or any combination.

In some cases, the length of a switch oligo may be at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249 or 250 nucleotides or longer.

In some cases, the length of a switch oligo may be at most about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249 or 250 nucleotides.

Once the contents of the cells are released into their respective partitions, the macromolecular components (e.g., macromolecular constituents of biological particles, such as RNA, DNA, or proteins) contained therein may be further processed within the partitions. In accordance with the methods and systems described herein, the macromolecular component contents of individual biological particles can be provided with unique identifiers such that, upon characterization of those macromolecular components they may be attributed as having been derived from the same biological particle or particles. The ability to attribute characteristics to individual biological particles or groups of biological particles is provided by the assignment of unique identifiers specifically to an individual biological particle or groups of biological particles. Unique identifiers, e.g., in the form of nucleic acid barcodes can be assigned or associated with individual biological particles or populations of biological particles, in order to tag or label the biological particle's macromolecular components (and as a result, its characteristics) with the unique identifiers. These unique identifiers can then be used to attribute the biological particle's components and characteristics to an individual biological particle or group of biological particles.

In some aspects, this is performed by co-partitioning the individual biological particle or groups of biological particles with the unique identifiers, such as described above (with reference to FIG. 2). In some aspects, the unique identifiers are provided in the form of nucleic acid molecules (e.g., oligonucleotides) that comprise nucleic acid barcode sequences that may be attached to or otherwise associated with the nucleic acid contents of individual biological particle, or to other components of the biological particle, and particularly to fragments of those nucleic acids. The nucleic acid molecules are partitioned such that as between nucleic acid molecules in a partition, the nucleic acid barcode sequences contained therein are the same, but as between different partitions, the nucleic acid molecule can, and do have differing barcode sequences, or at least represent a large number of different barcode sequences across all of the partitions in a analysis. In some aspects, only one nucleic acid barcode sequence can be associated with a partition, although in some cases, two or more different barcode sequences may be present.

The nucleic acid barcode sequences can include from about 6 to about 20 or more nucleotides within the sequence of the nucleic acid molecules (e.g., oligonucleotides). The nucleic acid barcode sequences can include from about 6 to about 20, 30, 40, 50, 60, 70, 80, 90, 100 or more nucleotides. In some cases, the length of a barcode sequence may be about 6, 7, 8, 9, 10, 11, 12, 13, 14, 15, 16, 17, 18, 19, 20 nucleotides or longer. In some cases, the length of a barcode sequence may be at least about 6, 7, 8, 9, 10, 11, 12, 13, 14, 15, 16, 17, 18, 19, 20 nucleotides or longer. In some cases, the length of a barcode sequence may be at most about 6, 7, 8, 9, 10, 11, 12, 13, 14, 15, 16, 17, 18, 19, 20 nucleotides or shorter. These nucleotides may be completely contiguous, i.e., in a single stretch of adjacent nucleotides, or they may be separated into two or more separate subsequences that are separated by 1 or more nucleotides. In some cases, separated barcode subsequences can be from about 4 to about 16 nucleotides in length. In some cases, the barcode subsequence may be about 4, 5, 6, 7, 8, 9, 10, 11, 12, 13, 14, 15, 16 nucleotides or longer. In some cases, the barcode subsequence may be at least about 4, 5, 6, 7, 8, 9, 10, 11, 12, 13, 14, 15, 16 nucleotides or longer. In some cases, the barcode subsequence may be at most about 4, 5, 6, 7, 8, 9, 10, 11, 12, 13, 14, 15, 16 nucleotides or shorter.

The co-partitioned nucleic acid molecules can also comprise other functional sequences useful in the processing of the nucleic acids from the co-partitioned biological particles. These sequences include, e.g., targeted or random/universal amplification primer sequences for amplifying the genomic DNA from the individual biological particles within the partitions while attaching the associated barcode sequences, sequencing primers or primer recognition sites, hybridization or probing sequences, e.g., for identification of presence of the sequences or for pulling down barcoded nucleic acids, or any of a number of other potential functional sequences. Other mechanisms of co-partitioning oligonucleotides may also be employed, including, e.g., coalescence of two or more droplets, where one droplet contains oligonucleotides, or microdispensing of oligonucleotides into partitions, e.g., droplets within microfluidic systems.

In an example, microcapsules, such as beads, are provided that each include large numbers of the above described barcoded nucleic acid molecules (e.g., barcoded oligonucleotides) releasably attached to the beads, where all of the nucleic acid molecules attached to a particular bead will include the same nucleic acid barcode sequence, but where a large number of diverse barcode sequences are represented across the population of beads used. Hydrogel beads, e.g., comprising polyacrylamide polymer matrices, may be used as a solid support and delivery vehicle for the nucleic acid molecules into the partitions, as they are capable of carrying large numbers of nucleic acid molecules, and may be configured to release those nucleic acid molecules upon exposure to a particular stimulus, as described elsewhere herein. In some cases, the population of beads provides a diverse barcode sequence library that includes at least about 1,000 different barcode sequences, at least about 5,000 different barcode sequences, at least about 10,000 different barcode sequences, at least about 50,000 different barcode sequences, at least about 100,000 different barcode sequences, at least about 1,000,000 different barcode sequences, at least about 5,000,000 different barcode sequences, or at least about 10,000,000 different barcode sequences, or more. Additionally, each bead can be provided with large numbers of nucleic acid (e.g., oligonucleotide) molecules attached. In particular, the number of molecules of nucleic acid molecules including the barcode sequence on an individual bead can be at least about 1,000 nucleic acid molecules, at least about 5,000 nucleic acid molecules, at least about 10,000 nucleic acid molecules, at least about 50,000 nucleic acid molecules, at least about 100,000 nucleic acid molecules, at least about 500,000 nucleic acids, at least about 1,000,000 nucleic acid molecules, at least about 5,000,000 nucleic acid molecules, at least about 10,000,000 nucleic acid molecules, at least about 50,000,000 nucleic acid molecules, at least about 100,000,000 nucleic acid molecules, at least about 250,000,000 nucleic acid molecules and in some cases at least about 1 billion nucleic acid molecules, or more. Nucleic acid molecules of a bead can include identical (or common) barcode sequences, different barcode sequences, or a combination of both. Nucleic acid molecules of a bead can include multiple sets of nucleic acid molecules. Nucleic acid molecules of a set can include identical barcode sequences. The identical barcode sequences can be different from barcode sequences of nucleic acid molecules of another set.

Moreover, when the population of beads is partitioned, the resulting population of partitions can also include a diverse barcode library that includes at least about 1,000 different barcode sequences, at least about 5,000 different barcode sequences, at least about 10,000 different barcode sequences, at least at least about 50,000 different barcode sequences, at least about 100,000 different barcode sequences, at least about 1,000,000 different barcode sequences, at least about 5,000,000 different barcode sequences, or at least about 10,000,000 different barcode sequences. Additionally, each partition of the population can include at least about 1,000 nucleic acid molecules, at least about 5,000 nucleic acid molecules, at least about 10,000 nucleic acid molecules, at least about 50,000 nucleic acid molecules, at least about 100,000 nucleic acid molecules, at least about 500,000 nucleic acids, at least about 1,000,000 nucleic acid molecules, at least about 5,000,000 nucleic acid molecules, at least about 10,000,000 nucleic acid molecules, at least about 50,000,000 nucleic acid molecules, at least about 100,000,000 nucleic acid molecules, at least about 250,000,000 nucleic acid molecules and in some cases at least about 1 billion nucleic acid molecules.

In some cases, it may be desirable to incorporate multiple different barcodes within a partition, either attached to a single or multiple beads within the partition. For example, in some cases, a mixed, but known set of barcode sequences may provide greater assurance of identification in the subsequent processing, e.g., by providing a stronger address or attribution of the barcodes to a partition, as a duplicate or independent confirmation of the output from a partition.

The nucleic acid molecules (e.g., oligonucleotides) are releasable from the beads upon the application of a particular stimulus to the beads. In some cases, the stimulus may be a photo-stimulus, e.g., through cleavage of a photo-labile linkage that releases the nucleic acid molecules. In other cases, a thermal stimulus may be used, where elevation of the temperature of the beads environment will result in cleavage of a linkage or other release of the nucleic acid molecules from the beads. In still other cases, a chemical stimulus can be used that cleaves a linkage of the nucleic acid molecules to the beads, or otherwise results in release of the nucleic acid molecules from the beads. In one case, such compositions include the polyacrylamide matrices described above for encapsulation of biological particles, and may be degraded for release of the attached nucleic acid molecules through exposure to a reducing agent, such as DTT.

In some aspects, provided are systems and methods for controlled partitioning. Droplet size may be controlled by adjusting certain geometric features in channel architecture (e.g., microfluidics channel architecture). For example, an expansion angle, width, and/or length of a channel may be adjusted to control droplet size.

Figure 4:
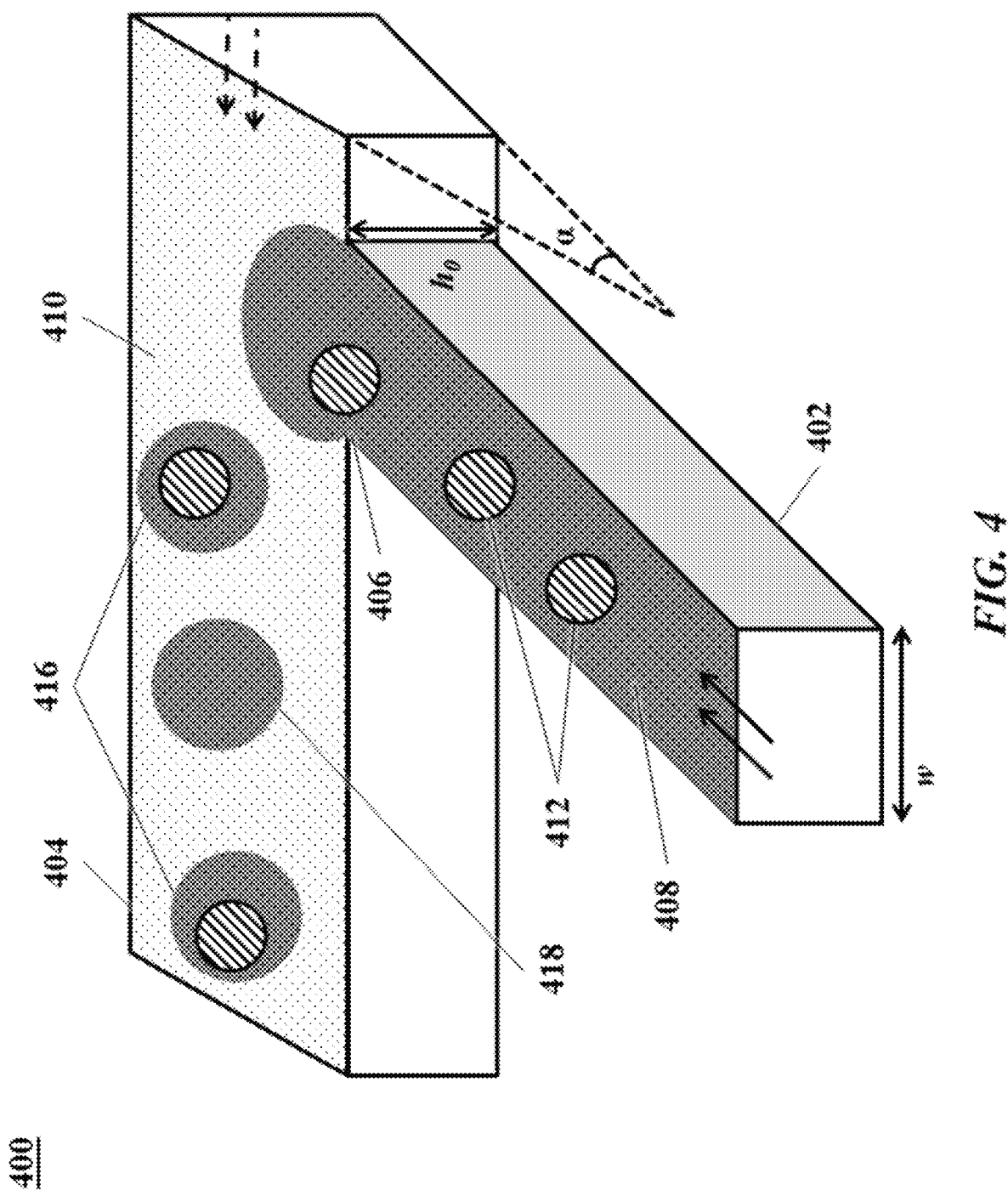
FIG. 4 shows an example of a microfluidic channel structure for the controlled partitioning of beads into discrete droplets.

FIG. 4 shows an example of a microfluidic channel structure for the controlled partitioning of beads into discrete droplets. A channel structure 400 can include a channel segment 402 communicating at a channel junction 406 (or intersection) with a reservoir 404. The reservoir 404 can be a chamber. Any reference to "reservoir," as used herein, can also refer to a "chamber." In operation, an aqueous fluid 408 that includes suspended beads 412 may be transported along the channel segment 402 into the junction 406 to meet a second fluid 410 that is immiscible with the aqueous fluid 408 in the reservoir 404 to create droplets 416, 418 of the aqueous fluid 408 flowing into the reservoir 404. At the junction 406 where the aqueous fluid 408 and the second fluid 410 meet, droplets can form based on factors such as the hydrodynamic forces at the junction 406, flow rates of the two fluids 408, 410, fluid properties, and certain geometric parameters (e.g., w, $h_0$, $\alpha$, etc.) of the channel structure 400. A plurality of droplets can be collected at the reservoir 404 by continuously injecting the aqueous fluid 408 from the channel segment 402 through the junction 406.

A discrete droplet generated may include a bead (e.g., as in occupied droplets 416). Alternatively, a discrete droplet generated may include more than one bead. Alternatively, a discrete droplet generated may not include any beads (e.g., as in unoccupied droplet 418). In some instances, a discrete droplet generated may contain one or more biological particles, as described elsewhere herein. In some instances, a discrete droplet generated may comprise one or more reagents, as described elsewhere herein.

In some instances, the aqueous fluid 408 can have a substantially uniform concentration or frequency of beads 412. The beads 412 can be introduced into the channel segment 402 from a separate channel (not shown in FIG. 4). The frequency of beads 412 in the channel segment 402 may be controlled by controlling the frequency in which the beads 412 are introduced into the channel segment 402 and/or the relative flow rates of the fluids in the channel segment 402 and the separate channel. In some instances, the beads can be introduced into the channel segment 402 from a plurality of different channels, and the frequency controlled accordingly.

In some instances, the aqueous fluid 408 in the channel segment 402 can comprise biological particles (e.g., described with reference to FIGS. 1 and 2). In some instances, the aqueous fluid 408 can have a substantially uniform concentration or frequency of biological particles. As with the beads, the biological particles can be introduced into the channel segment 402 from a separate channel. The frequency or concentration of the biological particles in the aqueous fluid 408 in the channel segment 402 may be controlled by controlling the frequency in which the biological particles are introduced into the channel segment 402 and/or the relative flow rates of the fluids in the channel segment 402 and the separate channel. In some instances, the biological particles can be introduced into the channel segment 402 from a plurality of different channels, and the frequency controlled accordingly. In some instances, a first separate channel can introduce beads and a second separate channel can introduce biological particles into the channel segment 402. The first separate channel introducing the beads may be upstream or downstream of the second separate channel introducing the biological particles.

The second fluid 410 can comprise an oil, such as a fluorinated oil, that includes a fluorosurfactant for stabilizing the resulting droplets, for example, inhibiting subsequent coalescence of the resulting droplets.

In some instances, the second fluid 410 may not be subjected to and/or directed to any flow in or out of the reservoir 404. For example, the second fluid 410 may be substantially stationary in the reservoir 404. In some instances, the second fluid 410 may be subjected to flow within the reservoir 404, but not in or out of the reservoir 404, such as via application of pressure to the reservoir 404 and/or as affected by the incoming flow of the aqueous fluid 408 at the junction 406. Alternatively, the second fluid 410 may be subjected and/or directed to flow in or out of the reservoir 404. For example, the reservoir 404 can be a channel directing the second fluid 410 from upstream to downstream, transporting the generated droplets.

The channel structure 400 at or near the junction 406 may have certain geometric features that at least partly determine the sizes of the droplets formed by the channel structure 400. The channel segment 402 can have a height, $h_0$ and width, w, at or near the junction 406. By way of example, the channel segment 402 can comprise a rectangular cross-section that leads to a reservoir 404 having a wider cross-section (such as in width or diameter). Alternatively, the cross-section of the channel segment 402 can be other shapes, such as a circular shape, trapezoidal shape, polygonal shape, or any other shapes. The top and bottom walls of the reservoir 404 at or near the junction 406 can be inclined at an expansion angle, a. The expansion angle, a, allows the tongue (portion of the aqueous fluid 408 leaving channel segment 402 at junction 406 and entering the reservoir 404 before droplet formation) to increase in depth and facilitate decrease in curvature of the intermediately formed droplet. Droplet size may decrease with increasing expansion angle. The resulting droplet radius, $R_d$, may be predicted by the following equation for the aforementioned geometric parameters of $h_0$, w, and $\alpha$:

$$R_d \approx 0.44\left(1 + 2.2\sqrt{\tan \alpha}\,\frac{w}{h_0}\right)\frac{h_0}{\sqrt{\tan \alpha}}$$

By way of example, for a channel structure with w=21 µm, h=21 µm, and $\alpha$=3°, the predicted droplet size is 121

μm. In another example, for a channel structure with w=25 μm, h=25 μm, and α=5°, the predicted droplet size is 123 μm. In another example, for a channel structure with w=28 μm, h=28 μm, and α=7°, the predicted droplet size is 124 μm.

In some instances, the expansion angle, a, may be between a range of from about 0.5° to about 4°, from about 0.1° to about 10°, or from about 0° to about 90°. For example, the expansion angle can be at least about 0.01, 0.1°, 0.2°, 0.3°, 0.4°, 0.5°, 0.6°, 0.7°, 0.8°, 0.9°, 1°, 2°, 3°, 4°, 5°, 6°, 7°, 8°, 9°, 10°, 15°, 20°, 20°, 25°, 30°, 35°, 40°, 45°, 50°, 55°, 60°, 65°, 70°, 75°, 80°, 85°, or higher. In some instances, the expansion angle can be at most about 89°, 88°, 87°, 86°, 85°, 84°, 83°, 82°, 81°, 80°, 75°, 70°, 65°, 60°, 55°, 50°, 45°, 40°, 35°, 30°, 25°, 20°, 15°, 10°, 9°, 8°, 7°, 6°, 5°, 4°, 3°, 2°, 1°, 0.1°, 0.01°, or less. In some instances, the width, w, can be between a range of from about 100 micrometers (μm) to about 500 μm. In some instances, the width, w, can be between a range of from about 10 μm to about 200 μm. Alternatively, the width can be less than about 10 μm. Alternatively, the width can be greater than about 500 μm. In some instances, the flow rate of the aqueous fluid 408 entering the junction 406 can be between about 0.04 microliters (μL)/minute (min) and about 40 μL/min. In some instances, the flow rate of the aqueous fluid 408 entering the junction 406 can be between about 0.01 microliters (μL)/minute (min) and about 100 μL/min. Alternatively, the flow rate of the aqueous fluid 408 entering the junction 406 can be less than about 0.01 μL/min. Alternatively, the flow rate of the aqueous fluid 408 entering the junction 406 can be greater than about 40 μL/min, such as 45 μL/min, 50 μL/min, 55 μL/min, 60 μL/min, 65 μL/min, 70 μL/min, 75 μL/min, 80 μL/min, 85 μL/min, 90 μL/min, 95 μL/min, 100 μL/min, 110 μL/min, 120, 130 μL/min, 140 μL/min, 150 μL/min, or greater. At lower flow rates, such as flow rates of about less than or equal to 10 microliters/minute, the droplet radius may not be dependent on the flow rate of the aqueous fluid 408 entering the junction 406.

In some instances, at least about 50% of the droplets generated can have uniform size. In some instances, at least about 55%, 60%, 65%, 70%, 75%, 80%, 85%, 90%, 95%, 96%, 97%, 98%, 99%, or greater of the droplets generated can have uniform size. Alternatively, less than about 50% of the droplets generated can have uniform size.

The throughput of droplet generation can be increased by increasing the points of generation, such as increasing the number of junctions (e.g., junction 406) between aqueous fluid 408 channel segments (e.g., channel segment 402) and the reservoir 404. Alternatively or in addition, the throughput of droplet generation can be increased by increasing the flow rate of the aqueous fluid 408 in the channel segment 402.

Figure 5:
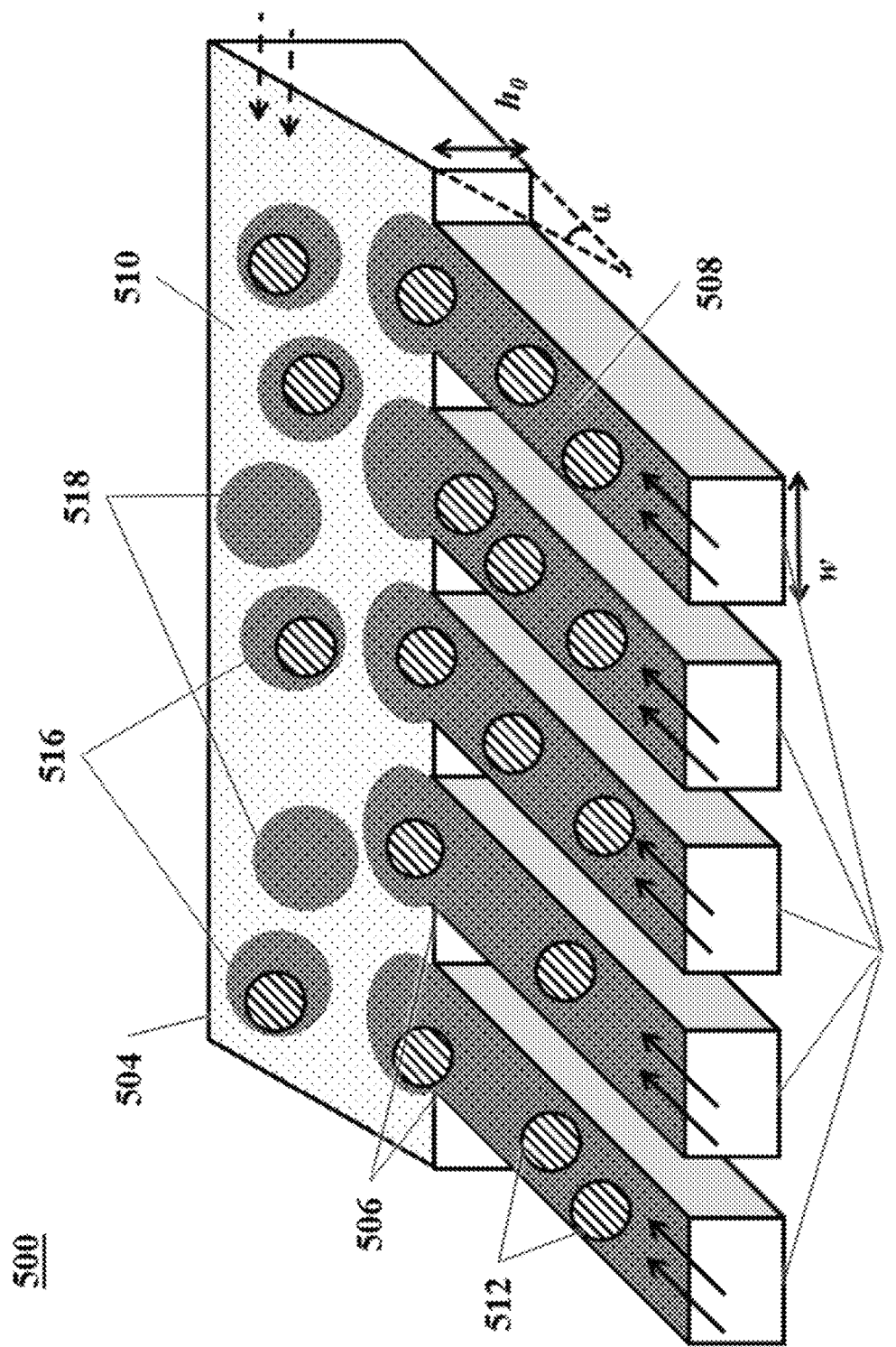
FIG. 5 shows an example of a microfluidic channel structure for increased droplet generation throughput.

FIG. 5 shows an example of a microfluidic channel structure for increased droplet generation throughput. A microfluidic channel structure 500 can comprise a plurality of channel segments 502 and a reservoir 504. Each of the plurality of channel segments 502 may be in fluid communication with the reservoir 504. The channel structure 500 can comprise a plurality of channel junctions 506 between the plurality of channel segments 502 and the reservoir 504. Each channel junction can be a point of droplet generation. The channel segment 402 from the channel structure 400 in FIG. 4 and any description to the components thereof may correspond to a channel segment of the plurality of channel segments 502 in channel structure 500 and any description to the corresponding components thereof. The reservoir 404 from the channel structure 400 and any description to the components thereof may correspond to the reservoir 504 from the channel structure 500 and any description to the corresponding components thereof.

Each channel segment of the plurality of channel segments 502 may comprise an aqueous fluid 508 that includes suspended beads 512. The reservoir 504 may comprise a second fluid 510 that is immiscible with the aqueous fluid 508. In some instances, the second fluid 510 may not be subjected to and/or directed to any flow in or out of the reservoir 504. For example, the second fluid 510 may be substantially stationary in the reservoir 504. In some instances, the second fluid 510 may be subjected to flow within the reservoir 504, but not in or out of the reservoir 504, such as via application of pressure to the reservoir 504 and/or as affected by the incoming flow of the aqueous fluid 508 at the junctions. Alternatively, the second fluid 510 may be subjected and/or directed to flow in or out of the reservoir 504. For example, the reservoir 504 can be a channel directing the second fluid 510 from upstream to downstream, transporting the generated droplets.

In operation, the aqueous fluid 508 that includes suspended beads 512 may be transported along the plurality of channel segments 502 into the plurality of junctions 506 to meet the second fluid 510 in the reservoir 504 to create droplets 516, 518. A droplet may form from each channel segment at each corresponding junction with the reservoir 504. At the junction where the aqueous fluid 508 and the second fluid 510 meet, droplets can form based on factors such as the hydrodynamic forces at the junction, flow rates of the two fluids 508, 510, fluid properties, and certain geometric parameters (e.g., w, $h_0$, α, etc.) of the channel structure 500, as described elsewhere herein. A plurality of droplets can be collected in the reservoir 504 by continuously injecting the aqueous fluid 508 from the plurality of channel segments 502 through the plurality of junctions 506. Throughput may significantly increase with the parallel channel configuration of channel structure 500. For example, a channel structure having five inlet channel segments comprising the aqueous fluid 508 may generate droplets five times as frequently than a channel structure having one inlet channel segment, provided that the fluid flow rate in the channel segments are substantially the same. The fluid flow rate in the different inlet channel segments may or may not be substantially the same. A channel structure may have as many parallel channel segments as is practical and allowed for the size of the reservoir. For example, the channel structure may have at least about 2, 3, 4, 5, 6, 7, 8, 9, 10, 20, 30, 40, 50, 60, 70, 80, 90, 100, 150, 500, 250, 300, 350, 400, 450, 500, 600, 700, 800, 900, 1000, 1500, 5000 or more parallel or substantially parallel channel segments.

The geometric parameters, w, $h_0$, and a, may or may not be uniform for each of the channel segments in the plurality of channel segments 502. For example, each channel segment may have the same or different widths at or near its respective channel junction with the reservoir 504. For example, each channel segment may have the same or different height at or near its respective channel junction with the reservoir 504. In another example, the reservoir 504 may have the same or different expansion angle at the different channel junctions with the plurality of channel segments 502. When the geometric parameters are uniform, beneficially, droplet size may also be controlled to be uniform even with the increased throughput. In some instances, when it is desirable to have a different distribution of droplet sizes, the geometric parameters for the plurality of channel segments 502 may be varied accordingly.

In some instances, at least about 50% of the droplets generated can have uniform size. In some instances, at least about 55%, 60%, 65%, 70%, 75%, 80%, 85%, 90%, 95%, 96%, 97%, 98%, 99%, or greater of the droplets generated can have uniform size. Alternatively, less than about 50% of the droplets generated can have uniform size.

Figure 6:
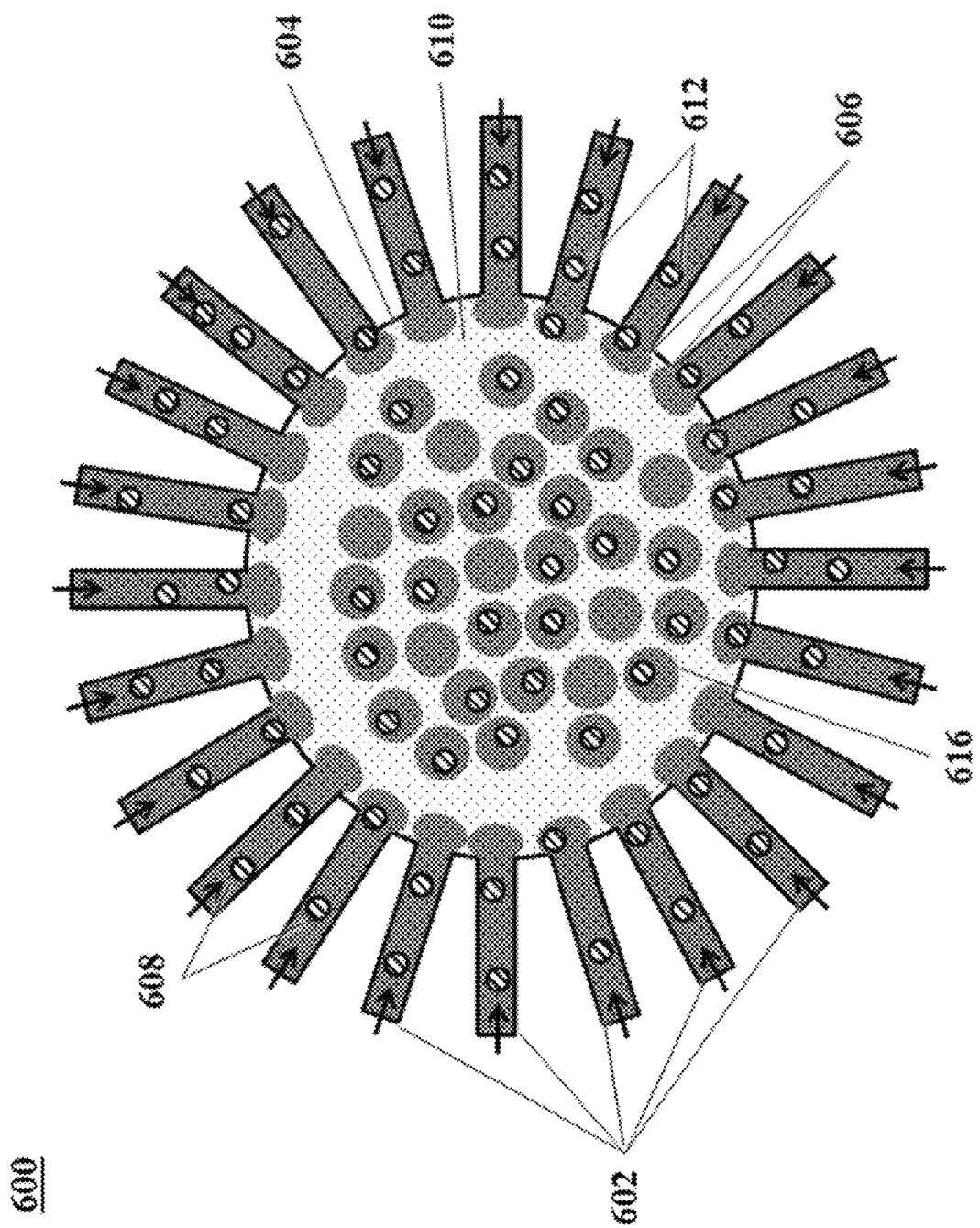
FIG. 6 shows another example of a microfluidic channel structure for increased droplet generation throughput.

FIG. 6 shows another example of a microfluidic channel structure for increased droplet generation throughput. A microfluidic channel structure 600 can comprise a plurality of channel segments 602 arranged generally circularly around the perimeter of a reservoir 604. Each of the plurality of channel segments 602 may be in fluid communication with the reservoir 604. The channel structure 600 can comprise a plurality of channel junctions 606 between the plurality of channel segments 602 and the reservoir 604. Each channel junction can be a point of droplet generation. The channel segment 402 from the channel structure 400 in FIG. 4 and any description to the components thereof may correspond to a channel segment of the plurality of channel segments 602 in channel structure 600 and any description to the corresponding components thereof. The reservoir 404 from the channel structure 400 and any description to the components thereof may correspond to the reservoir 604 from the channel structure 600 and any description to the corresponding components thereof.

Each channel segment of the plurality of channel segments 602 may comprise an aqueous fluid 608 that includes suspended beads 612. The reservoir 604 may comprise a second fluid 610 that is immiscible with the aqueous fluid 608. In some instances, the second fluid 610 may not be subjected to and/or directed to any flow in or out of the reservoir 604. For example, the second fluid 610 may be substantially stationary in the reservoir 604. In some instances, the second fluid 610 may be subjected to flow within the reservoir 604, but not in or out of the reservoir 604, such as via application of pressure to the reservoir 604 and/or as affected by the incoming flow of the aqueous fluid 608 at the junctions. Alternatively, the second fluid 610 may be subjected and/or directed to flow in or out of the reservoir 604. For example, the reservoir 604 can be a channel directing the second fluid 610 from upstream to downstream, transporting the generated droplets.

In operation, the aqueous fluid 608 that includes suspended beads 612 may be transported along the plurality of channel segments 602 into the plurality of junctions 606 to meet the second fluid 610 in the reservoir 604 to create a plurality of droplets 616. A droplet may form from each channel segment at each corresponding junction with the reservoir 604. At the junction where the aqueous fluid 608 and the second fluid 610 meet, droplets can form based on factors such as the hydrodynamic forces at the junction, flow rates of the two fluids 608, 610, fluid properties, and certain geometric parameters (e.g., widths and heights of the channel segments 602, expansion angle of the reservoir 604, etc.) of the channel structure 600, as described elsewhere herein. A plurality of droplets can be collected in the reservoir 604 by continuously injecting the aqueous fluid 608 from the plurality of channel segments 602 through the plurality of junctions 606. Throughput may significantly increase with the substantially parallel channel configuration of the channel structure 600. A channel structure may have as many substantially parallel channel segments as is practical and allowed for by the size of the reservoir. For example, the channel structure may have at least about 2, 3, 4, 5, 6, 7, 8, 9, 10, 20, 30, 40, 50, 60, 70, 80, 90, 100, 150, 200, 250, 300, 350, 400, 450, 500, 600, 700, 800, 900, 1000, 1500, 5000 or more parallel or substantially parallel channel segments. The plurality of channel segments may be substantially evenly spaced apart, for example, around an edge or perimeter of the reservoir. Alternatively, the spacing of the plurality of channel segments may be uneven.

The reservoir 604 may have an expansion angle, a (not shown in FIG. 6) at or near each channel junction. Each channel segment of the plurality of channel segments 602 may have a width, w, and a height, $h_0$, at or near the channel junction. The geometric parameters, w, $h_0$, and a, may or may not be uniform for each of the channel segments in the plurality of channel segments 602. For example, each channel segment may have the same or different widths at or near its respective channel junction with the reservoir 604. For example, each channel segment may have the same or different height at or near its respective channel junction with the reservoir 604.

The reservoir 604 may have the same or different expansion angle at the different channel junctions with the plurality of channel segments 602. For example, a circular reservoir (as shown in FIG. 6) may have a conical, dome-like, or hemispherical ceiling (e.g., top wall) to provide the same or substantially same expansion angle for each channel segments 602 at or near the plurality of channel junctions 606. When the geometric parameters are uniform, beneficially, resulting droplet size may be controlled to be uniform even with the increased throughput. In some instances, when it is desirable to have a different distribution of droplet sizes, the geometric parameters for the plurality of channel segments 602 may be varied accordingly.

In some instances, at least about 50% of the droplets generated can have uniform size. In some instances, at least about 55%, 60%, 65%, 70%, 75%, 80%, 85%, 90%, 95%, 96%, 97%, 98%, 99%, or greater of the droplets generated can have uniform size. Alternatively, less than about 50% of the droplets generated can have uniform size. The beads and/or biological particle injected into the droplets may or may not have uniform size.

Figure 7A:
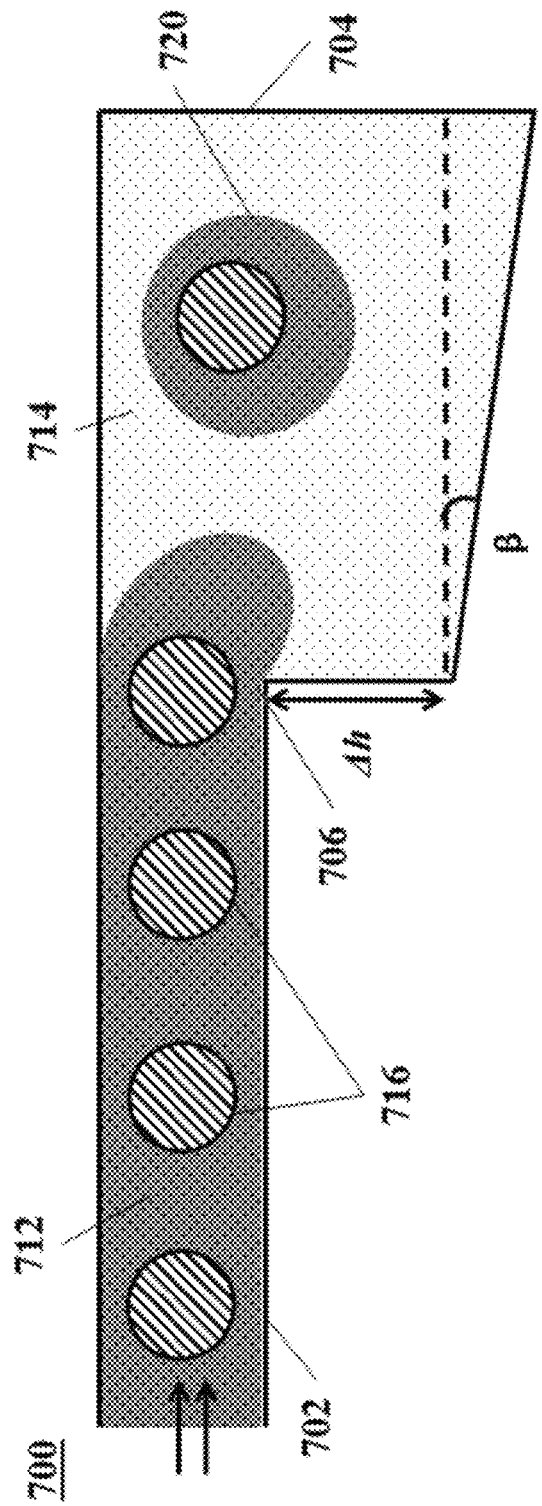
FIG. 7A shows a cross-section view of another example of a microfluidic channel structure with a geometric feature for controlled partitioning.
Figure 7B:
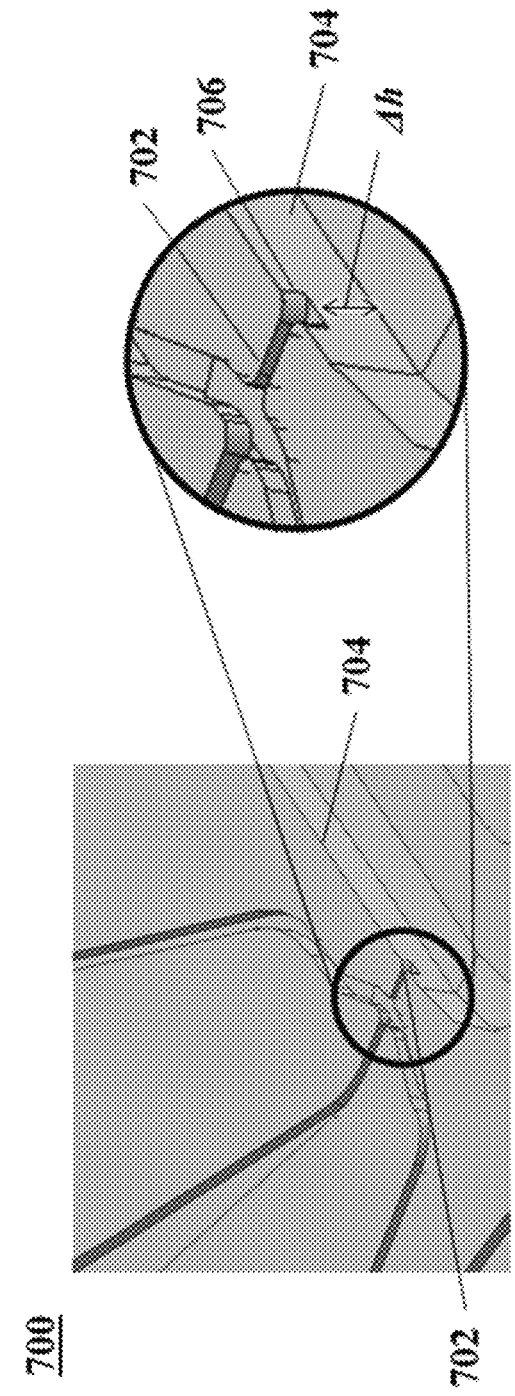
FIG. 7B shows a perspective view of the channel structure of FIG. 7A.

FIG. 7A shows a cross-section view of another example of a microfluidic channel structure with a geometric feature for controlled partitioning. A channel structure 700 can include a channel segment 702 communicating at a channel junction 706 (or intersection) with a reservoir 704. In some instances, the channel structure 700 and one or more of its components can correspond to the channel structure 100 and one or more of its components. FIG. 7B shows a perspective view of the channel structure 700 of FIG. 7A.

An aqueous fluid 712 comprising a plurality of particles 716 may be transported along the channel segment 702 into the junction 706 to meet a second fluid 714 (e.g., oil, etc.) that is immiscible with the aqueous fluid 712 in the reservoir 704 to create droplets 720 of the aqueous fluid 712 flowing into the reservoir 704. At the junction 706 where the aqueous fluid 712 and the second fluid 714 meet, droplets can form based on factors such as the hydrodynamic forces at the junction 706, relative flow rates of the two fluids 712, 714, fluid properties, and certain geometric parameters (e.g., $\Delta h$, etc.) of the channel structure 700. A plurality of droplets can be collected in the reservoir 704 by continuously injecting the aqueous fluid 712 from the channel segment 702 at the junction 706.

A discrete droplet generated may comprise one or more particles of the plurality of particles 716. As described elsewhere herein, a particle may be any particle, such as a bead, cell bead, gel bead, biological particle, macromolecular constituents of biological particle, or other particles. Alternatively, a discrete droplet generated may not include any particles.

In some instances, the aqueous fluid 712 can have a substantially uniform concentration or frequency of particles 716. As described elsewhere herein (e.g., with reference to FIG. 4), the particles 716 (e.g., beads) can be introduced into the channel segment 702 from a separate channel (not shown in FIG. 7). The frequency of particles 716 in the channel segment 702 may be controlled by controlling the frequency in which the particles 716 are introduced into the channel segment 702 and/or the relative flow rates of the fluids in the channel segment 702 and the separate channel. In some instances, the particles 716 can be introduced into the channel segment 702 from a plurality of different channels, and the frequency controlled accordingly. In some instances, different particles may be introduced via separate channels. For example, a first separate channel can introduce beads and a second separate channel can introduce biological particles into the channel segment 702. The first separate channel introducing the beads may be upstream or downstream of the second separate channel introducing the biological particles.

In some instances, the second fluid 714 may not be subjected to and/or directed to any flow in or out of the reservoir 704. For example, the second fluid 714 may be substantially stationary in the reservoir 704. In some instances, the second fluid 714 may be subjected to flow within the reservoir 704, but not in or out of the reservoir 704, such as via application of pressure to the reservoir 704 and/or as affected by the incoming flow of the aqueous fluid 712 at the junction 706. Alternatively, the second fluid 714 may be subjected and/or directed to flow in or out of the reservoir 704. For example, the reservoir 704 can be a channel directing the second fluid 714 from upstream to downstream, transporting the generated droplets.

The channel structure 700 at or near the junction 706 may have certain geometric features that at least partly determine the sizes and/or shapes of the droplets formed by the channel structure 700. The channel segment 702 can have a first cross-section height, $h_1$, and the reservoir 704 can have a second cross-section height, $h_2$. The first cross-section height, $h_1$, and the second cross-section height, $h_2$, may be different, such that at the junction 706, there is a height difference of 4 h. The second cross-section height, $h_2$, may be greater than the first cross-section height, $h_1$. In some instances, the reservoir may thereafter gradually increase in cross-section height, for example, the more distant it is from the junction 706. In some instances, the cross-section height of the reservoir may increase in accordance with expansion angle, β, at or near the junction 706. The height difference, Δh, and/or expansion angle, β, can allow the tongue (portion of the aqueous fluid 712 leaving channel segment 702 at junction 706 and entering the reservoir 704 before droplet formation) to increase in depth and facilitate decrease in curvature of the intermediately formed droplet. For example, droplet size may decrease with increasing height difference and/or increasing expansion angle.

The height difference, Δh, can be at least about 1 μm. Alternatively, the height difference can be at least about 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 200, 300, 400, 500 μm or more. Alternatively, the height difference can be at most about 500, 400, 300, 200, 100, 90, 80, 70, 60, 50, 45, 40, 35, 30, 25, 20, 19, 18, 17, 16, 15, 14, 13, 12, 11, 10, 9, 8, 7, 6, 5, 4, 3, 2, 1 μm or less. In some instances, the expansion angle, β, may be between a range of from about 0.5° to about 4°, from about 0.1° to about 10°, or from about 0° to about 90°. For example, the expansion angle can be at least about 0.01°, 0.1°, 0.2°, 0.3°, 0.4°, 0.5°, 0.6°, 0.7°, 0.8°, 0.9°, 1°, 2°, 3°, 4°, 5°, 6°, 7°, 8°, 9°, 10°, 15°, 20°, 25°, 30°, 35°, 40°, 45°, 50°, 55°, 60°, 65°, 70°, 75°, 80°, 85°, or higher. In some instances, the expansion angle can be at most about 89°, 88°, 87°, 86°, 85°, 84°, 83°, 82°, 81°, 80°, 75°, 70°, 65°, 60°, 55°, 50°, 40°, 35°, 30°, 25°, 20°, 15°, 10°, 9°, 8°, 7°, 6°, 5°, 4°, 3°, 2°, 1°, 0.1°, or less.

In some instances, the flow rate of the aqueous fluid 712 entering the junction 706 can be between about 0.04 microliters (μL)/minute (min) and about 40 μL/min. In some instances, the flow rate of the aqueous fluid 712 entering the junction 706 can be between about 0.01 microliters (μL)/minute (min) and about 100 μL/min. Alternatively, the flow rate of the aqueous fluid 712 entering the junction 706 can be less than about 0.01 μL/min. Alternatively, the flow rate of the aqueous fluid 712 entering the junction 706 can be greater than about 40 μL/min, such as 45 μL/min, 50 μL/min, 55 μL/min, 60 μL/min, 65 μL/min, 70 μL/min, 75 μL/min, 80 μL/min, 85 μL/min, 90 μL/min, 95 μL/min, 100 μL/min, 110 μL/min, 120 μL/min, 130 μL/min, 140 μL/min, 150 μL/min, or greater. At lower flow rates, such as flow rates of about less than or equal to 10 microliters/minute, the droplet radius may not be dependent on the flow rate of the aqueous fluid 712 entering the junction 706. The second fluid 714 may be stationary, or substantially stationary, in the reservoir 704. Alternatively, the second fluid 714 may be flowing, such as at the above flow rates described for the aqueous fluid 712.

In some instances, at least about 50% of the droplets generated can have uniform size. In some instances, at least about 55%, 60%, 65%, 70%, 75%, 80%, 85%, 90%, 95%, 96%, 97%, 98%, 99%, or greater of the droplets generated can have uniform size. Alternatively, less than about 50% of the droplets generated can have uniform size.

While FIGS. 7A and 7B illustrate the height difference, Δh, being abrupt at the junction 706 (e.g., a step increase), the height difference may increase gradually (e.g., from about 0 μm to a maximum height difference). Alternatively, the height difference may decrease gradually (e.g., taper) from a maximum height difference. A gradual increase or decrease in height difference, as used herein, may refer to a continuous incremental increase or decrease in height difference, wherein an angle between any one differential segment of a height profile and an immediately adjacent differential segment of the height profile is greater than 90°. For example, at the junction 706, a bottom wall of the channel and a bottom wall of the reservoir can meet at an angle greater than 90°. Alternatively or in addition, a top wall (e.g., ceiling) of the channel and a top wall (e.g., ceiling) of the reservoir can meet an angle greater than 90°. A gradual increase or decrease may be linear or non-linear (e.g., exponential, sinusoidal, etc.). Alternatively or in addition, the height difference may variably increase and/or decrease linearly or non-linearly. While FIGS. 7A and 7B illustrate the expanding reservoir cross-section height as linear (e.g., constant expansion angle, β), the cross-section height may expand non-linearly. For example, the reservoir may be defined at least partially by a dome-like (e.g., hemispherical) shape having variable expansion angles. The cross-section height may expand in any shape.

The channel networks, e.g., as described above or elsewhere herein, can be fluidly coupled to appropriate fluidic components. For example, the inlet channel segments are fluidly coupled to appropriate sources of the materials they are to deliver to a channel junction. These sources may include any of a variety of different fluidic components, from simple reservoirs defined in or connected to a body structure of a microfluidic device, to fluid conduits that deliver fluids from off-device sources, manifolds, fluid flow units (e.g., actuators, pumps, compressors) or the like. Likewise, the outlet channel segment (e.g., channel segment 208, reservoir 604, etc.) may be fluidly coupled to a receiving vessel or conduit for the partitioned cells for subsequent processing. Again, this may be a reservoir defined in the body of a microfluidic device, or it may be a fluidic conduit for delivering the partitioned cells to a subsequent process operation, instrument or component.

The methods and systems described herein may be used to greatly increase the efficiency of single cell applications and/or other applications receiving droplet-based input. For example, following the sorting of occupied cells and/or appropriately-sized cells, subsequent operations that can be performed can include generation of amplification products, purification (e.g., via solid phase reversible immobilization (SPRI)), further processing (e.g., shearing, ligation of functional sequences, and subsequent amplification (e.g., via PCR)). These operations may occur in bulk (e.g., outside the partition). In the case where a partition is a droplet in an emulsion, the emulsion can be broken and the contents of the droplet pooled for additional operations. Additional reagents that may be co-partitioned along with the barcode bearing bead may include oligonucleotides to block ribosomal RNA (rRNA) and nucleases to digest genomic DNA from cells. Alternatively, rRNA removal agents may be applied during additional processing operations. The configuration of the constructs generated by such a method can help minimize (or avoid) sequencing of the poly-T sequence during sequencing and/or sequence the 5' end of a polynucleotide sequence. The amplification products, for example, first amplification products and/or second amplification products, may be subject to sequencing for sequence analysis. In some cases, amplification may be performed using the Partial Hairpin Amplification for Sequencing (PHASE) method.

A variety of applications require the evaluation of the presence and quantification of different biological particle or organism types within a population of biological particles, including, for example, microbiome analysis and characterization, environmental testing, food safety testing, epidemiological analysis, e.g., in tracing contamination or the like.

Computer Systems

Figure 25:
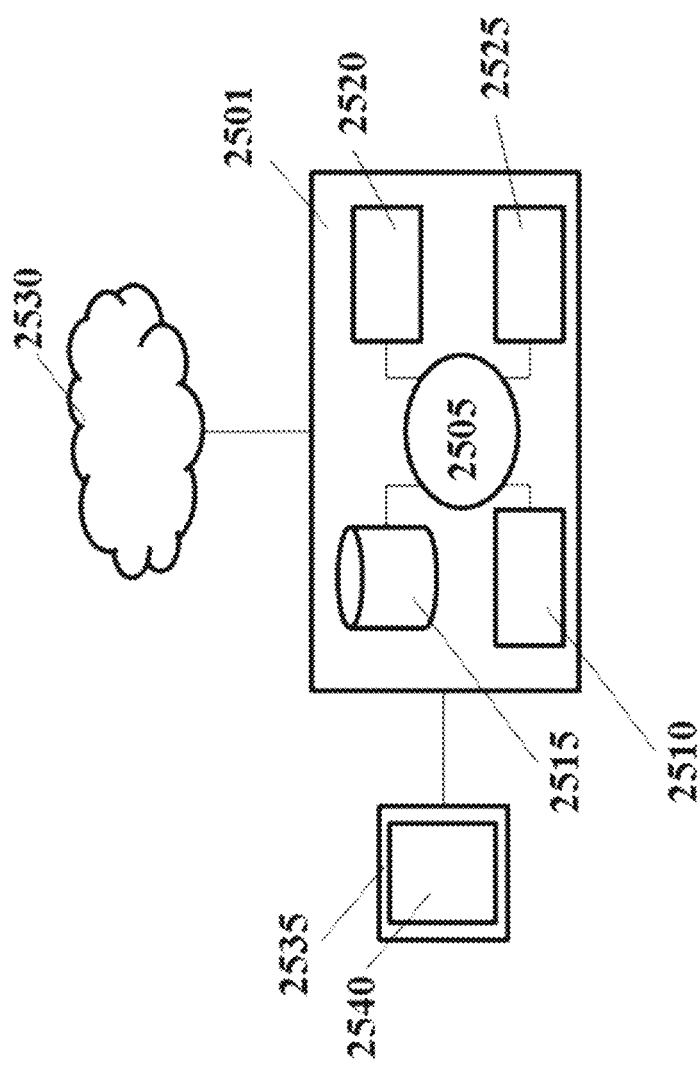
FIG. 25 shows a computer system that is programmed or otherwise configured to implement methods provided herein.

The present disclosure provides computer systems that are programmed to implement methods of the disclosure. FIG. 25 shows a computer system 2501 that is programmed or otherwise configured to implement one or more of the methods described herein. For example, computer system 2501 may be programmed or otherwise configured to control a microfluidics system (e.g., fluid flow), (ii) sort occupied droplets from unoccupied droplets, (iii) polymerize droplets, (iv) perform sequencing applications, and/or (v) generate and maintain sequencing libraries. The computer system 2501 can regulate various aspects of the present disclosure, such as, for example, regulating fluid flow rate in one or more channels in a microfluidic structure, regulating polymerization application units, etc. The computer system 2501 can be an electronic device of a user or a computer system that is remotely located with respect to the electronic device. The electronic device can be a mobile electronic device.

The computer system 2501 includes a central processing unit (CPU, also "processor" and "computer processor" herein) 2505, which can be a single core or multi core processor, or a plurality of processors for parallel processing. The computer system 2501 also includes memory or memory location 2510 (e.g., random-access memory, read-only memory, flash memory), electronic storage unit 2515 (e.g., hard disk), communication interface 2520 (e.g., network adapter) for communicating with one or more other systems, and peripheral devices 2525, such as cache, other memory, data storage and/or electronic display adapters. The memory 2510, storage unit 2515, interface 2520 and peripheral devices 2525 are in communication with the CPU 2505 through a communication bus (solid lines), such as a motherboard. The storage unit 2515 can be a data storage unit (or data repository) for storing data. The computer system 2501 can be operatively coupled to a computer network ("network") 2530 with the aid of the communication interface 2520. The network 2530 can be the Internet, an internet and/or extranet, or an intranet and/or extranet that is in communication with the Internet. The network 2530 in some cases is a telecommunication and/or data network. The network 2530 can include one or more computer servers, which can enable distributed computing, such as cloud computing. The network 2530, in some cases with the aid of the computer system 2501, can implement a peer-to-peer network, which may enable devices coupled to the computer system 2501 to behave as a client or a server.

The CPU 2505 can execute a sequence of machine-readable instructions, which can be embodied in a program or software. The instructions may be stored in a memory location, such as the memory 2510. The instructions can be directed to the CPU 2505, which can subsequently program or otherwise configure the CPU 2505 to implement methods of the present disclosure. Examples of operations performed by the CPU 2505 can include fetch, decode, execute, and writeback.

The CPU 2505 can be part of a circuit, such as an integrated circuit. One or more other components of the system 2501 can be included in the circuit. In some cases, the circuit is an application specific integrated circuit (ASIC).

The storage unit 2515 can store files, such as drivers, libraries and saved programs. The storage unit 2515 can store user data, e.g., user preferences and user programs. The computer system 2501 in some cases can include one or more additional data storage units that are external to the computer system 2501, such as located on a remote server that is in communication with the computer system 2501 through an intranet or the Internet.

The computer system 2501 can communicate with one or more remote computer systems through the network 2530. For instance, the computer system 2501 can communicate with a remote computer system of a user (e.g., operator). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 2501 via the network 2530.

Methods as described herein can be implemented by way of machine (e.g., computer processor) executable code stored on an electronic storage location of the computer system 2501, such as, for example, on the memory 2510 or electronic storage unit 2515. The machine executable or machine readable code can be provided in the form of software. During use, the code can be executed by the processor 2505. In some cases, the code can be retrieved from the storage unit 2515 and stored on the memory 2510 for ready access by the processor 2505. In some situations, the electronic storage unit 2515 can be precluded, and machine-executable instructions are stored on memory 2510.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 2501, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 2501 can include or be in communication with an electronic display 2535 that comprises a user interface (UI) 2540 for providing, for example, results of sequencing analysis, etc. Examples of UIs include, without limitation, a graphical user interface (GUI) and web-based user interface.

Methods and systems of the present disclosure can be implemented by way of one or more algorithms. An algorithm can be implemented by way of software upon execution by the central processing unit 2505. The algorithm can, for example, perform a nucleic acid sequencing assay, etc.

Devices, systems, compositions and methods of the present disclosure may be used for various applications, such as, for example, processing a single analyte (e.g., RNA, DNA, or protein) or multiple analytes (e.g., DNA and RNA, DNA and protein, RNA and protein, or RNA, DNA and protein) from a single cell. For example, a biological particle (e.g., a cell or cell bead) is partitioned in a partition (e.g., droplet), and multiple analytes from the biological particle are processed for subsequent processing. The multiple analytes may be from the single cell. This may enable, for example, simultaneous proteomic, transcriptomic and genomic analysis of the cell.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method comprising:
   (a) providing a partition comprising (i) a biological particle comprising (I) a tagmented fragment of a deoxyribonucleic acid (DNA) molecule and (II) a ribonucleic acid (RNA) molecule, (ii) a first nucleic acid barcode molecule comprising a first barcode sequence, (iii) a second nucleic acid barcode molecule comprising a second barcode sequence, and (iv) a splint molecule, wherein said first nucleic acid barcode molecule comprises an overhang sequence, and wherein said splint molecule comprises a first sequence complementary to a sequence of said tagmented fragment and a second sequence complementary to said overhang sequence; and
   (b) within said partition: (i) hybridizing said sequence of said tagmented fragment to said splint molecule, and hybridizing said overhang sequence of said first nucleic acid barcode molecule to said splint molecule to generate a first barcoded nucleic acid product comprising (I) said first barcode sequence or a complement thereof and (II) a sequence of said DNA molecule; and (ii) using said RNA molecule and said second nucleic acid barcode molecule to generate a second barcoded nucleic acid product comprising (I) said second barcode sequence or a complement thereof and (II) a complementary DNA (cDNA) sequence of said RNA molecule.

2. The method of claim 1, wherein said biological particle is a cell, a cell bead, or a cell nucleus.

3. The method of claim 1, further comprising lysing or permeabilizing said biological particle within said partition to provide access to said tagmented fragment and said RNA molecule.

4. The method of claim 1, further comprising, prior to (a), contacting an open chromatin structure of said biological particle with a transposase-nucleic acid complex to yield said biological particle comprising said tagmented fragment.

5. The method of claim 4, wherein said transposase-nucleic acid complex comprises a first adapter and a second adapter and wherein said tagmented fragment comprises a sequence of said DNA molecule flanked by said first adapter and said second adapter.

6. The method of claim 5, wherein (b)(i) comprises hybridizing said splint molecule to said first adapter or said second adapter of said tagmented fragment, and ligating said first nucleic acid barcode molecule and said tagmented fragment to generate said first barcoded nucleic acid product.

7. The method of claim 5, wherein said first adapter comprises a first transposon end sequence and a first primer sequence and wherein said second adapter comprises a second transposon end sequence and a second primer sequence.

8. The method of claim 7, wherein (b)(i) comprises:
hybridizing said splint molecule to said first primer sequence or said second primer sequence of said tagmented fragment.

9. The method of claim 8, further comprising, prior to said ligating, using a kinase to phosphorylate said tagmented fragment or said first nucleic acid barcode molecule.

10. The method of claim 9, wherein said kinase is a polynucleotide kinase (PNK).

11. The method of claim 7, wherein said first primer sequence or said second primer sequence is single stranded.

12. The method of claim 1, further comprising subjecting said first barcoded nucleic acid product to one or more nucleic acid extension reactions.

13. The method of claim 12, wherein said one or more nucleic acid extension reactions comprise attaching one or more functional sequences to said first barcoded nucleic acid product.

14. The method of claim 13, wherein said one or more functional sequences comprise one or more flow cell adapter sequences, one or more sequencing primer sequences, one or more sequencing primer binding sequences, or one or more sample index sequences.

15. The method of claim 1, wherein said second nucleic acid barcode molecule comprises a capture sequence complementary to said RNA molecule and wherein (b)(ii) comprises hybridizing said capture sequence to said RNA molecule and reverse transcribing said RNA molecule to generate said second barcoded nucleic acid product.

16. The method of claim 15, wherein said capture sequence comprises a polythymine (poly-T) sequence.

17. The method of claim 1, wherein said partition further comprises a primer comprising a sequence complementary to said RNA molecule and wherein (b)(ii) comprises hybridizing said primer to said RNA molecule, reverse transcribing said RNA molecule to generate a cDNA molecule, performing a template switching reaction onto said second nucleic acid barcode molecule, and extending said cDNA molecule to generate said second barcoded nucleic acid product.

18. The method of claim 17, wherein said sequence complementary to said RNA molecule comprises a polythymine (poly-T) sequence.

19. The method of claim 17, wherein said reverse transcribing comprises use of an enzyme with terminal transferase activity that appends a polynucleotide sequence to a 3' end of said cDNA molecule and wherein said second nucleic acid barcode molecule comprises a sequence complementary to said polynucleotide sequence to facilitate said template switching reaction.

20. The method of claim 19, wherein said polynucleotide sequence comprises a polycytosine (polyC) sequence and wherein said sequence complementary to said polynucleotide sequence comprises a polyguanine (polyG) sequence.

21. The method of claim 20, wherein said polyG sequence comprises a ribonucleotide.

22. The method of claim 1, wherein said partition is a droplet.

23. The method of claim 1, wherein said partition is a well.

24. The method of claim 1, wherein said first barcode sequence and said second barcode sequence are a same sequence.

25. The method of claim 1, wherein said first barcode sequence and said second barcode sequence are different.

26. The method of claim 1, wherein said tagmented fragment or said first nucleic acid barcode molecule comprises a 5' phosphate.

27. The method of claim 1, wherein said first nucleic acid barcode molecule and said second nucleic acid barcode molecule are coupled to a bead.

28. The method of claim 27, wherein said bead is a gel bead.

29. The method of claim 27, wherein said first nucleic acid barcode molecule and said second nucleic acid barcode molecule are releasable from said bead upon application of a stimulus.

30. The method of claim 27, wherein said first nucleic acid barcode molecule and said second nucleic acid barcode molecule are each coupled to said bead via a labile bond.

* * * * *